(12) United States Patent  (10) Patent No.: US 7,425,634 B2
Miyazawa et al.  (45) Date of Patent: Sep. 16, 2008

(54) BENZIMIDAZOLE COMPOUND

(75) Inventors: Shuhei Miyazawa, Tsukuba (JP);
Masanobu Shinoda, Tsukuba (JP);
Tetsuya Kawahara, Tsukuba (JP);
Nobuhisa Watanabe, Tsukuba (JP);
Hitoshi Harada, Tsukuba (JP); Daisuke Iida, Tsukuba (JP); Hiroki Terauchi, Tsukuba (JP); Junichi Nagakawa, Tsukuba (JP); Hideaki Fujisaki, Tsukuba (JP); Atsuhiko Kubota, Tsukuba (JP); Masato Ueda, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/520,838

(22) Filed: Sep. 14, 2006

(65) Prior Publication Data

US 2007/0010542 A1  Jan. 11, 2007

Related U.S. Application Data

(63) Continuation-in-part of application No. 11/403,815, filed on Apr. 14, 2006, now abandoned.

(60) Provisional application No. 60/675,848, filed on Apr. 29, 2005.

(30) Foreign Application Priority Data

Apr. 15, 2005 (JP) ............... 2005-117643

(51) Int. Cl.
C07D 401/12 (2006.01)
(52) U.S. Cl. .................. 546/273.7
(58) Field of Classification Search ........... 546/273.7
See application file for complete search history.

(56) References Cited

U.S. PATENT DOCUMENTS

| 4,808,596 | A | 2/1989 | Matsuishi et al. |
| 5,039,806 | A | 8/1991 | Brändström et al. |
| 5,430,042 | A | 7/1995 | Lindberg et al. |
| 2004/0266828 | A1 | 12/2004 | Garvey et al. |

FOREIGN PATENT DOCUMENTS

| EP | 0 187 977 A1 | 7/1986 |
| EP | 0 254 588 A1 | 1/1988 |
| JP | 59-181277 A | 10/1984 |
| JP | 62-207271 A | 9/1987 |
| JP | 63-146882 A | 6/1988 |
| JP | 1-190682 A | 7/1989 |
| JP | 2-22273 A | 1/1990 |
| JP | 5-177268 A | 5/1993 |
| JP | 5-507713 A | 11/1993 |
| WO | WO-91/19712 A1 | 12/1991 |
| WO | WO-00/50037 A1 | 8/2000 |
| WO | WO-2004/035020 A2 | 4/2004 |

OTHER PUBLICATIONS

Vippagunta et al., "Crystalline Solids", Advanced Drug Delivery Reviews, 48 (2001), 3-26.*
Guiillory "Generation of, etc.," in Brittain (ed.), Polymorphism in Pharmaceutical Solids, 95, Marcel Dekker, NY, 1999, 183-226.*
N.J.V. Bell et al.; Appropriate Acid Suppression for the Management of Gastro-Oesophageal Reflux Diease; Digestion 1992; 51(supp 1): 59-67.
Matsuishi et al. II, "Preparation of, etc.", CA 112:77192 (1990). Abstract: JP 62-207271, Sep. 11, 1987.

* cited by examiner

*Primary Examiner*—Patricia L Morris
(74) *Attorney, Agent, or Firm*—Birch, Stewart, Kolasch and Birch, LLP

(57) ABSTRACT

An object of the present invention is to provide a novel chemical compound useful as a therapeutic or prophylactic agent for acid-related diseases, having an excellent inhibitory effect against gastric acid secretion, an excellent effect of maintaining the inhibitory effect against gastric acid secretion, thereby maintaining intragastric pH high for a long time, and having more safety and appropriate physicochemical stability.

Provided is a compound represented by

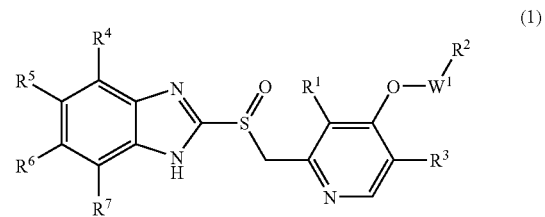

where $R^1$ and $R^3$ may be the same or different and each represent a hydrogen atom or a C1-C6 alkyl group; $R^2$ represents (5,5-dimethyl-1,3-dioxan-2-yl)methoxy group, 5,7-dioxaspiro[2.5]oct-6-ylmethoxy group, 1,5,9-trioxaspiro[5.5]undec-3-ylmethoxy group, or (2,2-dimethyl-1,3-dioxan-5-yl)methoxy group;
$R^4$, $R^5$, $R^6$ and $R^7$ represent a hydrogen atom, halogen atom, C1-C6 alkyl group, C1-C6 haloalkyl group, C1-C6 alkoxy group or C1-C6 haloalkoxy group; and $W^1$ represents a single bond, methylene or ethylene group,
a salt thereof or a solvate of these.

2 Claims, No Drawings

BENZIMIDAZOLE COMPOUND

CROSS-REFERENCE TO RELATED APPLICATION

The application is a continuation-in-part of U.S. patent application Ser. No. 11/403,815 filed Apr. 14, 2006, now abandoned, which is a non-provisional application of U.S. patent application Ser. No. 60/675,848 filed Apr. 29, 2005.

BACKGROUND OF THE INVENTION

1. Field of the Invention

The present invention relates to a benzimidazole compound or a salt thereof, or a solvate of these, useful as a gastric acid secretion inhibitor.

The present invention also relates to a benzimidazole compound or a salt thereof, or a solvate of these, useful as a therapeutic agent or prophylactic agent for acid-related diseases or symptoms (especially gastroesophageal reflux diseases, symptomatic gastroesophageal reflux diseases, gastric ulcers and duodenal ulcers).

2. Description of Related Art

Peptic ulcers such as gastric ulcer and duodenal ulcer are conceivably caused by the disruption of the balance between aggressive factors, such as acid and pepsin, and defensive factors, such as the mucus and blood flow, leading to autodigestion.

The peptic ulcer is principally treated by medical care, so that various drug therapies have been tried as the medical care. Particularly, in recent years, a medicament capable of specifically inhibiting $H^+/K^+$-ATPase, which is an enzyme present in the parietal cells and responsible for the final stage of gastric acid secretion, thereby suppressing gastric acid secretion and inhibiting autodigestion, has been developed and put to clinical use. Examples of such a medicament include omeprazole, esomeprazole, pantoprazole, lansoprazole, and rabeprazole.

These medicaments have excellent therapeutic effects; however, a medicament that more persistently inhibits gastric acid secretion, is safer, and is appropriately physicochemically stable has been still desired to be developed. In particular, it is also suggested that the cure rate of gastroesophageal reflux disease may be improved by maintaining the intragastric pH at a high value for a long time (Non-Patent Document 1).

Compounds particularly relevant to the present invention are described in Patent Documents 1 and 2. However, the compounds disclosed in these patent documents differ in chemical structure from the compounds specifically described in the present invention.

Patent Document 1: WO 91/19712
Patent Document 2: JP-A-59-181277
Non-Patent Document 1: Digestion 1992; 51 (suppl 1): 59-67

BRIEF SUMMARY OF THE INVENTION

An object of the present invention is to provide a novel compound having an excellent inhibitory effect against gastric acid secretion, useful as a therapeutic or prophylactic agent for acid-related diseases or symptoms and being excellent in maintaining the inhibitory effect against gastric acid secretion, thereby maintaining the intragastric pH high for a long time.

The present inventors have conducted intensive studies with the view toward attaining the aforementioned objects. As a result, they found that a benzimidazole compound having a novel chemical structure has an excellent inhibitory effect against gastric acid secretion, is excellent in maintaining the inhibitory effect against gastric acid secretion, thereby maintaining the intragastric pH at a high value for a long time, and particularly useful as a therapeutic or prophylactic agent for gastroesophageal reflux disease, symptomatic gastroesophageal reflux disease, gastric ulcer and duodenal ulcer. Based on these findings, the present invention was achieved.

DETAILED DESCRIPTION OF THE INVENTION

More particularly, the present invention provides a compound having the following formula (1) or a salt thereof, or a solvate of these.

[Formula 1]

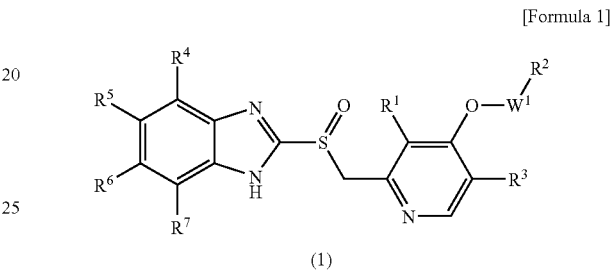

(1)

Furthermore, the present invention provides a medicament containing a compound having the formula (1) above or a salt thereof, or a solvate of these.

The present invention also provides a gastric acid secretion inhibitor containing a compound having the formula (1) above or a salt thereof, or a solvate of these.

The present invention further provides a pharmaceutical composition containing a compound having the formula (1) above or a salt thereof, or a solvate of these or use of a compound having the formula (1) above or a salt thereof, or a solvate of these for producing a pharmaceutical composition.

Further additionally, the present invention is directed to a therapeutic agent or prophylactic agent for acid-related diseases or symptoms, such as gastric ulcer, duodenal ulcer, anastomotic ulcer, gastroesophageal reflux disease (including gastroesophageal reflux disease with repeated relapses and recurrences), Zollinger-Ellison syndrome, symptomatic gastroesophageal reflux disease, endoscopically negative gastroesophageal reflux disease, non-erosive gastroesophageal reflux disease, gastroesophageal regurgitation, NUD (non-ulcer dyspepsia), abnormal sensation in the throat, Barrett's esophagus, NSAID-induced ulcer, gastritis, gastric bleeding, hemorrhagic gastritis, gastrointestinal bleeding, peptic ulcer, bleeding ulcer, stress ulcer, gastric hyperacidity, dyspepsia, gastroparesis, elderly person's ulcer, intractable ulcer, acute gastric mucosal lesion, heartburn, pyrosis of sleep apnea syndrome, bruxism, gastralgia, heavy stomach feeling, gagging, nausea, temporomandibular joint arthrosis, or erosive gastritis, and containing a compound having the general formula (1) above or a salt thereof or a solvate of these.

Preferable examples of acid-related diseases or symptoms may include gastric ulcer, duodenal ulcer, anastomotic ulcer, gastroesophageal reflux disease, Zollinger-Ellison syndrome, symptomatic gastroesophageal reflux disease, endoscopically negative gastroesophageal reflux disease, non-erosive gastroesophageal reflux disease, and acute gastric mucosal lesion. More preferable examples may include gastroesophageal reflux disease, symptomatic gastroesophageal reflux disease, gastric ulcer, and duodenal ulcer. Further more preferable examples may include (1) gastroesophageal reflux disease or symptomatic gastroesophageal reflux disease and (2) gastric ulcer, or duodenal ulcer.

On the other hand, the present invention is directed to an bactericidal agent or an auxiliary bactericidal agent against *Helicobacter pylori*, containing a compound having the formula (1) above or a salt thereof, or a solvate of these.

Note that the "prophylactic agent" mentioned above includes, other than a prophylactic agent administering before onset of a disease or symptom, a maintenance therapeutic agent and a recurrence preventing agent after cure.

Furthermore, the "auxiliary bactericidal agent" mentioned above refers to an agent that controls the working environment of a bactericidal agent difficult to work under the acidic conditions so as to produce the effect.

In the formula (1), $R^1$ and $R^3$ may be the same or different and represents a hydrogen atom or a C1 to C6 alkyl group; and $R^2$ is represented by the [formula 2], which may have 1 to 4 groups selected from Group A1 below.

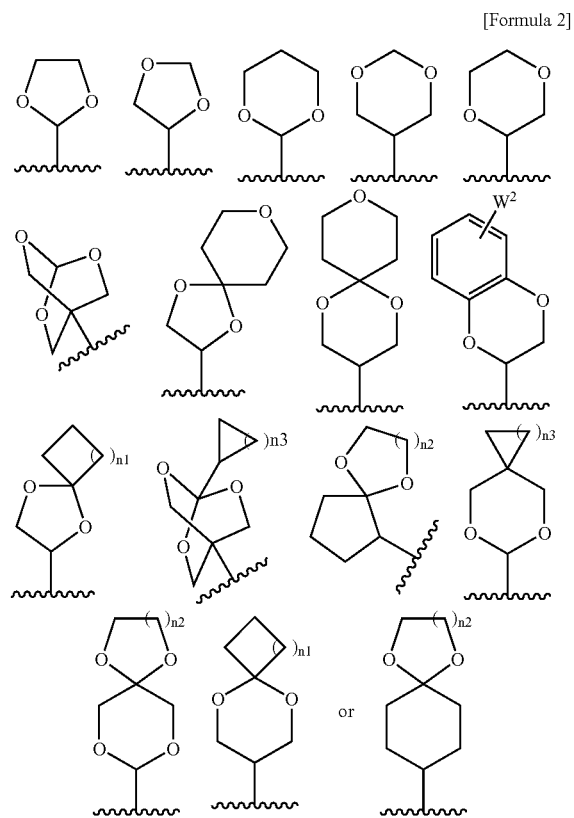

[Formula 2]

Group A1 is the group consisting of a halogen atom, a C1-C6 alkyl group, C1-C6 alkoxy group, C1-C6 haloalkyl group, C1-C6 alkoxy- C1-C6 alkyl group, and hydroxyl group.

$R_4$, $R_5$, $R_6$ and $R_7$ may be the same or different and each represent a hydrogen atom, a hydroxyl group, halogen atom, C1-C6 alkyl group, C1-C6 haloalkyl group, C1-C6 alkoxy group or C1-C6 haloalkoxy group, or a combination of $R_5$ and $R_6$ represents methylenedioxy group or ethylenedioxy group, and $W^1$ represents a single bond, or a C1 to C8 straight or branched alkylene group.

$W^2$ represents a hydrogen atom, C1-C6 alkyl group or halogen atom (with the proviso that, occurrence of $W^2$ on a benzene ring may be 1 to 3, and may be the same or different);

n1 represents 1 to 5, n2 represents 1 to 4, and n3 represents 1 to 6.

The "C1-C6 alkyl group" used herein refers to a linear or branched alkyl group having 1 to 6 carbon atoms, such as a methyl group, ethyl group, n-propyl group, isopropyl group, n-butyl group, isobutyl group, s-butyl group, t-butyl group, n-pentyl group, isopentyl group, 2-methylbutyl group, neopentyl group, 1-ethylpropyl group, n-hexyl group, isohexyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 1-ethylbutyl group or 2-ethylbutyl group.

The "halogen atom" used herein refers to a fluorine atom, chlorine atom, bromine atom or iodine atom.

The "C1-C6 alkoxy group" used herein refers to a linear or branched alkoxy group having 1 to 6 carbon atoms such as a methoxy group, ethoxy group, propoxy group, isopropoxy group, butoxy group, isobutoxy group, s-butoxy group, t-butoxy group, pentoxy group, isopentoxy group, 2-methylbutoxy group, neopentoxy group, hexyloxy group, 4-methylpentoxy group, 3-methylpentoxy group, 2-methylpentoxy group, 3,3-dimethylbutoxy group, 2,2-dimethylbutoxy group, 1,1-dimethylbutoxy group, 1,2-dimethylbutoxy group, 1,3-dimethylbutoxy group or 2,3-dimethylbutoxy group.

The "C1-C6 haloalkyl group" used herein refers to a C1-C6 alkyl group having 1 to 5 substituents of halogen atoms as mentioned above, for example, including a monofluoromethyl group, monochloromethyl group, monobromomethyl group, monoiodomethyl group, difluoromethyl group, dichloromethyl group, dibromomethyl group, diiodomethyl group, trifluoromethyl group, trichloromethyl group, tribromomethyl group, triiodomethyl group, 1-fluoroethyl group, 2-fluoroethyl group, 2,2,2-trifluoroethyl group, 1-chloroethyl group, 2-chloroethyl group, 2,2,2-trichloroethyl group, 1-fluoropropyl group, 2-bromopropyl group, 1-bromobutyl group, 1-chloropentyl group, and 1-fluorohexyl group.

The "C1-C6 haloalkoxy group" used herein refers to a C1-C6 alkoxy group having 1 to 5 substituents of halogen atoms mentioned above, for example including a monofluoromethyloxy group, monochloromethyloxy group, monobromomethyloxy group, monoiodomethyloxy group, difluoromethyloxy group, dichloromethyloxy group, dibromomethyloxy group, diiodomethyloxy group, trifluoromethyloxy group, trichloromethyloxy group, tribromomethyloxy group, triiodomethyloxy group, 1-fluoroethyloxy group, 2-fluoroethyloxy group, 2,2,2-trifluoroethyloxy group, 1-chloroethyloxy group, 2-chloroethyloxy group, 2,2,2-trichloroethyloxy group, 1-fluoropropyloxy group, 2-bromopropyloxy group, 1-bromobutyloxy group, 1-chloropentyloxy group, and 1-fluorohexyloxy group.

The "C1-C6 alkoxy-C1-C6 alkyl group" used herein refers to a C1-C6 alkyl group having a single substituent of a C1-C6 alkoxy group mentioned above, for example, including a methoxymethyl group, ethoxymethyl group, propoxymethyl group, 2-methoxyethyl group, 2-ethoxyethyl group, 1-methoxyethyl group, 3-methoxypropyl group, 3-ethoxypropyl group, 4-methoxybutyl group, 4-ethoxybutyl group, 4-propoxybutyl group, 5-methoxypentyl group, 5-ethoxypentyl group, 5-propoxypentyl group, 6-methoxyhexyl group, and 6-ethoxyhexyl group.

The "C1-C8 straight chain and branched chain alkylene chain" used herein refers to a methylene, ethylene, trimethylene, tetramethylene, pentamethylene, hexamethylene, propylene(1-methylethylene), 1-methyltrimethylene, or 2-methyltrimethylene.

The "C1-C6 alkyl group" of $R^1$ mentioned above is preferably a methyl group.

The "C1-C6 alkyl group" of $R^3$ mentioned above is preferably a methyl group.

The "halogen atom" of $R^4$, $R^5$, $R^6$ and $R^7$ mentioned above is preferably a fluorine or chlorine atom, and more preferably, a fluorine atom.

The "C1-C6 alkyl group" of $R^4$, $R^5$, $R^6$ and $R^7$ mentioned above is preferably a methyl group or ethyl group, and more preferably, a methyl group.

The "C1-C6 haloalkyl group" of $R^4$, $R^5$, $R^6$ and $R^7$ mentioned above is preferably a monofluoromethyl group, difluoromethyl group or trifluoromethyl group, and more preferably, a monofluoromethyl group.

The "C1-C6 alkoxy group" of $R^4$, $R^5$, $R^6$ and $R^7$ mentioned above is preferably a methoxy group or ethoxy group, and more preferably, a methoxy group.

The "C1-C6 haloalkoxy group" of $R^4$, $R^5$, $R^6$ and $R^7$ mentioned above is preferably a monofluoromethyloxy group, monochloromethyloxy group, difluoromethyloxy group, dichloromethyloxy group, trifluoromethyloxy group or trichloromethyloxy group, and more preferably, a monofluoromethyloxy group or difluoromethyloxy group.

The "halogen atom" of Group A1 is preferably a fluorine atom.

The "C1-C6 alkyl group" of the A1 group mentioned above is preferably a methyl group, ethyl group or propyl group, more preferably, a methyl group or ethyl group, and most preferably, a methyl group.

The "C1-C6 alkoxy group" of the A1 group mentioned above is preferably a methoxy group or ethoxy group, and more preferably, a methoxy group.

The "C1-C6 haloalkyl group" of the A1 group mentioned above is preferably a fluoromethyl group or difluoromethyl group, and more preferably, a fluoromethyl group.

The "C1-C6 alkoxy-C1-C6 alkyl group" of the A1 group mentioned above is preferably a methoxymethyl group or ethoxymethyl group.

$W^1$ mentioned above is preferably a single bond, methylene group or ethylene group, and more preferably, a methylene group.

The "C1-C6 alkyl group" of $W^2$ mentioned above is preferably a methyl group.

The "halogen atom" of $W^2$ mentioned above is preferably fluorine atom or chlorine atom, and more preferably, a fluorine atom.

The number of substituents present on a benzene ring of $W^2$ mentioned above is preferably one.

$W^2$ mentioned above is preferably a hydrogen atom.

n1 mentioned above is preferably 1 to 3, and more preferably, 1 or 2.

n2 mentioned above is preferably 1 or 2, and more preferably, 1.

n3 mentioned above is preferably 1 to 4, and more preferably, 1 or 2.

In the specification, the structure of a compound sometimes represents a certain isomer for convenience; however, the present invention includes all isomers structurally generated such as geometrical isomers, optical isomers, rotational isomers, stereoisomers, tautomers and mixtures thereof, and thus is not limited by the expression of a representative formula. Any one of isomers or a mixture of isomers is acceptable. Therefore, a compound according to the present invention may sometimes have an optically active substance and a racemic form, which will not limit the present invention and included both of them in the present invention. A compound may sometimes have a crystalline polymorphism, which will not limit the present invention. A single crystalline substance as well as a mixture of crystalline substances is acceptable. Furthermore, examples of a compound according to the present invention may include anhydrous and solvates (particularly hydrates). Moreover, a so-called metabolite produced by in-vivo degradation of a compound (1) according to the present invention may be included in the present invention. In addition, the present invention includes compounds (so-called prodrugs) producing a compound (1) according to the present invention by being metabolized in vivo through oxidation, reduction, hydrolysis, and conjugation, etc.

In a compound according to the present invention represented by the formula (1) mentioned above, a salt is formed at an NH group of the 1st or 3rd positions of a benzimidazole skeleton.

The "salt" is not particularly limited as long as it is pharmaceutically acceptable. Examples of such a salt include inorganic base salts and organic base salts.

Preferable examples of the inorganic base salts include alkaline metals salts such as sodium salt, potassium salt, and lithium salt; alkaline earth metal salts such as calcium salt and magnesium salt; transition metal salts such as zinc salt; aluminium salt; and ammonium salt. Preferable examples of the organic salts include diethyl amine salt, diethanol amine salt, meglumine salt and N,N'-dibenzylethylenediamine salt.

The "solvate" of the present invention is not particularly limited as long as it is pharmaceutically acceptable. Examples of such a solvate include a hydrate, ethanol solvate, and acetone solvate. Preferable example is a hydrate.

Of the compounds represented by the formula (1) of the present invention, preferable compounds include (2) a compound where $R^1$ is a hydrogen atom or a methyl group or a salt thereof, or a solvate of these;

(3) a compound where $R^1$ is a methyl group, or a salt thereof, or a solvate of these;

(4) a compound where $R^2$ is a group represented by

[Formula 3]

-continued

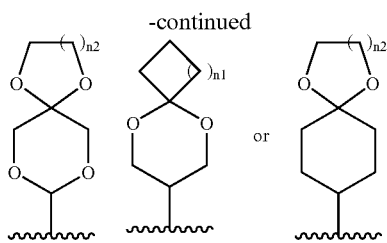

wherein $W^2$ represents a hydrogen atom, C1-C6 alkyl group or halogen atom (with the proviso that, occurrence of $W^2$ on a benzene ring may be 1 to 3, and may be the same or different); n1 represents 1 to 5, n2 represents 1 to 4; and n3 represents 1 to 6, the group optionally having 1 or 2 groups selected from the group A2 consisting of a fluorine atom, methyl group, ethyl group, propyl group, methoxy group and monofluoromethyl group;

or a salt thereof, or a solvate of these;

(5) a compound where $R^2$ is represented by

[Formula 4]

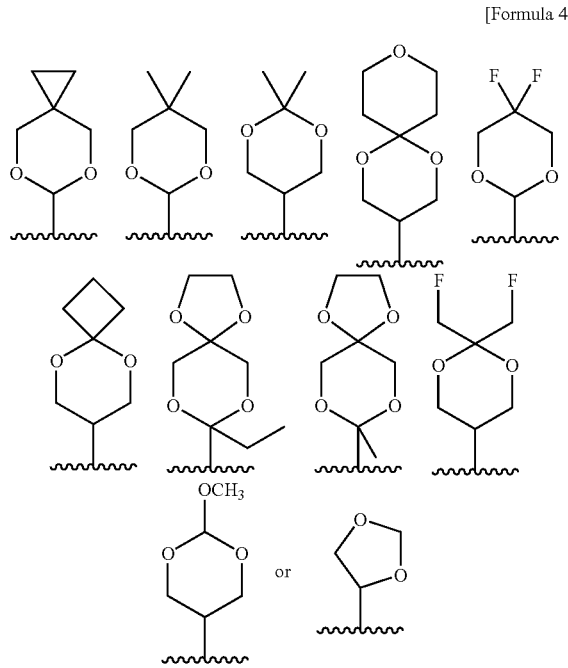

or a salt thereof, or a solvate of these;

(6) a compound where $R^2$ is represented by

[Formula 5]

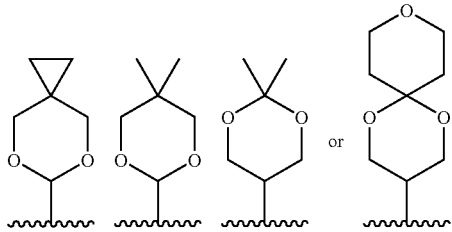

or a salt thereof or a solvate of these;

(7) a compound where $R^3$ is a hydrogen atom or a methyl group, or a salt thereof or a solvate of these;

(8) a compound where $R^3$ is a methyl group, or a salt thereof or a solvate of these;

(9) a compound where $R^4$ is a hydrogen atom, hydroxyl group, methyl group, ethyl group, methoxy group, ethoxy group, or a fluorine atom, or a salt thereof, or a solvate of these;

(10) a compound where $R^4$ is a hydrogen atom, methyl group, or a fluorine atom, or a salt thereof, or a solvate of these;

(11) a compound where $R^4$ is a hydrogen atom, or a salt thereof, or a solvate of these;

(12) a compound where $R^5$ is a hydrogen atom, hydroxyl group, methyl group, ethyl group, methoxy group, ethoxy group, or a fluorine atom, or a salt thereof, or a solvate of these;

(13) a compound where $R^5$ is a hydrogen atom, methyl group, or a fluorine atom, or a salt thereof, or a solvate of these;

(14) a compound where $R^5$ is a hydrogen atom, or a salt thereof, or a solvate of these;

(15) a compound where $R^6$ is a hydrogen atom, hydroxyl group, methyl group, ethyl group, methoxy group, ethoxy group, or a fluorine atom, or a salt thereof, or a solvate of these;

(16) a compound where $R^6$ is a hydrogen atom, methyl group, or a fluorine atom, or a salt thereof, or a solvate of these;

(17) a compound where $R^6$ is a hydrogen atom, or a salt thereof, or a solvate of these;

(18) a compound where $R^7$ is a hydrogen atom, hydroxyl group, methyl group, ethyl group, methoxy group, ethoxy group, or a fluorine atom, or a salt thereof, or a solvate of these;

(19) a compound where $R^7$ is a hydrogen atom, methyl group, or a fluorine atom, or a salt thereof, or a solvate of these;

(20) a compound where $R^7$ is a hydrogen atom, or a salt thereof, or a solvate of these;

(21) a compound where $W^1$ is a single bond, a methylene group, or ethylene group, or a salt thereof, or a solvate of these;

(22) a compound where $W^1$ is a methylene group, or a salt thereof, or a solvate of these;

(23) a compound where $W^2$ is a hydrogen atom, or a salt thereof, or a solvate of these;

(24) a compound where n1 is 1 to 3, or a salt thereof, or a solvate of these;

(25) a compound where n1 is 1 or 2, or a salt thereof, or a solvate of these;

(26) a compound where n2 is 1 or 2, or a salt thereof, or a solvate of these;

(27) a compound where n3 is 1 to 4, or a salt thereof, or a solvate of these; and

(28) a compound where n3 is 1 or 2, or a salt thereof, or a solvate of these.

Furthermore, use may be preferably made of a compound or a salt thereof, or a solvate of these satisfying the following conditions in any combination: R1 is selected from (2) or (3); R2 is selected from (4) to (6); R3 is selected from (7) or (8); R4 is selected from (9) to (11); R5 is selected from (12) to (14); R6 is selected from (15) to (17); R7 is selected from (18) to (20); and $W^1$ is selected from (21) or (22), $W^2$ is selected from (23), n1 is selected from (24) or (25), n2 is selected from (26), n3 is selected from (27) or (28).

Of the specific compounds or salts thereof or solvates of these, suitable compounds of the present invention include 2-(((4-((5,5-dimethyl-1,3-dioxan-2-yl)methoxy)-3-methylpyridin-2-yl)methyl)sulfinyl)-1H-benzimidazole;
2-(((4-(5,7-dioxaspiro[2.5]oct-6-ylmethoxy)-3-methylpyridin-2-yl)methyl)sulfinyl)-1H-benzimidazole;
2-(((3-methyl-4-(1,5,9-trioxaspiro[5.5]undec-3-ylmethoxy)pyridin-2-yl)methyl)sulfinyl)-1H-benzimidazole;
2-(((4-((2,2-dimethyl-1,3-dioxan-5-yl)methoxy)-3,5-dimethylpyridin-2-yl)methyl)sulfinyl)-1H-benzimidazole;
2-(((3-methyl-4-(2-(8-methyl-1,4,7,9-tetraoxaspiro[4.5]dec-8-yl)ethoxy)pyridin-2-yl)methyl)sulfinyl)-1H-benzimidazole;
2-(((4-(5,9-dioxaspiro[3.5]non-7-yloxy)pyridin-2-yl)methyl)sulfinyl)-1H-benzimidazole;
2-(((4-(2-(8-ethyl-1,4,7,9-tetraoxaspiro[4.5]dec-8-yl)ethoxy)-3-methylpyridin-2-yl)methyl)sulfinyl)-1H-benzimidazole;
2-(((4-(1,3-dioxolan-4-ylmethoxy)-3-methylpyridin-2-yl)methyl)sulfinyl)-1H-benzimidazole;
2-(((4-((2,2-bis(fluoromethyl)-1,3-dioxan-5-yl)methoxy)-3-methylpyridin-2-yl)methyl)sulfinyl)-1H-benzimidazole;
2-(((4-(5,9-dioxaspiro[3.5]non-7-yloxy)-3-methylpyridin-2-yl)methyl)sulfinyl)-1H-benzimidazole;
2-(((4-((2-methoxy-1,3-dioxan-5-yl)methoxy)-3-methylpyridin-2-yl)methyl)sulfinyl)-1H-benzimidazole;
2-(((3-methyl-4-((8-methyl-1,4,7,9-tetraoxaspiro[4.5]dec-8-yl)methoxy)pyridin-2-yl)methyl)sulfinyl)-1H-benzimidazole;
2-(((4-(5,9-dioxaspiro[3.5]non-7-ylmethoxy)pyridin-2-yl)methyl)sulfinyl-1H-benzimidazole; or
2-(((4-((5,5-difluoro-1,3-dioxan-2-yl)methoxy)-3-methylpyridin-2-yl)methyl)sulfinyl)-1H-benzimidazole; or salts thereof, or solvates (particularly, their sodium salts unhydrate or hydrate of their sodium salt) of these.

Further suitable compounds of the present invention include
2-(((4-((5,5-dimethyl-1,3-dioxan-2-yl)methoxy)-3-methylpyridin-2-yl)methyl)sulfinyl)-1H-benzimidazole;
2-(((4-(5,7-dioxaspiro[2.5]oct-6-ylmethoxy)-3-methylpyridin-2-yl)methyl)sulfinyl)-1H-benzimidazole;
2-(((3-methyl-4-(1,5,9-trioxaspiro[5.5]undec-3-ylmethoxy)pyridin-2-yl)methyl)sulfinyl)-1H-benzimidazole; or
2-(((4-((2,2-dimethyl-1,3-dioxan-5-yl)methoxy)-3,5-dimethylpyridin-2-yl)methyl)sulfinyl)-1H-benzimidazole; or salts thereof, or solvates of these (particularly, anhydrous or hydrates of their sodium salts).

Of the optical isomers (presently exist) of the compounds mentioned above, use is more preferably made of a compound exhibiting more excellent inhibitory effect against gastric acid secretion or a compound more excellent in persistency of inhibitory effect against gastric acid secretion.

[Advantages of the Invention]

The compound of the present invention has an excellent inhibitory effect against gastric acid secretion, more excellent persistency of inhibitory effect against gastric acid secretion, maintains the intragastric pH high for a long time, and has safer and appropriately physicochemical stability. Therefore, the compound is useful as a medicine, particularly as a therapeutic agent or prophylactic agent for acid-related diseases or symptoms and as a bactericidal agent or auxiliary bactericidal agent against *Helicobacter pylori*.

[Best Mode for Carrying out the Invention]

The compound of the present invention can be produced by any one of the methods described below; however, the production method of the present invention is not limited to these.

A compound (1) according to the present invention can be produced by Method A below.

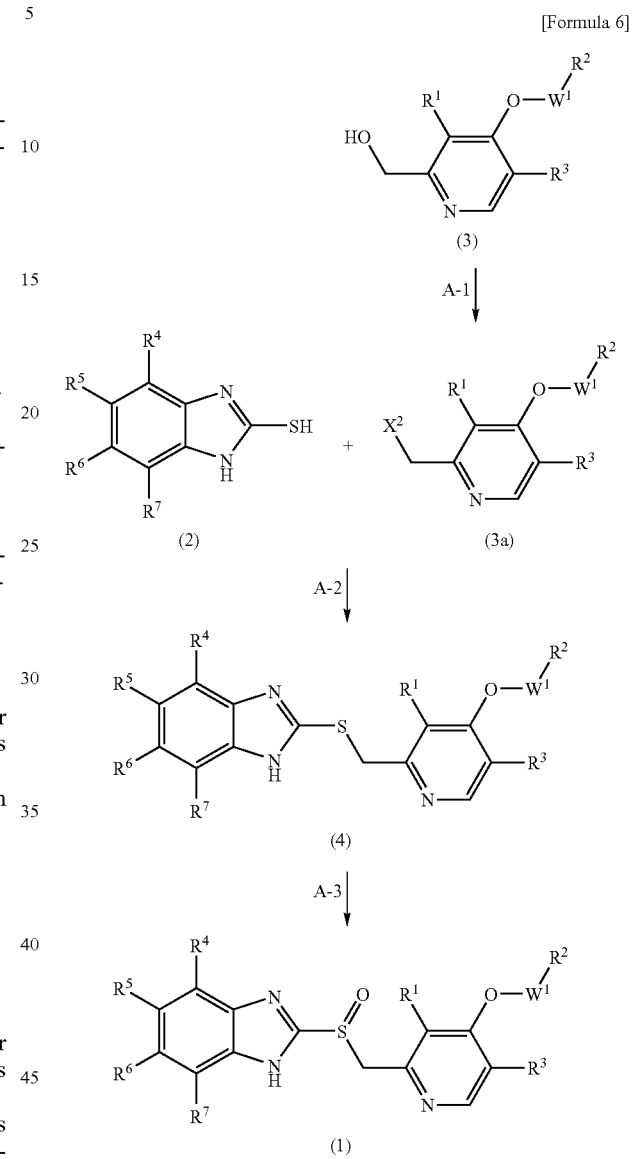

where $R^1$, $R^2$, $R^3$, $R^4$, $R^5$, $R^6$, $R^7$, and $W^1$ are the same as defined above and $X^2$ represents a leaving group.

Examples of the leaving group of $X^2$ include sulfonyloxy groups such as methanesulfonyloxy, p-toluenesulfonyloxy, and trifluoromethanesulfonyloxy, halogen groups such as chlorine, bromine, and iodine, acyloxy groups such as acetyloxy, trifluoroacetyloxy, and propionyloxy, and preferably methanesulfonyloxy and p-toluenesulfonyloxy, chlorine or acetyloxy is used.

Now, individual steps of Method A will be explained below.

(A-1 Step) Introduction of a Leaving Group or Halogenation (1) Reaction for Introducing a Leaving Group In this step, a compound (3) is reacted with a leaving group introduction agent in the absence of a solvent or in an inert solvent and in the presence of a base to produce a compound (3a) or a salt thereof.

The solvent that is used herein is not particularly limited as long as it can dissolve a starting material to some extent and does not inhibit the reaction. Examples of such a solvent include halogenated hydrocarbons such as chloroform, dichloromethane, 1,2-dichloroethane, and carbon tetrachloride; aromatic hydrocarbons such as benzene, toluene and benzotrifluoride; ethers such as diethyl ether, diisopropyl ether, tetrahydrofuran, dioxane, dimethoxyethane, and diethylene glycol dimethyl ether; amides such as formamide, N,N-dimethyl formamide, N,N-dimethyl acetamide, hexamethylphosphoric triamide; and pyridine; and solvent mixtures of these. Preferably, it is halogenated hydrocarbons, ethers, or a solvent mixture of ethers and aromatic hydrocarbons, and most preferably, dichloromethane, tetrahydrofuran, or a solvent mixture of tetrahydrofuran and toluene.

Examples of the leaving-group introducing agent that is used herein include sulfonylating agents such as methanesulfonyl chloride, p-toluenesulfonyl chloride, trifluoromethanesulfonyl chloride, N-phenyl-bis(trifluoromethanesulfonimide). Preferably, methanesulfonyl chloride or p-toluenesulfonyl chloride, and most preferably methanesulfonyl chloride is used.

Examples of the base that is used herein include tertiary alkylamines such as trimethylamine and triethylamine; pyridine, potassium carbonate, sodium carbonate, sodium hydroxide, and potassium hydroxide. Preferably, triethylamine or sodium hydroxide, and most preferably, triethylamine is used.

The reaction temperature varies depending upon the starting material, solvent, leaving-group introducing agent, and base. The reaction temperature is generally from $-50°$ C. to $100°$ C., and preferably from $-20°$ C. to $40°$ C.

The reaction time varies depending upon the starting material, solvent, leaving-group introducing agent, base, and reaction temperature. The reaction time is generally from 15 minutes to 12 hours, and more preferably, from 30 minutes to 2 hours.

The compound obtained in this step may not be particularly isolated and directly subjected to the next step.

(2) Halogenation (Taking Chlorination as a Representative Example)

In this step, a compound (3) is reacted with a chlorinating agent in the absence of a solvent or in an inert solvent and in the presence or absence of a base to produce a compound (3a).

The solvent that is used herein is not particularly limited as long as it can dissolve a starting material to some extent and does not inhibit the reaction. Examples of such a solvent include halogenated hydrocarbons such as chloroform, dichloromethane, 1,2-dichloroethane, and carbon tetrachloride; aromatic hydrocarbons such as benzene, toluene, and benzotrifluoride; and ethers such as diethyl ether, diisopropyl ether, tetrahydrofuran, dioxane, dimethoxyethane, and diethylene glycol dimethyl ether. Preferably a halogenated hydrocarbon or an aromatic hydrocarbon, and most preferably, dichloromethane, chloroform, or toluene is used. Examples of the chlorinating agent that is used herein include methanesulfonyl chloride, oxalyl chloride, thionyl chloride, phosphorus oxychloride, phosphorus trichloride, phosphorus pentachloride and hydrochloric acid; and preferably, thionyl chloride or hydrochloric acid is used. Examples of the base that is used herein include tertiary alkylamines such as trimethylamine and triethylamine; and pyridine; etc. Preferably, triethylamine is used.

The reaction temperature varies depending upon the starting material, solvent, and chlorinating agent. The reaction temperature is generally from $-20°$ C. to $30°$ C., and preferably from $0°$ C. to $10°$ C.

The reaction time varies depending upon the starting material, solvent, chlorinating agent, and reaction temperature. The reaction time is generally, from 10 minutes to 6 hours, and preferably, 10 minutes to 2 hours.

The compound in this step may not be particularly isolated and directly subjected to the next step.

Bromination is performed by use of a reagent such as bromine/red phosphorus, phosphorus tribromide, and phosphorus pentabromide. Iodization is performed by use of a reagent such as iodine/red phosphorus. Alternatively, a bromide and iodide can be obtained by reacting a reagent such as sodium bromide and sodium iodide respectively with the leaving group synthesized in the A-1 step.

(A-2 Step) Thioetherification

In this step, a compound (2) is reacted with a compound (3a) or a salt thereof (particularly, a hydrochloride salt(s)) in the absence of a solvent or in an inert solvent and in the presence or absence of a base, to produce a compound (4).

The solvent that is used herein is not particularly limited as long as it can dissolve a starting material to some extent and does not inhibit the reaction. Examples of such a solvent include alcohols such as methanol, ethanol, n-propanol, isopropanol, n-butanol, isobutanol, t-butanol, isoamyl alcohol, diethylene glycol, glycerin, octanol, cycohexanol, and methylcellosolve; halogenated hydrocarbons such as chloroform, dichloromethane, 1,2-dichloroethane, and carbon tetrachloride; ethers such as diethyl ether, diisopropyl ether, tetrahydrofuran, dioxane, dimethoxy ethane, and diethylene glycol dimethyl ether; aromatic hydrocarbons such as benzene and toluene; N,N-dimethyl formamide; dimethylsulfoxide; water; and solvent mixtures of these. Preferably, dichloromethane, an alcohol, an ether or solvent mixtures of an ether and toluene, and most preferably, methanol, tetrahydrofuran or solvent mixtures of tetrahydrofuran and toluene is used.

Examples of the base that is used herein include inorganic bases such as sodium hydride, potassium hydride, lithium carbonate, sodium carbonate, potassium, carbonate, lithium hydroxide, sodium hydroxide, and potassium hydroxide; organic bases such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di (t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). Preferably, an inorganic base such as sodium hydride, potassium hydride, lithium hydroxide, sodium hydroxide, or potassium hydroxide, or triethylamine, and most preferably, sodium hydroxide or triethylamine is used.

The reaction temperature varies depending upon the starting material, solvent, and base; and is generally from $0°$ C. to $100°$ C., and preferably from $10°$ C. to $50°$ C.

The reaction time varies depending upon the starting material, solvent, base, and reaction temperature; and is generally from 30 minutes to 3 days.

(A-3 Step) Oxidation

In this step, a compound (4) is reacted with an oxidizing agent in the presence or absence of a solvent to produce a compound (1).

The solvent that is used herein is not particularly limited as long as it can dissolve a starting material to some extent and does not inhibit the reaction. Examples of such a solvent include alcohols such as methanol, ethanol, n-propanol, iso-propanol, n-butanol, isobutanol, t-butanol, isoamyl alcohol, diethylene glycol, glycerin, octanol, cyclohexanol, and methyl cellosolve; aromatic hydrocarbons such as benzene and toluene; halogenated hydrocarbons such as chloroform, dichloromethane, 1,2-dichloroethane, and carbon tetrachloride; amides such as formamide, N,N-dimethylformamide, N,N-dimethylacetamide, and hexamethylphosphoric triamide; nitriles such as acetonitrile. Preferably, an aromatic hydrocarbon, an alcohol, a halogenated hydrocarbon or a solvent mixture of these, and most preferably, toluene, a solvent mixture of toluene and methanol or dichloromethane is used.

Examples of the oxidizing agent that is used herein include hydrogen peroxide, t-butyl hydroperoxide, cumene hydroperoxide, sodium periodate, peracetic acid, perbenzoic acid, 3-chloroperbenzoic acid, urea hydrogen peroxide addition compound (($NH_2)_2CO.H_2O_2$). Preferably, 3-chloroperbenzoic acid or cumene hydroperoxide is used.

Note that the asymmetric oxidation may be performed in accordance with the methods described in the following documents; WO96/02535, WO2001/83473, WO2004/087702, WO2004/052881, WO2004/052882, Adv. Synth. Catal. 2005, 347, 19-31, Chem. Rev. 2003, 103, 3651-3705, Tetrahedron Lett. 2004, 45, 9249-9252, Angew. Chem. Int. Ed. 2004, 43, 4225-4228, and Tetrahedron Asymmetry 2003, 14, 407-410.

More specifically, asymmetric oxidation is performed by reacting a compound (4) and an oxidizing agent in the presence of an asymmetry induction agent or an asymmetry induction catalyst.

Examples of the oxidizing agent include peroxides such as hydrogen peroxide, tert-butyl hydroperoxide, urea hydroperoxide, and cumene hydroperoxide. In particular, when an asymmetry induction agent or asymmetry induction catalyst contains titanium, zirconium or hafnium, cumene hydroxyperoxide is used. When it contains vanadium, hydrogen peroxide is used.

The oxidizing agent that is used herein may be present in an amount exceeding that of the compound (4), preferably fall within the range of 1.01 to 10 mole equivalents. In particular, when an asymmetry induction agent or asymmetry induction catalyst contains titanium, 1.05 equivalents of oxidizing agent is used. When an asymmetry induction agent or asymmetry induction catalyst contains zirconium or hafnium, 1.2 equivalents of oxidizing agent is used. When it contains vanadium, 1.1 equivalents of oxidizing agent is generally used.

Examples of such an asymmetry induction agent or asymmetry induction catalyst include (1) optically active titanium complexes such as complexes of an optically active diol and titanium (IV) alkoxide and water or an alcohol;

(2) optically active zirconium complexes such as complexes of an optically active diol and zirconium (IV) alkoxide (water may be present or not present);

(3) optically active hafnium complex such as complexes of an optically active diol and hafnium (IV) alkoxide;

(4) optically active vanadium complex such as complexes of an optically active Schiff base and vanadyl acetylacetone;

(5) optically active iron complexes such as complexes of an optically active Schiff base and iron (III) acetylacetonate;

(6) optically active manganese complexes (for example, salen-manganese complex) such as complexes of an optically active Schiff base and manganese; and (7) optically active tungsten complexes such as complexes of an optically active Cinchona alkaloid and tungsten (III).

Examples of the optical active diol include (1) alkyl diols such as tartaric acid esters, for example, (+) or (−) dimethyl tartrate, diethyl tartrate, diisopropyl tartrate and d butyl tartrate; and tartaramide such as tetramethyltartaramide; and (2) aromatic diol such as (R)- or (S)-binaphthol.

Examples of the optically active Schiff base include Schiff bases derived from substituted salicyl aldehydes such as (S)-(−)-2-(3,5-di-tert-butylsalicylideneamino)-3,3-dimethyl-1-butanol, and (1R,2S)-1-((2-hydroxy-3,5-di-tert-butylbenzylidene)amino)indan-2-ol, and salen type Schiff bases.

When asymmetric oxidation is performed, if necessary, a base may be added. Examples of the base that is used is not particularly limited as long as it does not inhibit a reaction and include inorganic bases and organic bases, preferably, tertiary amines such as diisopropylethylamine and triethylamine, and most preferably, diisopropylethylamine. The base is generally added in an amount of 0.1 to 1 equivalent relative to a compound (4).

Note that an asymmetry induction agent or asymmetry induction catalyst containing vanadium is used, generally no base is used.

Examples of the solvent that is used in asymmetric oxidation include aromatic hydrocarbons such as toluene, benzene, and xylene; halogenated hydrocarbons such as dichloromethane and chloroform; esters such as ethyl acetate, and tert-butyl methyl ether. Particularly when an asymmetry induction agent or asymmetry induction catalyst containing titanium, zirconium or hafnium is used, toluene or tert-butyl-methyl ether is preferably used. When an asymmetry induction agent or asymmetry induction catalyst containing vanadium is used, acetonitrile or dichloromethane is preferably used. When an asymmetry induction catalyst containing titanium is used, addition of water is effective. The amount of water including water contained in a solvent, reactive agent (excluding an oxidizing agent) and substrate preferably falls within the range of 0.1 to 0.33 equivalents relative to a compound (4), and most preferably, 0.13 to 0.25 equivalents. The content of water may be controlled by molecular sieves 3A.

When a complex of titanium (IV) alkoxide and an alcohol is synthesized, isopropanol is effectively used as the alcohol, usually in an amount of 1.2 equivalents relative to titanium.

The reaction temperature varies depending upon the starting material, solvent, and oxidizing agent; and is generally from −100° C. to 100° C., and preferably from −70° C. to 70° C.

The reaction time varies depending upon the starting material, solvent, an oxidizing agent, and reaction temperature; and is generally, from 15 minutes to 72 hours, and more preferably, from 30 minutes to 24 hours.

The compound obtained above can be converted into a salt by a conventional method. More specifically, a compound (1) is reacted with a base in the presence or absence of a solvent. As a solvent, use may be made of acetonitrile; an alcohol such as methanol or ethanol; water or a solvent mixture of these, and preferably, a solvent mixture of ethanol and water. As a base, use may be made of an alkaline metal hydroxide such as lithium hydroxide, sodium hydroxide, or potassium hydroxide; an alkaline earth metal hydroxide such as magnesium hydroxide; and an alkoxide such as sodium methoxide, sodium t-butoxide, sodium t-pentoxide or magnesium methoxide. Preferably, an aqueous solution of sodium hydroxide is used. The reaction temperature is generally from −50 to 50°

C., and preferably from 10 to 40° C. The reaction time is generally from 1 minute to 2 hours and preferably from 1 minute to 1 hour.

Alternatively, an alkaline metal salt such as a sodium salt and potassium salt may be subjected to a salt exchange reaction with a metal chloride or a metal sulfate such as barium chloride, magnesium chloride, magnesium sulfate, or zinc sulfate in the presence or absence of a solvent to convert into the corresponding metal salts such as a barium salt, magnesium salt, and zinc salt.

After a compound (4) is oxidized, a compound (1) can be subjected to converting into a salt without subjecting an isolation operation to obtain a metal salt.

As a compound (2) and a compound (3), which are intermediates in Method A, use may be made of commercially available compounds or compounds easily produced from commercially available compound(s) in accordance with a conventional method which one skilled in the art usually performed. Especially, a compound (3) can be produced in accordance with Method B as mentioned below.

Method B

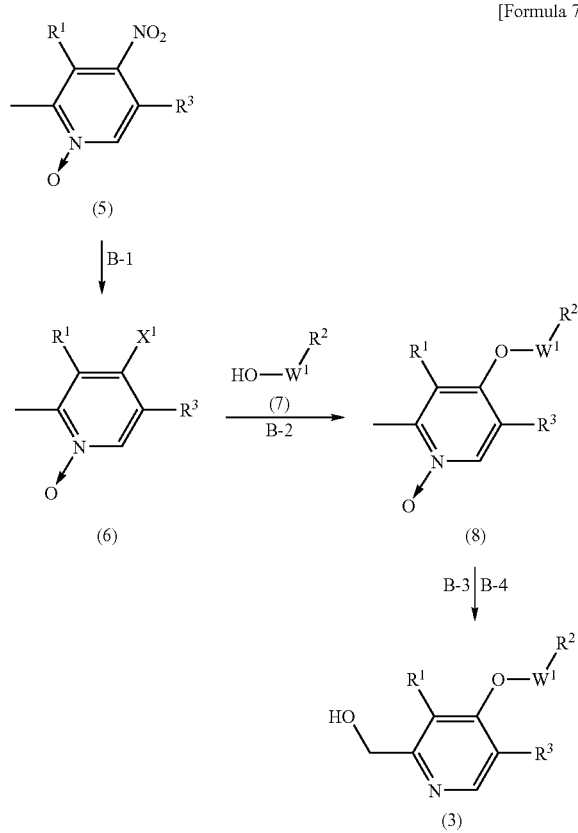

[Formula 7]

In the formula, $R^1$, $R^2$, $R^3$, and $W^1$ are the same as defined above; and $X^1$ represents a halogen atom, preferably chlorine atom, bromine atom, or iodine atom, and more preferably a chlorine atom.

Now, individual steps of Method B will be explained below.

(B-1 Step) Halogenation (Taking Chlorination as a Representative Reaction)

In this step, a compound (5) is reacted with a chlorinating agent in the absence of a solvent or in an inert solvent to produce a compound (6).

In this step, the reaction is desirably performed in the chlorinating agent generally without using a solvent. However, when a solvent is used, the solvent is not particularly limited as long as it can dissolve a starting material to some extent and does not inhibit the reaction. Examples of such a solvent include halogenated hydrocarbons such as chloroform, dichloromethane, 1,2-dichloroethane, and carbon tetrachloride; and ethers such as diethyl ether, diisopropyl ether, tetrahydrofuran, dioxane, and dimethoxy ethane, and diethylene glycoldimethyl ether.

Examples of the chlorinating agent that is used herein include acetyl chloride, oxalyl chloride, thionyl chloride, phosphorus oxychloride, phosphorus trichloride, and phosphorus pentachloride, and preferably acetyl chloride is used.

The reaction temperature varies depending upon the starting material, solvent, and chlorinating agent; and is generally from −50° C. to 30° C., and preferably from −30° C. to 10° C.

The reaction time varies depending upon the starting material, solvent, chlorinating agent, and reaction temperature; and is generally, from 30 minutes to 8 hours, and more preferably, from 1 to 5 hours.

When bromination is performed, a reagent such as acetyl bromide, hydrogen bromide, bromine/red phosphorus, phosphorus tribromide, and phosphorus pentabromide is used. When iodization is performed, a reagent such as iodine/red phosphorus is used or bromination is performed and thereafter sodium iodide is reacted.

(B-2 Step) $R^2$—$W^1$—O Group Introduction Reaction

In this step, a compound (6) is reacted with an alcohol (7), that is, $R^2$—$W^1$—OH group (where $R^2$ and $W^1$ are the same as defined above) in the absence of a solvent or in an inert solvent and in the presence of a base, to produce a compound (8).

The solvent that is used herein is not particularly limited as long as it can dissolve a starting material to some extent and does not inhibit the reaction. Examples of such a solvent include aliphatic hydrocarbons such as hexane, heptane, ligroin, and petroleum ether; halogenated hydrocarbons such as chloroform, dichloromethane, 1,2-dichloroethane, and carbon tetrachloride; aromatic hydrocarbons such as benzene and toluene; ethers such as diethyl ether, diisopropyl ether, tetrahydrofuran, dioxane, dimethoxyethane, and diethylene glycol dimethyl ether; amides such as formamide, N,N-dimethylformamide, N,N-dimethylacetamide, hexamethylphosphoric triamide, and N-methylpyrrolidone; dimethylsulfoxide; water; and solvent mixtures of these. Preferably, dimethylsulfoxide, an ether, or an amide, and most preferably, dimethylsulfoxide, is used.

Examples of the base that is used herein include alkaline metal carbonates such as lithium carbonate, sodium carbonate, and potassium carbonate; alkaline metal hydroxides such as lithium hydroxide, sodium hydroxide and potassium hydroxide; metal alkoxides such as lithium methoxide, sodium methoxide, sodium ethoxide, and potassium-t-butoxide; alkaline metal hydrides such as lithium hydride, sodium hydride, and potassium hydride; alkaline metal alkoxides prepared by an alkaline metal; n-butyl lithium; and lithium diisopropylamide. Preferably, alkaline metal hydride, and most preferably, sodium hydride is used.

The reaction temperature varies depending upon the starting material, solvent, and base; and is generally from 0° C. to 100° C., and preferably 10° C. to 100° C. in the case where the alcohol (7), that is, $R^2$—$W^1$—OH is a primary alcohol; and from 50 to 100° C. in the case where the alcohol is a secondary alcohol.

The reaction time varies depending upon the starting material, solvent, base, and reaction temperature; and is generally, from 15 minutes to 48 hours, and more preferably, from 30 minutes to 12 hours.

(B-3 Step) Rearrangement to Acetic Acid Ester

In this step, a compound (8) is reacted with acetic anhydride in the absence of a solvent and in the presence or absence of a base to produce an acetate of compound (3).

Examples of the base that is used herein include tertiary amines such as trimethylamine, diisopropylethylamine and triethylamine; and pyridine; etc. Preferably, triethylamine is used.

The reaction temperature varies depending upon the starting material and solvent; and is generally from 20° C. to 150° C., and preferably from 20° C. to 60° C. in the presence of a base, and from 50 to 100° C. in the absence of a base.

The reaction time varies depending upon the starting material, solvent, and reaction temperature; and is generally, from 10 minutes to 6 hours, and preferably, from 30 minutes to 5 hours.

After the reaction, a residue obtained by distilling acetic anhydride is usually subjected directly to the next step. Alternatively, acetate is subjected to step A-2 of Method A to obtain a compound (4).

(B-4 Step) Hydrolysis Reaction

In this step, the compound obtained in the B-3 step is reacted with a base in the presence or absence of a solvent to produce a compound (3).

The solvent that is used herein is not particularly limited as long as it can dissolve a starting material to some extent and does not inhibit the reaction. Examples of such a solvent include water; alcohols such as methanol, ethanol, n-propanol, isopropanol, n-butanol, isobutanol, t-butanol, isoamyl alcohol, diethyleneglycol, glycerin, octanol, cyclohexanol, and methyl cellosolve; aliphatic hydrocarbons such as hexane, heptane, ligroin, and petroleum ether; ethers such as diethyl ether, diisopropyl ether, tetrahydrofuran, dioxane, dimethoxyethane, and diethyleneglycol dimethyl ether; halogenated hydrocarbons such as chloroform, dichloromethane, 1,2-dichloroethane, and carbon tetrachloride; amides such as formamide, N,N-dimethylformamide; N,N-dimethylacetamide, and hexamethylphosphoric triamide; and solvent mixtures of these. Preferably, an alcohol or a solvent mixture of an alcohol and water, and most preferably, a solvent mixture of methanol and water is used.

Examples of the base that is used herein include alkaline metal carbonates such as lithium carbonate, sodium carbonate, and potassium carbonate; alkaline metal hydroxides such as lithium hydroxide, sodium hydroxide and potassium hydroxide; metal alkoxides such as lithium methoxide, sodium methoxide, sodium ethoxide, and potassium-t-butoxide; and ammonias such as aqueous ammonia, and concentrated ammonia-methanol, etc. Preferably, an alkaline metal hydroxide, and most preferably, sodium hydroxide is used.

The reaction temperature varies depending upon the starting material, solvent, and base; and is generally from 0° C. to 60° C., and preferably from 10° C. to 40° C.

The reaction time varies depending upon the starting material, solvent, base, and reaction temperature; and is generally, from 10 minutes to 6 hours.

In each of the methods, after completion of the reaction in each step, a target compound can be obtained from a reaction mixture in accordance with a conventional method.

For example, in the case where a whole reaction mixture is a solution, a target compound is obtained by returning the temperature of the reaction mixture if needed to room temperature or cooling the reaction mixture on ice, neutralizing an acid, alkali, oxidizing agent, or reducing agent, and adding water and an organic solvent such as ethyl acetate nonmiscible to water and non-reactive with a target compound, thereby separating a layer containing the target compound, and thereafter, adding a solvent nonmiscible to the obtained layer and non-reactive to the target compound, washing the layer containing the target compound, and separating the layer. In addition, if the obtained layer is an organic layer, the desired compound can be obtained by drying the organic layer by use of a dehydration agent such as potassium carbonate, anhydrous magnesium sulfate or anhydrous sodium sulfate and distilling away a solvent. On the other hand, if the obtained layer is an water layer, the desired compound can be obtained by subjecting the layer to electrically desalting and freeze dry steps.

Alternatively, when the whole reaction mixture is a solution, and if possible, a target compound can be obtained by distilling away other compounds (e.g., solvent, reagent) under normal pressure or reduced pressure.

Furthermore, when only a target compound is precipitated as solid or the whole reaction mixture is a liquid and only a target compound is precipitated in the course of the recovering process, the target compound can be obtained by a filtration, washing the filtered target compound with an appropriate solvent, and drying. Further, the target compound can be obtained from the filtrate in the same manner as the case where the whole reaction mixture is a solution, additionally.

Moreover, when a reagent(s) or a catalyst alone is present as solid into the reaction mixture, or in the case where the whole reaction mixture is a solution, besides a reagent(s) or a catalyst alone is precipitated as solid in the course of the recovering process and the target compound is dissolved in the solvent, the target compound can be obtained by filtering off the reagent(s) or catalyst, washing the filtered reagent(s) or catalyst with an adequate organic or inorganic solvent, combining the washing liquid and the filtrate, treating the mixture in the same manner as in case where the whole reaction mixture is a solution.

In particular, in the case where other compounds besides a target compound contained in the reaction mixture do not inhibit the reaction of the next step, the mixture can be directly used in the next step without isolating the target compound.

To improve the purity of the target compound obtained in the aforementioned step, a recrystallization method, various chromatographic methods and a distillation method may be appropriately applied.

When the obtained target compound is a solid, the purity of the target compound is generally improved by the recrystallization method. In the recrystallization method, a single solvent or a solvent mixture of a plurality of solvents nonreactive to the target compound may be used. More specifically, a target compound can be recrystallized by first dissolving a target compound in a single solvent or a solvent mixture of a plurality of solvents at room temperature or with heating, and then, cooling the resultant solution by ice water, etc, stirring it or standing it alone at room temperature, or adding a solvent in which the target dissolves at a low solubility, thereby recovering a crystallized target compound from the solution.

The purity of a target compound can be improved by various chromatographic methods. Generally, use may be made of silica gel column chromatography using weak acidic silica gels such as silica gel 60 (70 to 230 meshes or 340 to 400 meshes) manufactured by Merck Ltd., BW-300 (300 meshes) manufactured by Fuji Silysia Chemical Ltd., or a disposable silica gel column cartridge for middle pressure liquid chromatography (High Frash column), manufactured by Yamazen Corporation. When a target compound is basic and excessively adsorbed by the silica gels mentioned above, use may be made of propyl amine coating silica gel (200 to 350 meshes) manufactured by Fuji Silysia Chemical Ltd., or NH silica gel as used in disposable silica gel column cartridge for middle pressure liquid chromatography, (High Frash, Amino) manufactured by Yamazen Corporation. Alternatively, when a target compound has bipolarity or must be eluted by a high polar solvent such as methanol, NAM-200H or NAM-300H (manufactured by NAM Laboratory) may be used. When a target compound is eluted by using any one of these silica gels and a single solvent or a solvent mixture of a plurality of solvents non-reactive with the target compound, and the solvent is removed, the target compound improved in purity can be obtained.

When the obtained target compound is a liquid, the purity of the target compound can be improved by the distillation method. In the distillation method, a target compound can be distilled at normal pressures or by reducing pressure at room temperature or while heating.

In the foregoing, a representative manufacturing method of a compound (1) has been explained. The starting compounds and reagents for use in manufacturing a compound according to the present invention may be a salt or a solvate such as a hydrate, vary depending upon the starting material and the solvent to be used, and are not particularly limited as long as they cannot inhibit the reaction. Needlessly to say, the solvent to be used varies depending upon the starting materials and the reagents and is not particularly limited as long as it does not inhibit the reaction and can dissolve a starting material to some extent. When a compound (1) according to the present invention can be obtained in a free form, it can be converted into a salt or a solvate, to which the compound (1) may be converted, in accordance with a conventional method.

When a compound (1) according to the present invention is obtained in the form of a salt or a solvate of the compound (1), the salt or the solvate can be converted into a free-form compound (1) in accordance with a conventional method.

Furthermore, various isomers (such as geometrical isomers, optical isomers, rotational isomers, stereoisomers, and tautomers) of a compound (1) according to the present invention are purified and isolated by a conventional separation means, for example, a recrystallization method, diastereomeric salt method, enzymatic separation method, various chromatographic methods (such as thin-layer chromatography, column chromatography, and gas chromatography).

When the compound of the present invention is used as a medicament, usually, the compound is mixed with appropriate additives to make a formulation, which is put to use. However, the case where the compound of the present is directly used as a medicament, is not eliminated.

Examples of such additives include an excipient, binder, lubricant, disintegrator, colorant, flavor and odor improver, emulsifier, surfactant, solubilizer, suspending agent, isotonizing agent, buffer, preservative, antioxidant, stabilizer, and absorption accelerator that are usually used in medicine. If desired, they can be used in combination.

Examples of the excipient include lactose, white sugar, glucose, cornstarch, mannitol, sorbitol, starch, α-starch, dextrin, crystalline cellulose, light anhydrous silicic acid, aluminium silicate, calcium silicate, magnesium aluminometasilicate, and calcium hydrogen phosphate.

Examples of the binder include polyvinyl alcohol, methylcellulose, ethylcellulose, gum Arabic, tragacanth, gelatin, shellac, hydroxypropylmethylcellulose, hydroxypropylcellulose, sodium carboxymethylcellulose, polyvinylpyrrolidone, and macrogol.

Examples of the lubricant include magnesium stearate, calcium stearate, sodium stearyl fumarate, talc, polyethylene glycol, and colloidal silica.

Examples of the disintegrator include crystalline cellulose, agar, gelatin, calcium carbonate, sodium hydrogen carbonate, calcium citrate, dextrin, pectin, low-substitution degree hydroxypropyl cellulose, carboxymethylcellulose, calcium carboxymethylcellulose, croscarmellose sodium, carboxymethyl starch, sodium carboxymethyl starch.

Examples of the colorant include pharmaceutical acceptable colorants such as iron sesquioxide, yellow iron sesquioxide, carmine, caramel, β-carotene, titanium oxide, talc, riboflavin sodium phosphate, and yellow aluminium lake.

Examples of the flavor and odor improver include cocoa powder, menthol, empasm, menthol oil, Borneo camphor, and cinnamon powder.

Examples of emulsifier or surfactant include stearyl triethanolamine, sodium lauryl sulfate, lauryl aminopropionic acid, lecithin, glycerin monostrearate, sucrose fatty acid ester, and glycerin fatty acid ester.

Examples of the solubilizer include polyethyleneglycol, propyleneglycol, benzyl benzoate, ethanol, cholesterol, triethanolamine, sodium carbonate, sodium citrate, polysorbate 80, and nicotinamide.

Examples of the suspending agent include, other than the aforementioned surfactants, hydrophilic polymers such as polyvinyl alcohol, polyvinyl pyrrolidone, methylcellulose, hydroxymethylcellulose, hydroxyethylcellulose, and hydroxypropylcellulose.

Examples of the isotonizing agent include glucose, sodium chloride, mannitol, and sorbitol.

Examples of the buffer include phosphate, acetate, carbonate, and citrate buffer solutions.

Examples of the preserve include methylparaben, propylparaben, chlorobutanol, benzyl alcohol, phenethyl alcohol, dehydroacetic acid, and sorbic acid.

Examples of the antioxidant include sulfite, ascrobate, and α-tocopherol.

As examples of the stabilizer, those generally used in medicine are mentioned.

As examples of the absorption accelerator, those generally used in medicine are mentioned.

Examples of the preparation include peroral agents such as a tablet, powder, granule, capsule, syrup, troche, and inhalant; external preparations such as a suppository, ointment, ointment for eyes, tape agent, eyedrop, nosedrop, eardrop, poultice, and lotion; and injections.

The peroral agents mentioned above are prepared by appropriately combining the compound of the present invention with the additives mentioned above Note that, if necessary, the surface of preparations may be coated.

The external preparations are formed by appropriately combining the compound of the present invention with the aforementioned additives, in particular, an excipient, binder, flavor and odor improver, emulsifier, surfactant, solubilizer, suspending agent, isotonizing agent, preservative, antioxidant, stabilizer and absorption accelerator.

The injections are prepared by appropriately combining the compound of the present invention with the aforementioned additives, in particular, an emulsifier, surfactant, solubilizer, suspending agent, isotonizing agent, buffer, preservative, antioxidant, stabilizer and absorption accelerator.

When the compound of the present invention is used as a medicament, the dose varies depending upon the symptom and age; however, generally 0.15 to 5000 mg (preferably, 0.5 to 1500 mg) in the case of a peroral agent, 0.5 to 1500 mg (preferably, 1.5 to 500 mg) in the case of an external preparation, 0.3 to 5000 mg (preferably 1 to 500 mg) in the case of an injection. The amount of the dose may be administered in a single time or by dividing into 2 to 6 times per day. Note that, in the cases of peroral agent and injection, the dose is the amount virtually administered, whereas in the external preparation, the dose indicates an amount virtually absorbed into a living body.

A compound (1) of the present invention can be produced by the method shown in Examples below. The effect of the compound can be confirmed by the method described in Test Examples (below). These Examples are described by way of example but will not limit the present invention in any manner.

The names of commercially available starting materials and reagents used in the Examples and manufacturers of those are shown below. The name of documents are shown in the column of available manufacturer, meaning that the compound is formed in accordance with the method described in the document.

Benzyloxyacetaldehyde (Aldrich),
2,2-Dimethyl-1,3-propandiol (Kanto Chemical Co., Inc.),
p-Toluenesulfonic acid monohydrate (Tokyo Kasei Kogyo Co., Ltd.),
20% Palladium hydroxide (Aldrich),
Sodium hydride, in oil (Wako Pure Chemical Industries Ltd.),
Acetone (Wako Pure Chemical Industries Ltd.)
4-Chloro-2,3-dimethylpyridine1-oxide (obtained from Sanyo Fine Co., Ltd.; however, it is a known compound disclosed in J. Med. Chem. 1998, 41, 1777-1788),
Acetic anhydride (Kanto Chemical Co., Inc.),
5N Aqueous sodium hydroxide solution (Wako Pure Chemical Industries Ltd.),
1N Aqueous sodium hydroxide solution (Wako Pure Chemical Industries Ltd.),
Triethylamine (Kanto Chemical Co., Inc., or Wako Pure Chemical Industries Ltd.),
Methanesulfonyl chloride (Tokyo Kasei Kogyo Co., Ltd.),
2-Mercaptobenzimidazole (Tokyo Kasei Kogyo Co., Ltd.),
3-Chloroperbenzoic acid (Tokyo Kasei Kogyo Co., Ltd.),
1,1-Bis(hydroxymethyl)cyclopropane (Aldrich)
Ethyl 3-oxohexanoate (ACROS)
Ethylene glycol (Tokyo Kasei Kogyo Co., Ltd.),
Lithium aluminum hydride (Wako Pure Chemical Industries Ltd.),
1,3-Dibenzyloxy-2-propanol (Aldrich)
Sulfur trioxide pyridine complex (Aldrich)
Triethyl orthoformate (Wako Pure Chemical Industries Ltd.),
Trimethyl orthoformate (Tokyo Kasei Kogyo Co., Ltd.),
Methyl propionylacetate (Aldrich)
Hydroxyacetone (Wako Pure Chemical Industries Ltd.),
Benzoyl chloride (Tokyo Kasei Kogyo Co., Ltd.),
D-(−)-diethyl tartrate (Tokyo Kasei Kogyo Co., Ltd.),
Toluene (dehydrated) (Kanto Chemical Co., Inc.),
Titanium (IV) isopropoxide (Kanto Chemical Co., Inc. or Aldrich),
N,N-Diisopropylethylamine (Aldrich or Nakarai Tesque)
Cumene hydroperoxide (Nakarai Tesque, Inc. or Aldrich)
L-(+)-Diethyl tartrate (Tokyo Kasei Kogyo Co., Ltd. or Aldrich),
2-(Hydroxymethyl)-1,3-propanediol (E-MERCK or Aldrich),
Tetrahydrofuran (dehydrated) (Kanto Chemical Co., Inc.),
1,3-Difluoroacetone (SYNQUEST)
1,3-Propanediol (Wako Pure Chemical Industries Ltd.),
((4R)-2,2-dimethyl-1,3-dioxolan-4-yl)methanol (Aldrich)
2,2-Dimethyl-1,3-dioxan-5-one (Tokyo Kasei Kogyo Co., Ltd.),
Benzyl bromide (E-MERCK)
Tetrabutylammonium iodide (Tokyo Kasei Kogyo Co., Ltd.),
DOWEX® 50W-X8 (Muromachi Kagaku Kogyo Kaisha, Ltd.)
Cyclobutanone (AVOCADO)
Tetrahydro-4H-pyran-4-one (Tokyo Kasei Kogyo Co., Ltd.),
Dichloromethane (dehydrated) (Kanto Chemical Co., Inc.),
70% Perchloric acid (Wako Pure Chemical Industries Ltd.),
2,3,5-Collidine (ACROS),
Sulfuric acid (Junsei Chemical Co., Ltd.),
Nitric acid, fuming (Wako Pure Chemical Industries Ltd.),
Acetyl chloride (Junsei Chemical Co., Ltd.),
N,N-dimethylformamide (Wako Pure Chemical Industries Ltd.),
0.1N Aqueous sodium hydroxide solution (Wako Pure Chemical Industries Ltd.),
Sodium hydroxide (Wako Pure Chemical Industries Ltd.),
p-Toluenesulfonyl chloride (Tokyo Kasei Kogyo Co., Ltd.),
Thionyl chloride (Wako Pure Chemical Industries Ltd.),
Potassium t-butoxide (Tokyo Kasei Kogyo Co., Ltd.),
Pentaerythritol (Tokyo Kasei Kogyo Co., Ltd.),
Triethyl orthoacetate (Tokyo Kasei Kogyo Co., Ltd.),
Triethyl orthopropionate (Tokyo Kasei Kogyo Co., Ltd.),
3-Pentanone (Tokyo Kasei Kogyo Co., Ltd.),
Cyclopentanone (Tokyo Kasei Kogyo Co., Ltd.),
Cyclohexanone (Tokyo Kasei Kogyo Co., Ltd.),
1,4-Cyclohexanedione monoethylene ketal (Tokyo Kasei Kogyo Co., Ltd.),
Cyclopropanecarbonitrile (Tokyo Kasei Kogyo Co., Ltd.),
Cyclobutanecarbonitrile (AVOCADO),
Benzyloxyacetaldehyde (Aldrich),
1-Benzyloxy-2-propanone (Aldrich),
Picolinic acid (Tokyo Kasei Kogyo Co., Ltd.),
2,2-Dimethyl-1,3-propanediol (Kanto Chemical Co., Inc.)
Ethyl acetoacetate (Tokyo Kasei Kogyo Co., Ltd.),
Methyl 4-methoxyacetoacetate (Tokyo Kasei Kogyo Co., Ltd.),
Ethyl iodide (Wako Pure Chemical Industries Ltd.)
Diisopropylamine (Aldrich),
n-Butyllithium (Kanto Chemical Co., Inc.),
Lithium aluminum hydride (Wako Pure Chemical Industries Ltd.),
Sodium borohydride (Kanto Chemical Co., Inc.),
2N Aqueous sodium hydroxide solution (Wako Pure Chemical Industries Ltd.),
Hydrogen gas (TOMOE SHOKAI Co., LTD),
Hydrochloric acid gas (TOMOE SHOKAI Co., LTD),
Ethyl 3-oxopentanoate (Aldrich),
1-Bromobutan-2-one (Trans World Chemicals, Inc.),
Potassium acetate (Wako Pure Chemical Industries Ltd.),
Potassium carbonate (Kanto Chemical Co., Inc.),
Methyl 4-methoxyacetoacetate (Tokyo Kasei Kogyo Co., Ltd.)
Dihydroxyacetone (E-MERCK),
Pyridine (Wako Pure Chemical Industries Ltd.),
Benzoyl chloride (Tokyo Kasei Kogyo Co., Ltd.),
1,8-Diazabicyclo[5.4.0]undec-7-ene (Aldrich),
Nonafluoro-1-butanesulfonyl fluoride (Tokyo Kasei Kogyo Co., Ltd.),
Sodium benzoate (Kanto Chemical Co., Inc.),
(Diethylamino)sulfur trifluoride (FLUKA),
28% Methanol solution of sodium methoxide (Wako Pure Chemical Industries Ltd.),
Benzyloxyacetaldehyde (Aldrich), 3-Hydroxy-2-methylpyridine (Aldrich)
N-Phenyltrifluoromethanesulfonimide (Tokyo Kasei Kogyo Co., Ltd.),
(Trimethylsilyl)acetylene (Aldrich),
Bis(triphenylphosphine)palladium (II) chloride (N.E. CHEMCAT),
Copper (I) iodide (Kanto Chemical Co., Inc.),
Tetrabutylammonium fluoride (1N tetrahydrofuran solution) (Aldrich),
10% Palladium/carbon (N.E. CHEMCAT),
3,4-Diamino-1-fluorobenzene (Lancaster),
Carbon disulfide (Wako Pure Chemical Industries Ltd.),
Formaldehyde dimethyl acetal (Tokyo Kasei Kogyo Co., Ltd.),
Lithium bromide (Aldrich)
p-Toluenesulfonic acid monohydrate (Tokyo Kasei Kogyo Co., Ltd.),
2-Methyl-6-nitroaniline (Wako Pure Chemical Industries Ltd.),
4-Nitro-2-picoline N-oxide (Lancaster),
0.1N Aqueous sodium hydroxide solution (Wako Pure Chemical Industries Ltd.),
5,5-Dimethyl-1,3-dioxane-2-ethanol (Aldrich),
Glycerol formal (Tokyo Kasei Kogyo Co., Ltd.),
2-Hydroxymethyl-1,4-benzodioxane (Aldrich),
2-(Allyloxy)ethanol (Tokyo Kasei Kogyo Co., Ltd.),
Iodine (Wako Pure Chemical Industries Ltd.),
18-Crown-6 (Wako Pure Chemical Industries Ltd.),
Zirconium (IV) isopropoxide/isopropanol complex (Aldrich),
(−)-Tetramethyl-(D)-tartaramide (Tokyo Kasei Kogyo Co., Ltd.),
Hafnium tetrabutoxide (Aldrich),
Vanadyl acetylacetone (Aldrich),
(S)-(−)-2-(3,5-Di-tert-butylsalicylideneamino)-3,3-Dimethyl-1-butanol (Aldrich),
30% Hydrogen peroxide (Kanto Chemical Co., Inc.),
3-Amino-4-nitrotoluene (Aldrich),
2-Methoxy-6-nitroaniline (J. of Chem. Soc. (1954) 2977-2978),
4-Amino-3-nitrobenzotrifluoride (ACROS),
4-(2-Hydroxyethyl)-2,2-dimethyl-1,3-dioxolane (Aldrich),
DL-α-0-Benzylglycerol (SIGMA),
3-Pentanone (Tokyo Kasei Kogyo Co., Ltd.),
1-Benzyloxy-2-propanone (Aldrich),
(+)-1,4-Dioxaspiro[4,5]decane-2-methanol (Aldrich)
4-Benzyloxy-2-butanone (FLUKA),
(R)-(+)-1,2,4-Butanetriol (Wako Pure Chemical Industries Ltd.),
(S)-(−)-1,2,4-Butanetriol (Wako Pure Chemical Industries Ltd.),
Methyl acetoacetate (Tokyo Kasei Kogyo Co., Ltd.)
6,7-Dihydro-1H-[1,4]dioxino[2',3':4,5]benzo[D]imidazole-2-thiol (MAYBRIDGE),
5-Nitro-1,3-benzodioxole (Tokyo Kasei Kogyo Co., Ltd.),
Tetramethylammonium nitrate (Aldrich),
Trifluoromethanesulfonic anhydride (Aldrich),
Methyl 2-cyclopentanonecarboxylate (Aldrich),
1,4-Cyclohexanedione mono-2,2-dimethyltrimethylene ketal (Aldrich).
Ethyl 4-cyclohexanonecarboxylate (Tokyo Kasei Kogyo Co., Ltd.)
Glycol aldehyde diethyl acetal (Lancaster),
Diethyl 1,1-cyclobutanedicarboxylate (Lancaster)

EXAMPLES

In the chemical formulas described in Examples, the atom labeled with reference mark * represents an asymmetric atom.

Example 1

2-(((4-((5,5-dimethyl-1,3-dioxan-2-yl)methoxy)-3-methylpyridin-2-yl)methyl)sulfinyl)-1H-benzimidazole sodium salt

[Formula 8]

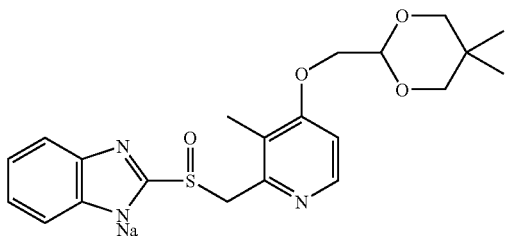

(1a) 2-((benzyloxy)methyl)-5,5-dimethyl-1,3-dioxane

[Formula 9]

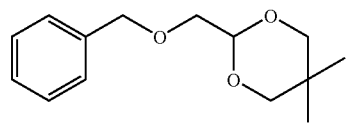

To a mixture of benzyloxyacetaldehyde (5 g, 33.3 mmol), 2,2-dimethyl-1,3-propanediol (4.16 g, 40 mmol) and toluene (70 ml), p-toluenesulfonic acid monohydrate (287 mg, 1.51 mmol) was added and refluxed for 4 hours while removing water by the Dean-Stark apparatus. After the reaction mixture was cooled to room temperature, triethylamine (4 ml) was added to the reaction mixture and the solvent was removed by evaporation. The residue was purified by silica gel column chromatography (silica gel: 200 g, elution solvent: ethyl acetate/heptane=1/9) to obtain the title compound (7.6 g, yield: 96.6%) as a colorless oil.

$^1$H NMR(400 MHz, CDCl$_3$)δ ppm; 0.73(3H, s), 1.19(3H, s), 3.46(2H, d, J=10 Hz), 3.55(2H, d, J=4 Hz), 3.64(2H, d, J=10 Hz), 4.60(2H, s), 4.66(1H, t, J=4 Hz), 7.26-7.35(5H, m).

(1b) (5,5-dimethyl-1,3-dioxan-2-yl)methanol

[Formula 10]

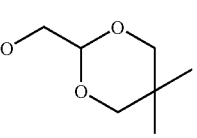

The 2-((benzyloxy)methyl)-5,5-dimethyl-1,3-dioxane (7.6 g, 32.2 mmol) obtained by the step (1a) was mixed with 20% palladium hydroxide (700 mg) and ethyl acetate (70 ml). The mixture was stirred in a hydrogen atmosphere overnight. The reaction mixture was allowed to stand for further 5 days in the same hydrogen atmosphere. The reaction vessel was purged with nitrogen, the catalyst was filtered off, and the solvent was distilled off to obtain the title compound (4 g, yield: 85%) as a white solid.

$^1$H NMR(400 MHz, CDCl$_3$)δppm; 0.75(3H, s), 1.20(3H, s), 1.88-1.95(1H, br), 3.47(2H, d, J=10 Hz), 3.63-3.66(4H, m), 4.54(1H, t, J=4 Hz).

(1c) 4-((5,5-dimethyl-1,3-dioxan-2-yl)methoxy)-2,3-dimethylpyridine1-oxide

[Formula 11]

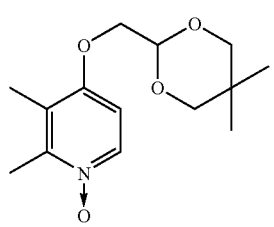

The (5,5-dimethyl-1,3-dioxan-2-yl)methanol (2 g, 13.7 mmol) obtained in the step (1b) was mixed with sodium hydride in oil (822 mg, 20.6 mmol as the content was regarded as 60%) and dimethylsulfoxide (20 ml). The mixture was stirred at room temperature for 30 minutes. To the reaction mixture, 4-chloro-2,3-dimethylpyridine1-oxide (2.16 g, 13.7 mmol) was added and stirred at 50° C. overnight, and further allowed to stand still for one day at room temperature. After dimethylsulfoxide was distilled off, methanol and NH silica gel were added to the residue and then methanol was distilled off. The mixture of the reaction mixture and NH silica gel was purified by silica gel column chromatography (NH silica gel: 200 g, elution solvent: ethyl acetate/heptane=1/1 to 4/1→methanol/ethyl acetate=1/9) to obtain the title compound (3.1 g, yield: 84.6%) as a light yellow oil.

$^1$H NMR(400 MHz, DMSO-d$_6$)δppm; 0.70(3H, s), 1.12 (3H, s), 2.12(3H, s), 2.34(3H, s), 3.49(2H, d, J=11 Hz), 3.59 (2H, d, J=11 Hz), 4.06(2H, d, J=4 Hz), 4.82(1H, t, J=4 Hz), 6.96(1H, d, J=7 Hz), 8.05(1H, d, J=7 Hz).

(1d) (4-((5,5-dimethyl-1,3-dioxan-2-yl)methoxy)-3-methylpyridin-2-yl)methanol

[Formula 12]

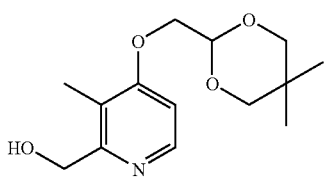

The 4-((5,5-dimethyl-1,3-dioxan-2-yl)methoxy)-2,3-dimethylpyridine1-oxide (3.1 g, 11.6 mmol) obtained by the step (1c) was mixed with acetic anhydride (9.87 ml, 104 mmol). After the mixture was stirred at 85° C. for 45 minutes, acetic anhydride was removed. The residue was dissolved in methanol (40 ml) and a 5N aqueous sodium hydroxide solution (5.1 ml, 25.5 mmol) was added to the mixture while cooling on ice. The mixture was stirred at room temperature for one hour. Methanol was distilled off and ice water was added to the residue, which was then extracted with ethyl acetate. The organic layer was washed with a saturated saline solution, dried over anhydrous magnesium sulfate. After the solvent was distilled off, the resultant mixture was purified by silica gel column chromatography (silica gel: 120 g, elution solvent: ethyl acetate/heptane=1/4 to 4/1) to obtain the title compound (1.23 g, yield: 39.7%) as a light yellow oil.

$^1$H NMR(400 MHz, CDCl$_3$)δppm; 0.77(3H, s), 1.23(3H, s), 2.07(3H, s), 3.52(2H, d, J=12 Hz), 3.69(2H, d, J=12 Hz), 4.12(2H, d, J=4 Hz), 4.65(2H, s), 4.85(1H, t, J=4 Hz), 6.73 (1H, d, J=6 Hz), 8.30(1H, d, J=6 Hz).

(1e) 2-(((4-((5,5-dimethyl-1,3-dioxan-2-yl)methoxy)-3-methylpyridin-2-yl)methyl)thio)-1H-benzimidazole

[Formula 13]

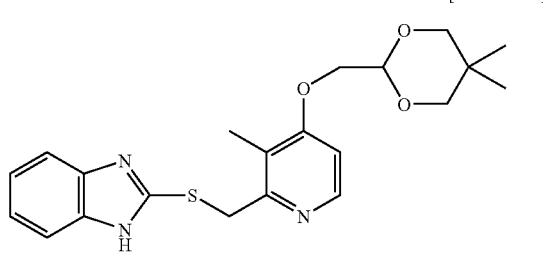

The (4-((5,5-dimethyl-1,3-dioxan-2-yl)methoxy)-3-methylpyridin-2-yl)methanol (500 mg, 1.87 mmol) obtained by the step (1d) was mixed with triethylamine (1.04 ml, 7.48 mmol) and tetrahydrofuran (15 ml). This mixture was cooled to −19° C. and methanesulfonyl chloride (217 μl, 2.81 mmol) was added thereto and then stirred at −19° C. for 30 minutes. Under the same conditions, 2-mercaptobenzimidazole (309 mg, 2.06 mmol) was added to the reaction mixture. After the reaction mixture was stirred overnight at room temperature, methanol and NH silica gel were added to the mixture, and then, the solvent was distilled off. The mixture of the reaction mixture and NH silica gel was purified by silica gel column chromatography (silica gel: 80 g, elution solvent: ethyl acetate/heptane=1/1 to 4/1→methanol/ethyl acetate=1/9) to obtain the title compound (599 mg, yield: 80.2%) as a light red foam.

$^1$H NMR(400 MHz, DMSO-d$_6$)δppm; 0.71(3H, s), 1.13 (3H, s), 2.21(3H, s), 3.50(2H, d, J=11 Hz), 3.59(2H, d, J=11 Hz), 4.09(2H, d, J=4 Hz), 4.69(2H, s), 4.84(1H, t, J=4 Hz), 6.98(1H, d, J=6 Hz), 7.11(2H, dd, J=3, 6 Hz), 7.36-7.51(2H, br), 8.22(1H, d, J=6 Hz).

(1f) 2-(((4-((5,5-dimethyl-1,3-dioxan-2-yl)methoxy)-3-methylpyridin-2-yl)methyl)sulfinyl)-1H-benzimidazole

[Formula 14]

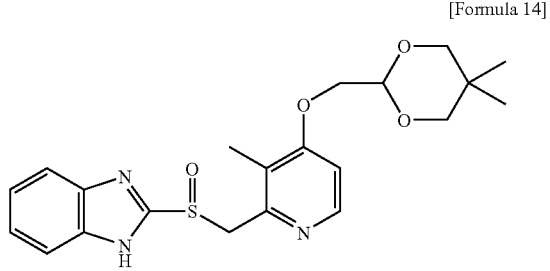

The 2-(((4-((5,5-dimethyl-1,3-dioxan-2-yl)methoxy)-3-methylpyridin-2-yl)methyl)thio)-1H-benzimidazole (599 mg, 1.5 mmol) obtained by the step (1e) was mixed with methanol (5 ml) and toluene (15 ml), and the mixture was cooled to −50° C. 3-chloroperbenzoic acid (358 mg, 1.35 mmol, as the content was regarded as 65%) dissolved in a solvent mixture of methanol and toluene was slowly added dropwise to the mixture, and stirred at −47° C. to −70° C. for 3 hours. A saturated aqueous solution of sodium hydrogen carbonate was added to the reaction mixture, which was then extracted with ethyl acetate. The organic layer was washed with a saturated saline solution, dried over potassium carbonate, and the solvent was distilled off. The residue was purified with silica gel column chromatography (NH silica gel: 40 g, elution solvent: dichloromethane/heptane=7/3→methanol/dichloromethan=3/97 to 1/9). To the obtained product, heptane (20 ml) and diethyl ether (2 ml) were added, the precipitate was obtained by filtration. In this manner, the title compound (475 mg, yield: 76.2%) was obtained as a light orange solid.

$^1$H NMR(400 MHz, DMSO-d$_6$)δppm; 0.71(3H, s), 1.12 (3H, s), 2.14(3H, s), 3.49(2H, d, J=11 Hz), 3.59(2H, d, J=11 Hz), 4.09(2H, d, J=4 Hz), 4.70(1H, d, J=13 Hz), 4.78(1H, d, J=13 Hz), 4.84(1H, t, J=4 Hz), 6.98(1H, d, J=6 Hz), 7.25-7.32 (2H, m), 7.60-7.66(2H, m), 8.20(1H, d, J=6 Hz).

(1g) 2-(((4-((5,5-dimethyl-1,3-dioxan-2-yl)methoxy)-3-methylpyridin-2-yl)methyl)sulfinyl)-1H-benzimidazole sodium salt

[Formula 15]

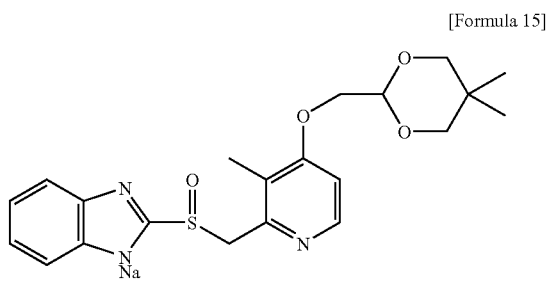

The 2-(((4-((5,5-dimethyl-1,3-dioxan-2-yl)methoxy)-3-methylpyridin-2-yl)methyl)sulfinyl)-1H-benzimidazole (475 mg, 1.14 mmol) obtained by the step (1f) was mixed with ethanol (15 ml). To the mixture, a 1N aqueous sodium hydroxide solution (1.14 ml, 1.14 mmol) was added and the solvent was distilled off. Ethanol was added to the residue, dissolved and distilled off. This operation was repeated twice. Diethyl ether was added to the residue and the resultant mixture was ultrasonically treated. The precipitate was obtained by filtration and dried by aspiration to obtain the title compound (445 mg, yield: 89.2%) as a light yellow solid.

$^1$H NMR(400 MHz, DMSO-d$_6$)δppm; 0.70(3H, s), 1.13 (3H, s), 2.18(3H, s), 3.50(2H, d, J=11Hz), 3.59(2H, d, J=11 Hz), 4.08(2H, d, J=4 Hz), 4.39(1H, d, J=13 Hz), 4.76(1H, d, J=13 Hz), 4.84(1H, t, J=4 Hz), 6.85(2H, dd, J=3, 6 Hz), 6.95(1H, d, J=6 Hz), 7.43(2H, dd, J=3, 6 Hz), 8.27(1H, d, J=6 Hz).

Example 2

2-(((4-(5,7-dioxaspiro[2.5]oct-6-ylmethoxy)-3-methylpyridin-2-yl)methyl)sulfinyl)-1H-benzimidazole sodium salt

[Formula 16]

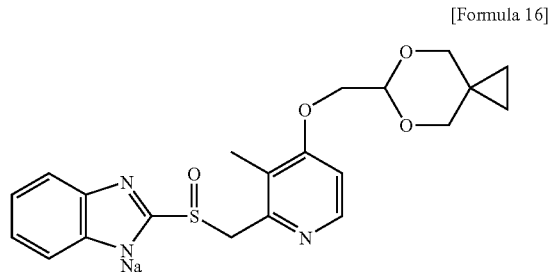

(2a) 6-((benzyloxy)methyl)-5,7-dioxasprio[2.5]octane

[Formula 17]

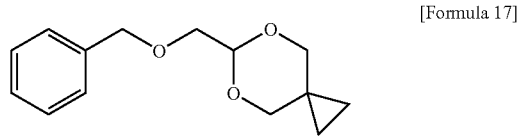

A mixture of benzyloxyacetaldehyde (5 g, 33.3 mmol), 1,1-bis(hydroxymethyl)cyclopropane (4.08 g, 40 mmol), p-toluenesulfonic acid monohydrate (287 mg, 1.51 mmol) and toluene (70 ml) was refluxed for 2 hours while removing water by the Dean-Stark apparatus. After the reaction mixture was cooled to room temperature, triethylamine (4 ml) was added to the reaction mixture and the solvent was distilled off. The residue was purified by silica gel column chromatography (silica gel: 200 g, elution solvent: ethyl acetate/heptane=5/95 to 1/9) to obtain the title compound (6.1 g, yield: 78.2%) as a light yellow oil.

$^1$H NMR(400 MHz, CDCl$_3$) δppm; 0.31-0.35(2H, m), 0.67-0.71(2H, m), 3.26(2H, d, J=12 Hz), 3.57(2H, d, J=4 Hz), 4.14(2H, d, J=12 Hz), 4.60(2H, s), 4.82(1H, t, J=4 Hz), 7.27-7.34(5H, m).

(2b) 5,7-dioxaspiro[2.5]oct-6-ylmethanol

[Formula 18]

The 6-((benzyloxy)methyl)-5,7-dioxasprio[2.5]octane (6.1 g, 26 mmol) obtained by the step (2a) was mixed with 20% palladium hydroxide (800 mg) and ethyl acetate (70 ml) and the mixture was stirred in a hydrogen atmosphere for 24 hours. The reaction vessel was purged with nitrogen and the catalyst was filtered off and then the solvent was distilled off to obtain the title compound (3.7 g, yield: 98.7%) as a colorless oil.

$^1$H NMR(400 MHz, CDCl$_3$) δppm; 0.33-0.37(2H, m), 0.68-0.72(2H, m), 3.28(2H, d, J=12 Hz), 3.68(2H, d, J=4 Hz), 4.16(2H, d, J=12 Hz), 4.73(1H, t, J=4 Hz).

(2c) 4-(5,7-dioxaspiro[2.5]oct-6-ylmethoxy)-2,3-dimethylpyridine1-oxide

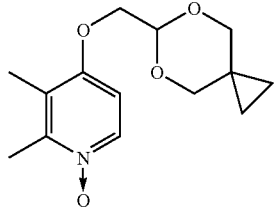

[Formula 19]

The 5,7-dioxaspiro[2.5]oct-6-ylmethanol (1.7 g, 11.8 mmol) obtained by the step (2b) was mixed with sodium hydride, in oil (708 mg, 17.7 mmol as the content was regarded as 60%) and dimethylsulfoxide (20 ml), and the mixture was stirred at room temperature for 30 minutes. To the reaction mixture, 4-chloro-2,3-dimethylpyridine1-oxide (1.86 g, 11.8 mmol) was added and stirred at 50° C. overnight. After dimethylsulfoxide was distilled off, methanol and NH silica gel were added to the residue and methanol was distilled off. The mixture of the reaction mixture and NH silica gel was purified by silica gel column chromatography (NH silica gel: 200 g, elution solvent: ethyl acetate/heptane=1/1 to 4/1→methanol/ethyl acetate=1/9 to 1/4) to obtain the title compound (1.8 g, yield: 57.5%) as a red oil.

$^1$H NMR(400 MHz, CDCl$_3$) δppm; 0.36-0.40(2H, m), 0.69-0.74(2H, m), 2.22(3H, s), 2.53(3H, s), 3.30(2H, d, J=12 Hz), 4.11(2H, d, J=4 Hz), 4.19(2H, d, J=12 Hz), 5.00(1H, t, J=4 Hz), 6.68(1H, d, J=7 Hz), 8.13(1H, d, J=7 Hz).

(2d) (4-(5,7-dioxaspiro[2.5]oct-6-ylmethoxy)-3-methylpyridin-2-yl)methanol

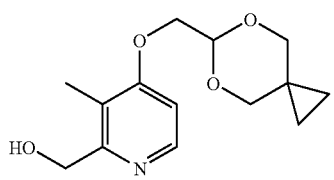

[Formula 20]

The 4-(5,7-dioxaspiro[2.5]oct-6-ylmethoxy)-2,3-dimethylpyridine1-oxide (1.8 g, 6.78 mmol) obtained by the step (2c) was mixed with acetic anhydride (5.77 ml, 61 mmol). The mixture was stirred at 85° C. for 45 minutes and then acetic anhydride was distilled off. The residue was cooled on ice and dissolved in methanol. To this, a 5N aqueous sodium hydroxide solution (2.98 ml, 14.9 mmol) was added under ice-cool and the mixture was stirred at room temperature for 2 hours. Methanol was distilled off and water was added to the residue, which was then extracted with ethyl acetate. The organic layer was washed with a saturated saline solution and dried over anhydrous magnesium sulfate, and thereafter the solvent was distilled off. Purification was performed by silica gel column chromatography (silica gel: 100 g, elution solvent: ethyl acetate/heptane=1/4 to 4/1). To the purified product, heptane (15 ml) was added and the mixture was refluxed. After the solution was confirmed to reach a homogeneous state, it was gradually cooled.

The precipitated product was obtained by filtration.

In this manner, the title compound (520 mg, yield: 28.9%) was obtained as a white solid.

$^1$H NMR(400 MHz, CDCl$_3$) δppm; 0.36-0.40(2H, m), 0.70-0.74(2H, m), 2.07(3H, s), 3.30(2H, d, J=11 Hz), 4.14 (2H, d, J=4 Hz), 4.20(2H, d, J=11 Hz), 4.64(2H, s), 4.86(1H, br s), 5.02(1H, t, J=4 Hz), 6.73(1H, d, J=6 Hz), 8.29(1H, d, J=6 Hz).

(2e) 2-(((4-(5,7-dioxaspiro[2.5]oct-6-ylmethoxy)-3-methylpyridin-2-yl)methyl)thio)-1H-benzimidazole

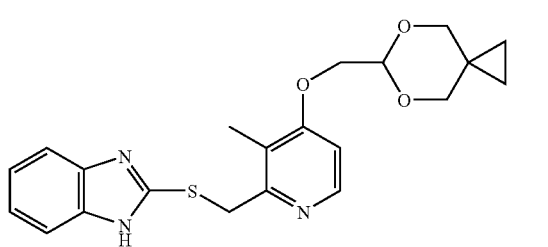

[Formula 21]

The (4-(5,7-dioxaspiro[2.5]oct-6-ylmethoxy)-3-methylpyridin-2-yl)methanol (520 mg, 1.96 mmol) obtained in the step (2d) was mixed with triethylamine (1.09 ml, 7.84 mmol) and tetrahydrofuran (10 ml) and the resultant mixture was cooled to −19° C. Methanesulfonyl chloride (228 μl, 2.94 mmol) was added to the mixture, which was stirred at −19° C. for 30 minutes. In the same conditions, 2-mercaptobenzimidazole (324 mg, 2.16=mol) was added to the reaction mixture. After the reaction mixture was stirred at room temperature for 2 days, methanol and NH silica gel were added to the mixture, and the solvent was distilled off. The mixture of the reaction mixture and NH silica gel was purified by silica gel column chromatography (silica gel: 80 g, elution solvent: ethyl acetate/heptane=4/6 to 7/3→methanol/ethyl acetate=1/9) to obtain the title compound (629 mg, yield: 80.7%) as a colorless foam.

$^1$H NMR(400 MHz, DMSO-d$_6$) δppm; 0.31-0.36(2H, m), 0.56-0.61(2H, m), 2.21(3H, s), 3.26(2H, d, J=12 Hz), 4.10-4.13(4H, m), 4.69(2H, s), 5.02(1H, t, J=5 Hz), 6.99(1H, d, J=6 Hz), 7.11(2H, dd, J=3, 6 Hz), 7.39-7.49(2H, br), 8.23(1H, d, J=6 Hz).

(2f) 2-(((4-(5,7-dioxaspiro[2.5]oct-6-ylmethoxy)-3-methylpyridin-2-yl)methyl)sulfinyl)-1H-benzimidazole

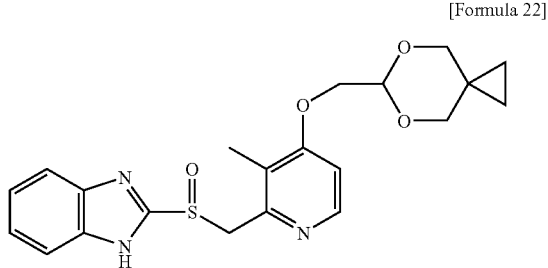

[Formula 22]

The 2-(((4-(5,7-dioxaspiro[2.5]oct-6-ylmethoxy)-3-methylpyridin-2-yl)methyl)thio)-1H-benzimidazole (629 mg, 1.58 mmol) obtained by the step (2e) was mixed with methanol (5 ml) and toluene (15 ml) and the mixture was cooled to −50° C. Then, 3-chloroperbenzoic acid (378 mg, 1.42 mmol as the content was regarded as 65%) dissolved in a solvent mixture of methanol and toluene was slowly added dropwise to the mixture, and stirred at −47° C. to −70° C. for 4 hours. A saturated aqueous solution of sodium hydrogen carbonate was added to the reaction mixture, which was then extracted with ethyl acetate. The organic layer was washed with a saturated saline solution, dried over potassium carbonate, and the solvent was distilled off. The residue was purified with silica gel column chromatography (NH silica gel: 40 g, elution solvent: dichloromethane/heptane=7/3→methanol/dichloromethan=3/97 to 1/9) to obtain the title compound (623 mg, yield: 95.4%) as a colorless foam.

$^1$H NMR(400 MHz, DMSO-$d_6$) δppm; 0.31-0.36(2H, m), 0.56-0.61(2H, m), 2.14(3H, s), 3.26(2H, d, J=11 Hz), 4.11-4.13(4H, m), 4.70(1H, d, J=14 Hz), 4.79(1H, d, J=14 Hz), 5.02(1H, t, J=4 Hz), 6.99(1H, d, J=6 Hz), 7.29(2H, dd, J=3, 6 Hz), 7.59-7.67(2H, br), 8.21(1H, d, J=6 Hz).

(2g) 2-(((4-(5,7-dioxaspiro[2.5]oct-6-ylmethoxy)-3-methylpyridin-2-yl)methyl)sulfinyl)-1H-benzimidazole sodium salt

[Formula 23]

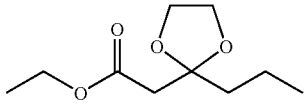

The 2-(((4-(5,7-dioxaspiro[2.5]oct-6-ylmethoxy)-3-methylpyridin-2-yl)methyl)sulfinyl)-1H-benzimidazole (623 mg, 1.51 mmol) obtained in the step (2f) was mixed with ethanol (15 ml). To the mixture, a 1N aqueous sodium hydroxide solution (1.51 ml, 1.51 mmol) was added and the solvent was distilled off. Ethanol was added to the residue and distilled off. This operation was repeated twice. Diethyl ether was added to the residue and the resultant mixture was ultrasonically treated. The precipitate was obtained by filtration and dried by aspiration to obtain the title compound (553 mg, yield: 84.1%) as a white solid.

$^1$H NMR(400 MHz, DMSO-$d_6$) δppm; 0.31-0.35(2H, m), 0.57-0.61(2H, m), 2.19(3H, s), 3.26(2H, d, J=11 Hz), 4.10 (2H, d, J=5 Hz), 4.12(2H, d, J=11 Hz), 4.37(1H, d, J=13 Hz), 4.82(1H, d, J=13 Hz), 5.02(1H, t, J=5 Hz), 6.84(2H, dd, J=3, 6 Hz), 6.95(1H, d, J=6 Hz), 7.42(2H, dd, J=3, 6 Hz), 8.27(1H, d, J=6 Hz).

Example 3

2-(((3-methyl-4-(2-(2-propyl-1,3-dioxolan-2-yl)ethoxy)pyridin-2-yl)methyl)sulfinyl)-1H-benzimidazole sodium salt

[Formula 24]

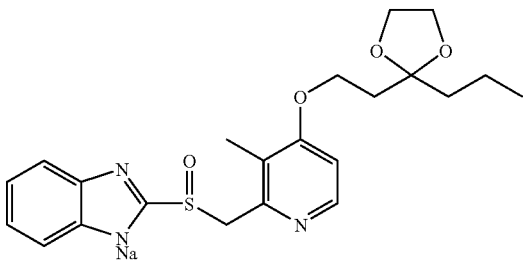

(3a) Ethyl(2-propyl-1,3-dioxolan-2-yl)acetate

[Formula 25]

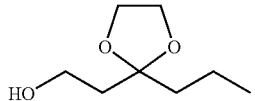

A mixture of ethyl 3-oxohexanoate (5 g, 31.6 mmol), ethylene glycol (3.92 g, 63.2 mmol) and triethyl orthoformate (4.68 g, 31.6 mmol), and p-toluenesulfonic acid monohydrate (544 mg, 2.86 mmol) was stirred at room temperature for 29 hours and 10 minutes. To the reaction mixture, water was added and the mixture was extracted with ethyl acetate. The organic layer was washed with a saturated saline solution, dried over magnesium sulfate, and filtered. The filtrate was concentrated under reduced press-re to obtain the title compound (6.2 g, 97%) as a colorless oil.

$^1$H NMR(400 MHz, CDCl$_3$) δppm; 0.93(3H, t, J=7 Hz), 1.27(3H, t, J=7 Hz), 1.39-1.48(2H, m), 1.78(2H, t, J=8 Hz), 2.64(2H, s), 3.94-4.02(4H, m), 4.15(2H, q, J=7H).

(3b) 2-(2-propyl-1,3-dioxolan-2-yl)ethanol

[Formula 26]

To tetrahydrofuran (100 ml) suspension of lithium aluminium hydride (1.17 g, 30.7 mmol), a tetrahydrofuran (20 ml) solution of the ethyl(2-propyl-1,3-dioxolan-2-yl)acetate (6.2 g, 30.7 mmol) obtained in the step (3a) was added under ice-cool. The mixture was stirred for 30 minutes under ice-cool, water (1.17 ml) and a 15% aqueous sodium hydroxide solution (1.17 ml) and water (3.51 ml) were sequentially added and stirred for 10 minutes. Sodium sulfate was added to the mixture, stirred and subjected to silica gel filtration. The filtrate was concentrated under reduced pressure and the residue was dissolved in a solution mixture containing n-heptane/ethyl acetate in a ratio of 2:1 and subjected to silica gel column chromatography (elution solvent: n-heptane/ethyl acetate=2/1) to obtain the title compound (3.82 g, 77.7%) as a colorless oil.

$^1$H NMR(400 MHz, CDCl$_3$) δppm; 0.93(3H, t, J=8 Hz), 1.33-1.43(2H, m), 1.60-1.65(2H,m), 1.92(2H, t, J=6 Hz), 2.83(1H, t, J=6 Hz), 3.74(2H, q, J=6 Hz), 3.95-4.03(4H, m).

(3c) 2,3-dimethyl-4-(2-(2-propyl-1,3-dioxolan-2-yl)ethoxy)pyridine1-oxide

[Formula 27]

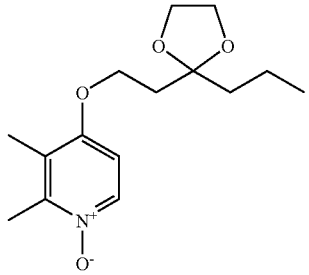

To a dimethylsulfoxide (22.5 ml) solution of the 2-(2-propyl-1,3-dioxolan-2-yl)ethanol (1.5 g, 9.35 mmol) obtained in the step (3b), sodium hydride, in oil (561 mg, 14 mmol as the content was regarded as 60%) and 4-chloro-2,3-dimethylpyridine1-oxide (1.33 g, 8.42 mmol) were added in a nitrogen stream and stirred at 60° C. for 2 hours. The mixture was allowed to stand at room temperature for 3 days and concentrated under reduced pressure. The residue was suspended in tetrahydrofuran. NH silica gel was added to the resultant mixture, which was then concentrated to dryness and subjected to NH silica gel column chromatography (elution solvent: n-heptane/ethyl acetate/methanol=1/1/0→0/1/0→0/10/1) to obtain the title compound (1.53 g, yield: 58.2%) as a light brown oil.

$^1$H NMR(400 MHz, CDCl$_3$) δppm; 0.94(3H, t, J=7 Hz), 1.38-1.49(2H, m), 1.62-1.67(2H,m), 2.14-2.20(2H, m), 2.19(3H, s), 2.53(3H, s), 3.92-4.01(4H, m), 4.10(2H, t, J=7 Hz), 6.64(1H, d, J=7 Hz), 8.13(1H, d, J=7 Hz).

(3d) (3-methyl-4-(2-(2-propyl-1,3-dioxolan-2-yl)ethoxy)pyridin-2-yl)methyl acetate

[Formula 28]

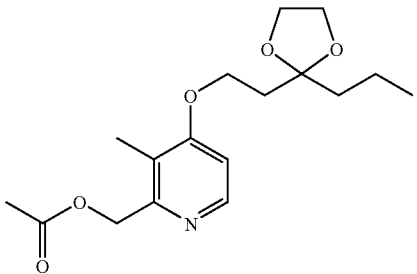

The 2,3-dimethyl-4-(2-(2-propyl-1,3-dioxolan-2-yl)ethoxy)pyridine1-oxide (1.53 g, 5.44 mmol) obtained in the step (3c) was mixed with acetic anhydride (30 ml) and the mixture was stirred at 80° C. overnight. The reaction mixture was concentrated under reduced pressure and the residue was dissolved in ethyl acetate and then subjected to silica gel column chromatography (elution solvent: n-heptane/ethyl acetate=1/1) to obtain the title compound (1.19 g, 67.6%) as a light yellow oil.

$^1$H NMR(400 MHz, CDCl$_3$) δppm; 0.94(3H, t, J=7 Hz), 1.39-1.49(2H, m), 1.64-1.69(2H,m), 2.12(3H, s), 2.16-2.20(2H, m), 2.18(3H, s), 3.93-4.00(4H, m), 4.12(2H, t, J=7 Hz), 5.20(2H,s), 6.73(1H, d, J=6 Hz), 8.31(1H, d, J=6 Hz).

(3e) (3-methyl-4-(2-(2-propyl-1,3-dioxolan-2-yl)ethoxy)pyridin-2-yl)methanol

[Formula 29]

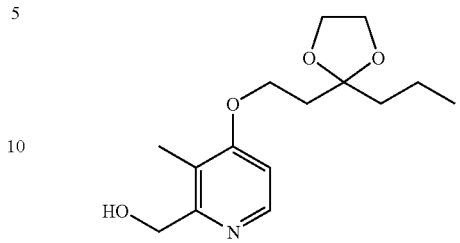

The (3-methyl-4-(2-(2-propyl-1,3-dioxolan-2-yl)ethoxy)pyridin-2-yl)methyl acetate (1.19 g, 3.68 mmol) obtained in the step (3d) was mixed with a 1N aqueous sodium hydroxide solution (5 ml) and methanol (10 ml). The mixture was stirred at room temperature for 3 hours and concentrated under reduced pressure. The residue was suspended in tetrahydrofuran and sodium sulfate was added to the suspension, and filtered. The filtrate was concentrated under reduced pressure. The residue was dissolved in a solution mixture containing heptane and ethyl acetate at a ratio of 2:1 and subjected to silica gel column chromatography (elution solvent: n-heptane/ethyl acetate=2/1) to obtain the title compound (0.88 g, 85%) as a colorless oil.

$^1$H NMR(400 MHz, CDCl$_3$) δppm; 0.94(3H, t, J=7 Hz), 1.39-1.49(2H, m), 1.64-1.69(2H,m), 2.03(3H, s), 2.18(2H, t, J=7 Hz), 3.93-4.01(4H, m), 4.14(2H, t, J=7 Hz), 4.65(2H, s), 4.89(1H, br s), 6.73(1H, d, J=6 Hz), 8.29(1H, d, J=6 Hz).

(3f) 2-(((3-methyl-4-(2-(2-propyl-1,3-dioxolan-2-yl)ethoxy)pyridin-2-yl)methyl)thio)-1H-benzimidazole

[Formula 30]

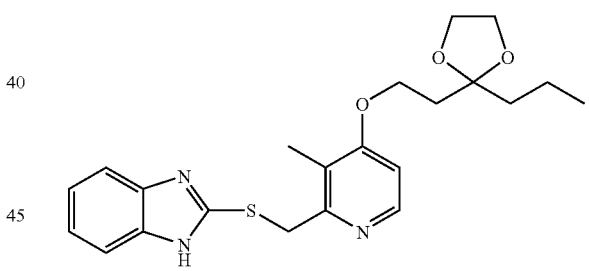

The (3-methyl-4-(2-(2-propyl-1,3-dioxolan-2-yl)ethoxy)pyridin-2-yl) methanol (450 mg, 1.6 mmol) obtained in the step (3e) was mixed with tetrahydrofuran (10 ml). The mixture was cooled on ice in a nitrogen atmosphere. To this, triethylamine (0.446 ml, 3.2 mmol), and methanesulfonyl chloride (0.186 ml, 2.4 mmol) were added and stirred for 50 minutes under ice-cooling. To the reaction mixture, 2-mercaptobenzimidazole (240 mg, 1.6 mmol) was added and stirred at room temperature overnight. To the reaction mixture, an aqueous solution of sodium hydrogen carbonate was added and extracted with ethyl acetate. The organic layer was washed with a saturated saline solution, dried over magnesium sulfate, and filtered. The filtrate was concentrated under reduced pressure. The residue was dissolved in ethyl acetate. After silica gel was added to the solution, the solution was concentrated. The dried residue was subjected to silica gel column chromatography (elution solvent: n-heptane/ethyl acetate=1/1→0/1) to obtain the title compound (528 mg, 79.8%) as a colorless viscous oil.

¹H NMR(400 MHz, CDCl₃) δppm; 0.94(3H, t, J=7 Hz), 1.39-1.50(2H, m), 1.63-1.68(2H, m), 2.20(2H, t, J=7 Hz), 2.26(3H, s), 3.93-4.01(4H, m), 4.16(2H, t, J=7 Hz), 4.37(2H, s), 6.78(1H, d, J=6 Hz), 7.16-7.20(2H, m), 7.50-7.59(2H, m), 8.35(1H, d, J=6 Hz).

(3g) 2-(((3-methyl-4-(2-(2-propyl-1,3-dioxolan-2-yl) ethoxy)pyridin-2-yl) methyl)sulfinyl)-1H-benzimidazole

[Formula 31]

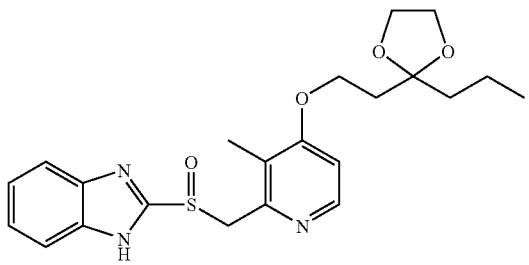

The 2-(((3-methyl-4-(2-(2-propyl-1,3-dioxolan-2-yl) ethoxy)pyridin-2-yl)methyl)thio)-1H-benzimidazole (482 mg, 1.17 mmol) obtained in the step (3f) was dissolved in a solvent mixture of toluene (30 ml) and methanol (3 ml). The mixture was cooled in a nitrogen atmosphere. To this mixture, a methanol solution (1.3 ml) of 3-chloroperbenzoic acid (311 mg, 1.17 mmol as the content was regarded as 65%) was added at an inner temperature of below −70° C. and stirred below −60° C. for 2 hours. To the reaction mixture, an aqueous solution of sodium hydrogen carbonate and ethyl acetate were added. The organic layer was separated and washed with a saturated saline solution, dried over anhydrous sodium sulfate, and filtered. The filtrate was concentrated under reduced pressure. The residue was dissolved in methylene chloride and subjected to silica gel column chromatography using NH silica gel (elution solvent: methylene chloride/methanol=1/0→100/1→100/5) to obtain the title compound (323 mg, yield: 64.3%).

¹H NMR(400 MHz, DMSO-d₆); 0.85(3H, t, J=7 Hz), 1.28-1.39(2H, m), 1.55-1.60(2H,m), 2.04(2H, t, J=7 Hz), 2.10(3H, s), 3.89-3.90(4H, m), 4.08(2H, t, J=7 Hz), 4.68(1H, d, J=13 Hz), 4.77(1H, d, J=13 Hz), 6.95(1H, d, J=6 Hz), 7.26-7.32 (2H, m), 7.59-7.67(2H, m), 8.20(1H, d, J=6 Hz).

(3h) 2-(((3-methyl-4-(2-(2-propyl-1,3-dioxolan-2-yl) ethoxy)pyridin-2-yl)methyl)sulfinyl)-1H-benzimidazole sodium salt

[Formula 32]

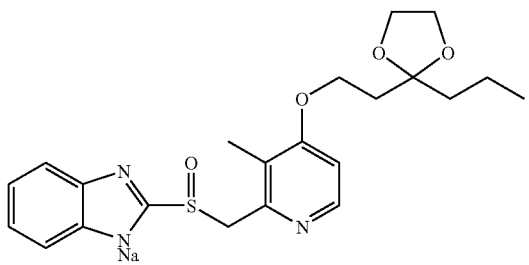

The 2-(((3-methyl-4-(2-(2-propyl-1,3-dioxolan-2-yl) ethoxy)pyridin-2-yl)methyl)sulfinyl)-1H-benzimidazole (323 mg, 0.752 mmol) obtained in the step (3 g) was mixed with ethanol (15 ml) and a 1N aqueous sodium hydroxide solution (0.752 ml, 0.752 mmol) and the mixture was stirred at room temperature for 10 minutes. The solvent was distilled off and the resultant residue was dissolved in ethanol and the solvent was again distilled off. Diethyl ether-ethanol-n-heptane was added to the residue and stirred at room temperature and then filtrated to obtain solid. In this manner, the title compound (315 mg, 92.8%) was obtained as a light yellow solid.

¹H NMR(400 MHz, DMSO-d₆); 0.85(3H, t, J=7 Hz), 1.29-1.39(2H, m), 1.56-1.63(2H, m), 2.05(2H, t, J=7 Hz), 2.15(3H, s), 3.83-3.91(4H, m), 4.07(2H, t, J=7 Hz), 4.40(1H, d, J=13 Hz), 4.76(1H, d, J=13 Hz), 6.84-6.90(2H, m), 6.92(1H, d, J=5 Hz), 7.41-7.47(2H, m), 8.25(1H, d, J=5 Hz).

Example 4

2-(((4-(2-(8-ethyl-1,4,7,9-tetraoxaspiro[4.5]dec-8-yl) ethoxy)-3-methylpyridin-2-yl)methyl)sulfinyl)-1H-benzimidazole sodium salt

[Formula 33]

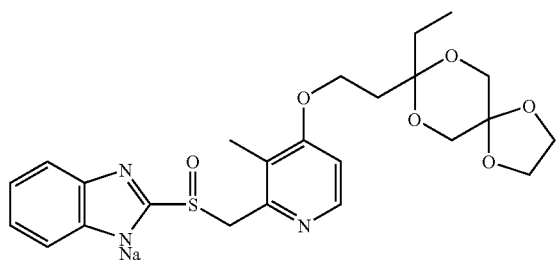

(4a) 1,3-bis(benzyloxy)acetone

[Formula 34]

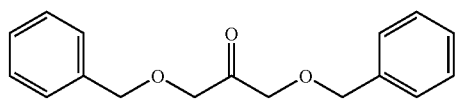

To a dichloromethane (200 ml) solution of 1,3 dibenzyloxy-2-propanol (52 g, 191 mmol), triethylamine (130 ml, 933 mmol), and dimethylsulfoxide (65 ml, 916 mmol), sulfur trioxide pyridine complex (131 g, 823 mmol) was added at 0° C. and stirred at 0° C. to room temperature for 2 hours. To the mixture, water and ethyl acetate were added. The organic layer was washed with 2N hydrochloric acid, water and an aqueous saline solution, dried over anhydrous sodium sulfate, and concentrated. As a result, the title compound (52.01 g, quantitative yield) was obtained as a brown oil.

¹H NMR(400 MHz, DMSO-d₆) δppm; 4.26(4H, s), 4.49 (4H, s), 7.25-7.38(10H, m).

(4b) 2,2-bis((benzyloxy)methyl)-1,3-dioxolane

[Formula 35]

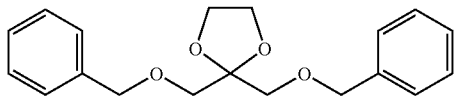

The 1,3-bis(benzyloxy)acetone (30 g, 111 mmol) obtained in the step (4a) was mixed with ethylene glycol (64 ml, 1,148 mmol) and triethyl orthoformate (19 ml, 114 mmol), and p-toluenesulfonic acid monohydrate (591 mg, 3.11 mmol). The mixture was stirred at 50° C. for 14 hours. To the mixture, a saturated aqueous solution of sodium hydrogen carbonate and ethyl acetate were added. The organic layer was washed with water and a saline solution, dried over anhydrous sodium sulfate, and concentrated. The obtained crude product was purified by silica gel column chromatography (elution solvent: heptane/ethyl acetate=1/0-4/1 gradient) and desired fractions were concentrated to obtain the title compound (28.46 g, yield: 81.6%) as a colorless oil.

$^1$H NMR(400 MHz, DMSO-$d_6$) δppm; 3.45(4H, s), 3.88 (4H, s), 4.50(4H, s), 7.22-7.35(10H, m).

(4c) 1,3-dioxolan-2,2-diyldimethanol

[Formula 36]

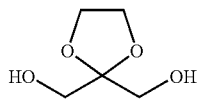

To an ethyl acetate (300 ml) solution of the 2,2-bis((benzyloxy)methyl)-1,3-dioxolane (28.5 g, 90.7 mmol) obtained in the step (4b), palladium hydroxide (20 wt % Pd (dry basis) on carbon, wet (water max. 50%)) (2.5 g) was added and stirred at room temperature for 39 hours in a hydrogen atmosphere. After the reaction mixture was purged with nitrogen, a catalyst was filtered off from the reaction mixture and washed with ethyl acetate. The filtrate was concentrated. To the obtained residue, ethyl acetate (300 ml) and palladium hydroxide (20 wt % Pd (dry basis) on carbon, wet (water max. 50%)) (2.5 g) were added and stirred at room temperature for 26 hours in a hydrogen atmosphere. After the reaction mixture was purged with nitrogen, a catalyst was filtered off and washed with ethyl acetate. The filtrate was concentrated to obtain the title compound (11.97 g, yield: 98.4%) as a colorless oil.

$^1$H NMR(400 MHz, DMSO-$d_6$) δppm; 3.32(4H, d, J=6 Hz), 3.85(4H, s), 4.63(2H, t, J=6 Hz).

(4d) methyl(8-ethyl-1,4,7,9-tetraoxaspiro[4.5]dec-8-yl)acetate

[Formula 37]

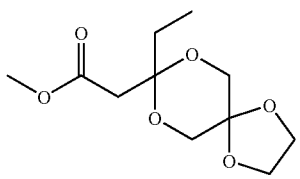

The 1,3-dioxolan-2,2-diyldimethanol (4 g, 29.8 mmol), which was obtained at another time in the same manner as described in the steps (4a)-(4c), was mixed with methyl propionylacetate (5.6 ml, 44.6 mmol) and triethyl orthoformate (5.2 ml, 31.3 mmol), and p-toluenesulfonic acid monohydrate (163 mg, 0.856 mmol). The mixture was stirred at room temperature for 3 hours. To the mixture, a saturated aqueous solution of sodium hydrogen carbonate and ethyl acetate were added. The organic layer was washed with water twice and with an aqueous saline solution, dried over anhydrous sodium sulfate and concentrated. The obtained crude product was purified by silica gel column chromatography (elution solvent: heptane/ethyl acetate=1/0-3/1-1/1 gradient) and a desired fraction(s) was concentrated to obtain the title compound (2.63 g, yield: 35.8%) as a colorless oil.

$^1$H NMR(400 MHz, DMSO-$d_6$) δppm; 0.84(3H, t, J=7 Hz), 1.75(2H, q, J=7 Hz), 2.76(2H, s), 3.56(3H, s), 3.58(2H, d, J=12 Hz), 3.68(2H, d, J=12 Hz), 3.80-3.89(4H, m).

(4e) 2-(8-ethyl-1,4,7,9-tetraoxaspiro[4.5]dec-8-yl)ethanol

[Formula 38]

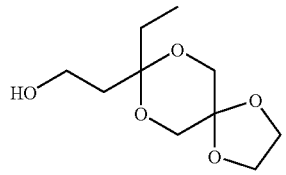

To a THF (40 ml) solution of the methyl(8-ethyl-1,4,7,9-tetraoxaspiro[4.5]dec-8-yl)acetate (2.63 g, 10.7 mmol) obtained in the step (4d), lithium aluminum hydride (487 mg, 12.8 mmol) was added at 0° C. and stirred at 0° C. to room temperature for 4 hours. Water (0.5 ml), a 2N aqueous sodium hydroxide solution (0.5 ml), water (1.5 ml) were sequentially added to terminate the reaction. Thereafter, anhydrous sodium sulfate and celite were added to the mixture, the resultant mixture was filtered by a glass filter, and washed with ethyl acetate. The filtrate was concentrated to obtain the title compound (2.34 g, quantitative yield) as a colorless oil.

$^1$H NMR(400 MHz, DMSO-$d_6$) δppm; 0.79(3H, t, J=7 Hz), 1.62(2H, q, J=7 Hz), 1.81(2H, t, J=8 Hz), 3.41(2H, dt, J=6, 8 Hz), 3.57(4H, s), 3.83(4H, s), 4.29(1H, t, J=6 Hz).

(4f) 4-(2-(8-ethyl-1,4,7,9-tetraoxaspiro[4.5]dec-8-yl)ethoxy)-2,3-dimethylpyridine1-oxide

[Formula 39]

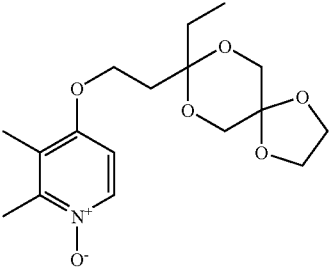

To a dimethyl sulfoxide (20 ml) solution of 2-(8-ethyl-1,4,7,9-tetraoxaspiro[4.5]dec-8-yl)ethanol (1.34 g, 6.14 mmol)

obtained in the step (4e), sodium hydride, in oil (295 mg, 7.37 mmol as the content was regarded as 60%) was added at room temperature in a nitrogen atmosphere. The mixture was stirred for 30 minutes under the same conditions. To the reaction mixture, 4-chloro-2,3-dimethylpyridine1-oxide (1.06 g, 6.75 mmol) was added at room temperature and the resultant mixture was stirred at 60° C. for 5.5 hours. The reaction mixture was concentrated and the residue was purified by silica gel column chromatography (NH silica gel, elution solvent: heptane, ethyl acetate/methanol=1/0-4/1 gradient) and a desired fraction(s) was concentrated to obtain the title compound (948 mg, yield: 45.5%) as a light yellow solid.

$^1$H NMR(400 Hz, DMSO-$d_6$) δppm; 0.83(3H, t, J=7 Hz), 1.73(2H, q, J=7 Hz), 2.09(3H, s), 2.12(2H, t, J=6 Hz), 2.32 (3H, s), 3.62(4H, s), 3.80-3.88(4H, m), 4.06(2H, t, J=6 Hz), 6.89(1H, d, J=8 Hz), 8.05(1H, d, J=8 Hz).

(4g) (4-(2-(8-ethyl-1,4,7,9-tetraoxaspiro[4.5]dec-8-yl)ethoxy)-3-methylpyridin-2-yl)methanol

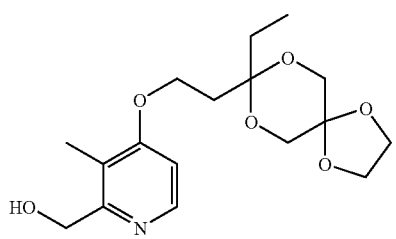

[Formula 40]

The 4-(2-(8-ethyl-1,4,7,9-tetraoxaspiro[4.5]dec-8-yl)ethoxy)-2,3-dimethylpyridine 1-oxide (947 mg, 2.79 mmol) obtained in the step (4f) was mixed with acetic anhydride (10 ml). To the mixture, triethylamine (0.6 ml, 4.3 mmol) was added and stirred at 50° C. for 2 hours. The reaction mixture was concentrated and methanol (10 ml) was added to the residue and thereafter, a 5N aqueous sodium hydroxide solution (7 ml) was added and stirred at room temperature for one hour. To the mixture, a saturated aqueous ammonium chloride solution (7 ml) was added and the pH of the resultant solution was adjusted to about 10. The reaction mixture was diluted with ethyl acetate and the organic layer was washed with a 2N aqueous sodium hydroxide solution, water, and a saline solution, dried over anhydrous sodium sulfate, and concentrated. The obtained crude product was purified by silica gel column chromatography (elution solvent: ethyl acetate/methanol=1/0-4/1 gradient) and a desired fraction(s) was concentrated to obtain the title compound (564 mg, yield: 59.6%) as a light yellow solid.

$^1$H NMR(400 MHz, DMSO-$d_6$) δppm; 0.84(3H, t, J=7 Hz), 1.74(2H, q, J=7 Hz), 2.08(3H, s), 2.14(2H, t, J=6 Hz), 3.63(4H, s), 3.78-3.89(4H, m), 4.08(2H, t, J=6 Hz), 4.50(2H, d, J=6 Hz), 4.96(1H, t, J=6 Hz), 6.90(1H, d, J=6 Hz), 8.20(1H, d, J=6 Hz).

(4h) 2-(((4-(2-(8-ethyl-1,4,7,9-tetraoxaspiro[4.5]dec-8-yl)ethoxy)-3-methylpyridin-2-yl)methyl)thio)-1H-benzimidazole

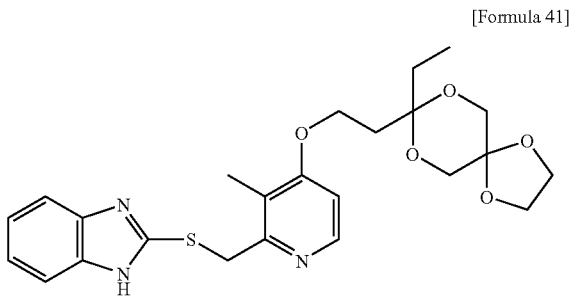

[Formula 41]

To a THF (10 ml) solution of the (4-(2-(8-ethyl-1,4,7,9-tetraoxaspiro[4.5]dec-8-yl)ethoxy)-3-methylpyridin-2-yl)methanol (560 mg, 1.65 mmol) obtained in the step (4g), triethylamine (0.48 ml, 3.44 mmol) was added at room temperature and thereafter, methanesulfonyl chloride (0.19 ml, 2.45 mmol) was added while cooling in an ice salt bath and stirred under the same conditions for 30 minutes. After the ice salt bath was removed, 2-mercaptobenzimidazole (248 mg, 1.65 mmol) was added and stirred at room temperature for 22 hours. After the reaction mixture was concentrated, NH silica gel was added to the residue and dried. The crude substance was purified by silica gel column chromatography (elution solvent: heptane/ethyl acetate=1/0, 1/1-0/1 gradient) and a desired fraction(s) was concentrated. The obtained foamy product was dissolved in chloroform and diethyl ether was added thereto. The resulting solid was collected by filtration to obtain the title compound (410 mg, yield: 52.7%) as a white solid.

$^1$H NMR(400 MHz, DMSO-$d_6$) δppm; 0.84(3H, t, J=7 Hz), 1.75(2H, q, J=7 Hz), 2.15(2H, t, J=6 Hz), 2.18(3H, s), 3.63(4H, s), 3.80-3.90(4H, m), 4.09(2H, t, J=6 Hz), 4.67(2H, s), 6.93(1H, d, J=6 Hz), 7.07-7.13(2H, m), 7.35-7.51(2H, m), 8.22(1H, d, J=6 Hz), 12.60(1H, br s).

(4i) 2-(((4-(2-(8-ethyl-1,4,7,9-tetraoxaspiro[4.5]dec-8-yl)ethoxy)-3-methylpyridin-2-yl)methyl)sulfinyl)-1H-benzimidazole

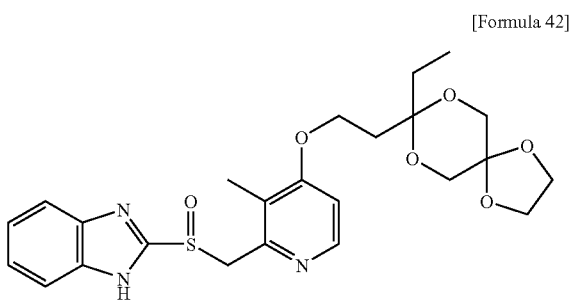

[Formula 42]

To a toluene (10.8 ml) and methanol (1.2 ml) solution of the 2-(((4-(2-(8-ethyl-1,4,7,9-tetraoxaspiro[4.5]dec-8-yl)ethoxy)-3-methylpyridin-2-yl)methyl)thio)-1H-benzimidazole (380 mg, 0.81 mmol) obtained in the step (4h), a toluene (2.7 ml) and methanol (0.3 ml) solution of 3-chloroperbenzoic acid (192 mg, 0.73 mmol as the content was regarded as 65%) was added dropwise at −70 to −60° C. for 10 minutes in a nitrogen atmosphere. The mixture was stirred for one hour in the same conditions. The reaction was terminated by adding a saturated aqueous solution (15 ml) of sodium hydrogen carbonate at the same temperature. The mixture was extracted with chloroform (50 ml) twice and the organic layer was dried over anhydrous sodium sulfate and concentrated. The obtained crude product was purified by silica gel column chromatography (NH silica gel: elusion solvent: ethyl acetate/methanol=1/0-4/1 gradient) and desired fractions were concentrated. The obtained foamy product was re-precipitated with chloroform and diethyl ether and filtered. The operation was repeated four times and the obtained solid was washed with diethyl ether and then dried to obtain the title compound (188 mg, 47.9% yield) as a white solid.

H NMR(400 MHz, DMSO-$d_6$) δppm; 0.83(3H, t, J=7 Hz), 1.74(2H, q, J=7 Hz), 2.10(3H, s), 2.14(2H, t, J=6 Hz), 3.63 (4H, s), 3.79-3.90(4H, m), 4.09(2H, t, J=6 Hz), 4.68(1H, d, J=13 Hz), 4.77(1H, d, J=13 Hz), 6.93(1H, d, J=6 Hz), 7.23-7.32(2H, m), 7.54-7.68(2H, m), 8.20(1H, d, J=6 Hz).

(4j) 2-(((4-(2-(8-ethyl-1,4,7,9-tetraoxaspiro[4.5]dec-8-yl)ethoxy)-3-methylpyridin-2-yl)methyl)sulfinyl)-1H-benzimidazole sodium salt

[Formula 43]

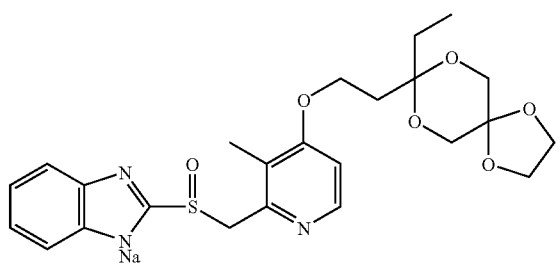

To an ethanol (2 ml) solution of the 2-(((4-(2-(8-ethyl-1,4,7,9-tetraoxaspiro[4.5]dec-8-yl)ethoxy)-3-methylpyridin-2-yl)methyl)sulfinyl)-1H-benzimidazole (188 mg, 0.39 mmol) obtained in the step (4i), a 1N aqueous sodium hydroxide solution (386 μl, 0.39 mmol) was added at room temperature, and the mixture was stirred for 10 minutes, and then concentrated. Methanol was added to the residue and concentration was performed. After this operation was repeated, diethyl ether was added to the residue and the obtained suspension was allowed to stand. After the supernatant liquid was removed, the residue was dried by a vacuum pump to obtain the title compound (190 mg, 96.6% yield) as a white solid.

$^1$H NMR(400 MHz, DMSO-$d_6$) δppm; 0.84(3H, t, J=8 Hz), 1.75(2H, q, J=8 Hz), 2.09-2.20(5H, m), 3.63(4H, s), 3.80-3.90(4H, m), 4.08(2H, t, J=6 Hz), 4.36(1H, d, J=13 Hz), 4.79(1H, d, J=13 Hz), 6.78-6.88(2H, m), 6.89(1H, d, J=5 Hz), 7.36-7.46(2H, m), 8.26(1H, d, J=5 Hz).

Example 5

2-(((3-methyl-4-((8-methyl-1,4,7,9-tetraoxaspiro [4.5]dec-8-yl)methoxy)pyridin-2-yl)methyl)sulfinyl)-1H-benzimidazole sodium salt

[Formula 44]

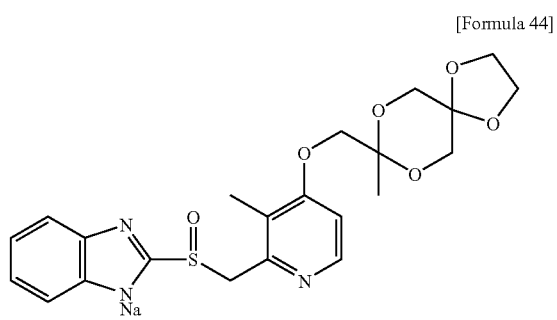

(5a) 2-oxopropyl benzoate

[Formula 45]

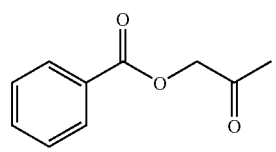

To a pyridine (25 ml) and THF (10 ml) solution of hydroxyacetone (5 g, 67.5 mmol), benzoyl chloride (12 ml, 103 mmol) was added dropwise at 0° C. in a nitrogen atmosphere and the mixture was stirred for 43 hours at room temperature. Ice was added to the reaction mixture, which was then diluted with ethyl acetate. The organic layer was washed with 1N hydrochloric acid, water, and a saline solution, dried over anhydrous sodium sulfate, and concentrated. The obtained crude product was purified by silica gel column chromatography (elution solvent: heptane/ethyl acetate=1/0-1/1 gradient). Desired fractions were concentrated to obtain the title compound (10.56 g, 87.8% yield) as a light yellow oil.

$^1$H NMR(400 MHz, DMSO-$d_6$) δppm; 2.14(3H, s), 5.01 (2H, s), 7.51-7.58(2H, m), 7.65-7.70(1H, m), 7.95-8.00(2H, m).

(5b) (8-methyl-1,4,7,9-tetraoxaspiro[4.5]dec-8-yl) methyl benzoate

[Formula 46]

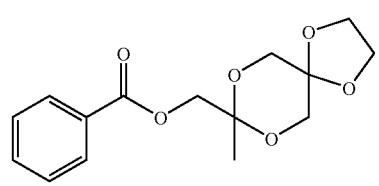

The 2-oxopropyl benzoate (4 g, 22.4 mmol) obtained in the step (5a) was mixed with 1,3-dioxolan-2,2-diyldimethanol (3 g, 22.4 mmol) obtained in the step (4c), triethyl orthoformate (3.8 ml, 22.8 mmol), and p-toluenesulfonic acid monohydrate (200 mg, 1.05 mmol). The mixture was stirred at room temperature for 13.5 hours. To the mixture, a saturated aqueous solution of sodium hydrogen carbonate and ethyl acetate were added. The organic layer was washed with water twice and with a saline solution, dried over anhydrous sodium sulfate, and concentrated. The obtained crude product was purified by silica gel column chromatography (elution solvent: heptane/ethyl acetate=1/0-1/1 gradient) and desired fractions were concentrated to obtain the title compound (1.92 g, 29.1% yield) as a colorless oil.

$^1$H NMR(400 MHz, DMSO-$d_6$) δppm; 1.41(3H, s), 3.64-3.76(4H, m), 3.80-3.88(4H, m), 4.33(2H, s), 7.50-7.57(2H, m), 7.64-7.70(1H, m), 7.92-8.00(2H, m).

(5c) (8-methyl-1,4,7,9-tetraoxaspiro[4.5]dec-8-yl)methanol

[Formula 47]

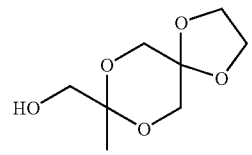

To a THF (10 ml) and methanol (5 ml) solution of the (8-methyl-1,4,7,9-tetraoxaspiro[4.5]dec-8-yl)methyl benzoate (1.92 g, 6.52 mmol) obtained in the step (5b), a 1N aqueous sodium hydroxide solution (10 ml, 10 mmol) was added and stirred at room temperature for one hour. The reaction mixture was extracted with dichloromethane (50 ml) four times, dried over anhydrous sodium sulfate, and then, concentrated. The obtained crude product was purified by silica gel column chromatography (elution solvent: heptane/ethyl acetate=1/1-0/1 gradient) and desired fractions were concentrated to obtain the title compound (1.12 g, 90.0% yield) as a white solid.

$^1$H NMR(400 MHz, DMSO-$d_6$) δppm; 1.24(3H, s), 3.33 (2H, d, J=6 Hz), 3.60(4H, s), 3.80-3.85(4H, m), 4.81(1H, t, J=6 Hz).

(5d) 2,3-dimethyl-4-((8-methyl-1,4,7,9-tetraoxaspiro [4.5]dec-8-yl)methoxy)pyridine 1-oxide

[Formula 48]

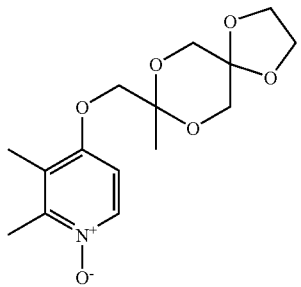

To a dimethylsulfoxide (15 ml) solution of the (8-methyl-1,4,7,9-tetraoxaspiro[4.5]dec-8-yl)methanol (1.11 g, 5.82 mmol) obtained in the step (5c), sodium hydride, in oil (326 mg, 8.15 mmol as the content was regarded as 60%) was added at room temperature in a nitrogen atmosphere. The mixture was stirred for 30 minutes in the same conditions. To the reaction mixture, 4-chloro-2,3-dimethylpyridine 1-oxide (917 mg, 5.82 mmol) was added at room temperature and the reaction mixture was stirred at 70° C. for 4.5 hours. The reaction mixture was concentrated and the residue was purified by silica gel column chromatography (elution solvent: ethyl acetate/methanol=1/0-5/2 gradient) and desired fractions were concentrated to obtain the title compound (1.20 g, 66.1% yield) as a brown oil.

$^1$H NMR(400 MHz, DMSO-$d_6$) δppm; 1.42(3H, s), 2.12 (3H, s), 2.33(3H, s), 3.65-3.75(4H, m), 3.85(4H, s), 4.07(2H, s), 7.00(1H, d, J=7 Hz), 8.07(1H, d, J=7 Hz).

(5e) (3-methyl-4-((8-methyl-1,4,7,9-tetraoxaspiro [4.5]dec-8-yl)methoxy)pyridin-2-yl)methanol

[Formula 49]

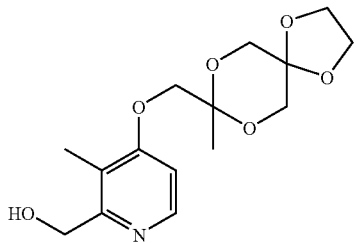

The 2,3-dimethyl-4-((8-methyl-1,4,7,9-tetraoxaspiro[4.5] dec-8-yl)methoxy)pyridine 1-oxide (1.20 g, 3.84 mmol) obtained in the step (5d) was mixed with acetic anhydride (10 ml). To the mixture, triethylamine (0.8 ml, 5.74 mmol) was added and the mixture was stirred at 50° C. for 2 hours. The reaction mixture was concentrated and methanol (10 ml) was added to the residue. Thereafter a 5N aqueous sodium hydroxide solution (7 ml) was added to the mixture, and stirred at room temperature for 30 minutes. To the resultant mixture, a saturated aqueous ammonium chloride solution (7 ml) was added and the pH was adjusted to about 10. The reaction mixture was diluted with ethyl acetate, and the organic layer was washed with a 2N aqueous sodium hydroxide solution, water, and a saline solution, dried over anhydrous sodium sulfate and concentrated. The obtained crude product was purified by silica gel column chromatography (elution solvent: ethyl acetate/methanol=1/0-4/1 gradient) and a desired fraction(s) was concentrated to obtain the title compound (312 mg, 26.1% yield) as a light yellow solid.

$^1$H NMR(400 MHz, DMSO-$d_6$) δppm; 1.44(3H, s), 2.11 (3H, s), 3.65-3.75(4H, m), 3.85(4H, s), 4.08(2H, s), 4.51(2H, d, J=5 Hz), 4.97(1H, t, J=5 Hz), 6.99(1H, d, J=6 Hz), 8.20(1H, d, J=6 Hz).

(5f) 2-(((3-methyl-4-((8-methyl-1,4,7,9-tetraoxaspiro [4.5]dec-8-yl)methoxy)pyridin-2-yl)methyl)thio)-1H-benzimidazole

[Formula 50]

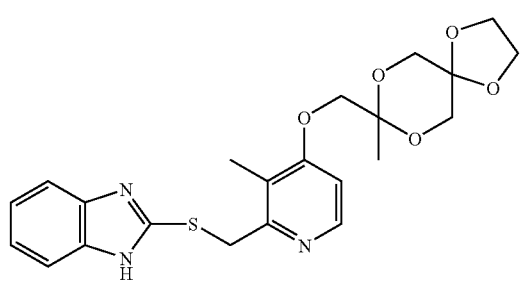

To a THF (7 ml) solution of the (3-methyl-4-((8-methyl-1,4,7,9-tetraoxaspiro[4.5]dec-8-yl)methoxy)pyridin-2-yl)

methanol (312 mg, 1.00 mmol) obtained in the step (5e), triethylamine (0.30 ml, 2.15 mmol) was added at room temperature, and then methanesulfonyl chloride (0.12 ml, 1.55 mmol) was added under cooling in an ice-salt bath and stirred for 30 minutes in the same conditions. To the reaction mixture, a saturated aqueous solution of sodium hydrogen carbonate and ethyl acetate were added. The aqueous layer was extracted with ethyl acetate. Organic layers were combined, washed with water and a saline solution, dried over anhydrous sodium sulfate, and concentrated. The obtained residue was dissolved in ethanol (6 ml). To the resultant solution, 2-mercaptobenzimidazole (150 mg, 1.00 mmol) and sodium hydroxide (160 mg, 4.00 mmol) were added and stirred at room temperature for 16.5 hours. After the reaction mixture was concentrated, NH silica gel was added to the residue and the mixture was dried. The obtained crude product was purified by silica gel column chromatography (elution solvent: heptane/ethyl acetate=1/0, 1/1-0/1 gradient) and desired fractions were concentrated to obtain the title compound (377 mg, 85.0% yield) as a white foam.

1H NMR(400 MHz, DMSO-$d_6$) δppm; 1.43(3H, s), 2.21 (3H, s), 3.66-3.76(4H, m), 3.85(4H, s), 4.09(2H, s), 4.68(2H, s), 7.02(1H, d, J=6 Hz), 7.07-7.14(2H, m), 7.37-7.50(2H, m), 8.22(1H, d, J=6 Hz), 12.59(1H, br s).

(5g) 2-(((3-methyl-4-((8-methyl-1,4,7,9-tetraoxaspiro[4.5]dec-8-yl)methoxy)pyridin-2-yl)methyl)sulfinyl)-1H-benzimidazole

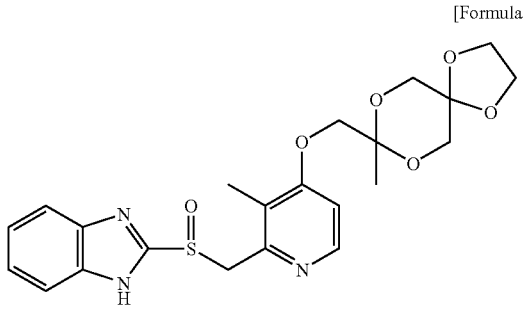

[Formula 51]

To a toluene (8.1 ml) and methanol (0.9 ml) solution of the 2-(((3-methyl-4-((8-methyl-1,4,7,9-tetraoxaspiro[4.5]dec-8-yl)methoxy)pyridin-2-yl)methyl)thio)-1H-benzimidazole (372 mg, 0.84 mmol) obtained in the step (5f), a toluene (2.7 ml) and methanol (0.3 ml) solution of 3-chloroperbenzoic acid (200 mg, 0.76 mmol as the content was regarded as 65%) was added dropwise at −55° C. to −50° C. for 10 minutes in a nitrogen atmosphere. The mixture was stirred at −60° C. to −50° C. for 1.5 hours. The reaction was terminated by adding 12 ml of a saturated aqueous solution of sodium hydrogen carbonate at the same temperature. The mixture was extracted with 50 ml of chloroform twice, and then, the organic layer was dried over anhydrous sodium sulfate and concentrated. The obtained crude product was purified by silica gel column chromatography (NH silica gel, elution solvent: ethyl acetate/methanol=1/0-4/1 gradient) and desired fractions were concentrated. The obtained white foam was re-precipitated with chloroform and diethyl ether and filtered. The operation was repeated twice to obtain the title compound (148 mg, 38.4% yield) as a white solid.

1H NMR(400 MHz, DMSO-$d_6$) δppm; 1.43(3H, s), 2.14 (3H, s), 3.65-3.77(4H, m), 3.85(4H, s), 4.09(2H, s), 4.69(1H, d, J=14 Hz), 4.78(1H, d, J=14 Hz), 7.02(1H, d, J=6 Hz), 7.20-7.32(2H, m), 7.53-7.70(2H, m), 8.20(1H, d, J=6 Hz).

(5h) 2-(((3-methyl-4-((8-methyl-1,4,7,9-tetraoxaspiro[4.5]dec-8-yl)methoxy)pyridin-2-yl)methyl)sulfinyl)-1H-benzimidazole sodium salt

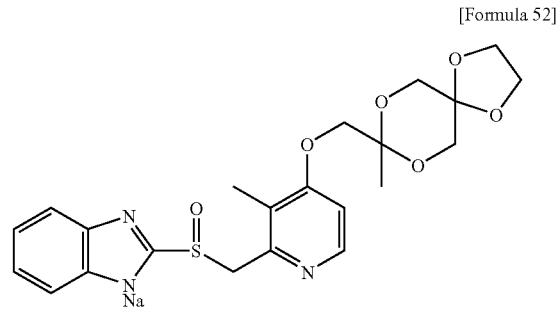

[Formula 52]

To an ethanol (4 ml) solution of the 2-(((3-methyl-4-((8-methyl-1,4,7,9-tetraoxaspiro[4.5]dec-8-yl)methoxy)pyridin-2-yl)methyl)sulfinyl)-1H-benzimidazole (147 mg, 0.32 mmol) obtained in the step (5g), a 1N aqueous sodium hydroxide solution (320 μl, 0.32 mmol) was added at room temperature and stirred for 10 minutes and thereafter, the mixture was concentrated. Methanol was added to the residue and concentrated. After this operation was repeated twice, diethyl ether was added and the obtained suspension was allowed to stand. After the supernatant liquid was discarded, the residue was dried by a vacuum pump to obtain the title compound (147 mg, 95.4% yield) as a white solid.

1H NMR(400 MHz, DMSO-$d_6$) δppm; 1.43(3H, s), 2.18 (3H, s), 3.66-3.76(4H, m), 3.85(4H, s), 4.07(2H, s), 4.36(1H, d, J=13 Hz), 4.81(1H, d, J=13 Hz), 6.78-6.88(2H, m), 6.99 (1H, d, J=6 Hz), 7.38-7.46(2H, m), 8.27(1H, d, J=6 Hz).

Example 6

2-(((4-((2-methoxy-1,3-dioxan-5-yl)methoxy)-3-methylpyridin-2-yl)methyl)sulfinyl)-1H-benzimidazole sodium salt

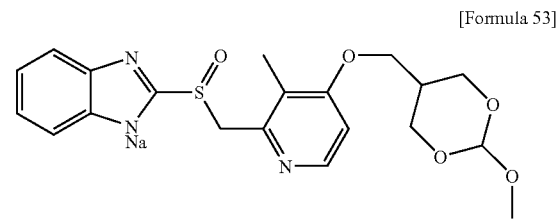

[Formula 53]

(6a) (2-methoxy-1,3-dioxan-5-yl)methanol

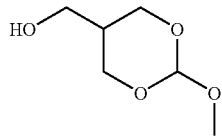

[Formula 54]

A mixture of 2-(hydroxymethyl)-1,3-propanediol (1.7 g, 16 mmol), trimethyl orthoformate (7 ml, 64.1 mmol), and p-toluenesulfonic acid monohydrate (275 mg, 1.6 mmol) was stirred at room temperature for 22 hours. To the reaction mixture, triethylamine (447 µl) was added and the mixture was concentrated. The residue was purified by silica gel column chromatography (elution solvent: heptane/ethyl acetate) to obtain the title compound (1.4 g, 59.1% yield), which is a cis and trans (1:1) mixture, as a light yellow oil.

$^1$H NMR(400 MHz, CDCl$_3$) δppm; 1.85-1.92(0.5H, m), 1.93-2.04(0.5H, m), 3.34(1.5H, s), 3.41(1.5H, s), 3.62-3.84 (3H, m), 3.90(1H, dd, J=4, 12 Hz), 4.03(1H, dd, J=6, 12 Hz), 4.27(1H, dd, J=4, 12 Hz), 5.22(0.5H, s), 5.25(0.5H, s).

(6b) 4-((2-methoxy-1,3-dioxan-5-yl)methoxy)-2,3-dimethylpyridine 1-oxide

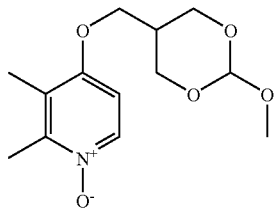

[Formula 55]

To a dimethylsulfoxide (10 ml) solution of the (2-methoxy-1,3-dioxan-5-yl)methanol (2.0 g, 13.5 mmol) obtained in the same manner of step (6a), sodium hydride, in oil (770 mg, 14.9 mmol as the content was regarded as 55%) was added at room temperature. To the mixture, 4-chloro-2,3-dimethylpyridine 1-oxide (2.13 g, 13.5 mmol) was added and the mixture was stirred at 60° C. for 2.5 hours. After the reaction mixture was cooled to room temperature, it was concentrated. The residue was purified by silica gel column chromatography (NH silica gel, elution solvent: ethyl acetate/methanol) to obtain the title compound (1.8 g, 49.5% yield), which was a cis and trans (1:1) mixture, as a yellow oil.

$^1$H NMR(400 MHz, CDCl$_3$) δppm; 2.12-2.30(1H, m), 2.20 (3H, s), 2.54(3H, s), 3.41(1.5H, s), 3.45(1.5H, s), 3.77 (1H, dd, J=4, 12 Hz), 4.01(1H, dd, J=4, 12 Hz), 4.08-4.26(3H, m), 4.39(1H, dd, J=4, 12 Hz), 5.28(0.5H, s), 5.29(0.5H, s), 6.65 (0.5H, d, J=8 Hz), 6.69(0.5H, d, J=8 Hz), 8.15(0.5H, d, j=8 Hz), 8.16(0.5H, d, J=8 Hz).

(6c) (4-((2-methoxy-1,3-dioxan-5-yl)methoxy)-3-methylpyridin-2-yl)methanol

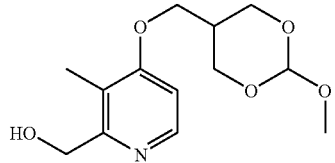

[Formula 56]

The 4-((2-methoxy-1,3-dioxan-5-yl)methoxy)-2,3-dimethylpyridine 1-oxide (1.8 g, 6.68 ml) obtained in the step (6b) was mixed with acetic anhydride (8 ml). The mixture was stirred at 100° C. for 2 hours. After cooled to room temperature, the reaction mixture was concentrated under reduced pressure. To the residue, methanol (10 ml) and a 5N aqueous sodium hydroxide solution (5 ml) were added and the mixture was stirred at room temperature for 15 hours. The reaction mixture was concentrated and the residue was separated with a saturated saline solution and ethyl acetate. The organic layer was dried over anhydrous magnesium sulfate, filtered, concentrated and the residue was purified by silica gel column chromatography (elution solvent: heptane/ethyl acetate, ethyl acetate/methanol) to obtain the title compound (0.41 g, yield: 22.8%), which is a cis and trans (1:1) mixture, as a yellow oil.

$^1$H NMR(400 MHz, CDCl$_3$) δppm; 2.04(3H, s), 2.12-2.22 (0.5H, m), 2.24-2.32(0.5H, m), 3.41(1.5H, s), 3.44(1.5H, s), 3.79(1H, dd, J=4, 12 Hz), 4.01(1H, dd, J=4, 12 Hz), 4.10-4.20 (2H, m), 4.23(1H, d, J=8 Hz), 4.38(1H, dd, J=4, 12 Hz), 4.66(2H, s), 4.86(1H, br s), 5.28(0.5H, s), 5.29(0.5H, s), 6.73(0.5H, d, J=8 Hz), 6.76(0.5H, d, J=8 Hz), 8.31(0.5H, d, J=8 Hz), 8.32(0.5H, d, J=8 Hz).

(6d) 2-(((4-((2-methoxy-1,3-dioxan-5-yl)methoxy)-3-methylpyridin-2-yl)methyl)thio)-1H-benzimidazole

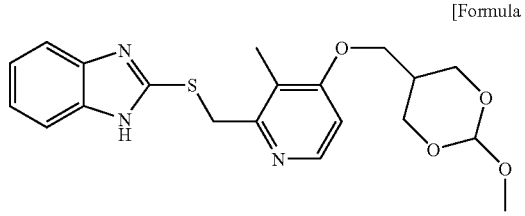

[Formula 57]

To a tetrahydrofuran (dehydrated) (10 ml) solution of the (4-((2-methoxy-1,3-dioxan-5-yl)methoxy)-3-methylpyridin-2-yl)methanol (0.41 g, 1.52 mmol) obtained in the step (6c) and triethylamine (1.06 ml, 7.61 mmol), methanesulfonyl chloride (176 µl, 2.27 mmol) was added dropwise under ice-cooling in a nitrogen atmosphere. The mixture was stirred for 1.5 hours in the same conditions. To the mixture, 2-mercaptobenzimidazole (228 mg, 1.52 mmol) was added and stirred at room temperature for 20 hours. The reaction mixture was poured into a saturated aqueous solution of sodium hydrogen carbonate and extracted with ethyl acetate. The organic layer was dried over anhydrous magnesium sulfate, filtered and concentrated. The residue was purified by silica gel column chromatography (elution solvent: heptane/ethyl acetate) to obtain the title compound (324 mg, 53.1% yield), which is a cis and trans (1:1) mixture, as a light yellow foam.

$^1$H NMR(400 MHz, CDCl$_3$) δppm; 2.12-2.24(1H, m), 2.27 (3H, s), 3.41(1.5H, s), 3.44(1.5H, s), 3.79(1H, dd, J=4, 12 Hz), 4.02(1H, dd, J=4, 12 Hz), 4.12-4.20(2H, m), 4.27(1H, d, J=8 Hz), 4.38(2H, s), 4.36-4.44(1H, m), 5.27(0.5H, s), 5.29 (0.5H, s), 6.78(0.5H, d, J=8 Hz), 6.82(0.5H, d, J=8 Hz), 7.15-7.24(2H, m), 7.43-7.50(1H, m), 7.58-7.67(1H, m), 8.35-8.44(1H, m).

(6e) 2-(((4-((2-methoxy-1,3-dioxan-5-yl)methoxy)-3-methylpyridin-2-yl)methyl)sulfinyl)-1H-benzimidazole

[Formula 58]

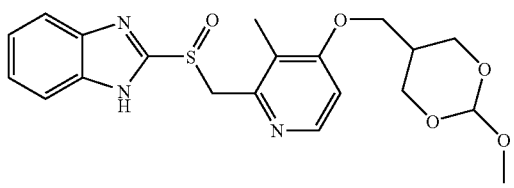

To a toluene/methanol (10:1) (20 ml) solution of the 2-(((4-((2-methoxy-1,3-dioxan-5-yl)methoxy)-3-methylpyridin-2-yl)methyl)thio)-1H-benzimidazole (324 mg, 807 μmol) obtained in the step (6d), a toluene/methanol (10:1) (5 ml) solution of 3-chloroperbenzoic acid (193 mg, 726 μmol as the content was regarded as 65%) was added dropwise at −50° C. to −60° C. for 5 minutes in a nitrogen atmosphere. The mixture was stirred for 2 hours in the same conditions. To the reaction mixture, a saturated aqueous solution of sodium hydrogen carbonate was added and the resultant mixture was extracted with ethyl acetate. The organic layer was dried over anhydrous sodium sulfate, filtered and concentrated. The residue was purified by silica gel column chromatography (NH silica gel, elution solvent: ethyl acetate/methanol) to obtain the title compound (222 mg, 65.9% yield), which is a cis and trans (1:1) mixture, as a light yellow foam.

MS m/e (ESI) 418 (MH)$^+$, 440(MNa)$^+$ (6f) 2-(((4-((2-methoxy-1,3-dioxan-5-yl)methoxy)-3-methylpyridin-2-yl)methyl)sulfinyl)-1H-benzimidazole sodium salt

[Formula 59]

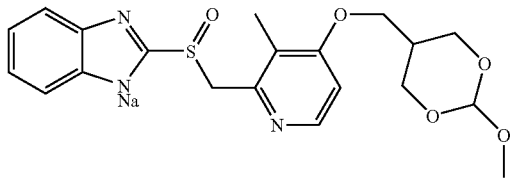

To an ethanol (10 ml) solution of the 2-(((4-((2-methoxy-1,3-dioxan-5-yl)methoxy)-3-methylpyridin-2-yl)methyl) sulfinyl)-1H-benzimidazole (222 mg, 532 μmol) obtained in the step (6e), a 1N aqueous sodium hydroxide solution (532 μl, 532 μmol) was added at room temperature and stirred for one hour. The mixture was concentrated and the residue was dissolved in ethanol. Thereafter, diethyl ether was added to the mixture and the mixture was ultrasonically treated. The resulting solid was collected by filtration in a nitrogen atmosphere. The solid was dried under reduced pressure to obtain the title compound (234 mg, yield: 83.4%), which was a cis and trans (1:1) mixture, as a light yellow solid.

$^1$H NMR(400 MHz, DMSO-d$_6$) δppm; 2.14-2.21(1H, m), 2.18(3H, s), 3.27(1.5H, s), 3.28(1.5H, s), 3.66-3.76(1H, m), 3.88-4.04(2H, m), 4.09(2H, dd, J=4, 12 Hz), 4.16-4.23(1H, m), 4.35(1H, d, J=13 Hz), 4.82(1H, d, J=13 Hz), 5.24(0.5H, s), 5.27(0.5H, s), 6.83(2H, dd, J=3, 6 Hz), 6.93(1H, d, J=6 Hz), 7.41(2H, dd, J=3, 6 Hz), 8.26(1H, d, J=6 Hz).

MS m/e (ESI) 440(MNa)$^+$

Example 7

2-(((4-((2,2-bis(fluoromethyl)-1,3-dioxan-5-yl)methoxy)-3-methylpyridin-2-yl)methyl)sulfinyl)-1H-benzimidazole sodium salt

[Formula 60]

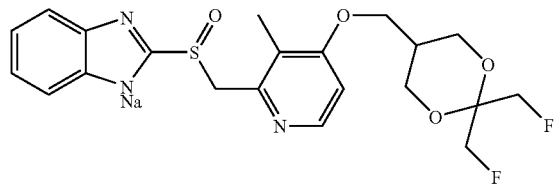

(7a) (2,2-bis(fluoromethyl)-1,3-dioxan-5-yl)methanol

[Formula 61]

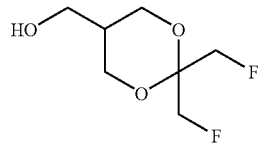

A mixture of 2-(hydroxymethyl)-1,3-propanediol (2.2 g, 20.7 mmol), 1,3-difluoroacetone (3.89 g, 41.4 mmol), trimethyl orthoformate (3.44 ml, 20.7 mmol), and p-toluenesulfonic acid monohydrate (356 mg, 2.07 mmol) was stirred at 60° C. for 10 hours. After completion of the reaction, triethylamine (577 μl) was added to the reaction mixture, which was then concentrated. The residue was purified by silica gel column chromatography (elution solvent: heptane/ethyl acetate) to obtain the title compound (1.6 g, yield: 43.4%) as a light yellow oil.

$^1$H NMR(400 MHz, CDCl$_3$) δppm; 1.97-2.10(1H, m), 3.72-3.82(2H, m), 3.87(2H, dd, J=4, 12 Hz), 4.10(2H, dd, J=4, 12 Hz), 4.46(2H, dd, J=2, 48 Hz), 4.57(2H, dd, J=2, 48 Hz).

(7b) 4-((2,2-bis(fluoromethyl)-1,3-dioxan-5-yl)methoxy)-2,3-dimethylpyridine 1-oxide

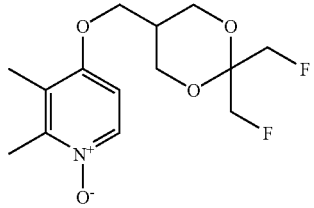

[Formula 62]

To a dimethylsulfoxide (10 ml) solution of the (2,2-bis(fluoromethyl)-1,3-dioxan-5-yl)methanol (1.6 g, 8.98 mmol) obtained in the step (7a), sodium hydride, in oil (431 mg, 9.88 mmol as the content was regarded as 55%) was added at room temperature. To the mixture, 4-chloro-2,3-dimethylpyridine 1-oxide (1.42 g, 8.98 mmol) was added and the mixture was stirred at 60° C. for 2 hours. After the reaction mixture was cooled to room temperature, it was concentrated under reduced pressure. The residue was purified by silica gel column chromatography (elution solvent: ethyl acetate/methanol) to obtain the title compound (1.63 g, yield: 60.6%) as a yellow oil.

$^1$H NMR(400 MHz, CDCl$_3$) δppm; 2.19(3H, s), 2.26-2.36 (1H, m), 2.54(3H, s), 3.99(2H, dd, J=4, 12 Hz), 4.13(2H, d, J=8 Hz), 4.21(2H, dd, J=4, 12 Hz), 4.45(2H, dd, J=2, 48 Hz), 4.62(2H, dd, J=2, 48 Hz), 6.64(1H, d, J=8 Hz), 8.14(1H, d, J=8 Hz).

(7c) (4-((2,2-bis(fluoromethyl)-1,3-dioxan-5-yl)methoxy)-3-methylpyridin-2-yl)methanol

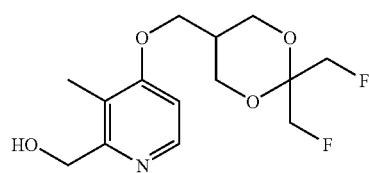

[Formula 63]

The 4-((2,2-bis(fluoromethyl)-1,3-dioxan-5-yl)methoxy)-2,3-dimethylpyridine 1-oxide (1.63 g, 5.37 mmol) obtained in the step (7b) was mixed with acetic anhydride (8 ml). The mixture was stirred at 100° C. for 2 hours, cooled to room temperature, and then, concentrated under reduced pressure. To the residue, methanol (10 ml) and a 5N aqueous sodium hydroxide solution (5 ml) were added and the mixture was stirred at room temperature for 3 hours. The reaction mixture was concentrated and the residue was separated between a saturated saline solution and ethyl acetate. The organic layer was dried over anhydrous magnesium sulfate, filtered, concentrated and the residue was purified by silica gel column chromatography (elution solvent: heptane/ethyl acetate, ethyl acetate/methanol) to obtain the title compound (385 mg, yield 23.6%) as a yellow oil.

$^1$H NMR(400 MHz, CDCl$_3$) δppm; 2.04(3H, s), 2.32-2.40 (1H, m), 4.01(2H, dd, J=4, 12 Hz), 4.16(2H, d, J=8 Hz), 4.21(2H, dd, J=4, 12 Hz), 4.48(2H, dd, J=2, 48 Hz), 4.62(2H, dd, J=2, 48 Hz), 4.66(2H, s), 4.84(1H, br s), 6.73(1H, d, J=8 Hz), 8.31(1H, d, J=8 Hz).

(7d) 2-(((4-((2,2-bis(fluoromethyl)-1,3-dioxan-5-yl)methoxy)-3-methylpyridin-2-yl)methyl)thio)-1H-benzimidazole

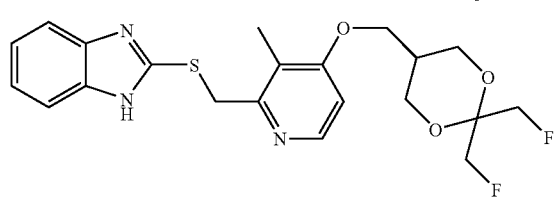

[Formula 64]

To a tetrahydrofuran (dehydrated) (20 ml) solution of the (4-((2,2-bis(fluoromethyl)-1,3-dioxan-5-yl)methoxy)-3-methylpyridin-2-yl)methanol (385 mg, 1.27 mmol) obtained in the step (7c) and triethylamine (885 μl, 6.35 mmol), methanesulfonyl chloride (177 μl, 2.29 mmol) was added dropwise under ice-cooling in a nitrogen atmosphere. The mixture was stirred for 1.0 hour in the same conditions. To the reaction mixture, 2-mercaptobenzimidazole (191 mg, 1.27 mmol) was added and stirred at room temperature for 10 hours. The reaction mixture was poured into a saturated aqueous solution of sodium hydrogen carbonate and extracted with ethyl acetate. The organic layer was dried over anhydrous magnesium sulfate, filtered and concentrated. The residue was purified by silica gel column chromatography (elution solvent: heptane/ethyl acetate) to obtain the title compound (305 mg, yield: 55.1%) as a light yellow foam.

$^1$H NMR(400 MHz, CDCl$_3$) δppm; 2.26(3H, s), 2.30-2.38 (1H, m), 4.01(2H, dd, J=4, 12 Hz), 4.18(2H, d, J=8 Hz), 4.22(2H, dd, J=4, 12 Hz), 4.38(2H, s), 4.46(2H, dd, J=2, 48 Hz), 4.62(2H, dd, J=2, 48 Hz), 6.79(1H, d, J=8 Hz), 7.15-7.23 (2H, m), 7.42-7.50(1H, m), 7.56-7.66(1H, m), 8.37(1H, d, J=8 Hz).

(7e) 2-(((4-((2,2-bis(fluoromethyl)-1,3-dioxan-5-yl)methoxy)-3-methylpyridin-2-yl)methyl)sulfinyl)-1H-benzimidazole

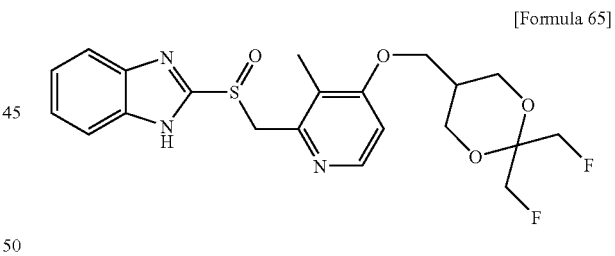

[Formula 65]

To a toluene/methanol (10:1) (20 ml) solution of the 2-(((4-((2,2-bis(fluoromethyl)-1,3-dioxan-5-yl)methoxy)-3-methylpyridin-2-yl)methyl)thio)-1H-benzimidazole (305 mg, 700 mmol) obtained in the step (7d), a toluene/methanol (10:1) (5 ml) solution of 3-chloroperbenzoic acid (167 mg, 630 μmol as the content was regarded as 65%) was added dropwise at −50° C. to −60° C. for 5 minutes in a nitrogen atmosphere. The mixture was stirred for 2 hours in the same conditions. To the reaction mixture, a saturated aqueous solution of sodium hydrogen carbonate was added and the resultant mixture was extracted with ethyl acetate. The organic layer was dried over anhydrous sodium sulfate, filtered and concentrated. The residue was purified by silica gel column chromatography (NH silica gel, elution solvent: ethyl acetate/methanol) to obtain the title compound (215 mg, yield: 68%) as a light yellow foam.

MS m/e (ESI) 452(MH)$^+$, 474(MNa)$^+$

(7f) 2-(((4-((2,2-bis(fluoromethyl)-1,3-dioxan-5-yl)methoxy)-3-methylpyridin-2-yl)methyl)sulfinyl)-1H-benzimidazole sodium salt

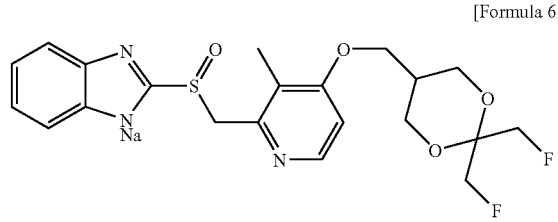

[Formula 66]

To an ethanol (10 ml) solution of the 2-(((4-((2,2-bis(fluoromethyl)-1,3-dioxan-5-yl)methoxy)-3-methylpyridin-2-yl)methyl)sulfinyl)-1H-benzimidazole (215 mg, 476 μmol) obtained in the step (7e), a 1N aqueous sodium hydroxide solution (476 μl, 476 μmol) was added at room temperature and stirred for one hour. After the mixture was concentrated and the residue was dissolved in ethanol, diethyl ether was added to the mixture. The mixture was ultrasonically treated and the resultant solid was collected by filtration in a nitrogen atmosphere. The solid was dried under reduced pressure to obtain the title compound (193 mg, yield: 85.6%) as a light yellow solid.

$^1$H NMR(400 MHz, DMSO-$d_6$) δppm; 2.17(3H, s), 2.18-2.28(1H, m), 3.84-3.94(2H, m), 4.06-4.18(2H, m), 4.12(2H, d, J=8 Hz), 4.37(1H, d, J=12 Hz), 4.50(2H, d, J=47 Hz), 4.58(2H, d, J=47 Hz), 4.81(1H, d, J=12 Hz), 6.80-6.90(2H, m), 6.94(1H, d, J=8 Hz), 7.38-7.48(2H, m), 8.27(1H, d, J=8 Hz).

Example 8

2-(((3-methyl-4-(2-(2-propyl-1,3-dioxan-2-yl)ethoxy)pyridin-2-yl)methyl)sulfinyl)-1H-benzimidazole sodium salt

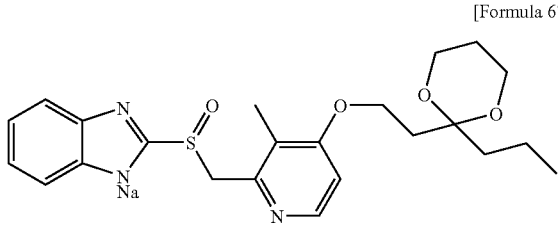

[Formula 67]

(8a) Ethyl(2-propyl-1,3-dioxan-2-yl)acetate

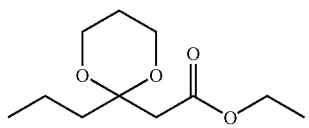

[Formula 68]

A mixture of ethyl 3-oxohexanoate (5 g, 31.6 mmol), 1,3-propanediol (3.61 g, 47.4 mmol), trimethyl orthoformate (5.78 ml, 34.8 mmol), and p-toluenesulfonic acid monohydrate (272 mg, 1.58 mmol) was stirred at room temperature for 22 hours. After completion of the reaction, triethylamine (881 μl, 6.32 mmol) was added to the reaction mixture which was then concentrated. The residue was purified by silica gel column chromatography (elution solvent: heptane/ethyl acetate) to obtain the title compound (5.5 g, yield: 80.5%) as a light yellow oil.

$^1$H NMR(400 MHz, CDCl$_3$) δppm; 0.94(3H, t, J=7 Hz), 1.27(3H, t, J=7 Hz), 1.40-1.54(2H, m), 1.55-1.68(2H, m), 1.74-1.90(2H, m), 2.82(2H, s), 3.87-4.06(4H, m), 4.15(2H, q, J=7 Hz).

(8b) 2-(2-propyl-1,3-dioxan-2-yl)ethanol

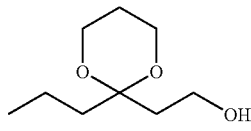

[Formula 69]

To a tetrahydrofuran (dehydrated) (30 ml) solution of the ethyl(2-propyl-1,3-dioxan-2-yl)acetate (5.5 g, 25.4 mmol) obtained in the step (8a), lithium aluminum hydride (578 mg, 15.2 mmol) was added portionwise under ice-cooling and stirred for one hour under ice cool. To the reaction mixture, water (0.6 ml), a 2N aqueous sodium hydroxide solution (0.6 ml), and water (1.8 ml) were sequentially added and the content was filtered through celite. The filtrate was concentrated under reduced pressure to obtain the title compound (4.4 g, yield 99.4%), which was a crude product, as a light yellow oil.

$^1$H NMR(400 MHz, CDCl$_3$) δppm; 0.97(3H, t, J=7 Hz), 1.22-1.42(4H, m), 1.82-2.00(4H, m), 3.78-3.96(4H, m), 3.96-4.08(2H, m).

(8c) 2,3-dimethyl-4-(2-(2-propyl-1,3-dioxan-2-yl)ethoxy)pyridine 1-oxide

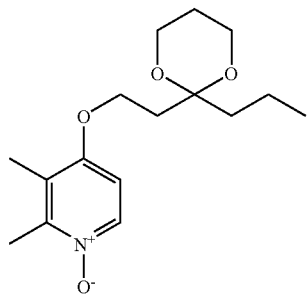

[Formula 70]

To a dimethylsulfoxide (20 ml) solution of the (2-(2-propyl-1,3-dioxan-2-yl)ethanol (4.4 g, 25.3 mmol) obtained in the step (8b), sodium hydride, in oil (1.1 g, 25.3 mmol as the content was regarded as 55%) was added at room temperature. To the mixture, 4-chloro-2,3-dimethylpyridine 1-oxide (3.19 g, 20.2 mmol) was added and the mixture was stirred at 60° C. for 1.5 hours. After cooled to room temperature, the mixture was concentrated under reduced pressure. The residue was purified by silica gel column chromatography (NH silica gel, elution solvent: heptane/ethyl acetate, ethyl acetate/methanol) to obtain the title compound (3.9 g, yield: 52.2%) as a light yellow oil.

$^1$H NMR(400 MHz, CDCl$_3$) δppm; 0.96(3H, t, J=7 Hz), 1.34-1.48(2H, m), 1.76-1.88(2H, m), 2.14-2.26(4H, m), 2.54 (3H, s), 2.62(3H, s), 3.82-3.90(2H, m), 3.92-4.04(2H, m), 4.17(2H, t, J=7 Hz), 6.69(1H, d, J=8 Hz), 8.14(1H, d, J=8 Hz).

(8d) (3-methyl-4-(2-(2-propyl-1,3-dioxan-2-yl)ethoxy)pyridin-2-yl)methanol

[Formula 71]

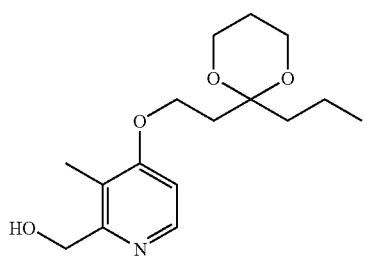

The 2,3-dimethyl-4-(2-(2-propyl-1,3-dioxan-2-yl)ethoxy) pyridine 1-oxide (3.9 g, 13.2 mmol) obtained in the step (8c) was mixed with acetic anhydride (16 ml). The mixture was stirred at 90° C. for 2 hours. After cooled to room temperature, the reaction mixture was concentrated under reduced pressure. To the residue, methanol (20 ml) and a 5N aqueous sodium hydroxide solution (10 ml) were added and the mixture was stirred at room temperature for 2 hours. The reaction mixture was concentrated and the residue was separated by use of a saturated saline solution and ethyl acetate. The organic layer was dried over anhydrous magnesium sulfate, filtered and concentrated, and the residue was purified by silica gel column chromatography (elution solvent: heptane/ethyl acetate, ethyl acetate/methanol) to obtain the title compound (1.69 g, yield: 43.3%) as a yellow oil.

$^1$H NMR(400 MHz, CDCl$_3$) δppm; 0.96(3H, t, J=7 Hz), 1.35-1.48(2H, m), 1.52-1.66(2H, m), 1.72-1.88(2H, m), 2.03 (3H, s), 2.22(2H, t, J=7 Hz), 3.82-4.04(4H, m), 4.19(2H, t, J=7 Hz), 4.65(2H, s), 6.77(1H, d, J=8 Hz), 8.29(1H, d, J=8 Hz).

(8e) 2-(((3-methyl-4-(2-(2-propyl-1,3-dioxan-2-yl)ethoxy)pyridin-2-yl)methyl)thio)-1H-benzimidazole

[Formula 72]

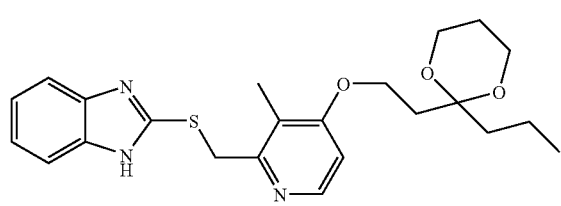

To a tetrahydrofuran (dehydrated) (30 ml) solution of the (3-methyl-4-(2-(2-propyl-1,3-dioxan-2-yl)ethoxy)pyridin-2-yl)methanol (445 ml, 1.51 mmol) obtained in the step (8d) and triethylamine (1.05 ml, 7.55 mmol), methanesulfonyl chloride (210 µl, 2.72 mmol) was added dropwise under ice-cooling in a nitrogen atmosphere and the mixture was stirred for one hour in the same conditions. To the reaction mixture, 2-mercaptobenzimidazole (227 mg, 1.51 mmol) was added and stirred at room temperature for 3 days. The reaction mixture was poured into a saturated aqueous solution of sodium hydrogen carbonate and extracted with ethyl acetate. The organic layer was dried over anhydrous magnesium sulfate, filtered and concentrated. The residue was purified by silica gel column chromatography (elution solvent: heptane/ethyl acetate, ethyl acetate/methanol) to obtain the title compound (417 mg, yield: 64.6%) as a light yellow foam.

$^1$H NMR(400 MHz, CDCl$_3$) δppm; 0.96(3H, t, J=7 Hz), 1.35-1.47(2H, m), 1.76-1.88(4H, m), 2.22(2H, t, J=7 Hz), 2.25(3H, s), 3.82-3.91(2H, m), 3.92-4.00(2H, m), 4.22(2H, t, J=7 Hz), 4.37(2H, s), 6.82(1H, d, J=8 Hz), 7.14-7.24(2H, m), 7.50-7.62(2H, m), 8.35(1H, d, J=8 Hz).

(8f) 2-(((3-methyl-4-(2-(2-propyl-1,3-dioxan-2-yl)ethoxy)pyridin-2-yl)methyl)sulfinyl)-1H-benzimidazole

[Formula 73]

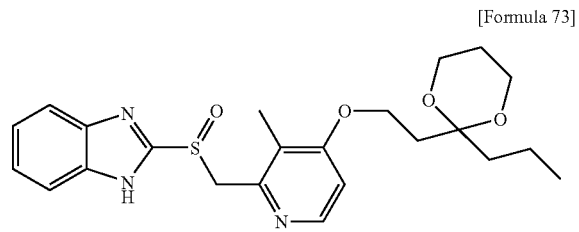

To a toluene-methanol (10:1) (30 ml) solution of the 2-(((3-methyl-4-(2-(2-propyl-1,3-dioxan-2-yl)ethoxy)pyridin-2-yl)methyl)thio)-1H-benzimidazole (417 mg, 975 µmol) obtained in the step (8e), a toluene/methanol (10:1) (5 ml) solution of 3-chloroperbenzoic acid (233 mg, 878 µmol as the content was regarded as 65%) was added dropwise at a temperature of −50° C. to −60° C. for 5 minutes in a nitrogen atmosphere. The reaction mixture was stirred for 2 hours in the same conditions. To the reaction mixture, a saturated aqueous solution of sodium hydrogen carbonate was added, which was extracted with ethyl acetate. After the organic layer was concentrated, the residue was purified by silica gel column chromatography (NH silica gel, elution solvent: ethyl acetate/methanol) to obtain the title compound (311 mg, yield: 71.9%), as a light yellow foam.

$^1$H NMR(400 MHz, CDCl$_3$) δppm; 0.95(3H, t, J=7 Hz), 1.34-1.47(2H, m), 1.70-1.88(4H, m), 2.17(3H, s), 2.20(2H, t, J=7 Hz), 3.82-3.92(2H, m), 3.92-4.00(2H, m), 4.17(2H, t, J=7 Hz), 4.65(1H, d, J=14 Hz), 4.82(1H, d, J=14 Hz), 6.78(1H, d, J=8 Hz), 7.28-7.38(2H, m), 7.30-7.62(2H, m), 8.30(1H, d, J=8 Hz).

(8g) 2-(((3-methyl-4-(2-(2-propyl-1,3-dioxan-2-yl)ethoxy)pyridin-2-yl)methyl)sulfinyl)-1H-benzimidazole sodium salt

[Formula 74]

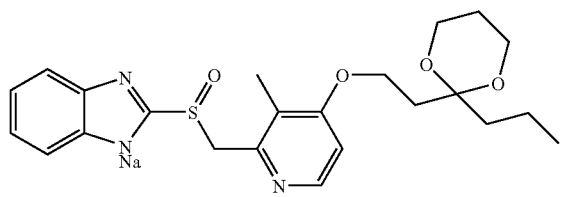

To an ethanol (6 ml) solution of the 2-(((3-methyl-4-(2-(2-propyl-1,3-dioxan-2-yl)ethoxy)pyridin-2-yl)methyl)sulfinyl)-1H-benzimidazole (311 mg, 701 μmol) obtained in the step (8f), a 1N aqueous sodium hydroxide solution (701 μl, 701 μmol) was added at room temperature and stirred for one hour. The mixture was concentrated and the residue was dissolved in ethanol. After diethyl ether was added to the solution, the solution was ultrasonically treated. The generated solid was collected by filtration in a nitrogen atmosphere, and the solid was dried under reduced pressure to obtain the title compound (283 mg, yield: 86.7%) as a light yellow solid.

$^1$H NMR(400 MHz, DMSO-d$_6$) δppm; 0.87(3H, t, J=7 Hz), 1.26-1.38(2H, m), 1.48-1.64(2H, m), 1.67-1.74(2H, m), 2.12-2.20(2H, m), 2.16(3H, s), 3.81(4H, t, J=7 Hz), 4.07(2H, t, J=7 Hz), 4.38(1H, d, J=13 Hz), 4.79(1H, d, J=13 Hz), 6.82-6.90(2H, m), 6.91(1H, d, J=8 Hz), 7.36-7.50(2H, m), 8.25(1H, d, J=8 Hz).

MS m/e (ESI) 466(MNa)$^+$.

Example 9

2-(((4-(5,9-dioxaspiro[3.5]non-7-yloxy)-3-methylpyridin-2-yl)methyl)sulfinyl)-1H-benzimidazole sodium salt

[Formula 75]

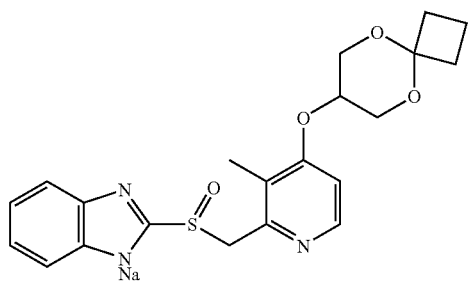

(9a) 2,2-dimethyl-1,3-dioxan-5-ol

[Formula 76]

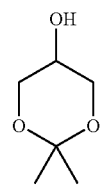

To a diethyl ether (150 ml) solution of 2,2-dimethyl-1,3-dioxan-5-one (15 g, 0.115 mol), lithium aluminum hydride (4.38 g, 0.115 mol) was added at 0 to 8° C. for one hour in a nitrogen atmosphere. To the reaction mixture, water (4.2 ml), a 5N aqueous sodium hydroxide solution (4.2 ml), and water (12.8 ml) were sequentially added dropwise at 0 to 10° C. The mixture was dried over anhydrous sodium sulfate, filtered and concentrated under reduced pressure to obtain the title compound (14.2 g, 93.4%) as a colorless oil.

$^1$H NMR(400 MHz, CDCl$_3$) δppm; 1.44(3H, s), 1.46(3H, s), 2.75-2.95(1H, br), 3.51-3.55(1H, m), 3.74-3.79(2H, m), 4.05-4.10(2H, m).

(9b) 5-(benzyloxy)-2,2-dimetheyl-1,3-dioxane

[Formula 77]

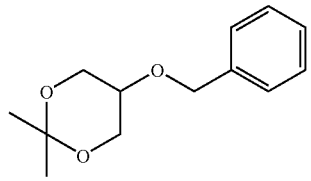

To a N,N-dimethylformamide (200 ml) solution of the 2,2-dimethyl-1,3-dioxan-5-ol (7.1 g, 0.054 mol) obtained in the step (9a), sodium hydride, in oil (2.81 g, 0.064 mol as the content was regarded as 55%) was added at 0° C. and stirred. After benzyl bromide (12.9 ml, 0.108 mol) and tetrabutylammonium iodide (220 mg, 0.001 mol) were added at the same temperature to the mixture, the mixture was stirred at room temperature for 1.5 hours. Water was added to the reaction mixture, which was then extracted with ethyl acetate three times. Organic layers were combined, washed five times with water and once with a saturated saline solution, dried over anhydrous sodium sulfate, and filtered. After NH silica gel was added, the resultant mixture was concentrated and purified by silica gel column chromatography (elution solvent: heptane, heptane/ethyl acetate=9/1, 4/1, ethyl acetate) to obtain the title compound (6.5 g, 54.5%) as a colorless oil.

$^1$H NMR(400 MHz, CDCl$_3$) δppm; 1.40(3H, s), 1.45(3H, s), 3.50-3.56(1H, m), 3.77(2H, dd, J=7, 12 Hz), 3.95(2H, dd, J=4, 12 Hz), 4.58(2H, s), 7.28-7.38(5H, m).

(9c) 2-(benzyloxy)propane-1,3-diol

[Formula 78]

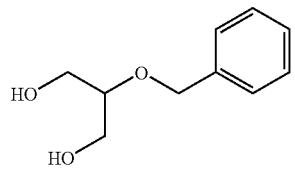

To a methanol (50 ml) solution of the 5-(benzyloxy)-2,2-dimethyl-1,3-dioxane (6.5 g, 29.2 mmol) obtained in the step (9b), DOWEX® 50W-X8 (5 g) was added and stirred at room temperature. After 2 hours, the reaction mixture was filtered and concentrated to obtain the title compound (5.0 g, 93.8%) as a colorless oil.

$^1$H NMR(400 MHz, CDCl$_3$) δppm; 3.60-3.65(1H, m), 3.74 (2H, dd, J=5, 12 Hz), 3.82(2H, dd, J=4, 12 Hz), 4.67(2H, s), 7.29-7.40(5H, m).

(9d) 7-(benzyloxy)-5,9-dioxaspiro[3.5]nonane

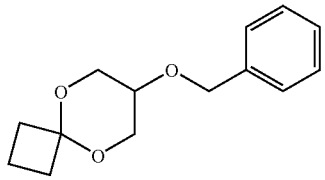
[Formula 79]

To a round-bottom flask containing a benzene (50 ml) solution of the 2-(benzyloxy)propane-1,3-diol (5.0 g, 27.4 mmol) obtained in the step (9c), cyclobutanone (2.33 ml, 30.6 mmol), and p-toluenesulfonic acid monohydrate (100 mg, 0.53 mmol), a reflux cooling tube equipped with the Dean-Stark water separator was attached. The mixture was under refluxed for 2 hours. To the resultant mixture, triethylamine (0.4 ml, 0.72 mmol) was added and the mixture was concentrated to obtain a crude product. The crude product was purified by silica gel column chromatography (NH silica gel, elution solvent: heptane, heptane/ethyl acetate=5/1) to obtain the title compound (6.3 g, yield: 98.2%) as a light yellow oil.

$^1$H NMR(400 MHz, CDCl$_3$) δppm; 1.70-1.79(2H, m), 2.20-2.29(4H, m), 3.44-3.50(1H, m), 3.64-3.69(2H, m), 3.92 (2H, dd, J=4, 12 Hz), 4.58(2H, s), 7.27-7.39(5H, m).

(9e) 5,9-dioxaspiro[3.5]nonan-7-ol

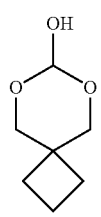
[Formula 80]

To a methanol (269 ml) solution of the 7-(benzyloxy)-5,9-dioxaspiro[3.5]nonane (6.3 g, 26.9 mmol) obtained in the step (9d), 20% palladium hydroxide (630 mg) was added and stirred for 13 hours in a hydrogen atmosphere. The reaction vessel was purged with nitrogen and insoluble matter was removed by filtration. The filtrate was concentrated to obtain a crude product. The crude product was purified by silica gel column chromatography (NH silica gel, elution solvent: heptane, heptane/ethyl acetate=5/1) to obtain the title compound (3.42 g, yield: 88.2%) as a colorless oil.

$^1$H NMR(400 MHz, CDCl$_3$) δppm; 1.72-1.82(2H, m), 2.21-2.31(4H, m), 2.71-2.88(1H, br), 3.50-3.56(1H, m), 3.71-3.76(2H, m), 3.93-3.98(2H, m).

(9f) 4-(5,9-dioxaspiro[3.5]non-7-yloxy)-2,3-dimethylpyridine 1-oxide

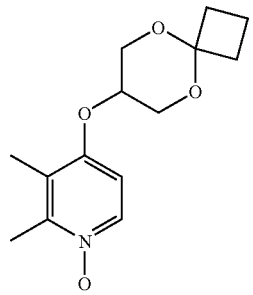
[Formula 81]

To a dimethyl formamide (30 ml) solution of the 5,9-dioxaspiro[3.5]nonan-7-ol (1.68 g, 11.7 mmol) obtained in the step (9e), sodium hydride, in oil (587 mg, 13.5 mmol as the content was regarded as 55%) was added at room temperature. The mixture was stirred at room temperature for 50 minutes. After 4-chloro-2,3-dimethylpyridine 1-oxide (1.84 g, 11.7 mmol) was added thereto, the mixture was stirred at 80° C. for 2 hours. The reaction mixture was concentrated and dimethylsulfoxide (30 ml) was added thereto and stirred at 80° C. After 12 hours, sodium hydride, in oil (587 mg, 13.5 mmol as the content was regarded as 55%) was added to the reaction mixture and stirred at 80° C. After one hour, the reaction mixture was concentrated and the residue was purified by silica gel column chromatography (NH silica gel, elution solvent: ethyl acetate, ethyl acetate/methanol=9/1) to obtain the title compound (2.00 g, yield: 64.4%) as a light yellow oil.

$^1$H NMR(400 MHz, CDCl$_3$) δppm; 1.76-1.82(2H, m), 2.24 (3H, s), 2.27-2.32(4H, m), 2.54(3H, s), 3.85(2H, dd, J=6, 12 Hz), 4.07(2H, dd, J=3, 12 Hz), 4.24-4.30(1H, m), 6.62(1H, d, J=7 Hz), 8.16(1H, d, J=7 Hz).

(9g) (4-(5,9-dioxaspiro[3.5]non-7-yloxy)-3-methylpyridin-2-yl)methanol

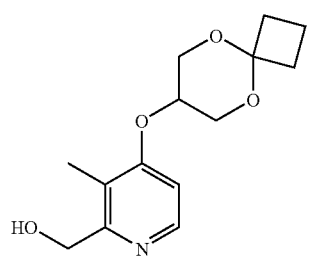
[Formula 82]

The 4-(5,9-dioxaspiro[3.5]non-7-yloxy)-2,3-dimethylpyridine 1-oxide (1.25 g, 4.71 mmol) obtained in the step (9f) was mixed with acetic anhydride (4.45 ml, 47.1 mmol). After the mixture was stirred at room temperature for one hour, it was cooled to 0° C. After triethylamine (656 μl, 4.71 mmol) was added, the mixture was stirred for one hour and stirred at room temperature for another one hour. After stirred at 50° C.

for 2 hours, the reaction mixture was concentrated and the residue was purified by silica gel column chromatography (NH silica gel, elution solvent: ethyl acetate/heptane=1/3). To the obtained product, methanol (30 ml) and a 5N aqueous sodium hydroxide solution (2.24 ml, 11.2 mol) were added, and the reaction mixture was stirred at room temperature for one hour. A saturated aqueous solution of ammonium chloride was added to the reaction mixture to adjust the pH of the solution to about 9 and thereafter concentrated. The resultant residue was extracted with ethyl acetate three times. Organic layers were combined, washed with a saturated saline solution, dried over anhydrous sodium sulfate, filtered and concentrated to obtain the title compound (630 mg, yield: 49.6%) as a light yellow oil.

$^1$H NMR(400 MHz, CDCl$_3$) δppm; 1.77-1.85(2H, m), 2.08 (3H, s), 2.26-2.35(4H, m), 3.85(2H, dd, J=6, 12 Hz), 4.11(2H, dd, J=4, 12 Hz), 4.38-4.44(1H, m), 4.68(2H, s), 6.72(1H, d, J=6 Hz), 8.31(1H, d, J=6 Hz).

(9h) 2-(((4-(5,9-dioxaspiro[3.5]non-7-yloxy)-3-methylpyridin-2-yl)methyl)thio)-1H-benzimidazole

[Formula 83]

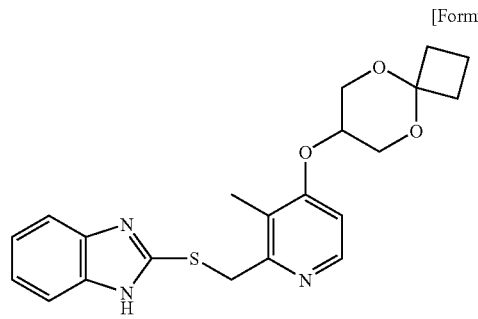

A tetrahydrofuran (20 ml) solution of the (4-(5,9-dioxaspiro[3.5]non-7-yloxy)-3-methylpyridin-2-yl)methanol (630 mg, 2.37 mmol) obtained in the step (9g) and triethylamine (0.66 ml, 4.74 mmol) was stirred at −10° C. After 10 minutes, methanesulfonyl chloride (275 μl, 3.56 mmol) was added at the same temperature and the resultant mixture was stirred in the same conditions for 30 minutes. To the reaction mixture, a saturated aqueous solution of sodium hydrogen carbonate was poured. The reaction mixture was extracted with ethyl acetate twice and organic layers were combined, washed with a saturated saline solution, dried over anhydrous sodium sulfate, filtered and concentrated. Dichloromethane (30 ml) was added to the residue to make a solution, and thereafter, 2-mercaptobenzimidazole (354 mg, 2.36 mmol) was added at room temperature. Furthermore, triethylamine (0.493 ml, 3.54 mmol) was added, and additionally, methanol was added until 2-mercaptobenzimidazole was dissolved. After the reaction mixture was stirred at room temperature for 2 hours, NH silica gel was added to the reaction mixture, which was then concentrated. The residue was subjected to silica gel column chromatography (elution solvent: heptane/ethyl acetate=1/1, ethyl acetate) to obtain the title compound (690 mg, yield: 73.6%) as a white solid.

$^1$H NMR(400 MHz, DMSO-d$_6$) δppm; 1.61-1.70(2H, m), 2.13-2.25(4H, m), 2.22(3H, s), 3.77(2H, dd, J=4, 12 Hz), 4.02(2H, dd, J=2, 12 Hz), 4.44-4.48(1H, m), 4.68(2H, s), 6.97(1H, d, J=6 Hz), 7.07-7.13(2H, m), 7.37-7.50(2H, m), 8.21(1H, d, J=6 Hz).

(9i) 2-(((4-(5,9-dioxaspiro[3.5]non-7-yloxy)-3-methylpyridin-2-yl)methyl)sulfinyl)-1H-benzimidazole

[Formula 84]

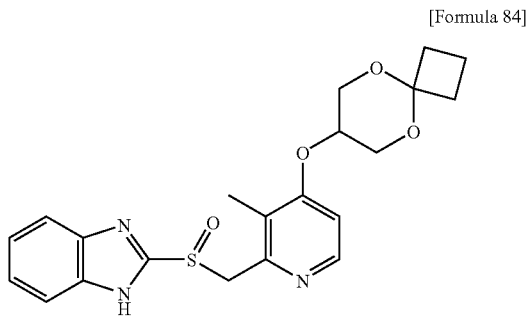

To a toluene (30 ml)/methanol (3 ml) solution of the 2-(((4-(5,9-dioxaspiro[3.5]non-7-yloxy)-3-methylpyridin-2-yl)methyl)thio)-1H-benzimidazole (290 mg, 0.73 mmol) obtained in the step (9h), a toluene/methanol (10:1) solution of 3-chloroperbenzoic acid (174 mg, 0.65 mmol as the content was regarded as 65%) was added at −70° C. in a nitrogen atmosphere. After the mixture was stirred at −50° C. for one hour, a saturated aqueous solution of sodium hydrogen carbonate was added. After the mixture was warmed to room temperature, the mixture was extracted with ethyl acetate twice. Organic layers were combined and dried over anhydrous sodium sulfate, filtered and concentrated. The residue was purified by silica gel column chromatography (NH silica gel, elution solvent: ethyl acetate, ethyl acetate/methanol=9/1). Fractions containing the title compound was collected by use of ethyl acetate and concentrated. After diethyl ether was added to the residue, the solvent was distilled off to obtain the title compound (230 mg, yield: 76.2%) as a white solid.

$^1$H NMR(400 MHz, DMSO-d$_6$) δppm; 1.60-1.70(2H, m), 2.15(3H, s), 2.12-2.25(4H, m), 3.73-3.81(2H, m), 3.98-4.06 (2H, m), 4.44-4.49(1H, m), 4.70(1H, d, J=14 Hz), 4.78(1H, d, J=14 Hz), 6.97(1H, d, J=6 Hz), 7.25-7.32(2H, m), 7.56-7.70 (2H, m), 8.19(1H, d, J=6 Hz).

(9j) 2-(((4-(5,9-dioxaspiro[3.5]non-7-yloxy)-3-methylpyridin-2-yl)methyl)sulfinyl)-1H-benzimidazole sodium salt

[Formula 85]

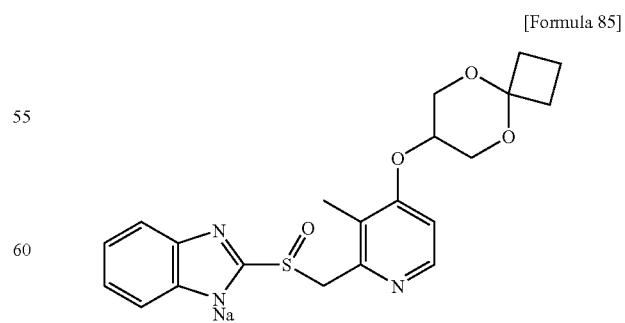

To an ethanol (20 ml) solution of the 2-(((4-(5,9-dioxaspiro [3.5]non-7-yloxy)-3-methylpyridin-2-yl)methyl)sulfinyl)-1H-benzimidazole (230 mg, 0.56 mmol) obtained in the step (9i), a 1N aqueous sodium hydroxide solution (0.56 ml, 0.56 mmol) was added at room temperature. The mixture was stirred for one hour and then concentrated. After the residue was subjected to azeotropic distillation with ethanol twice, it was suspended with diethyl ether, the resultant solid was collected by filtration and dried to obtain the title compound (190 mg, yield: 91%) as a white solid.

$^1$H NMR(400 MHz, DMSO-d$_6$) δppm; 1.60-1.70(2H, m), 2.13-2.27(4H, m), 2.22(3H, s), 3.74-3.81(2H, m), 3.99-4.06 (2H, m), 4.37(1H, d, J=13 Hz), 4.42-4.50 (1H, m), 4.85(1H, d, J=13 Hz), 6.82-6.88 (2H, m), 6.94(1H, d, J=6 Hz), 7.40-7.46 (2H, m), 8.25(1H, d, J=6 Hz).

Example 10

2-(((3-methyl-4-(1,5,9-trioxaspiro[5.5]undec-3-ylmethoxy)pyridin-2-yl)methyl)sulfinyl)-1H-benzimidazole sodium salt

[Formula 86]

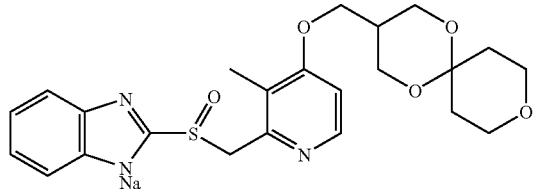

(10a) 1,5,9-trioxaspiro[5.5]undec-3-ylmethanol

[Formula 87]

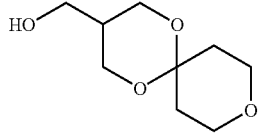

A mixture of 2-(hydroxymethyl)-1,3-propanediol (3.3 g, 31.1 mmol), tetrahydro-4H-pyran-4-one (3.12 g, 31.2 mmol), p-toluenesulfonic acid monohydrate (268 mg, 1.41 mmol) and benzene (68.3 ml) was refluxed in a round bottom flask equipped with a cooling tube and Dean-Stark for 6 hours. After cooled to room temperature, triethylamine (1 ml) was added to the reaction mixture and the mixture was concentrated. The residue was purified by silica gel column chromatography (silica gel: 200 g, elution solvent: heptane, heptane/ethyl acetate=1/1, 1/3) to obtain the title compound (3.80 g, yield: 64.9%) as a colorless oil.

$^1$H NMR(400 MHz, DMSO-d$_6$) δppm; 1.67-1.82(5H, m), 3.35-3.42(2H, m), 3.49-3.57(4H, m), 3.65(2H, dd, J=7, 12 Hz), 3.86(2H, dd, J=4, 12 Hz), 4.56(1H, t, J=5 Hz).

(10b) 2,3-dimethyl-4-(1,5,9-trioxaspiro[5.5]undec-3-ylmethoxy)pyridine 1-oxide

[Formula 88]

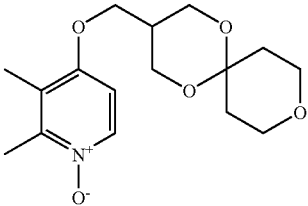

To a dimethylsulfoxide (30 ml) solution of the 1,5,9-trioxaspiro[5.5]undec-3-ylmethanol (3.80 g, 20.2 mmol) obtained in the step (10a), sodium hydride, in oil (770 mg, 19.3 mmol as the content was regarded as 60%) was added at room temperature. The mixture was stirred at room temperature for 30 minutes in a nitrogen atmosphere. To the mixture, 4-chloro-2,3-dimethylpyridine 1-oxide (2.6 g, 16.5 mmol) was added, the mixture was stirred at 60° C. for 2.5 hours. After cooled to room temperature, the reaction mixture was concentrated. The residue was purified by silica gel column chromatography (NH silica gel: 200 g, elution solvent: heptane, heptane/ethyl acetate=1/1, 1/3, ethyl acetate, ethyl acetate/methanol=10/1) to obtain the title compound (3.38 g, yield: 66.2%) as a pale yellow gum.

$^1$H NMR(400 MHz, DMSO-d$_6$) δppm; 1.78(2H, t, J=5 Hz), 1.85(2H, t, J=5 Hz), 2.07-2.20(1H, m), 2.13(3H, s), 2.35(3H, s), 3.52-3.60(4H, m), 3.80(2H, dd, J=6, 12 Hz), 4.04(2H, dd, J=4, 12 Hz), 4.11(2H, d, J=7 Hz), 6.97(1H, d, J=7 Hz), 8.08(1H, d, J=7 Hz).

(10c) (3-methyl-4-(1,5,9-trioxaspiro[5.5]undec-3-ylmethoxy)pyridin-2-yl)methanol

[Formula 89]

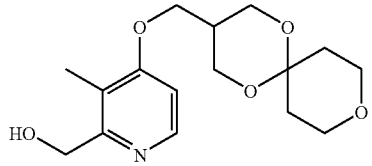

The 2,3-dimethyl-4-(1,5,9-trioxaspiro[5.5]undec-3-ylmethoxy)pyridine 1-oxide (3.31 g, 10.7 mmol) obtained in the step (10b) was mixed with acetic anhydride (30 ml, 331 mmol). The mixture was stirred at 85° C. for 1 hour and 55 minutes. After cooled to a room temperature, the reaction mixture was concentrated. To the residue, methanol (50 ml) and a 5N aqueous sodium hydroxide solution (30 ml, 150 mmol) were added and the mixture was stirred at room temperature for one hour. The reaction mixture was concentrated and the residue was separated between water and ethyl acetate. The organic layer was washed twice with a 1N aqueous sodium hydroxide solution, dried over anhydrous magnesium sulfate, filtered, and concentrated to obtain the title compound (1.97 g, yield: 59.5%) as a brown oil.

$^1$H NMR(400 MHz, DMSO-d$_6$) δppm; 1.78(2H, t, J=5 Hz), 1.85(2H, t, J=5 Hz), 2.09-2.20(1H, m), 2.12(3H, s), 3.50-3.62(4H, m), 3.82(2H, dd, J=6, 12 Hz), 4.05(2H, dd, J=4, 12 Hz), 4.14(2H, d, J=7 Hz), 4.53(2H, d, J=6 Hz), 4.99 (1H, t, J=6 Hz), 6.97(1H, d, J=6 Hz), 8.24(1H, d, J=6 Hz).

(10d) 2-(((3-methyl-4-(1,5,9-trioxaspiro[5.5]undec-3-ylmethoxy)pyridin-2-yl)methyl)thio)-1H-benzimidazole

[Formula 90]

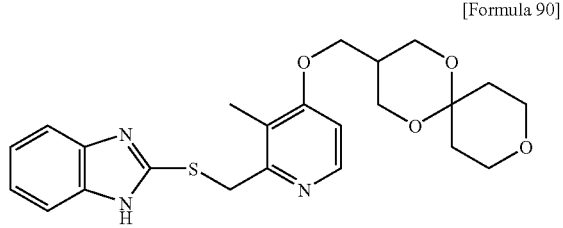

To a dichloromethane (dehydrated) (20 ml) solution of the (3-methyl-4-(1,5,9-trioxaspiro[5.5]undec-3-ylmethoxy)pyridin-2-yl)methanol (1.26 g, 4.07 mmol) obtained in the step (10c) and triethylamine (1.13 ml, 8.14 mmol), methanesulfonyl chloride (473 μl, 6.11 mmol) was added dropwise at 1° C. to 4° C. for 20 minutes in a nitrogen atmosphere. The mixture was stirred for 40 minutes in the same conditions. The reaction mixture was poured into a saturated aqueous solution of sodium hydrogen carbonate. The aqueous layer was extracted with dichloromethane. Organic layers were combined, dried over anhydrous sodium sulfate, filtered and concentrated. The residue was mixed with 2-mercaptobenzimidazole (595 mg, 3.96 mmol). The mixture was stirred in methanol (15 ml) at room temperature for 17 hours and 45 minutes. NH silica gel (10 g) was added to the reaction mixture and the mixture was concentrated. The residue was subjected to silica gel column chromatography (silica gel: 15 g, elution solvent: heptane/ethyl acetate=50/50, 25/75, ethyl acetate, ethyl acetate/methanol=10/1) to obtain a mixture of the title compound and 2-mercaptobenzimidazole. The mixture was further purified by silica gel column chromatography (silica gel: 15 g, elution solvent: heptane/ethyl acetate=50/50, 25/75, ethyl acetate, ethyl acetate/methanol=10/1). The obtained oil was suspended in hexane, concentrated to obtain the title compound (994 mg, yield; 56.8%) as a colorless foam.

$^1$H NMR(400 MHz, DMSO-$d_6$) δppm; 1.78(2H, t, J=5 Hz), 1.85(2H, t, J=5 Hz), 2.10-2.20(1H, m), 2.22(3H, s), 3.52-3.60(4H, m), 3.82(2H, dd, J=6, 12 Hz), 4.05(2H, dd, J=4, 12 Hz), 4.15(2H, d, J=7 Hz), 4.70(2H, s), 6.99(1H, d, J=6 Hz), 7.09-7.16(2H, m), 7.38-7.53(2H, br), 8.25(1H, d, J=6 Hz), 12.62(1H, br s).

(10e) 2-(((3-methyl-4-(1,5,9-trioxaspiro[5.5]undec-3-ylmethoxy)pyridin-2-yl)methyl)sulfinyl)-1H-benzimidazole

[Formula 91]

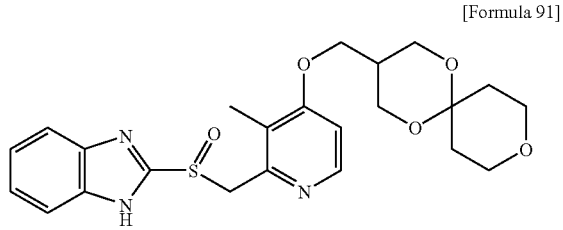

To a toluene (30 ml)-methanol (3 ml) solution of the 2-(((3-methyl-4-(1,5,9-trioxaspiro[5.5]undec-3-ylmethoxy)pyridin-2-yl)methyl)thio)-1H-benzimidazole (974 mg, 2.21 mmol) obtained in the step (10d), a toluene (1 ml)-methanol (1 ml) solution of 3-chloroperbenzoic acid (528 mg, 1.99 mmol as the content was regarded as 65%) was added dropwise at −65° C. for 5 minutes in a nitrogen atmosphere. The mixture was stirred for 55 minutes in the same conditions. To the reaction mixture, a saturated aqueous solution of sodium hydrogen carbonate was added. The organic layer was dried over anhydrous sodium sulfate, filtered and concentrated. The residue was purified by silica gel column chromatography (NH silica gel: 20 g, elution solvent: dichloromethane, dichloromethane/methanol=10/1). The fractions containing the title compound were collected with ethyl acetate and concentrated. After diethyl ether was added to the residue, the solvent was distilled off to obtain the title compound (725 mg, yield: 71.7%) as a pale grayish solid.

$^1$H NMR(400 MHz, DMSO-$d_6$) δppm; 1.78(2H, t, J=5 Hz), 1.85(2H, t, J=5 Hz), 2.05-2.21(1H, m), 2.14(3H, s), 3.48-3.62(4H, m), 3.81(2H, dd, J=6, 12 Hz), 4.05(2H, dd, J=4, 12 Hz), 4.15(2H, d, J=7 Hz), 4.71(1H, d, J=14 Hz), 4.80(1H, d, J=14 Hz), 6.99(1H, d, J=6 Hz), 7.26-7.36(2H, m), 7.58-7.72(2H, br), 8.23(1H, d, J=6 Hz).

(10f) 2-(((3-methyl-4-(1,5,9-trioxaspiro[5.5]undec-3-ylmethoxy)pyridin-2-yl)methyl)sulfinyl)-1H-benzimidazole sodium salt

[Formula 92]

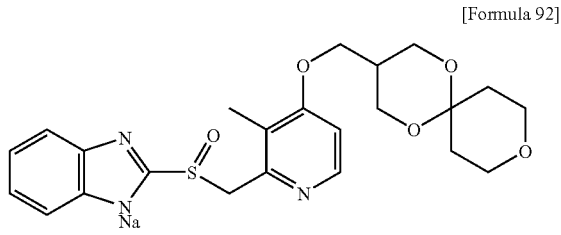

To an ethanol (15 ml) solution of the 2-(((3-methyl-4-(1,5,9-trioxaspiro[5.5]undec-3-ylmethoxy)pyridin-2-yl)methyl)sulfinyl)-1H-benzimidazole (708 mg, 1.55 mmol) obtained in the step (10e), a 1N aqueous sodium hydroxide solution (1.54 ml, 1.55 mmol as the concentration was regarded as 1.004M) was added at room temperature and the mixture was concentrated. The residue was subjected to azeotropic distillation with ethanol twice. After the residue was suspended with diethyl ether, ultrasonically treated, and allowed to stand, the supernatant liquid was removed. This washing process was repeated further twice. The residue was dried under reduced pressure to obtain the title compound (635 mg, yield: 85.4%) as a white solid.

$^1$H NMR(400 MHz, DMSO-$d_6$) δppm; 1.79(2H, t, J=5 Hz), 1.85(2H, t, J=5 Hz), 2.10-2.23(1H, m), 2.19(3H, s), 3.50-3.62(4H, m), 3.78-3.87(2H, m), 4.05(2H, dd, J=4, 12 Hz), 4.14(2H, d, J=7 Hz), 4.40(1H, d, J=13 Hz), 4.78(1H, d, J=13 Hz), 6.82-6.90(2H, m), 6.96(1H, d, J=6 Hz), 7.42-7.48(2H, m), 8.29(1H, d, J=6 Hz).

Example 11

2-(((4-((2,2-dimethyl-1,3-dioxan-5-yl)methoxy)-3,5-dimethylpyridin-2-yl)methyl)sulfinyl)-1H-benzimidazole sodium salt

[Formula 93]

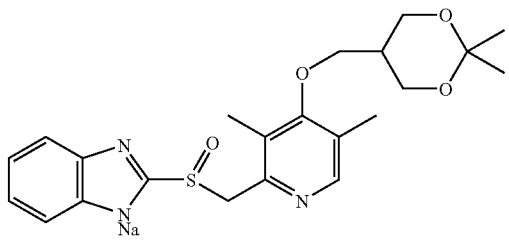

(11a)(2,2-dimethyl-1,3-dioxan-5-yl)methanol

[Formula 94]

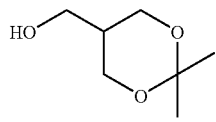

A mixture of 2-(hydroxymethyl)-1,3-propanediol (4.09 g, 38.5 mmol), acetone (130 ml, 1768 mmol) and 70% perchloric acid (1.37 g, 9.55 mmol) was stirred at room temperature for 21 hours. After the pH of the reaction mixture was adjusted with concentrated aqueous ammonia to 9, the reaction mixture was concentrated. The residue was purified by silica gel column chromatography (silica gel: 100 g, elution solvent: heptane, heptane/ethyl acetate=1/3) to obtain the title compound (4.83 g, yield: 85.8%) as a colorless oil.

$^1$H NMR(400 MHz, DMSO-d$_6$) δppm; 1.29(3H, s), 1.30 (3H, s), 1.64-1.74(1H, m), 3.35-3.41(2H, m), 3.61(2H, dd, J=7, 12 Hz), 3.82(2H, dd, J=4, 12 Hz), 4.54(1H, t, J=5 Hz).

(11b) 2,3,5-trimethylpyridine 1-oxide

[Formula 95]

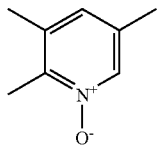

To a dichloromethane (dehydrated) (150 ml) solution of a 2,3,5-collidine (11.0 g, 90.8 mmol), 3-chloroperbenzoic acid (24.8 g, 93.4 mmol as the content was regarded as 65%) was added at 1° C. in a nitrogen atmosphere. The mixture was stirred while the temperature was gradually raised to room temperature for 13.5 hours. After the reaction mixture was concentrated, the residue was purified by silica gel column chromatography (NH silica gel: 200 g, elution solvent: heptane/ethyl acetate=50/50, ethyl acetate, ethyl acetate/methanol=20/1) to obtain a crude product of the title compound as a pale yellow oil. After the crude product was diluted with ethyl acetate and a saturated aqueous solution of sodium hydrogen carbonate, the mixture was concentrated. The residue was purified by silica gel column chromatography (NH silica gel: 300 g, elution solvent: heptane, heptane/ethyl acetate=50/50, ethyl acetate, ethyl acetate/methanol=20/1) to obtain the title compound (11.0 g, yield: 88.3%) as a white solid.

$^1$H NMR(400 MHz, DMSO-d$_6$) δppm; 2.15(3H, s), 2.23 (3H, s), 2.27(3H, s), 6.97(1H, s), 7.99(1H, s).

(11c) 2,3,5-trimethyl-4-nitropyridine 1-oxide

[Formula 96]

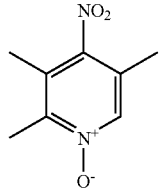

The 2,3,5-trimethylpyridine1-oxide (11.0 g, 80.2 mmol) obtained in the step (11b) was mixed with sulfuric acid (34.1 g, 348 mmol). After fuming nitric acid (5.50 ml, 133 mmol) was added dropwise to this mixture at room temperature, the mixture was stirred at 80° C. for 9 hours. The reaction mixture was cooled to room temperature and thereafter poured into ice. The obtained aqueous solution was extracted with chloroform three times. Organic layers were combined and dried over anhydrous magnesium sulfate, filtered and concentrated to obtain the title compound (13.6 g, yield: 93.1%) as a yellow solid.

$^1$H NMR(400 MHz, DMSO-d$_6$) δppm; 2.16(3H, s), 2.20 (3H, s), 2.36(3H, s), 8.35(1H, s).

(11d) 4-chloro-2,3,5-trimethylpyridine 1-oxide

[Formula 97]

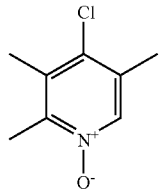

The 2,3,5-trimethyl-4-nitropyridine1-oxide (13.4 g, 73.6 mmol) obtained in the step (11c) was added to acetyl chloride (80 ml, 1,125 mmol) at −30° C. in a nitrogen atmosphere. The mixture was stirred at −30° C. to room temperature for 4 hours and 20 minutes. After the reaction mixture was concentrated, the residue was subjected to silica gel column chromatography (NH silica gel: 300 g, elution solvent: heptane, heptane/ethyl acetate=50/50, ethyl acetate, ethyl acetate/methanol=10/1) to obtain fractions containing a pure product of the title compound and fractions containing a crude product of the title compound.

The fractions containing a crude product of the title compound was concentrated. The residue was suspended in ethyl acetate and the resulting precipitate was collected by filtration, washed with ethyl acetate and diethyl ether to obtain the title compound (Lot A, 1.58 g) as a white solid. The filtrate was concentrated. The residue was dissolved in chloroform and washed with a saturated aqueous solution of sodium hydrogen carbonate, dried over anhydrous sodium sulfate, filtered and concentrated. The residue was suspended in diethyl ether. The resulting precipitate was collected by filtration, washed with diethyl ether to obtain the title compound (Lot B, 2.69 g) as a pale brown solid.

The fractions containing a pure product of the title compound were concentrated. The residue was dissolved in chloroform, washed with a saturated aqueous solution of sodium hydrogen carbonate, dried over anhydrous sodium sulfate, filtered and concentrated to obtain the title compound (Lot C, 6.56 g) as a pale white solid.

The yield of the obtained title compounds of 3 lots was 85.7% in total.

Lot A: $^1$H NMR(400 MHz, DMSO-$d_6$) δppm; 2.24(3H, s), 2.35(3H, s), 2.39(3H, s), 8.25(1H, s).

Lot B: $^1$H NMR(400 MHz, DMSO-$d_6$) δppm; 2.24(3H, s), 2.35(3H, s), 2.39(3H, s), 8.25(1H, s).

Lot C: $^1$H NMR(400 MHz, DMSO-$d_6$) δppm; 2.24(3H, s), 2.35(3H, s), 2.39(3H, s), 8.25(1H, s).

(11e) 4-((2,2-dimethyl-1,3-dioxan-5-yl)methoxy)-2,3,5-trimethylpyridine 1-oxide

[Formula 98]

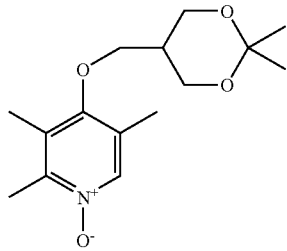

To a dimethylsulfoxide (50 ml) solution of the (2,2-dimethyl-1,3-dioxan-5-yl)methanol (4.78 g, 32.7 mmol) obtained in the step (11a), sodium hydride, in oil (1.26 g, 31.5 mmol as the content was regarded as 60%) was added at room temperature. The mixture was stirred at room temperature for 15 minutes in a nitrogen atmosphere. To the mixture, the 4-chloro-2,3,5-trimethylpyridine 1-oxide (Lot C, 4.50 g, 26.2 mmol) obtained in the step (11d) was added and the mixture was stirred at 60° C. for 8 hours and 10 minutes. After cooled to room temperature, the reaction mixture was concentrated. The residue was purified by silica gel column chromatography (NH silica gel: 300 g, elution solvent: heptane, heptane/ethyl acetate=1/1, 1/3, ethyl acetate, ethyl acetate/methanol=10/1) to obtain the title compound (5.06 g, yield: 68.6%) as a yellow oil.

$^1$H NMR(400 MHz, DMSO-$d_6$) δppm; 1.33(3H, s), 1.36 (3H, s), 2.05-2.13(1H, m), 2.14(3H, s), 2.17(3H, s), 2.31(3H, s), 3.77-3.86(4H, m), 4.01(2H, dd, J=4, 12 Hz), 8.07(1H, s).

(11f) (4-((2,2-dimethyl-1,3-dioxan-5-yl)methoxy)-3,5-dimethylpyridin-2-yl)methanol

[Formula 99]

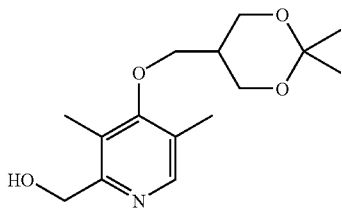

The 4-((2,2-dimethyl-1,3-dioxan-5-yl)methoxy)-2,3,5-trimethylpyridine 1-oxide (5.06 g, 18 mmol) obtained in the step (11e) was mixed with acetic anhydride (50 ml, 529 mmol) and the mixture was stirred at 85° C. for 1.5 hours. After cooled to room temperature, the reaction mixture was concentrated. Methanol (50 ml) and a 5N aqueous sodium hydroxide solution (50 ml, 250 mmol) were added to the residue and the mixture was stirred at room temperature for 30 minutes. The reaction mixture was concentrated and the residue was separated between water and ethyl acetate. The organic layer was washed with a 1N aqueous sodium hydroxide solution twice and dried over anhydrous magnesium sulfate, filtered and concentrated to obtain the title compound (3.02 g, yield: 59.6%) as a brown oil.

$^1$H NMR(400 MHz, DMSO-$d_6$) δppm; 1.33(3H, s), 1.37 (3H, s), 2.05-2.16(1H, m), 2.20(6H, s), 3.82(2H, dd, J=6, 12 Hz), 3.86(2H, d, J=8 Hz), 4.02(2H, dd, J=4, 12 Hz), 4.51(2H, d, J=6 Hz), 4.98(1H, t, J=6 Hz), 8.16(1H, s).

(11g) 2-(((4-((2,2-dimethyl-1,3-dioxan-5-yl)methoxy)-3,5-dimethylpyridin-2-yl)methyl)thio)-1H-benzimidazole

[Formula 100]

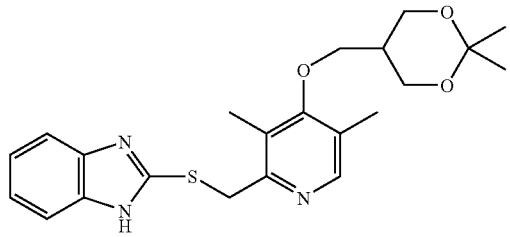

To a tetrahydrofuran (15 ml) solution of the (4-((2,2-dimethyl-1,3-dioxan-5-yl)methoxy)-3,5-dimethylpyridin-2-yl)methanol (504 mg, 1.79 mmol) obtained in the step (11f) and triethylamine (500 μl, 3.58 mmol), methanesulfonyl chloride (208 μl, 2.69 mmol) was added dropwise at 1° C. to 3° C. for 15 minutes in a nitrogen atmosphere. The reaction mixture was stirred for 1 hour and 25 minutes in the same conditions. After 2-mercaptobenzimidazole (271 mg, 1.8 mmol) was added, the mixture was stirred at room temperature for 64 hours and 20 minutes. The reaction mixture was separated between ethyl acetate and a saturated aqueous solution of sodium hydrogen carbonate. The organic layer was dried over anhydrous magnesium sulfate, filtered and concentrated. The residue was purified by silica gel column chromatography (silica gel: 30 g, elution solvent: heptane/ethyl acetate=42/58, 22/78, ethyl acetate) to obtain the title compound (442 mg, yield: 59.7%) as a colorless foam.

$^1$H NMR(400 MHz, DMSO-$d_6$) δppm; 1.33(3H, s), 1.36 (3H, s), 2.05-2.16(1H, m), 2.20(3H, s), 2.28(3H, s), 3.81(2H, dd, J=6, 12 Hz), 3.87(2H, d, J=7 Hz), 4.02(2H, dd, J=4, 12 Hz), 4.69(2H, s), 7.09-7.16(2H, m), 7.41-7.50(2H, m), 8.18 (1H, s).

(11h) 2-(((4-((2,2-dimethyl-1,3-dioxan-5-yl)methoxy)-3,5-dimethylpyridin-2-yl)methyl)sulfinyl)-1H-benzimidazole

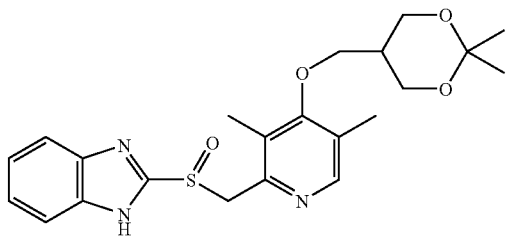

[Formula 101]

To a toluene (20 ml)-methanol (2 ml) solution of the 2-(((4-((2,2-dimethyl-1,3-dioxan-5-yl)methoxy)-3,5-dimethylpyridin-2-yl)methyl)thio)-1H-benzimidazole (424 mg, 1.03 mmol) obtained in the step (11g), a toluene (1 ml)-methanol (1 ml) solution of 3-chloroperbenzoic acid (246 mg, 0.927 mmol as the content was regarded as 65%) was added dropwise at −65° C. for 5 minutes in a nitrogen atmosphere. The mixture was stirred for 45 minutes in the same conditions. To the reaction mixture, a saturated aqueous solution of sodium hydrogen carbonate was added and the mixture was extracted with ethyl acetate. The organic layer was dried over anhydrous sodium sulfate, filtered and concentrated. The residue was purified by silica gel column chromatography (NH silica gel: 20 g, elution solvent: dichloromethane, dichloromethane/methanol=10/1). The fractions containing the title compound were collected with ethyl acetate and concentrated. To the residue, diethyl ether was added. The resulting precipitate was collected by filtration and washed with diethyl ether to obtain the title compound (274 mg, yield: 61.9%) as a white solid.

$^1$H NMR(400 MHz, DMSO-$d_6$) δppm; 1.32(3H, s), 1.36 (3H, s), 2.02-2.13(1H, m), 2.16(3H, s), 2.20(3H, s), 3.74-3.84 (4H, m), 4.00(2H, dd, J=4, 12 Hz), 4.70(1H, d, J=14 Hz), 4.79(1H, d, J=14 Hz), 7.26-7.33(2H, m), 7.60-7.70(2H, m), 8.18(1H, s).

(11i) 2-(((4-((2,2-dimethyl-1,3-dioxan-5-yl)methoxy)-3,5-dimethylpyridin-2-yl)methyl)sulfinyl)-1H-benzimidazole sodium salt

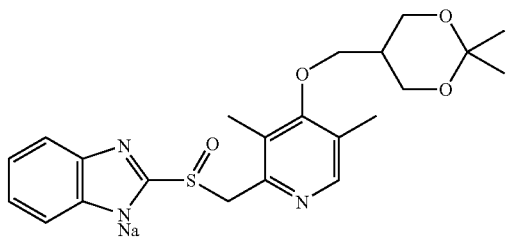

[Formula 102]

To an ethanol (10 ml) solution of the 2-(((4-((2,2-dimethyl-1,3-dioxan-5-yl)methoxy)-3,5-dimethylpyridin-2-yl)methyl)sulfinyl)-1H-benzimidazole (274 mg, 0.638 mmol) obtained in the step (11h), a 1N aqueous sodium hydroxide solution (635 μl, 0.638 mmol as the concentration was regarded as 1.004M) was added at room temperature and the mixture was concentrated. The residue was subjected to azeotropic distillation with ethanol twice. After the residue was suspended in diethyl ether, the mixture was ultrasonically treated and concentrated to obtain the title compound (260 mg, yield: 90.3%) as a white solid.

$^1$H NMR(400 MHz, DMSO-$d_6$) δppm; 1.33(3H, s), 1.36 (3H, s), 2.03-2.14(1H, m), 2.20(3H, s), 2.21(3H, s), 3.76-3.87 (4H, m), 4.00(2H, dd, J=4, 11 Hz), 4.39(1H, d, J=13 Hz), 4.75(1H, d, J=13 Hz), 6.81-6.91(2H, m), 7.40-7.48(2H, m), 8.23(1H, s).

Example 12

2-(((4-((2,2-dimethyl-1,3-dioxan-5-yl)methoxy)-3-methylpyridin-2-yl)methyl)sulfinyl)-1H-benzimidazole sodium salt

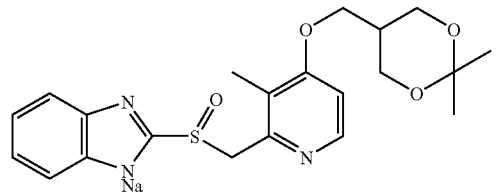

[Formula 103]

(12a) 4-((2,2-dimethyl-1,3-dioxan-5-yl)methoxy)-2,3-dimethylpyridine 1-oxide

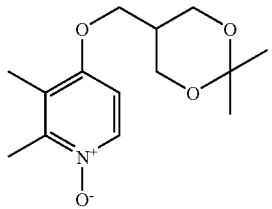

[Formula 104]

To a dimethyl sulfoxide (30 ml) solution of the (2,2-dimethyl-1,3-dioxan-5-yl)methanol (3.27 g, 22.4 mmol) separately obtained in the same manner as in the step (11a) in example 11, sodium hydride, in oil (837 mg, 20.9 mmol as the content was regarded as 60%) was added at room temperature. The mixture was stirred at room temperature for 15 minutes in a nitrogen atmosphere. To the mixture, 4-chloro-2,3-dimethylpyridine 1-oxide (3.03 g, 19.2 mmol) was added, and the mixture was stirred at 60° C. for 3 hours and 20 minutes. After cooled to room temperature, the reaction mixture was concentrated. The residue was purified by silica gel column chromatography (NH silica gel: 250 g, elution solvent: ethyl acetate, ethyl acetate/methanol=10/1) to obtain the title compound (3.84 g, yield: 74.8%) as a pale brown solid.

$^1$H NMR(400 MHz, DMSO-$d_6$) δppm; 1.31(3H, s), 1.35 (3H, s), 2.00-2.12(1H, m), 2.12(3H, s), 2.33 (3H, s), 3.74(2H, dd, J=6, 12 Hz), 3.97(2H, dd, J=4, 12 Hz), 4.08(2H, d, J=7 Hz), 6.94(1H, d, J=7 Hz), 8.05(1H, d, J=7 Hz).

(12b) (4-((2,2-dimethyl-1,3-dioxan-5-yl)methoxy)-3-methylpyridin-2-yl)methanol

[Formula 105]

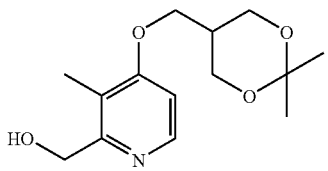

The 4-((2,2-dimethyl-1,3-dioxan-5-yl)methoxy)-2,3-dimethylpyridine 1-oxide (3.84 g, 14.4 mmol) obtained in the step (12a) was mixed with acetic anhydride (50 ml, 530 mmol). The mixture was stirred at 85° C. for 1.5 hours. After cooled to room temperature, the reaction mixture was concentrated. To the residue, methanol (50 ml) and a 5N aqueous sodium hydroxide solution (20 ml, 100 mmol) were added and the mixture was stirred at room temperature for 2.5 hours. The reaction mixture was concentrated and the residue was partitioned between water and ethyl acetate. The organic layer was washed with a 1N aqueous sodium hydroxide solution twice, dried over anhydrous sodium sulfate, filtered and concentrated to obtain the title compound (2.97 g, yield: 77.2%) as a brown solid.

$^1$H NMR(400 MHz, DMSO-$d_6$) δppm; 1.31(3H, s), 1.34 (3H, s), 2.03-2.14(1H, m), 2.10(3H, s), 3.76(2H, dd, J=6, 12 Hz), 3.98(2H, dd, J=4, 12 Hz), 4.10(2H, d, J=7 Hz), 4.51(2H, d, J=5 Hz), 4.97(1H, t, J=5 Hz), 6.95(1H, d, J=6 Hz), 8.22(1H, d, J=6 Hz).

(12c) 2-(((4-((2,2-dimethyl-1,3-dioxan-5-yl)methoxy)-3-methylpyridin-2-yl)methyl)thio)-1H-benzimidazole

[Formula 106]

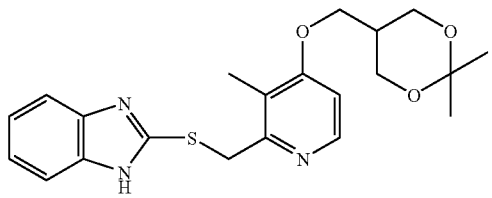

To a dichloromethane (dehydrated) (20 ml) solution of the (4-((2,2-dimethyl-1,3-dioxan-5-yl)methoxy)-3-methylpyridin-2-yl)methanol (1.03 g, 3.85 mmol) obtained in the step (12b) and triethylamine (1.07 ml, 7.7 mmol), methanesulfonyl chloride (447 μl, 5.78 mmol) was added dropwise at a temperature of 1° C. to 4° C. for 10 minutes under nitrogen atmosphere. The mixture was stirred for one hour and 25 minutes in the same conditions. The reaction mixture was poured into a saturated aqueous solution of sodium hydrogen carbonate. The aqueous layer was extracted with dichloromethane. Organic layers were combined, dried over anhydrous sodium sulfate, filtered and concentrated. The residue was mixed with 2-mercaptobenzimidazole (586 mg, 3.9 mmol) and the mixture was stirred in methanol (20 ml) at room temperature for 2 hours and 40 minutes. NH silica gel (15 g) was added to the reaction mixture, which was then concentrated. The residue was subjected to silica gel column chromatography (NH silica gel: 20 g, elution solvent: heptane/ethyl acetate=1/1, 1/3, ethyl acetate) to obtain a mixture of the title compound and 2-mercaptobenzimidazole. The mixture was further purified by silica gel column chromatography (silica gel: 30 g, elution solvent: heptane/ethyl acetate=50/50, 25/75, ethyl acetate) to obtain the title compound (771 mg, yield: 50.1%) as a colorless foam.

$^1$H NMR(400 MHz, DMSO-$d_6$) δppm; 1.31(3H, s), 1.34 (3H, s), 2.03-2.15(1H, m), 2.20(3H, s), 3.76(2H, dd, J=6, 12 Hz), 3.98(2H, dd, J=4, 12 Hz), 4.11(2H, d, J=7 Hz), 4.68(2H, s), 6.97(1H, d, J=6 Hz), 7.06-7.14(2H, m), 7.35-7.51(2H, br), 8.23(1H, d, J=6 Hz), 12.60 (1H, br s).

(12d) 2-(((4-((2,2-dimethyl-1,3-dioxan-5-yl)methoxy)-3-methylpyridin-2-yl)methyl)sulfinyl)-1H-benzimidazole

[Formula 107]

To a toluene (45 ml)-methanol (5 ml) solution of the 2-(((4-((2,2-dimethyl-1,3-dioxan-5-yl)methoxy)-3-methylpyridin-2-yl)methyl)thio)-1H-benzimidazole (766 mg, 1.92 mmol) obtained in the step (12c), a toluene (0.5 ml)-methanol (0.5 ml) solution of 3-chloroperbenzoic acid (459 mg, 1.73 mmol as the content was regarded as 65%) was added dropwise at −65° C. for 5 minutes in a nitrogen atmosphere. The mixture was stirred in the same conditions for one hour and 20 minutes. To the reaction mixture, a saturated aqueous solution of sodium hydrogen carbonate was added. The aqueous layer was extracted with ethyl acetate and chloroform (three times). Organic layers were combined, dried over anhydrous sodium sulfate, filtered and concentrated. The residue was purified by silica gel column chromatography (NH silica gel: 30 g, elution solvent: dichloromethane, dichloromethane/methanol=20/1). The fractions containing the title compound were collected, concentrated to obtain the title compound (688 mg, yield: 86.2%) as a light brown foam.

$^1$H NMR(400 MHz, DMSO-$d_6$) δppm; 1.31(3H, s), 1.34 (3H, s), 2.03-2.12(1H, m), 2.12(3H, s), 3.75(2H, dd, J=6, 12 Hz), 3.98(2H, dd, J=4, 12 Hz), 4.11 (2H, d, J=7 Hz), 4.69(1H, d, J=14 Hz), 4.78(1H, d, J=14 Hz), 6.97(1H, d, J=6 Hz), 7.24-7.34(2H, m), 7.57-7.70(2H, m), 8.20(1H, d, J=6 Hz).

(12e) 2-(((4-((2,2-dimethyl-1,3-dioxan-5-yl)methoxy)-3-methylpyridin-2-yl)methyl)sulfinyl)-1H-benzimidazole sodium salt

[Formula 108]

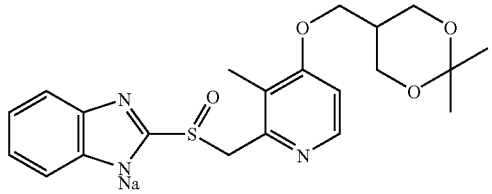

To an ethanol (10 ml) solution of the 2-(((4-((2,2-dimethyl-1,3-dioxan-5-yl)methoxy)-3-methylpyridin-2-yl)methyl)sulfinyl)-1H-benzimidazole (688 mg, 1.66 mmol) obtained in the step (12d), a 1N aqueous sodium hydroxide solution (1.65 ml, 1.66 mmol as the concentration was regarded as 1.004M) was added at room temperature and the mixture was concentrated. The residue was subjected to azeotropic distillation with ethanol twice. After the residue was suspended in diethyl ether, the mixture was ultrasonically treated and allowed to stand. Thereafter, the supernatant liquid was removed. This washing process was repeated further twice and the residue was dried under reduced pressure to obtain the title compound (701 mg, yield: 96.5%) as a white solid.

$^1$H NMR(400 MHz, DMSO-$d_6$) δppm; 1.32(3H, s), 1.34 (3H, s), 2.04-2.13(1H, m), 2.17(3H, s), 3.72-3.81(2H, m), 3.98(2H, dd, J=4, 12 Hz), 4.10(2H, d, J=7 Hz), 4.38(1H, d, J=13 Hz), 4.76(1H, d, J=13 Hz), 6.80-6.89(2H, m), 6.94(1H, d, J=5 Hz), 7.39-7.47(2H, m), 8.28(1H, d, J=5 Hz).

Example 13

2-(((4-(5,9-dioxaspiro[3.5]non-7-ylmethoxy)-3,5-dimethylpyridin-2-yl)methyl)sulfinyl)-1H-benzimidazole sodium salt

[Formula 109]

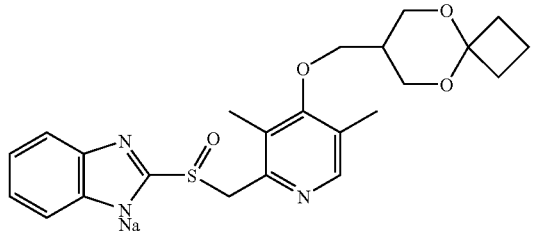

(13a) 5,9-dioxasprio[3.5]non-7-ylmethanol

[Formula 110]

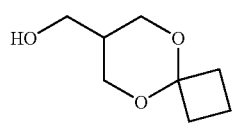

A mixture of 2-(hydroxymethyl)-1,3-propanediol (5.58 g, 52.6 mmol), cyclobutanone (3.69 g, 52.6 mmol), p-toluenesulfonic acid monohydrate (550 mg, 2.89 mmol) and benzene (92.9 ml) was refluxed in a round-bottom flask equipped with a cooling tube and Dean-Stark for 8 hours and 35 minutes. After the reaction mixture was cooled to room temperature, triethylamine (1 ml) was added to the reaction mixture and the mixture was concentrated. The residue was purified by silica gel column chromatography (silica gel: 300 g, elution solvent: heptane, heptane/ethyl acetate=1/1). The fractions containing the title compound were collected with ethyl acetate and concentrated. The residue was dissolved in diethyl ether and then the mixture was concentrated to obtain the title compound (6.08 g, yield: 73.1%) as a pale yellow oil.

$^1$H NMR(400 MHz, DMSO-$d_6$) δppm; 1.58-1.68(2H, m), 1.68-1.77(1H, m), 2.07-2.16(4H, m), 3.32-3.39(2H, m), 3.52 (2H, dd, J=7, 12 Hz), 3.78(2H, dd, J=4, 12 Hz), 4.56(1H, t, J=5 Hz).

(13b) 4-(5,9-dioxasprio[3.5]non-7-ylmethoxy)-2,3,5-trimethylpyridine 1-oxide

[Formula 111]

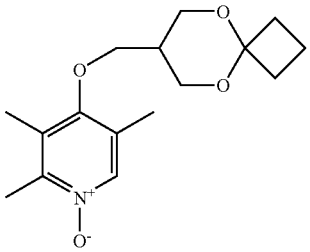

To a dimethylsulfoxide (20 ml) solution of the 5,9-dioxasprio[3.5]non-7-ylmethanol (2.20 g, 13.9 mmol) obtained in the step (13a), sodium hydride, in oil (524 mg, 13.1 mmol as the content was regarded as 60%) was added at room temperature. The mixture was stirred at room temperature for 45 minutes in a nitrogen atmosphere. To the mixture, 4-chloro-2,3,5-trimethylpyridine 1-oxide (Lot C, 1.94 g, 11.3 mmol) obtained in the step (11d) in example 11 was added, the mixture was stirred at 60° C. for 2 hours and 50 minutes. After cooled to room temperature, the reaction mixture was concentrated. The residue was purified by silica gel column chromatography (NH silica gel: 100 g, elution solvent: heptane, heptane/ethyl acetate=1/1, ethyl acetate, ethyl acetate/methanol=20/1) to obtain the title compound (1.97 g, yield: 59.4%) as a brown oil.

$^1$H NMR(400 MHz, DMSO-$d_6$) δppm; 1.60-1.71(2H, m), 2.07-2.22(5H, m), 2.12(3H, s), 2.16(3H, s), 2.30(3H, s), 3.74 (2H, dd, J=7, 12 Hz), 3.78(2H, d, J=7 Hz), 3.94(2H, dd, J=4, 12 Hz), 8.05(1H, s).

(13c) (4-(5,9-dioxasprio[3.5]non-7-ylmethoxy)-3,5-dimethylpyridin-2-yl)methanol

[Formula 112]

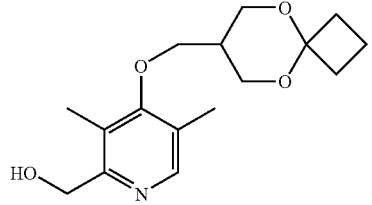

The 4-(5,9-dioxasprio[3.5]non-7-ylmethoxy)-2,3,5-trimethylpyridine1-oxide (1.97 g, 6.72 mmol) obtained in the step (13b) was mixed with acetic anhydride (20 ml, 212 mmol). The mixture was stirred at 85° C. for 1.5 hours. After cooled to room temperature, the reaction mixture was concentrated. To the residue, methanol (20 ml) and a 5N aqueous sodium hydroxide solution (20 ml, 100 mmol) were added and the mixture was stirred at room temperature for 45 minutes. The reaction mixture was concentrated and the residue was partitioned between water and ethyl acetate. The organic layer was washed with a 2N aqueous sodium hydroxide solution, dried over anhydrous magnesium sulfate, filtered and concentrated to obtain the title compound (1.69 g, yield: 85.7%) as a brown oil.

$^1$H NMR(400 MHz, DMSO-d$_6$) δppm; 1.60-1.70(2H, m), 2.08-2.25(5H, m), 2.18(6H, s), 3.75(2H, dd, J=6, 12 Hz), 3.83(2H, d, J=7 Hz), 3.95(2H, dd, J=4, 12 Hz), 4.50(2H, d, J=5 Hz), 4.97(1H, t, J=5 Hz), 8.14(1H, s).

(13d) 2-(((4-(5,9-dioxasprio[3.5]non-7-ylmethoxy)-3,5-dimethylpyridin-2-yl)methyl)thio)-1H-benzimidazole

[Formula 113]

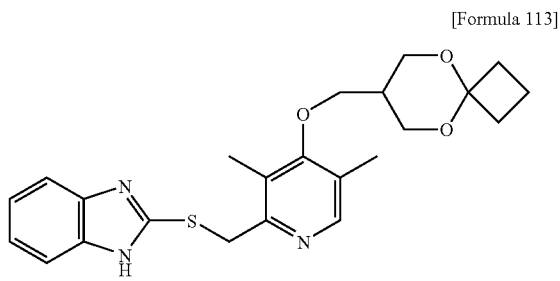

To a dichloromethane (dehydrated) (15 ml) and tetrahydrofuran (5 ml) solution of the (4-(5,9-dioxasprio[3.5]non-7-ylmethoxy)-3,5-dimethylpyridin-2-yl)methanol (450 mg, 1.53 mmol) obtained in the step (13c) and triethylamine (427 μl, 3.06 mmol), methanesulfonyl chloride (178 μl, 2.3 mmol) was added dropwise at 1° C. to 4° C. for 10 minutes in a nitrogen atmosphere. The mixture was stirred for 50 minutes in the same conditions. The reaction mixture was poured into a saturated aqueous solution of sodium hydrogen carbonate. The aqueous layer was extracted with dichloromethane. Organic layers were combined, dried over anhydrous sodium sulfate, filtered and concentrated. The residue was mixed with 2-mercaptobenzimidazole (235 mg, 1.56 mmol) and the mixture was stirred in methanol (20 ml) at room temperature for 2 hours and 30 minutes. NH silica gel (15 g) was added to the reaction mixture, which was then concentrated. The residue was subjected to silica gel column chromatography (silica gel: 30 g, elution solvent: heptane/ethyl acetate=42/58, 22/78, ethyl acetate) to the title compound (507 mg, yield: 77.9%) as a colorless foam.

$^1$H NMR(400 MHz, DMSO-d$_6$) δppm; 1.60-1.71(2H, m), 2.08-2.22(5H, m), 2.19(3H, s), 2.28(3H, s), 3.76(2H, dd, J=6, 12 Hz), 3.84(2H, d, J=7 Hz), 3.95(2H, dd, J=4, 12 Hz), 4.69(2H, s), 7.06-7.19(2H, m), 7.37-7.56(2H, br), 8.18(1H, s), 12.60(1H, br s).

(13e) 2-(((4-(5,9-dioxasprio[3.5]non-7-ylmethoxy)-3,5-dimethylpyridin-2-yl)methyl)sulfinyl)-1H-benzimidazole

[Formula 114]

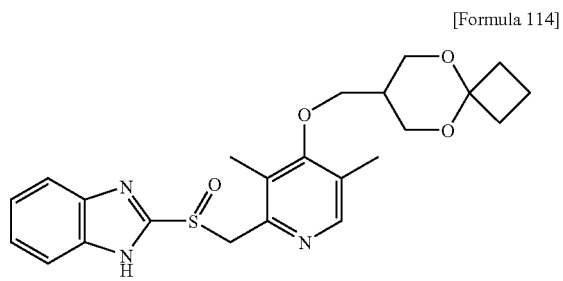

To a toluene (20 ml)-methanol (2 ml) solution of the 2-(((4-(5,9-dioxasprio[3.5]non-7-ylmethoxy)-3,5-dimethylpyridin-2-yl)methyl)thio)-1H-benzimidazole (499 mg, 1.17 mmol) obtained in the step (13d), a toluene (1 ml)-methanol (1 ml) solution of 3-chloroperbenzoic acid (280 mg, 1.05 mmol as the content was regarded as 65%) was added dropwise at −65° C. for 5 minutes in a nitrogen atmosphere. The mixture was stirred in the same conditions for 55 minutes. To the reaction mixture, a saturated aqueous solution of sodium hydrogen carbonate was added. The mixture was extracted with ethyl acetate. The organic layer was dried over anhydrous sodium sulfate, filtered and concentrated. The residue was purified by silica gel column chromatography (NH silica gel: 20 g, elution solvent: dichloromethane, dichloromethane/methanol=20/1). The fractions containing the title compound were collected with ethyl acetate, and concentrated. To the residue, diethyl ether was added and then the mixture was concentrated to obtain the title compound (445 mg, yield: 86.1%) as a colorless foam.

$^1$H NMR(400 MHz, DMSO-d$_6$) δppm; 1.60-1.70(2H, m), 2.06-2.23(5H, m), 2.14(3H, s), 2.18(3H, s), 3.67-3.82(4H, m), 3.93(2H, dd, J=4, 12 Hz), 4.70(1H, d, J=14 Hz), 4.78(1H, d, J=14 Hz), 7.25-7.34(2H, m), 7.58-7.70(2H, m), 8.18 (1H, s).

(13f) 2-(((4-(5,9-dioxasprio[3.5]non-7-ylmethoxy)-3,5-dimethylpyridin-2-yl)methyl)sulfinyl)-1H-benzimidazole sodium salt

[Formula 115]

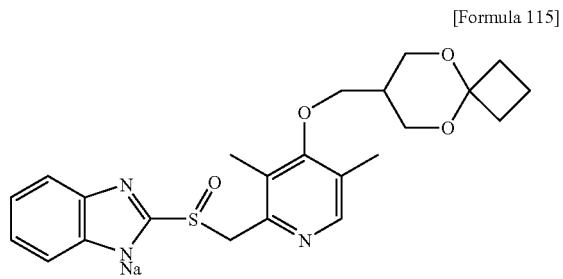

To an ethanol (10 ml) solution of the 2-(((4-(5,9-dioxasprio[3.5]non-7-ylmethoxy)-3,5-dimethylpyridin-2-yl)methyl)sulfinyl)-1H-benzimidazole (445 mg, 1.01 mmol) obtained in the step (13e), a 1N aqueous sodium hydroxide solution (1.01 ml, 1.01 mmol as the concentration was regarded as 1.004M) was added at room temperature and the mixture was concentrated. The residue was subjected to azeotropic distillation with ethanol twice. After the residue was suspended with diethyl ether, the mixture was ultrasonically treated and concentrated to obtain the title compound (420 mg, yield: 89.7%) as a white solid.

$^1$H NMR(400 MHz, DMSO-d$_6$) δppm; 1.58-1.70(2H, m), 2.07-2.25(5H, m), 2.19(6H, s), 3.68-3.82(4H, m), 3.94(2H, dd, J=4, 12 Hz), 4.34-4.41(1H, m), 4.70-4.77(1H, m), 6.82-6.89(2H, m), 7.41-7.47(2H, m), 8.22(1H, s).

Example 14

2-(((4-(((4R)-2,2-dimethyl-1,3-dioxolan-4-yl)methoxy)-3-methylpyridin-2-yl)methyl)sulfinyl)-1H-benzimidazole sodium salt

[Formula 116]

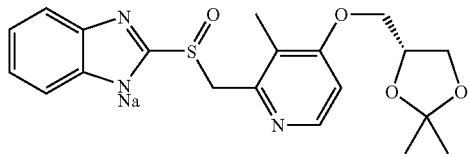

(14a) 4-(((4R)-2,2-dimethyl-1,3-dioxolan-4-yl)methoxy)-2,3-dimethylpyridine 1-oxide

[Formula 117]

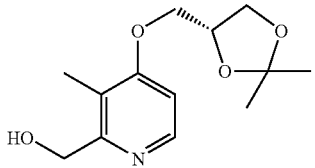

To a dimethylsulfoxide (48 ml) solution of the ((4R)-2,2-dimethyl-1,3-dioxolan-4-yl)methanol (4.87 g, 39.7 mmol), sodium hydride, in oil (1.73 g, 39.6 mmol as the content was regarded as 55%) was added at room temperature. To the mixture, 4-chloro-2,3-dimethylpyridine 1-oxide (4.8 g, 30.5 mmol) was added, the mixture was stirred at 60° C. for 2 hours. After cooled to room temperature, the reaction mixture was concentrated under reduced pressure. The residue was purified by silica gel column chromatography (NH silica gel, elution solvent: ethyl acetate/methanol) to obtain the title compound (10.5 g, yield: 136%) as a yellow oil.

$^1$H NMR(400 MHz, CDCl$_3$) δppm; 1.40(3H, s), 1.45(3H, s), 2.21(3H, s), 2.54(3H, s), 3.93(1H, dd, J=6, 8 Hz), 4.01(1H, dd, J=5, 10 Hz), 4.07(1H, dd, J=5, 10 Hz), 4.17(1H, dd, J=6, 8 Hz), 4.48(1H, quint, J=6 Hz), 6.65(1H, d, J=8 Hz), 8.15(1H, d, J=8 Hz).

(14b) (4-(((4R)-2,2-dimethyl-1,3-dioxolan-4-yl)methoxy)-3-methylpyridin-2-yl)methanol

[Formula 118]

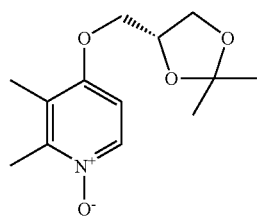

The 4-(((4R)-2,2-dimethyl-1,3-dioxolan-4-yl)methoxy)-2,3-dimethylpyridine 1-oxide (10.5 g, 41.5 mmol) obtained in the step (14a) was mixed with acetic anhydride (20 ml). The mixture was stirred at 80° C. for one hour. After cooled to room temperature, the reaction mixture was concentrated under reduced pressure. To the residue, methanol (40 ml) and a 5N aqueous sodium hydroxide solution (20 ml) were added and the mixture was stirred at room temperature for 1.5 hours. The reaction mixture was concentrated and the residue was partitioned between a saturated saline solution and ethyl acetate. The organic layer was dried over anhydrous magnesium sulfate, filtered and concentrated and the residue was purified by silica gel column chromatography (elution solvent: ethyl acetate/methanol) to obtain the title compound (3.77 g, yield: 41.9%) as a yellow oil.

$^1$H NMR(400 MHz, CDCl$_3$) δppm; 1.41(3H, s), 1.46(3H, s), 2.5(3H, s), 3.95(1H, dd, J=6, 8 Hz), 4.03(1H, dd, J=5, 10 Hz), 4.11(1H, dd, J=5, 10 Hz), 4.18(1H, dd, J=6, 8 Hz), 4.49(1H, quint, J=6 Hz), 4.65(2H, s), 4.84(1H, br s), 6.71(1H, d, J=8 Hz), 8.29(1H, d, J=8 Hz).

(14c) 2-(((4-(((4R)-2,2-dimethyl-1,3-dioxolan-4-yl)methoxy)-3-methylpyridin-2-yl)methyl)thio)-1H-benzimidazole

[Formula 119]

To a tetrahydrofuran (dehydrated), (50 ml) solution of the (4-(((4R)-2,2-dimethyl-1,3-dioxolan-4-yl)methoxy)-3-methylpyridin-2-yl)methanol (3.77 g, 14.9 mmol) obtained in the step (14b) and triethylamine (4.15 ml, 29.8 mmol), methanesulfonyl chloride (1.73 ml, 22.4 mmol) was added dropwise under ice-cooling in a nitrogen atmosphere, and the mixture was stirred for 1.5 hours in the same conditions. The reaction mixture was poured into a saturated aqueous solution of sodium hydrogen carbonate and extracted with ethyl acetate. The organic layer was dried over anhydrous magnesium sulfate and the solvent was distilled off. From the obtained residue (3.8 g, the yield of a crude product: 77%), a portion of 1.2 g (3.62 mmol) was taken and dissolved in ethanol (20 ml), and 2-mercaptobenzimidazole (598 mg, 3.98 mmol) was added thereto and the mixture was stirred at room temperature for 14 hours. The reaction mixture was poured into a saturated aqueous solution of the sodium hydrogen carbonate and extracted with ethyl acetate. The organic layer was dried over anhydrous magnesium sulfate, filtered and concentrated. The residue was purified by silica gel column chromatography (NH silica gel, elution solvent: heptane/ ethyl acetate) to obtain the title compound (580 mg, yield: 41.6%) as a light yellow foam.

¹H NMR(400 MHz, CD₃OD) δppm; 1.37(3H, s), 1.39(3H, s), 2.33(3H, s), 3.94(1H, dd, J=6, 8 Hz), 4.19(1H, dd, J=6, 8 Hz), 4.32(1H, dd, J=5, 11Hz), 4.40(1H, dd, J=4, 11Hz), 4.52-4.60(1H, m), 4.75(2H, s), 7.25(2H, dd, J=3, 6 Hz), 7.39(1H, d, J=8 Hz), 7.53(2H, dd, J=3, 6 Hz), 8.47(1H, d, J=8 Hz).

(14d) 2-(((4-(((4R)-2,2-dimethyl-1,3-dioxolan-4-yl)methoxy)-3-methylpyridin-2-yl)methyl)sulfinyl)-1H-benzimidazole

[Formula 120]

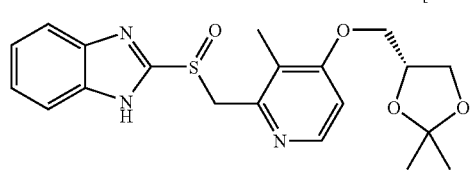

To a toluene-methanol (10:1) (22 ml) solution of the 2-(((4-(((4R)-2,2-dimethyl-1,3-dioxolan-4-yl)methoxy)-3-methylpyridin-2-yl)methyl)thio)-1H-benzimidazole (580 mg, 1.5 mmol) obtained in the step (14c), a toluene-methanol (10:1) (11 ml) solution of 3-chloroperbenzoic acid (353 mg, 1.33 mmol as the content was regarded as 65%) was added dropwise at −50° C. to −60° C. for 5 minutes in a nitrogen atmosphere. The mixture was stirred in the same condition for 3 hours. To the reaction mixture, a saturated aqueous solution of sodium hydrogen carbonate was added and extracted with ethyl acetate. The organic layer was concentrated and the residue was purified by silica gel column chromatography (NH silica gel, elution solvent: ethyl acetate/methanol) to obtain the title compound (330 mg, yield: 54.8%) as a light yellow foam. This compound was converted into a sodium salt in accordance with the operation below and confirmed for the structure thereof.

(14e) 2-(((4-(((4R)-2,2-dimethyl-1,3-dioxolan-4-yl)methoxy)-3-methylpyridin-2-yl)methyl)sulfinyl)-1H-benzimidazole sodium salt

[Formula 121]

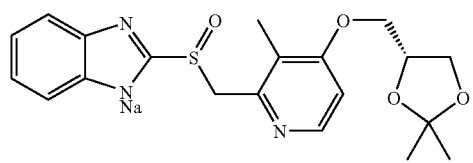

To an ethanol (6 ml) solution of the 2-(((4-(((4R)-2,2-dimethyl-1,3-dioxolan-4-yl)methoxy)-3-methylpyridin-2-yl)methyl)sulfinyl)-1H-benzimidazole (330 mg, 822 μmol) obtained in the step (14d), a 1N aqueous sodium hydroxide solution (822 μl, 822 μmol) was added at room temperature and the mixture was stirred for 30 minutes. After the mixture was concentrated and diethyl ether was added to the residue, the mixture was ultrasonically treated. The generated solid was collected by filtration in a nitrogen atmosphere. The solid was dried under reduced pressure to obtain the title compound (314 mg, yield: 90.2%) as a light yellow solid.

¹H NMR(400 MHz, DMSO-d₆) δppm; 1.30(3H, s), 1.36 (3H, s), 2.19(3H, s), 3.80(1H, dd, J=6, 8 Hz), 4.02-4.14(3H, m), 4.37(1H, d, J=14 Hz), 4.43(1H, quint, J=6 Hz), 4.79(1H, d, J=14 Hz), 6.83(2H, dd, J=3, 6 Hz), 6.93(1H, d, J=6 Hz), 7.42(2H, dd, J=3, 6 Hz), 8.36(1H, d, J=6 Hz).

(14f) Optical isomer (short in retention time) of 2-(((4-(((4R)-2,2-dimethyl-1,3-dioxolan-4-yl)methoxy)-3-methylpyridin-2-yl)methyl)sulfinyl)-1H-benzimidazole

[Formula 122]

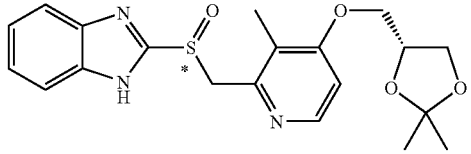

To a toluene (dehydrated)(0.5 ml) and water (1.73 μl, 95.9 μmol) mixed solution of the 2-(((4-(((4R)-2,2-dimethyl-1,3-dioxolan-4-yl)methoxy)-3-methylpyridin-2-yl)methyl)thio)-1H-benzimidazole (84 mg, 218 μmol) obtained in the step (14c), L(+)-diethyl tartrate (32.9 μl, 192 μmol) was added and stirred at 50° C. for 15 minutes in a nitrogen atmosphere. Titanium (IV) isopropoxide (28.3 μl, 95.9 μmol) was added to the reaction mixture and stirred for further one hour. After the reaction mixture was cooled on ice, N,N-diisopropylethylamine (33.4 μl, 192 μmol) was added and cumene hydroperoxide (121 μl, 654 μmol as the content was regarded as 80%) was added dropwise in a nitrogen atmosphere and stirred at 0° C. to room temperature for 17 hours. A saturated aqueous solution of sodium hydrogen carbonate was added to the reaction mixture and the mixture was extracted with ethyl acetate. The organic layer was dried over anhydrous sodium sulfate and the solvent was distilled off under reduced pressure. The residue was purified by silica gel column chromatography (NH silica gel, elution solvent: ethyl acetate/methanol) to obtain the title compound (45 mg, yield: 51.4%) as a light yellow foam. This compound was converted into a sodium salt in accordance with the operation below and confirmed for the structure.

(14g) Sodium salt of an optical isomer (short in retention time) of 2-(((4-(((4R)-2,2-dimethyl-1,3-dioxolan-4-yl)methoxy)-3-methylpyridin-2-yl)methyl)sulfinyl)-1H-benzimidazole

[Formula 123]

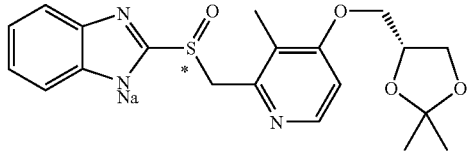

To an ethanol (3 ml) solution of an optical isomer (short in retention time) of 2-(((4-(((4R)-2,2-dimethyl-1,3-dioxolan-4-yl)methoxy)-3-methylpyridin-2-yl)methyl)sulfinyl)-1H-benzimidazole (45 mg, 112 μmol) obtained in the step (14f), a 1N aqueous sodium hydroxide solution (112 μl, 112 mmol) was added at room temperature and the mixture was stirred for 30 minutes. After the mixture was concentrated and diethyl ether was added to the residue, the mixture was ultrasonically treated. The generated solid was collected by filtration in a nitrogen atmosphere. The solid was dried under reduced pressure to obtain the title compound (22 mg, yield: 46.4%) as a light yellow solid.

$^1$H NMR(400 MHz, DMSO-d$_6$) δppm; 1.30(3H, s), 1.35 (3H, s), 2.19(3H, s), 3.80(1H, dd, J=6, 8 Hz), 4.02-4.14(3H, m), 4.37(1H, d, J=13 Hz), 4.42(1H, quint, J=5 Hz), 4.79(1H, d, J=13 Hz), 6.83(2H, dd, J=3, 6 Hz), 6.93(1H, d, J=6 Hz), 7.42(2H, dd, J=3, 6 Hz), 8.26(1H, d, J=6 Hz).

HPLC:

(Conditions) column: CHIRALCEL OD-H (manufactured by Daicel Chemical Industries Ltd.)(0.46 cmφ×25 cm), eluant: hexane/ethanol=4/1 (v/v), flow rate: 0.3 ml/min, Detection: UV (254 nm)

(Analysis results): retention time: 31.6 minutes, diastereomeric excess: 92% de (14h) Optical Isomer (Long in Retention Time) of 2-(((4-(((4R)-2,2-dimethyl-1,3-dioxolan-4-yl)methoxy)-3-methylpyridin-2-yl)methyl)sulfinyl)-1H-benzimidazole

[Formula 124]

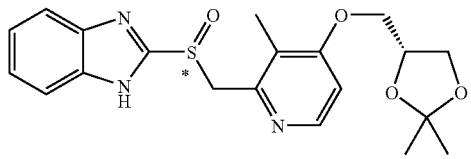

To a toluene (dehydrated)(1.0 ml) and water (3.5 μl, 194 μmol) solution of the 2-(((4-(((4R)-2,2-dimethyl-1,3-dioxolan-4-yl)methoxy)-3-methylpyridin-2-yl)methyl)thio)-1H-benzimidazole (170 mg, 441 μmol) obtained in the step (14c), D-(−)-diethyl tartrate (66.6 μl, 389 μmol) was added and stirred at 50° C. for 15 minutes in a nitrogen atmosphere. To the reaction mixture, titanium (IV) isopropoxide (57.3 μl, 194 μmol) was added and stirred for further one hour. After the reaction mixture was cooled on ice, N,N-diisopropylethylamine (67.6 μl, 389 μmol) was added to the reaction mixture and cumene hydroperoxide (245 μl, 1.32 mmol as the content was regarded as 80%) was added dropwise thereto in a nitrogen atmosphere and the mixture was stirred at 0° C. to room temperature for 17 hours. A saturated aqueous solution of sodium hydrogen carbonate was added to the reaction mixture and extracted with ethyl acetate. After the organic layer was dried over sodium sulfate, the solvent was distilled off under reduced pressure. The residue was purified by silica gel column chromatography (NH silica gel, elution solvent: ethyl acetate/methanol) to obtain the title compound (104 mg, yield: 58.7%) as a light yellow foam. This compound was converted into a sodium salt in accordance with the operations below and confirmed for the structure.

(14i) Sodium Salt of the Optical Isomer (Long in Retention Time) of 2-(((4-(((4R)-2,2-dimethyl-1,3-dioxolan-4-yl)methoxy)-3-methylpyridin-2-yl)methyl)sulfinyl)-1H-benzimidazole

[Formula 125]

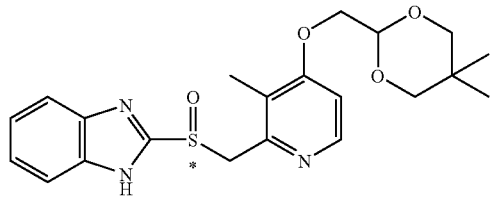

To an ethanol (3 ml) solution of the optical isomer (long in retention time) of 2-(((4-(((4R)-2,2-dimethyl-1,3-dioxolan-4-yl)methoxy)-3-methylpyridin-2-yl)methyl)sulfinyl)-1H-benzimidazole (104 mg, 259 μmol) obtained in the step (14h), a 1N aqueous sodium hydroxide solution (259 μl, 259 μmol) was added at room temperature and the mixture was stirred for 30 minutes. After the mixture was concentrated and diethyl ether was added to the residue, the mixture was ultrasonically treated. The generated solid was collected by filtration in a nitrogen atmosphere. The solid was dried under reduced pressure to obtain the title compound (99 mg, yield: 90%) as a light yellow solid.

$^1$H NMR(400 MHz, DMSO-d$_6$) δppm; 1.30(3H, s), 1.35 (3H, s), 2.19(3H, s), 3.80(1H, dd, J=6, 8 Hz), 4.02-4.14(3H, m), 4.37(1H, d, J=13 Hz), 4.42(1H, quint, J=5 Hz), 4.79(1H, d, J=13 Hz), 6.82-6.88(2H, m), 6.93(1H, d, J=6 Hz), 7.38-7.46(2H, m), 8.26(1H, d, J=6 Hz).

HPLC:

(Conditions) column: CHIRALCEL OD-H (manufactured by Daicel Chemical Industries Ltd.)(0.46 cmφ×25 cm), eluant: hexane/ethanol=4/1 (v/v), flow rate: 0.3 ml/min, Detection: UV (254 nm)

(Analysis results): retention time: 35.9 minutes, diastereomeric excess: 89% de

Example 15

A Sodium Salt of an Optical Isomer (Long in Retention Time) of 2-(((4-((5,5-dimethyl-1,3-dioxan-2-yl)methoxy)-3-methylpyridin-2-yl)methyl)sulfinyl)-1H-benzimidazole

[Formula 126]

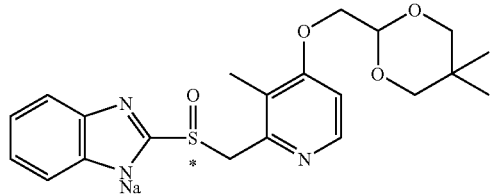

(15a) Optical Isomer (Long in Retention Time) of 2-(((4-((5,5-dimethyl-1,3-dioxan-2-yl)methoxy)-3-methylpyridin-2-yl)methyl)sulfinyl)-1H-benzimidazole

[Formula 127]

A toluene (dehydrated)(2.8 ml)-water (1.4 μl, 0.0777 mmol) suspension of 2-(((4-((5,5-dimethyl-1,3-dioxan-2-yl)methoxy)-3-methylpyridin-2-yl)methyl)thio)-1H-benzimidazole (250 mg, 0.626 mmol) obtained in the same manner as in the steps (1a) to (1e) of Example 1 and D-(−)-diethyl tartrate (47 μl, 0.275 mmol) was stirred at 50° C. for 30 minutes in a nitrogen atmosphere. Toluene (dehydrated)(1.2 ml) was further added to the mixture, which was stirred for 30 minutes in the same conditions. Titanium (IV) isopropoxide (37 μl, 0.125 mmol) was added and the resultant mixture was stirred for one hour in the same conditions. After cooled to room temperature and N,N-diisopropylethylamine (35 μl, 0.201 mmol) was added to the mixture, the resultant mixture was stirred for 10 minutes under ice-cooling. After cumene hydroperoxide (360 μl, 1.95 mmol as the content was regarded as 80%) was added dropwise at an inner temperature of 0° C. to 2° C., for 5 minutes, the mixture was stirred at an inner temperature of 0° C. to 3° C. for 4 hours. After the reaction was terminated by a saturated aqueous solution of sodium hydrogen carbonate, ethyl acetate and water were added thereto. The aqueous layer separated was extracted with ethyl acetate. Organic layers were combined, washed with water, a saturated saline solution, dried over anhydrous sodium sulfate and concentrated. The obtained residue was purified by silica gel column chromatography (NH silica gel, elution solvent: ethyl acetate/methanol=1/0-4/1 gradient). Desired fractions were concentrated to obtain the title compound (203 mg, content: 88.9%, yield: 69.4%) as a light brown foam.

$^1$H NMR(400 MHz, DMSO-d$_6$) δppm; 0.69(3H, s), 1.11 (3H, s), 2.13(3H, s), 3.48(2H, d, J=11 Hz), 3.58(2H, d, J=11 Hz), 4.08(2H, d, J=4 Hz), 4.69(1H, d, J=14 Hz), 4.77(1H, d, J=14 Hz), 4.83(1H, t, J=4 Hz), 6.97(1H, d, J=6 Hz), 7.24-7.32 (2H, m), 7.58-7.67(2H, m), 8.20(1H, d, J=6 Hz).

HPLC:
(Conditions) column: CHIRALCEL OD-H (manufactured by
Daicel Chemical Industries Ltd.)(0.46 cmφ×25 cm),
eluant: hexane/ethanol=4/1 (v/v), flow rate: 0.6 ml/min,
Detection: UV (254 nm)
(Analysis results): retention time: 18.9 minutes,
enantiomeric excess: 87% ee (15b) A Sodium Salt of the Optical Isomer (Long in Retention Time) of 2-(((4-((5,5-dimethyl-1,3-dioxan-2-yl)methoxy)-3-methylpyridin-2-yl)methyl)sulfinyl)-1H-benzimidazole

[Formula 128]

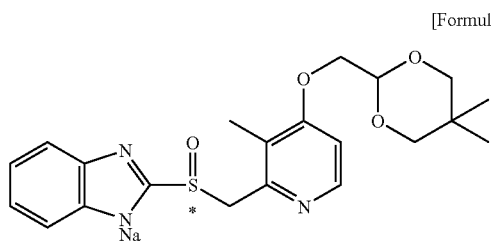

To an ethanol (3 ml) solution of an optical isomer (long in retention time) of the 2-(((4-((5,5-dimethyl-1,3-dioxan-2-yl)methoxy)-3-methylpyridin-2-yl)methyl)sulfinyl)-1H-benzimidazole (200 mg, content: 88.9%, 0.428 mmol) obtained in the step (15a), a 1N aqueous sodium hydroxide solution (428 μl, 0.428 mmol) was added at room temperature and the mixture was stirred for 10 minutes in the same conditions. After the mixture was concentrated and ethanol was added to the residue, the mixture was subjected to azeotropic distillation and suspended with diethyl ether. The suspension was ultrasonically treated and allowed to stand. The supernatant liquid was removed and then the residue was dried to obtain the title compound (145 mg, 77.4% yield) as a light yellow solid.

$^1$H NMR(400 MHz, DMSO-d$_6$) δppm; 0.68(3H, s), 1.11 (3H, s), 2.17(3H, s), 3.48(2H, d, J=11 Hz), 3.58(2H, d, J=11 Hz), 4.06(2H, d, J=4 Hz), 4.37(1H, d, J=13 Hz), 4.80(1H, d, J=13 Hz), 4.83(1H, t, J=4 Hz), 6.81-6.88(2H, m), 6.93(1H, d, J=6 Hz), 7.39-7.46(2H, m), 8.25(1H, d, J=6 Hz).

HPLC:
(Conditions) column: CHIRALCEL OD-H (manufactured by Daicel Chemical Industries Ltd.)(0.46 cmφ×25 cm),
eluant: hexane/ethanol=4/1 (v/v), flow rate: 0.6 ml/min,
Detection: UV (254 nm)
(Analysis results): retention time: 18.4 minutes,
enantiomeric excess: 87.4% ee
specific rotation: α$_D^{25.5}$=−123.83(c=0.5, EtOH)

Example 16

Sodium Salt of Optical Isomer (Short in Retention Time) of 2-(((4-((5,5-dimethyl-1,3-dioxan-2-yl)methoxy)-3-methylpyridin-2-yl)methyl)sulfinyl)-1H-benzimidazole

[Formula 129]

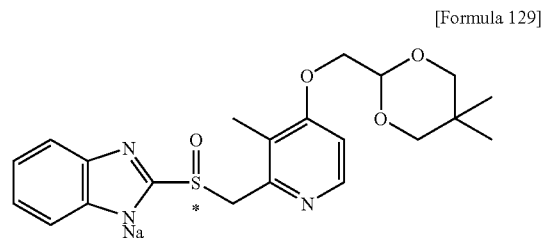

(16a) Optical Isomer (Short in Retention Time) of 2-(((4-((5,5-dimethyl-1,3-dioxan-2-yl)methoxy)-3-methylpyridin-2-yl)methyl)sulfinyl)-1H-benzimidazole

[Formula 130]

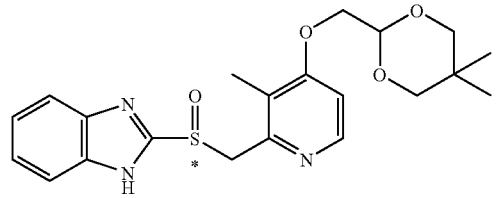

A toluene (dehydrated)(4.0 ml)-water (1.4 μl, 0.0777 mmol) suspension of 2-(((4-((5,5-dimethyl-1,3-dioxan-2-yl)methoxy)-3-methylpyridin-2-yl)methyl)thio)-1H-benzimidazole (250 mg, 0.626 mmol) obtained in the same manner as in the steps (1a) to (1e) of Example 1 and L-(+)-diethyl tartrate (47 μl, 0.274 mmol) was stirred at 50° C. for 10 minutes in a nitrogen atmosphere. Titanium (IV) isopropoxide (37 μl, 0.125 mmol) was added and the resultant mixture was stirred for one hour in the same conditions. After cooled to room temperature N,N-diisopropylethylamine (35 μl, 0.201 mmol) was added to the mixture, and the resultant mixture was stirred for 15 minutes under ice-cooling. After cumene hydroperoxide (360 μl, 1.95 mmol as the content was regarded as 80%) was added dropwise at an inner temperature of 0° C. to 2° C., for 5 minutes, the mixture was stirred at an inner temperature of 0° C. to 3° C. for 4 hours. After the reaction was terminated by a saturated aqueous solution of sodium hydrogen carbonate, ethyl acetate and water were added thereto. The aqueous layer separated was extracted with ethyl acetate. Organic layers were combined, washed with water and a saturated saline solution, dried over anhydrous sodium sulfate and concentrated. The obtained residue was purified by silica gel column chromatography (NH silica gel, elution solvent: ethyl acetate/methanol=1/0-4/1 gradient). Desired fractions were concentrated to obtain the title compound (208 mg, content: 90.9%, yield: 72.7%) as a light brown foam.

$^1$H NMR(400 MHz, DMSO-d$_6$) δppm; 0.69(3H, s), 1.11 (3H, s), 2.13(3H, s), 3.48(2H, d, J=11 Hz), 3.58(2H, d, J=11 Hz), 4.08(2H, d, J=4 Hz), 4.68(1H, d, J=14 Hz), 4.77(1H, d, J=14 Hz), 4.83(1H, t, J=4 Hz), 6.97(1H, d, J=6 Hz), 7.22-7.32 (2H, m), 7.57-7.68(2H, m), 8.20(1H, d, J=6 Hz).

HPLC:
(Conditions) column: CHIRALCEL OD-H (manufactured by
Daicel Chemical Industries Ltd.) (0.46 cmφ×25 cm),
eluant: hexane/ethanol=4/1 (v/v), flow rate: 0.6 ml/min, Detection: UV (254 nm)
(Analysis results): retention time: 15.2 minutes,
enantiomeric excess: 84.2% ee (16b) A Sodium Salt of the Optical Isomer (Short in Retention Time) of 2-(((4-((5,5-dimethyl-1,3-dioxan-2-yl)methoxy)-3-methylpyridin-2-yl)methyl)sulfinyl)-1H-benzimidazole

[Formula 131]

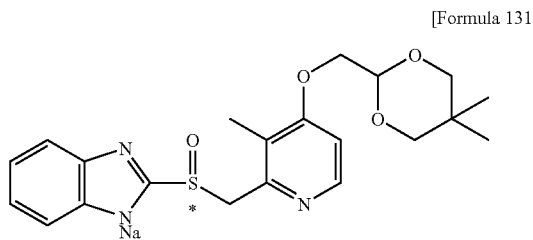

To an ethanol (3 ml) solution of the optical isomer (short in retention time) of the 2-(((4-((5,5-dimethyl-1,3-dioxan-2-yl) methoxy)-3-methylpyridin-2-yl)methyl)sulfinyl)-1H-benzimidazole (206 mg, content: 90.9%, 0.451 mmol) obtained in the step (16a), a 1N aqueous sodium hydroxide solution (451 μl, 0.451 mmol) was added at room temperature and the mixture was stirred for 15 minutes in the same conditions. After the reaction mixture was concentrated and ethanol was added to the residue, the mixture was subjected to azeotropic distillation and suspended with diethyl ether. The suspension was ultrasonically treated and allowed to stand. The supernatant liquid was removed and then the residue was dried to obtain the title compound (126 mg, 63.9% yield) as a light yellow solid.

$^1$H NMR(400 MHz, DMSO-d$_6$) δppm; 0.69(3H, s), 1.11 (3H, s), 2.17(3H, s), 3.48(2H, d, J=11 Hz), 3.58(2H, d, J=11 Hz), 4.06(2H, d, J=4 Hz), 4.36(1H, d, J=13 Hz), 4.81(1H, d, J=13 Hz), 4.83(1H, t, J=4 Hz), 6.79-6.87(2H, m), 6.93(1H, d, J=6 Hz), 7.37-7.46(2H, m), 8.25(1H, d, J=6 Hz).

HPLC:
(Conditions) column: CHIRALCEL OD-H (manufactured by Daicel Chemical Industries Ltd.)(0.46 cmφ×25 cm),
eluant: hexane/ethanol=4/1 (v/v), flow rate: 0.6 ml/min, Detection: UV (254 nm)
(Analysis results): retention time: 15.8 minutes,
enantiomeric excess: 85.0% ee
specific rotation: α$_D$$^{26.3}$=+116.94(c=0.5, EtOH)

Example 17

Sodium Salt of an Optical Isomer (Short in Retention Time) of 2-(((3-methyl-4-(1,5,9-trioxaspiro[5.5]undec-3-ylmethoxy)pyridin-2-yl)methyl)sulfinyl)-1H-benzimidazole sodium salt

[Formula 132]

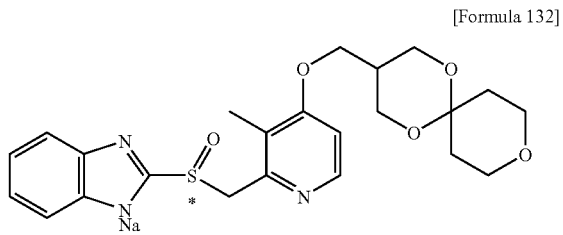

(17a) Optical Isomer (Short in Retention Time) of 2-(((3-methyl-4-(1,5,9-trioxaspiro[5.5]undec-3-ylmethoxy)pyridin-2-yl)methyl)sulfinyl)-1H-benzimidazole

[Formula 133]

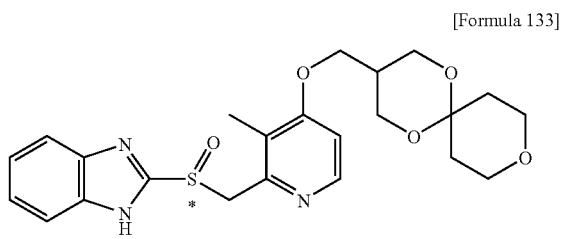

To a toluene (dehydrated)(1.5 ml)-water (1.47 μl, 81.5 μmol) solution of the 2-(((3-methyl-4-(1,5,9-trioxaspiro[5.5] undec-3-ylmethoxy)pyridin-2-yl)methyl)thio)-1H-benzimidazole (300 mg, 679 mmol) separately obtained in the same manner as described in the steps (10a) to (10d) of Example 10, L-(+)-diethyl tartrate (51.2 μl, 299 μmol) was added and the mixture was stirred at 50° C. for 5 minutes in a nitrogen atmosphere. Titanium (IV) isopropoxide (40.1 μl, 136 μmol) was added and the resultant mixture was stirred for further one hour. After cooled on ice and N,N-diisopropylethylamine (37.8 μl, 217 μmol) was added, and cumene hydroperoxide (376 μl, 2.04 mmol as the content was regarded as 80%) was added dropwise in a nitrogen atmosphere, the mixture was stirred at 0° C. to room temperature for 5.5 hours. After a saturated aqueous solution of sodium hydrogen carbonate was added, the reaction mixture was extracted with ethyl acetate. The organic layer was dried over sodium sulfate, the solvent was distilled off under reduced pressure. The obtained residue was purified by silica gel column chromatography (NH silica gel, elution solvent: ethyl acetate/methanol) to obtain the title compound (256 mg, yield: 82.4%) as a light yellow foam.

$^1$H NMR(400 MHz, CDCl$_3$) δppm; 1.85(2H, t, J=5 Hz), 2.01(2H, t, J=5 Hz), 2.12-2.21(1H, m), 2.21(3H, s), 3.66-3.78 (4H, m), 3.86(2H, dd, J=4, 12 Hz), 4.06-4.24(4H, m), 4.64

(1H, d, J=14 Hz), 4.83(1H, d, J=14 Hz), 6.77(1H, d, J=6 Hz), 7.26-7.40(2H, m), 7.50-7.80(2H, br), 8.32(1H, d, J=6 Hz).

(17b) A Sodium Salt of the Optical Isomer (Short in Retention Time) of 2-(((3-methyl-4-(1,5,9-trioxaspiro[5.5]undec-3-ylmethoxy)pyridin-2-yl)methyl)sulfinyl)-1H-benzimidazole

[Formula 134]

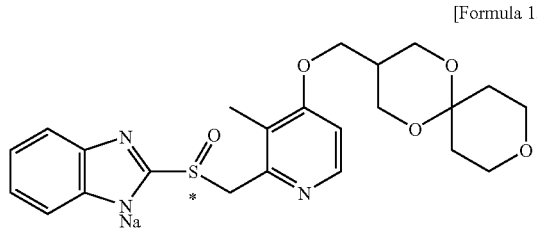

To an ethanol (10 ml) solution of the optical isomer (short in retention time) of 2-(((3-methyl-4-(1,5,9-trioxaspiro[5.5]undec-3-ylmethoxy)pyridin-2-yl)methyl)sulfinyl)-1H-benzimidazole (256 mg, 599 μmol) obtained in the step (17a), a 1N aqueous sodium hydroxide solution (559 μl, 559 μmol) was added at room temperature, which was stirred for 30 minutes. After the mixture was concentrated and diethyl ether was added to the residue, the mixture was ultrasonically treated. The generated solid was collected by filtration in a nitrogen atmosphere. The solid was dried under reduced pressure to obtain the title compound (147 mg, yield: 54.8%) as a light yellow solid.

$^1$H NMR(400 MHz, DMSO-$d_6$) δppm; 1.74-1.86(4H, m), 2.08-2.23(1H, m), 2.18(3H, s), 3.50-3.62(4H, m), 3.76-3.84 (2H, m), 4.02(2H, dd, J=4, 12 Hz), 4.11(2H, d, J=7 Hz), 4.37(1H, d, J=13 Hz), 4.81(1H, d, J=13 Hz), 6.80-6.92(2H, m), 6.93(1H, d, J=6 Hz), 7.38-7.48(2H, m), 8.25(1H, d, J=6 Hz).

HPLC:

(Conditions) column: CHIRALCEL OD-H (manufactured by

Daicel Chemical Industries Ltd.)(0.46 cmφ×25 cm), eluant: hexane/ethanol=4/1 (v/v), flow rate: 0.6 ml/min, Detection: UV (254 nm)

(Analysis results): retention time: 29.6 minutes, enantiomeric excess: 85.8% ee

Example 18

Sodium Salt of an Optical Isomer (Long in Retention Time) of 2-(((3-methyl-4-(1,5,9-trioxaspiro[5.5]undec-3-ylmethoxy)pyridin-2-yl)methyl)sulfinyl)-1H-benzimidazole

[Formula 135]

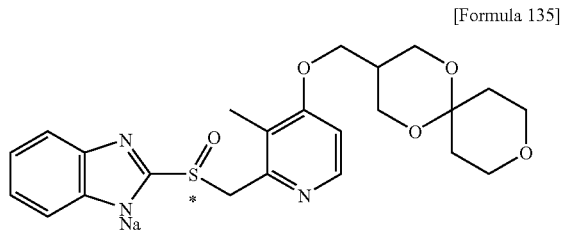

(18a) Optical Isomer (Long in Retention Time) of 2-(((3-methyl-4-(1,5,9-trioxaspiro[5.5]undec-3-ylmethoxy)pyridin-2-yl)methyl)sulfinyl)-1H-benzimidazole

[Formula 136]

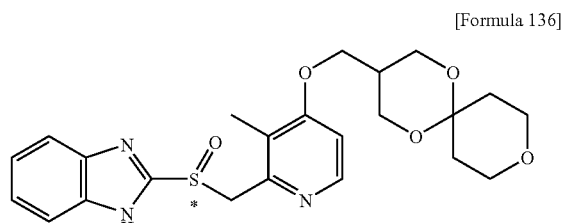

To a toluene (dehydrated)(1.5 ml)-water (1.35 μl, 74.8 μmol) solution of 2-(((3-methyl-4-(1,5,9-trioxaspiro[5.5]undec-3-ylmethoxy)pyridin-2-yl)methyl)thio)-1H-benzimidazole (150 mg, 340 mmol), which was separately obtained in the same manner as described in the steps (10a) to (10d) of Example 10, D-(−)-diethyl tartrate (51.2 μl, 299 μmol) was added and the mixture was stirred at 50° C. for 5 minutes in a nitrogen atmosphere. Titanium (IV) isopropoxide (44.2 μl, 150 μmol) was added and the resultant mixture was stirred for further one hour. After the mixture was cooled on ice, N,N-diisopropylethylamine (39.1 μl, 224 μmol) was added, and cumene hydroperoxide (188 μl, 1.02 mmol as the content was regarded as 80%) was added dropwise in a nitrogen atmosphere, the mixture was stirred at 0° C. to room temperature for 7 hours. After a saturated aqueous solution of sodium hydrogen carbonate was added to the reaction mixture, the reaction mixture was extracted with ethyl acetate. The organic layer was dried over sodium sulfate, the solvent was distilled off under reduced pressure. The obtained residue was purified by silica gel column chromatography (NH silica gel, elution solvent: ethyl acetate/methanol) to obtain the title compound (68 mg, yield: 43.7%) as a light yellow foam.

$^1$H NMR(400 MHz, CDCl$_3$) δppm; 1.85(2H, t, J=5 Hz), 2.01(2H, t, J=5 Hz), 2.12-2.22(1H, m), 2.21(3H, s), 3.66-3.78 (4H, m), 3.89(2H, dd, J=4, 12 Hz), 4.06-4.26(4H, m), 4.65 (1H, d, J=14 Hz), 4.83(1H, d, J=14 Hz), 6.79(1H, d, J=6 Hz), 7.28-7.42(2H, m), 7.50-7.80(2H, br), 8.33(1H, d, J=6 Hz).

(18b) Sodium Salt of the Optical Isomer (Long in Retention Time) of 2-(((3-methyl-4-(1,5,9-trioxaspiro[5.5]undec-3-ylmethoxy)pyridin-2-yl)methyl)sulfinyl)-1H-benzimidazole

[Formula 137]

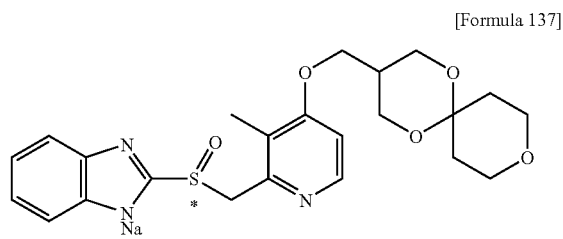

To an ethanol (10 ml) solution of the optical isomer (long retention time) of the 2-(((3-methyl-4-(1,5,9-trioxaspiro[5.5]undec-3-ylmethoxy)pyridin-2-yl)methyl)sulfinyl)-1H-benzimidazole (68 mg, 149 μmol) obtained in the step (18a), a 1N aqueous sodium hydroxide solution (149 μl, 149 μmol) was added at room temperature, which was stirred for 30 minutes. After the mixture was concentrated and diethyl ether was added to the residue, the mixture was ultrasonically treated. The resultant solid was collected by filtration in a nitrogen atmosphere. The solid was dried under reduced pressure to obtain the title compound (36 mg, yield: 54.8%) as a light yellow solid.

$^1$H NMR(400 MHz, DMSO-d$_6$) δppm; 1.77(2H, t, J=6 Hz), 1.83(2H, t, J=6 Hz), 2.08-2.23(1H, m), 2.17(3H, s), 3.50-3.60(4H, m), 3.76-3.86(2H, m), 4.02(2H, dd, J=4, 12 Hz), 4.11(2H, d, J=7 Hz), 4.37(1H, d, J=13 Hz), 4.81(1H, d, J=13 Hz), 6.85(2H, dd, J=3, 6 Hz), 6.93(1H, d, J=6 Hz), 7.42(1H, dd, J=3, 6 Hz), 8.26(1H, d, J=6 Hz).

HPLC:

(Conditions) column: CHIRALCEL OD-H (manufactured by Daicel Chemical Industries Ltd.)(0.46 cmφ×25 cm), eluant: hexane/ethanol=4/1 (v/v), flow rate: 0.6 ml/min, Detection: UV (254 nm)

(Analysis results): retention time: 36.7 minutes, enantiomeric excess: 36% ee

Example 19

Sodium Salt of an Optical Isomer (Long in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 138]

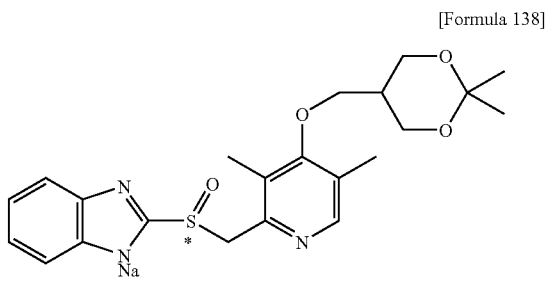

(19a) Optical Isomer (Long in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 139]

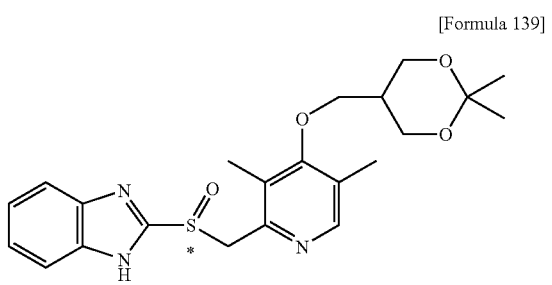

A toluene (dehydrated)(2.22 ml)-water (2.3 μl, 0.128 mmol) solution of the 2-(((4-((2,2-dimethyl-1,3-dioxan-5-yl)methoxy)-3,5-dimethylpyridin-2-yl)methyl)thio)-1H-benzimidazole (444 mg, 1.07 mmol) separately obtained in the same manner as described in the steps (11a) to (11g) of Example 11 and D-(−)-diethyl tartrate (80.6 μl, 0.471 mmol) was stirred at 50° C. for 10 minutes in a nitrogen atmosphere. Titanium (IV) isopropoxide (63.2 μl, 0.214 mmol) was added and the resultant mixture was stirred for further one hour in the same conditions. After the mixture was cooled to room temperature and N,N-diisopropylethylamine (59.6 μl, 0.342 mmol) was added, the resultant mixture was cooled to 0° C. After cumene hydroperoxide (611 μl, 3.31 mmol as the content was regarded as 80%) was added dropwise for 5 minutes at 0° C. to 2° C., the mixture was stirred at 0° C. to 7° C. for 3 hours and 35 minutes in an nitrogen atmosphere. After a saturated aqueous solution of sodium hydrogen carbonate was added to the reaction mixture, the mixture was extracted with ethyl acetate. The organic layer was dried over anhydrous sodium sulfate, filtered, and concentrated. The residue was purified by silica gel column chromatography (NH silica gel: 20 g, elution solvent: dichloromethane, dichloromethane/methanol=20/1). The fractions containing the title compound were collected with ethyl acetate and concentrated to obtain the title compound (388 mg, yield: 84.4%) as a colorless foam.

$^1$H NMR(400 MHz, DMSO-d$_6$) δppm; 1.32(3H, s), 1.36 (3H, s), 2.02-2.13(1H, m), 2.16(3H, s), 2.20(3H, s), 3.74-3.85 (4H, m), 4.00(2H, dd, J=4, 12 Hz), 4.70(1H, d, J=14 Hz), 4.79(1H, d, J=14 Hz), 7.26-7.34(2H, m), 7.59-7.70(2H, m), 8.18(1H, s).

HPLC:

(Conditions) column: CHIRALPAK AD-H (manufactured by Daicel Chemical Industries Ltd.)(0.46 cmφ×25 cm), eluant: hexane/ethanol=1/1 (v/v), flow rate: 0.6 ml/mm, Detection: UV (254 nm)

(Analysis results): retention time: 17.8 minutes, enantiomer excess: 94.4% ee (19b) Sodium Salt of the Optical Isomer (Long in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 140]

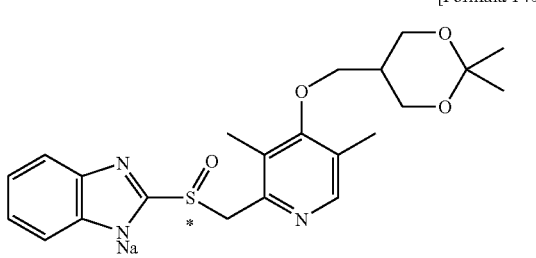

To an ethanol (10 ml) solution of the optical isomer (long in retention time) of the 2-(((4-((2,2-dimethyl-1,3-dioxan-5-yl)methoxy)-3,5-dimethylpyridin-2-yl)methyl)sulfinyl)-1H-benzimidazole (379 mg, 0.882 mmol) obtained in the step (19a), a 1N aqueous sodium hydroxide solution (878 μl, 0.882 mmol as the concentration was regarded as 1.004M) was added at room temperature and the mixture was concentrated. The residue was subjected to azeotropic distillation with ethanol. The residue was suspended in diethyl ether, ultrasonically treated, concentrated to obtain the title compound (365 mg, yield: 91.7%) as a white solid.

$^1$H NMR(400 MHz, DMSO-d$_6$) δppm; 1.33(3H, s), 1.36 (3H, s), 2.03-2.13(1H, m), 2.20(3H, s), 2.21(3H, s), 3.76-3.88

(4H, m), 4.00(2H, dd, J=4, 12 Hz), 4.38(1H, d, J=13 Hz), 4.75(1H, d, J=13 Hz), 6.81-6.90(2H, m), 7.40-7.47(2H, m), 8.23(1H, s).

HPLC:

(Conditions) column: CHIRALPAK AD-H (manufactured by Daicel Chemical Industries Ltd.)(0.46 cmφ×25 cm), eluant: hexane/ethanol=1/1 (v/v), flow rate: 0.6 ml/min, Detection: UV (254 nm)

(Analysis results): retention time: 17.0 minutes, enantiomer excess: 94.9% ee specific rotation: $\alpha_D^{27.4}$=−76.29(c=0.5, EtOH)

Example 20

Sodium Salt of an Optical Isomer (Short in Retention Time) of 2-(((4-(2,2-dimethyl-1,3-dioxan-5-yl)methoxy-3,5-dimethylpyridin-2-yl)methyl)sulfinyl)-1H-benzimidazole

[Formula 141]

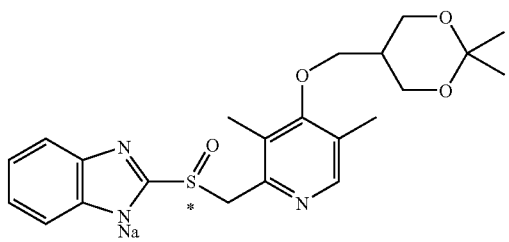

(20a) Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 142]

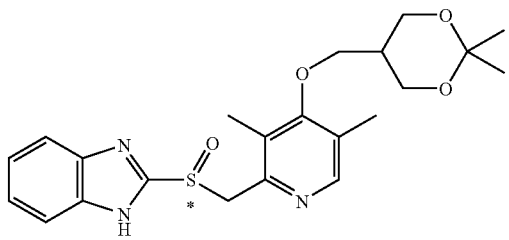

A toluene (dehydrated)(2.96 ml)-water (3.09 μl, 0.172 mmol) solution of the 2-(((4-((2,2-dimethyl-1,3-dioxan-5-yl)methoxy)-3,5-dimethylpyridin-2-yl)methyl)thio)-1H-benzimidazole (591 mg, 1.43 mmol) separately obtained in the same manner as described in the steps (11a) to (11g) of Example 11 and L-(+)-diethyl tartrate (108 μl, 0.629 mmol) was stirred at 50° C. for 5 minutes in a nitrogen atmosphere. Titanium (IV) isopropoxide (84.4 μl, 0.286 mmol) was added and the resultant mixture was stirred for one hour in the same conditions. After the mixture was cooled to room temperature and N,N-diisopropylethylamine (79.7 μl, 0.458 mmol) was added, the resultant mixture was cooled to 0° C. After cumene hydroperoxide (816 μl, 4.42 mmol as the content was regarded as 80%) was added dropwise for 10 minutes at 0° C. to 1° C., the mixture was stirred for 3 hours and 10 minutes in the same conditions. After a saturated aqueous solution of sodium hydrogen carbonate was added to the reaction mixture, the mixture was extracted with ethyl acetate. The organic layer was dried over anhydrous sodium sulfate, filtered, and concentrated. The residue was purified by silica gel column chromatography (NH silica gel: 20 g, elution solvent: dichloromethane, dichloromethane/methanol=20/1). The fractions containing the title compound were collected with ethyl acetate and concentrated to obtain the title compound (498 mg, yield: 81.1%) as a colorless foam.

$^1$H NMR(400 MHz, DMSO-d$_6$) δppm; 1.32(3H, s), 1.36 (3H, s), 2.02-2.12(1H, m), 2.16(3H, s), 2.20(3H, s), 3.74-3.84 (4H, m), 4.00(2H, dd, J=4, 12 Hz), 4.70(1H, d, J=14 Hz), 4.79(1H, d, J=14 Hz), 7.26-7.34(2H, m), 7.58-7.70(2H, m), 8.18(1H, s).

HPLC:

(Conditions) column: CHIRALPAK AD-H (manufactured by Daicel Chemical Industries Ltd.)(0.46 cmφ×25 cm), eluant: hexane/ethanol=1/1 (v/v), flow rate: 0.6 ml/min, Detection: UV (254 nm)

(Analysis results): retention time: 14.6 minutes, enantiomer excess: 95.4% ee (20b) Sodium Salt of the Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 143]

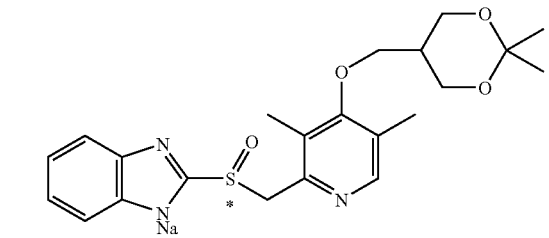

To an ethanol (10 ml) solution of the optical isomer (short in retention time) of the 2-(((4-((2,2-dimethyl-1,3-dioxan-5-yl)methoxy)-3,5-dimethylpyridin-2-yl)methyl)sulfinyl)-1H-benzimidazole (480 mg, 1.12 mmol) obtained in the step (20a), a 1N aqueous sodium hydroxide solution (1.12 ml, 1.12 mmol as the concentration was regarded as 1.004M) was added at room temperature and the mixture was concentrated. The residue was subjected to azeotropic distillation with ethanol. The residue was suspended in diethyl ether, the suspension was ultrasonically treated, concentrated to obtain the title compound (447 mg, yield: 88.4%) as a white solid.

$^1$H NMR(400 MHz, DMSO-d$_6$) δppm; 1.33(3H, s), 1.36 (3H, s), 2.03-2.14(1H, m), 2.21(6H, s), 3.76-3.87(4H, m), 4.00(2H, dd, J=4, 12 Hz), 4.39(1H, d, J=13 Hz), 4.74(1H, d, J=13 Hz), 6.82-6.90(2H, m), 7.40-7.48(2H, m), 8.23(1H, s).

HPLC:

(Conditions) column: CHIRALPAK AD-H (manufactured by Daicel Chemical Industries Ltd.)(0.46 cmφ×25 cm), eluant: hexane/ethanol=1/1 (v/v), flow rate: 0.6 ml/min, Detection: UV (254 nm)

(Analysis results): retention time: 14.4 minutes, enantiomeric excess: 95.4% ee

Example 21

2-(((4-(6,10-dioxaspiro[4.5]dec-8-ylmethoxy)-3-methylpyridin-2-yl)methyl)sulfinyl)-1H-benzimidazole sodium salt

[Formula 144]

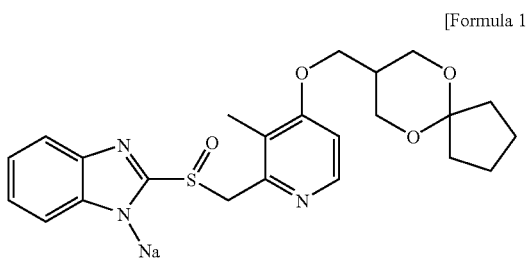

(21a) 6,10-dioxaspiro[4.5]dec-8-ylmethanol

[Formula 145]

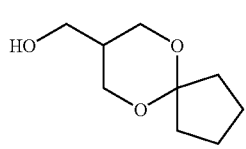

The same procedure as in the step (7a) of Example 7 was repeated using 2-(hydroxymethyl)-1,3-propanediol and cyclopentanone to obtain the title compound (2.8 g, yield: 87%) as yellow oil.

$^1$H NMR(400 MHz, CDCl$_3$) δppm; 1.51-1.55(1H, m), 1.62-1.72(4H, m), 1.83-1.94(4H, m), 3.73-3.80(4H, m), 3.99 (2H, dd, J=4, 12 Hz).

(21b) 2-(((4-(6,10-dioxaspiro[4.5]dec-8-ylmethoxy)-3-methylpyridin-2-yl)methyl)sulfinyl)-1H-benzimidazole sodium salt

[Formula 146]

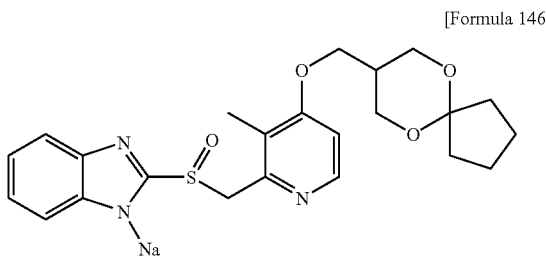

The same procedure as in the steps (6b) to (6f) of Example 6 was repeated using 6,10-dioxaspiro[4.5]dec-8-ylmethanol obtained in the step (21a) to obtain the title compound (180 mg, total yield: 8.1%) as a light yellow solid.

$^1$H NMR(400 MHz, DMSO-d$_6$) δppm; 1.52-1.62(4H, m), 1.75-1.86(4H, m), 2.08-2.16(1H, m), 2.17(3H, s), 3.72-3.82 (2H, m), 3.92-4.02(2H, m), 4.09(2H, d, J=7 Hz), 4.36(1H, d, J=13 Hz), 4.80(1H, d, J=13 Hz), 6.83(2H, dd, J=3, 6 Hz), 6.93(1H, d, J=6 Hz), 7.42(2H, dd, J=3, 6 Hz), 8.27(1H, d, J=6 Hz).

Example 22

2-(((4-(5,9-dioxaspiro[3.5]non-7-ylmethoxy)-3-methylpyridin-2-yl)methyl)sulfinyl)-1H-benzimidazole sodium salt

[Formula 147]

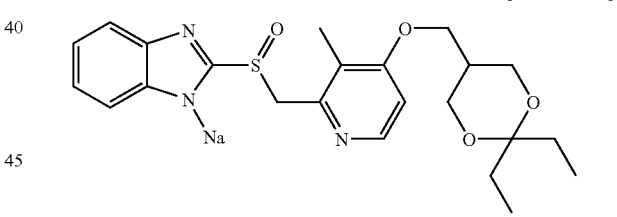

The same procedure as in the steps (21a) and (21b) of Example 21 was repeated using 2-(hydroxymethyl)-1,3-propanediol and cyclobutanone to obtain the title compound (265 mg, total yield: 6.2%) as a light yellow solid.

$^1$H NMR(400 MHz, DMSO-d$_6$) δppm; 1.58-1.70(2H, m), 2.06-2.22(5H, m), 2.17(3H, s), 3.66-3.76(2H, m), 3.86-3.96 (2H, m), 4.07(2H, d, J=6 Hz), 4.37(1H, d, J=13 Hz), 4.79(1H, d, J=13 Hz), 6.85(2H, dd, J=3, 6 Hz), 6.93(1H, d, J=6 Hz), 7.44(2H, dd, J=3, 6 Hz), 8.26(1H, d, J=6 Hz).

Example 23

2-(((4-((2,2-diethyl-1,3-dioxan-5-yl)methoxy)-3-methylpyridin-2-yl)methyl)sulfinyl)-1H-benzimidazole sodium salt

[Formula 148]

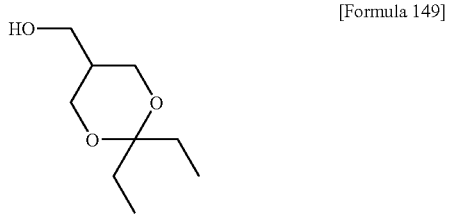

(23a) (2,2-diethyl-1,3-dioxan-5-yl)methanol

[Formula 149]

The same procedure as in the step (7a) of Example 7 was repeated using 2-(hydroxymethyl)-1,3-propanediol, and 3-pentanone to obtain the title compound (1.5 g, yield: 46%) as a light yellow oil.

¹H NMR(400 MHz, CDCl₃) δppm; 0.87(3H, t, J=7 Hz), 0.88(3H, t, J=7 Hz), 1.46-1.51(1H, m), 1.70(2H, q, J=7 Hz), 1.78(2H, q, J=7 Hz), 3.70-3.88(4H, m), 3.96-4.10(2H, m).

(23b) 2-(((4-((2,2-diethyl-1,3-dioxan-5-yl)methoxy)-3-methylpyridin-2-yl)methyl)sulfinyl)-1H-benzimidazole sodium salt

[Formula 150]

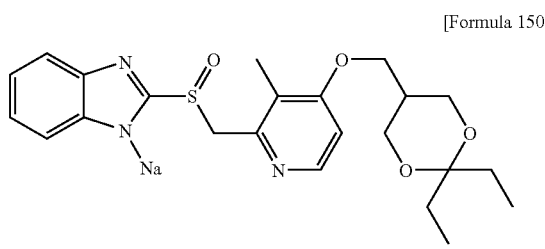

The same procedure as in the steps (6b) to (6f) of Example 6 was repeated using (2,2-diethyl-1,3-dioxan-5-yl)methanol obtained in the step (23a) to obtain the title compound (164 mg, total yield: 9.7%) as a light yellow solid.

¹H NMR(400 MHz, DMSO-d₆) δppm; 0.80(6H, t, J=7 Hz), 1.63(2H, q, J=7 Hz), 1.70(2H, q, J=7 Hz), 2.01-2.12(1H, m), 2.18(3H, s), 3.50-3.80(2H, m), 3.94-4.20(2H, m), 4.12 (2H, d, J=7 Hz), 4.37(1H, d, J=13 Hz), 4.81(1H, d, J=13 Hz), 6.84(2H, dd, J=3, 6 Hz), 6.92(1H, d, J=6 Hz), 7.42(2H, dd, J=3, 6 Hz), 8.26(1H, d, J=6 Hz).

Example 24

2-(((3-methyl-4-((1-methyl-2,6,7-trioxabicyclo[2.2.2]oct-4-yl)methoxy)pyridin-2-yl)methyl)sulfinyl)-1H-benzimidazole sodium salt

[Formula 151]

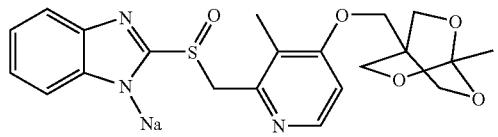

(24a) (1-methyl-2,6,7-trioxabicyclo[2.2.2]oct-4-yl)methanol

[Formula 152]

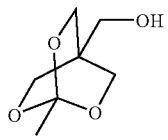

A mixture of pentaerythritol (15 g, 110 mmol), triethyl orthoacetate (20.2 ml, 110 mmol), and p-toluenesulfonic acid monohydrate (947 mg, 5.5 mmol) was stirred at 100° C. for 30 minutes. The temperature of the mixture was further raised to 130° C. and the mixture was stirred for 30 minutes. To the reaction mixture, triethylamine (1.53 ml, 11 mmol) was added and the reaction mixture was concentrated. The residue was purified by silica gel column chromatography (elution solvent: heptane/ethyl acetate) to obtain the title compound (8.5 g, yield: 48.2%) as a light yellow solid.

¹H NMR(400 MHz, CDCl₃) δppm; 1.47(3H, s), 3.46(2H, d, J=4 Hz), 4.02(6H, s).

(24b) 2,3-dimethyl-4-((1-methyl-2,6,7-trioxabicyclo[2.2.2]oct-4-yl)methoxy)pyridine 1-oxide

[Formula 153]

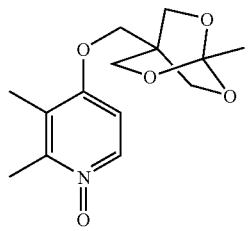

To a dimethylsulfoxide solution (30 ml) of the (1-methyl-2,6,7-trioxabicyclo[2.2.2]oct-4-yl)methanol (4.5 g, 28.1 mmol) obtained in the step (24a), sodium hydride, in oil (1.29 g, 29.5 mmol as the content was regarded as 55%) was added at room temperature. To the mixture, 4-chloro-2,3-dimethylpyridine 1-oxide (3.99 g, 25.3 mmol) was added, which was stirred at 60° C. for 3 hours. After cooled to room temperature, the reaction mixture was concentrated under reduced pressure. The residue was purified by silica gel column chromatography (elution solvent: ethyl acetate/methanol) to obtain the title compound (7.46 g, yield: 81%) as a yellow oil.

¹H NMR(400 MHz, CDCl₃) δppm; 1.50(3H, s), 2.20(3H, s), 2.54(3H, s), 3.77(2H, s), 4.15(6H, s), 6.53(1H, d, J=6 Hz), 8.14(1H, d, J=6 Hz).

(24c) (3-methyl-4-((1-methyl-2,6,7-trioxabicyclo[2.2.2]oct-4-yl)methoxy)pyridin-2-yl)methanol

[Formula 154]

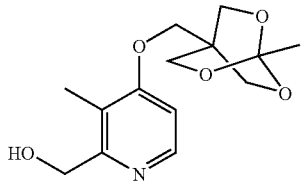

A mixture of 2,3-dimethyl-4-((1-methyl-2,6,7-trioxabicyclo[2.2.2]oct-4-yl)methoxy)pyridine 1-oxide (6.4 g, 22.8 mmol) obtained in the step (24b) and acetic anhydride (20 ml) was stirred at 80° C. for one hour. After cooled to room temperature, the reaction mixture was concentrated under reduced pressure. To the residue, methanol (30 ml) and a 5N aqueous sodium hydroxide solution (10 ml) was added and the mixture was stirred at room temperature for 15 hours. The reaction mixture was concentrated and ethyl acetate was added to the residue. The mixture was washed with a saturated saline solution. The organic layer was dried over anhydrous magnesium sulfate, filtrated, and concentrated. The resultant residue (solid) was washed with diethyl ether and collected by filtration to obtain the title compound (1.5 g, yield: 28.7%) as a yellow solid.

¹H NMR(400 MHz, CDCl₃) δppm; 1.50(3H, s), 2.04(3H, s), 3.80(2H, s), 4.15(6H, s), 4.65(2H, s), 4.77(1H, br s), 6.60 (1H, d, J=6 Hz), 8.29(1H, d, J=6 Hz).

(24d) 2-(((3-methyl-4-((1-methyl-2,6,7-trioxabicyclo[2.2.2]oct-4-yl)methoxy)pyridin-2-yl)methyl)thio)-1H-benzimidazole

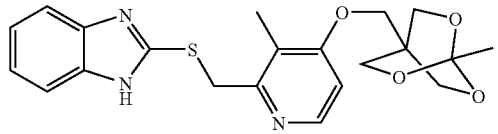

[Formula 155]

To a tetrahydrofuran (dehydrated, 20 ml) solution of the (3-methyl-4-((1-methyl-2,6,7-trioxabicyclo[2.2.2]oct-4-yl)methoxy)pyridin-2-yl)methanol (0.37 g, 1.32 mmol) obtained in the step (24c) and triethylamine (0.368 ml, 2.64 mmol), methanesulfonyl chloride (153 μl, 1.98 mmol) was added dropwise in a nitrogen atmosphere at 1° C. to 4° C. The resultant mixture was stirred under the same conditions for 1.5 hours. Further, 2-mercaptobenzimidazole (204 mg, 1.52 mmol) was added to the mixture and stirred at room temperature for 18 hours. After the reaction mixture was concentrated, the residue was purified by silica gel column chromatography (elution solvent: ethyl acetate/methanol) to obtain the title compound (230 mg, yield: 40.9%) as a light yellow foam.

$^1$H NMR(400 MHz, CDCl$_3$) δppm; 1.50(3H, s), 2.27(3H, s), 3.80(2H, s), 4.15(6H, s), 4.38(2H, s), 6.65(1H, d, J=6 Hz), 7.15-7.21(2H, m), 7.36-7.68(2H, m), 8.35(1H, d, J=6 Hz).

(24e) 2-(((3-methyl-4-((1-methyl-2,6,7-trioxabicyclo[2.2.2]oct-4-yl)methoxy)pyridin-2-yl)methyl)sulfinyl)-1H-benzimidazole

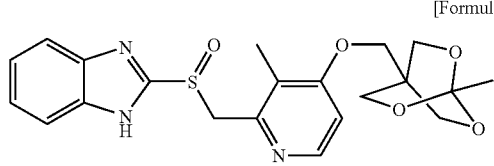

[Formula 156]

To a toluene-methanol (10:1) solution (20 ml) of the 2-(((3-methyl-4-((1-methyl-2,6,7-trioxabicyclo[2.2.2]oct-4-yl)methoxy)pyridin-2-yl)methyl)thio)-1H-benzimidazole (230 mg, 556 μmol) obtained in the step (24d), a toluene-methanol (10:1) solution (5 ml) of 3-chloroperbenzoic acid (133 mg, 0.5 mmol as the content was regarded as 65%) was added dropwise in a nitrogen atmosphere at −50° C. to −60° C. for 5 minutes and the mixture was stirred under the same conditions for 3.5 hours. To the reaction mixture, a saturated aqueous sodium hydrogen carbonate solution was added, which was extracted with ethyl acetate. The organic layer was dried over anhydrous sodium sulfate, filtrated and concentrated. The residue was purified by silica gel column chromatography (NH silica gel, elution solvent: ethyl acetate/methanol) to obtain the title compound (143 mg, yield: 59.9%) as light a yellow foam.

$^1$H NMR(400 MHz, CDCl$_3$) δppm; 1.50(3H, s), 2.17(3H, s), 3.76(2H, s), 4.12(6H, s), 4.63(1H, d, J=14 Hz), 4.79(1H, d, J=14 Hz), 6.60(1H, d, J=6 Hz), 7.30-7.38(2H, m), 7.47-7.56 (1H, m), 7.76-7.86(1H, m), 8.30(1H, d, J=6 Hz), 11.05(1H, br s).

(24f) 2-(((3-methyl-4-((1-methyl-2,6,7-trioxabicyclo[2.2.2]oct-4-yl)methoxy)pyridin-2-yl)methyl)sulfinyl)-1H-benzimidazole sodium salt

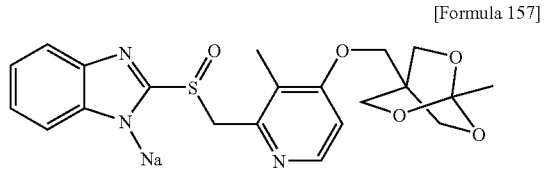

[Formula 157]

To an ethanol (5 ml) solution of the 2-(((3-methyl-4-((1-methyl-2,6,7-trioxabicyclo[2.2.2]oct-4-yl)methoxy)pyridin-2-yl)methyl)sulfinyl)-1H-benzimidazole (143 mg, 333 μmol) obtained in the step (24e), a 1N aqueous sodium hydroxide solution (333 μl, 333 μmol) was added at room temperature and the mixture was stirred for 0.5 hours. The mixture was concentrated and the residue was dissolved in ethanol. Thereafter, diethyl ether was added to the solution, and sonicated. The generated solid was filtrated in a nitrogen atmosphere and dried under reduced pressure to obtain the title compound (150 mg, yield: 100%) as a light yellow solid.

$^1$H NMR(400 MHz, DMSO-d$_6$) δppm; 1.33(3H, s), 2.19 (3H, s), 3.92(2H, s), 4.04(6H, s), 4.35(1H, d, J=15 Hz), 4.82 (1H, d, J=15 Hz), 6.82-6.87(3H, m), 7.42(2H, dd, J=3, 6 Hz), 8.26(1H, d, J=6 Hz).

Example 25

2-(((4-(1,5-dioxaspiro[5.5]undec-3-ylmethoxy)-3-methylpyridin-2-yl)methyl)sulfinyl)-1H-benzimidazole sodium salt

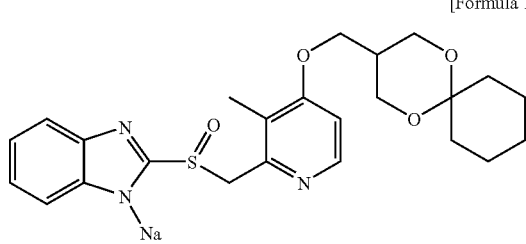

[Formula 158]

(25a) 1,5-dioxaspiro[5.5]undec-3-ylmethanol

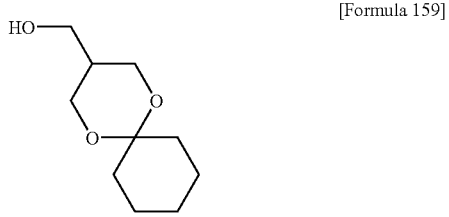

[Formula 159]

The same procedure as in the step (1a) of Example 1 was repeated using 2-(hydroxymethyl)-1,3-propanediol and cyclohexanone to obtain the title compound (2.26 g, yield: 65%) as a light yellow oil.

¹H NMR(400 MHz, CDCl₃) δppm; 1.37-1.46(2H, m), 1.47-1.57(4H, m), 1.68-1.76(2H, m), 1.77-1.90(3H, m), 3.74-3.81(4H, m), 4.02(2H, dd, J=4, 12 Hz).

(25b) 2-(((4-(1,5-dioxaspiro[5.5]undec-3-yl-methoxy)-3-methylpyridin-2-yl)methyl)sulfinyl)-1H-benzimidazole sodium salt

[Formula 160]

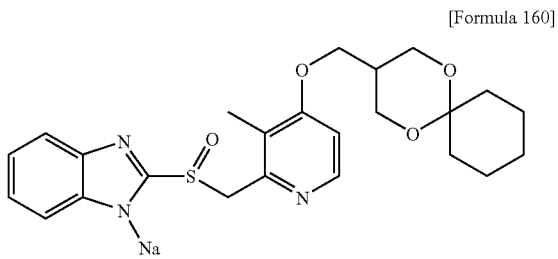

The same procedure as in the steps (6b) to (6f) of Example 6 was repeated using 1,5-dioxaspiro[5.5]undec-3-ylmethanol obtained in the step (25a) to obtain the title compound (125 mg, total yield: 8.4%) as a light yellow solid.

¹H NMR(400 MHz, DMSO-d₆) δppm; 1.30-1.48(6H, m), 1.64-1.76(4H, m), 2.06-2.15(1H, m), 2.18(3H, s), 3.73-3.82 (2H, m) 3.96-4.03(2H, m), 4.11(2H, d, J=7 Hz), 4.44(1H, d, J=13 Hz), 4.81(1H, d, J=13 Hz), 6.90-6.98(3H, m), 7.47(2H, dd, J=3, 6 Hz), 8.25(1H, d, J=6 Hz).

Example 26

2-(((4-((2,2-dimethyl-1,3-dioxan-5-yl)oxy)-3-methylpyridin-2-yl)methyl)sulfinyl)-1H-benzimidazole sodium salt

[Formula 161]

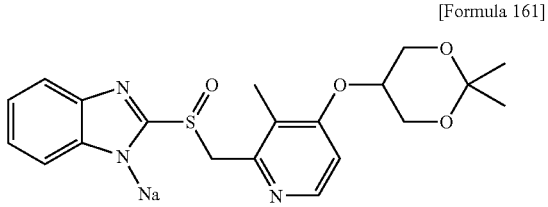

The same procedure as in the steps (6d), (6e), and (6f) of Example 6 was repeated using 2,2-dimethyl-1,3-dioxan-5-ol obtained in the step (9a) to obtain the title compound (530 mg, total yield: 18%) as a light yellow solid.

¹H NMR(400 MHz, DMSO-d₆) δppm; 1.34(3H, s), 1.40 (3H, s), 2.23(3H, s), 3.79(2H, dd, J=3, 12 Hz), 4.12(2H, dd, J=3, 12 Hz), 4.39(1H, d, J=13 Hz), 4.46-4.54(1H, m), 4.82 (1H, d, J=13 Hz), 6.86-6.94(3H, m), 7.42-7.48(2H, m), 8.23 (1H, d, J=6 Hz).

Example 27

2-(((4-(1,4-dioxaspiro[4.5]dec-8-yloxy)-3-methylpyridin-2-yl)methyl)sulfinyl)-1H-benzimidazole sodium salt

[Formula 162]

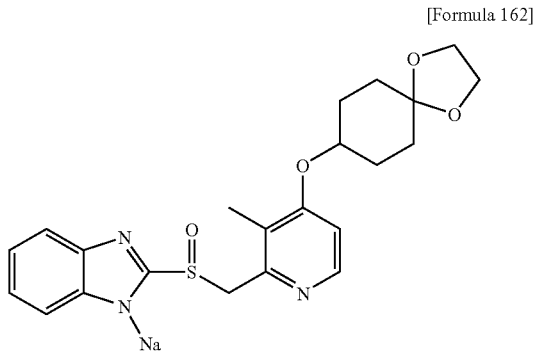

(27a) 1,4-dioxaspiro[4.5]decan-8-ol

[Formula 163]

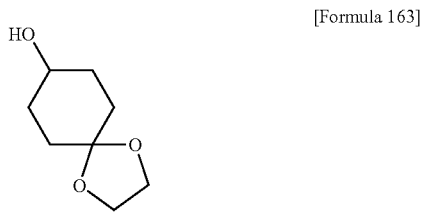

The same manner as in Example 9a was repeated using 1,4-cyclohexanedione monoethylene ketal to obtain the title compound (2.6 g, yield: 79%) as a light yellow oil.

¹H NMR(400 MHz, CDCl₃) δppm; 1.53-1.71(4H, m), 1.77-1.93(4H, m), 3.75-3.85(1H, m), 3.93-3.96(4H,m).

(27b) 2-(((4-(1,4-dioxaspiro[4.5]dec-8-yloxy)-3-methylpyridin-2-yl)methyl)sulfinyl)-1H-benzimidazole sodium salt

[Formula 164]

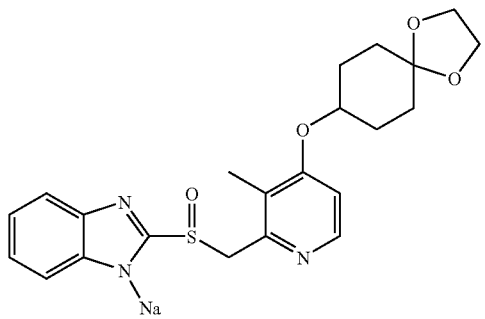

The same procedure as in the steps (6b) to (6f) of Example 6 was repeated using 1,4-dioxaspiro[4.5]decan-8-ol obtained in the step (27a) to obtain the title compound (230 mg, total yield: 7.3%) as a light yellow solid.

¹H NMR(400 MHz, DMSO-d₆) δppm; 1.57-1.94(8H, m), 2.17(3H, s), 3.87(4H, s), 4.35(1H, d, J=13 Hz), 4.62-4.68(1H, m), 4.79(1H, d, J=13 Hz), 6.84(2H, dd, J=3, 6 Hz), 6.97(1H, d, J=6 Hz), 7.43(2H, dd, J=3, 6 Hz), 8.23(1H, d, J=6 Hz).

Example 28

2-(((4-(2-(2,2-dimethyl-1,3-dioxan-5-yl)ethoxy)-3-methylpyridin-2-yl)methyl)sulfinyl)-1H-benzimidazole sodium salt

[Formula 165]

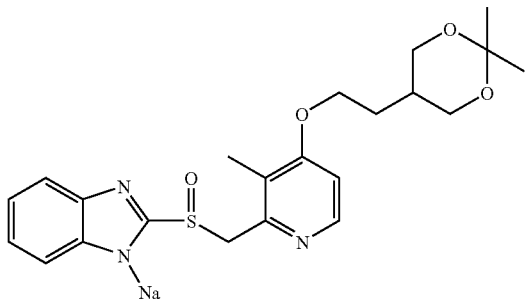

(28a) 2-(2,2-dimethyl-1,3-dioxan-5-yl)ethanol

[Formula 166]

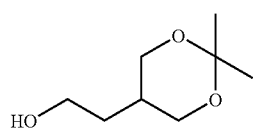

To an acetone (30 ml) solution of the 2-(hydroxymethyl)butane-1,4-diol (3.4 g, 28.3 mmol) obtained in accordance with the method described in J. Med. Chem., 30 (9), 1636-1642 (1987), p-toluenesulfonic acid monohydrate (244 mg, 2.83 mmol) was added at room temperature and the mixture was stirred for 15 hours. To the reaction mixture, triethylamine (394 μl, 2.83 mmol) was added and the mixture was concentrated. The residue was purified by silica gel column chromatography (elution solvent: heptane/ethyl acetate) to obtain the title compound (1.0 g, yield: 22%) as a light yellow oil.

$^1$H NMR(400 MHz, CDCl$_3$) δppm; 1.42(6H, s), 1.54-1.62 (2H, m), 1.90-2.02(1H, m), 3.58-3.76(4H, m), 3.94(2H, dd, J=4, 12 Hz).

(28b) 2-(((4-(2-(2,2-dimethyl-1,3-dioxan-5-yl)ethoxy)-3-methylpyridin-2-yl)methyl)sulfinyl)-1H-benzimidazole sodium salt

[Formula 167]

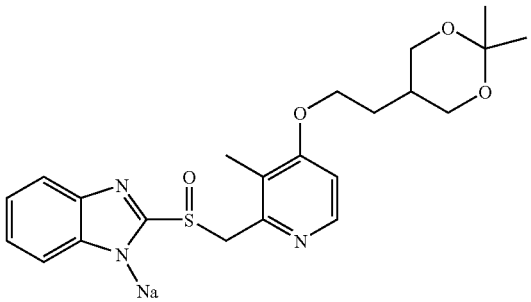

The same procedure as in the steps (6b) to (6f) of Example 6 was repeated using 2-(2,2-dimethyl-1,3-dioxan-5-yl)ethanol obtained in the step (28a) to obtain the title compound (58 mg, total yield: 2.0%) as a light yellow solid.

$^1$H NMR(400 MHz, DMSO-d$_6$) δppm; 1.28(3H, s), 1.34 (3H, s), 1.64-1.72(2H, m), 1.83-1.92(1H, m), 2.16(3H, s), 3.54-3.63(2H, m), 3.83(2H, dd, J=4, 16 Hz), 4.06(2H, t, J=6 Hz), 4.38(1H, d, J=13 Hz), 4.75(1H, d, J=13 Hz), 6.85(2H, dd, J=3, 6 Hz), 6.91(1H, d, J=6 Hz), 7.43(2H, dd, J=3, 6 Hz), 8.26(1H, d, J=6 Hz).

Example 29

2-(((4-((1-ethyl-2,6,7-trioxabicyclo[2.2.2]oct-4-yl)methoxy)-3-methylpyridin-2-yl)methyl)sulfinyl)-1H-benzimidazole sodium salt

[Formula 168]

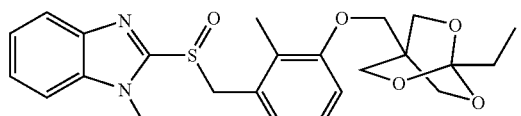

(29a) (1-ethyl-2,6,7-trioxabicyclo[2.2.2]oct-4-yl)methanol

[Formula 169]

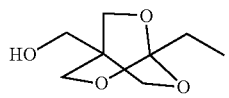

The same manner as in Example 24 was repeated using triethyl orthopropionate (15 g, 110 mmol) to obtain the title compound (14 g, yield: 73%) as a light yellow oil.

$^1$H NMR(400 MHz, CDCl$_3$) δppm; 0.96(3H, t, J=7 Hz), 1.71(2H, q, J=7 Hz), 3.47(2H, d, J=4 Hz), 4.02(6H, s).

(29b) 2-(((4-((1-ethyl-2,6,7-trioxabicyclo[2.2.2]oct-4-yl)methoxy)-3-methylpyridin-2-yl)methyl)sulfinyl)-1H-benzimidazole sodium salt

[Formula 170]

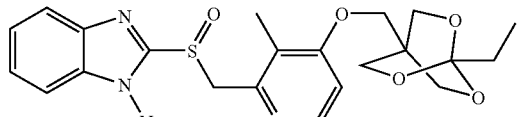

The same manner as in Example 24 was repeated using (1-ethyl-2,6,7-trioxabicyclo[2.2.2]oct-4-yl)methanol obtained in the step (29a) to obtain the title compound (145 mg, total yield: 1.7%) as a light yellow solid.

$^1$H NMR(400 MHz, DMSO-d$_6$) δppm; 0.86(3H, t, J=7 Hz), 1.59(2H, q, J=7 Hz), 2.19(3H, s), 3.92(2H, s), 4.04(6H, s), 4.35(1H, d, J=13 Hz), 4.82(1H, d, J=13 Hz), 6.80-6.90(3H, m), 7.42(2H, dd, J=3, 6 Hz), 8.26(1H, d, J=6 Hz)

Example 30

2-(((3-methyl-4-(2-(2-methyl-1,3-dioxan-2-yl)ethoxy)pyridin-2-yl)methyl)sulfinyl)-1H-benzimidazole sodium salt

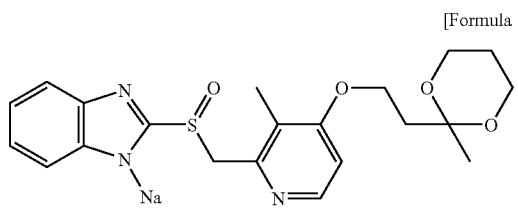

[Formula 171]

(30a) 2-(2-methyl-1,3-dioxan-2-yl)ethanol

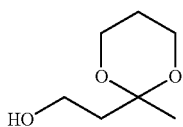

[Formula 172]

The same procedure as in the steps (8a) and (8b) of Example 8, was repeated using ethyl acetoacetate to obtain the title compound (5.4 g, total yield: 49%) as a light yellow oil.

$^1$H NMR(400 MHz, CDCl$_3$) δppm; 1.49(3H, s), 1.91(2H, t, J=6 Hz), 1.90-2.40(2H, m), 3.00(1H, t, J=6 Hz), 3.80-4.06 (6H, m).

(30b) 2-(((3-methyl-4-(2-(2-methyl-1,3-dioxan-2-yl)ethoxy)pyridin-2-yl)methyl)sulfinyl)-1H-benzimidazole sodium salt

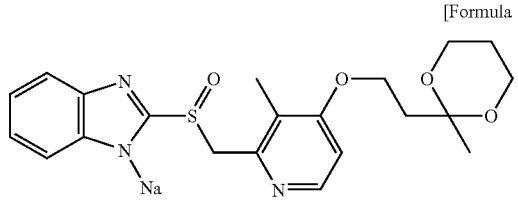

[Formula 173]

The same procedure as in the steps (8c) to (8g) of Example 8, was repeated using 2-(2-methyl-1,3-dioxan-2-yl)ethanol obtained in the step (30a) to obtain the title compound (113 mg, total yield: 2.5%) as a light yellow solid.

$^1$H NMR(400 MHz, DMSO-d$_6$) δppm; 1.39(3H, s), 1.46-1.70(2H, m), 2.12-2.19(2H, m), 2.16(3H, s), 3.76-3.90(4H, m), 4.11(2H, t, J=7 Hz), 4.38(1H, d, J=13 Hz), 4.79(1H, d, J=13 Hz), 6.82-6.92(2H, m), 6.90(1H, d, J=6 Hz), 7.38-7.48 (2H, m), 8.24(1H, d, J=6 Hz).

Example 31

2-(((4-(2-(5,9-dioxaspiro[3.5]non-7-yl)ethoxy)-3-methylpyridin-2-yl)methyl)sulfinyl)-1H-benzimidazole sodium salt

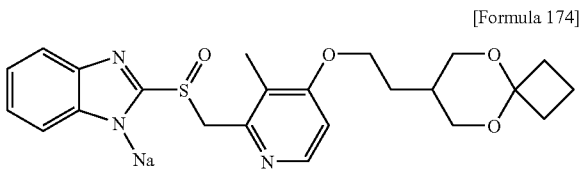

[Formula 174]

The same manner as in Example 28 was repeated using cyclobutanone to obtain the title compound (80 mg, total yield: 0.8%) as a light yellow solid.

$^1$H NMR(400 MHz, DMSO-d$_6$) δppm; 1.57-1.67(4H, m), 1.86-1.96(1H, m), 2.05-2.18(4H, m), 2.16(3H, s), 3.40-3.50 (2H, m), 3.82(2H, dd, J=4, 11 Hz), 4.06(2H, t, J=7 Hz), 4.38(1H, d, J=13 Hz), 4.78(1H, d, J=13 Hz), 6.85(2H, dd, J=3, 6 Hz), 6.90(1H, d, J=6 Hz), 7.43(2H, dd, J=3, 6 Hz), 8.26(1H, d, J=6 Hz).

Example 32

2-(((4-(1,3-dioxan-2-ylmethoxy)-3-methylpyridin-2-yl)methyl)sulfinyl)-1H-benzimidazole sodium salt

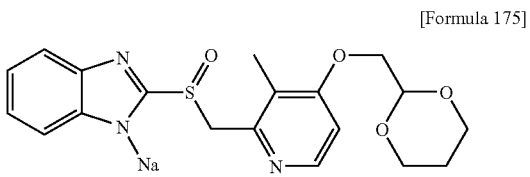

[Formula 175]

(32a) 2-((benzyloxy)methyl)-1,3-dioxane

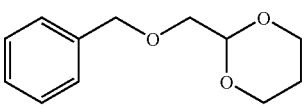

[Formula 176]

A mixture of benzyloxyacetaldehyde (3.6 g, 24 mmol), 1,3-propanediol (5.2 ml, 72 mmol), triethyl orthoformate (4 ml, 24 mmol), and p-toluenesulfonic acid monohydrate (414 mg, 2.45 mmol) was stirred at room temperature for 17 hours. To the reaction mixture, triethylamine (669 μl, 4.8 mmol) was added, which was concentrated. The residue was purified by silica gel column chromatography (elution solvent: heptane/ethyl acetate) to obtain the title compound (2.9 g, yield: 58%) as a light yellow oil.

$^1$H NMR(400 MHz, CDCl$_3$) δppm; 1.22(1H, t, J=7 Hz), 2.04-2.20(1H, m), 3.49(2H, d, J=4 Hz), 3.80(2H, dt, J=2, 12 Hz), 4.14(2H, dd, J=5, 11 Hz), 4.59(2H, s), 4.76(1H, t, J=4 Hz), 7.20-7.42(5H, m).

(32b) 1,3-dioxan-2-ylmethanol

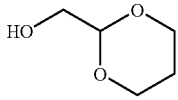
[Formula 177]

To a methanol (50 ml) solution of the 2-((benzyloxy)methyl)-1,3-dioxane (2.9 g, 13.9 mmol) obtained in the step (32a), 10% palladium carbon (760 mg) was added and the mixture was stirred at room temperature in a hydrogen atmosphere for 2 days. The reaction mixture was filtrated by celite and washed with ethyl acetate. Thereafter, the solvent of the filtrate was distilled off under reduced pressure to obtain a crude product of the title compound (860 mg, yield: 52.4%) as a light yellow oil.

$^1$H NMR(400 MHz, CDCl$_3$) δppm; 1.34-1.44(1H, m), 1.86 (1H, t, J=5 Hz), 2.04-2.20(1H, m), 3.60(2H, dd, J=4, 6 Hz), 3.82(2H, dt, J=2, 12 Hz), 4.15(2H, dd, J=5, 11 Hz), 4.66(1H, t, J=5 Hz).

(32c) 2-(((4-(1,3-dioxan-2-ylmethoxy)-3-methylpyridin-2-yl)methyl)sulfinyl)-1H-benzimidazole sodium salt

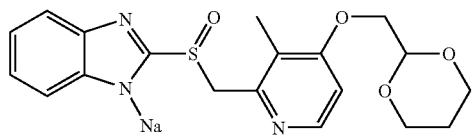
[Formula 178]

The same procedure as in the steps (6b) to (6f) of Example 6 was repeated using 1,3-dioxan-2-ylmethanol obtained in the step (32b) to obtain the title compound (148 mg, total yield:10%) as a light yellow solid.

$^1$H NMR(400 MHz, DMSO-d$_6$) δppm; 1.33-1.42(1H, m), 1.84-1.98(1H, m), 2.16(3H, s), 3.74-3.84(2H, m), 3.98-4.08 (4H, m), 4.37(1H, d, J=13 Hz), 4.80(1H, d, J=13 Hz), 4.92 (1H, t, J=4 Hz), 6.84(2H, dd, J=3, 6 Hz), 6.91(1H, d, J=6 Hz), 7.42(2H, dd, J=3, 6 Hz), 8.25(1H, d, J=6 Hz).

Example 33

2-(((3-methyl-4-((2-methyl-1,3-dioxan-2-yl)methoxy)pyridin-2-yl)methyl)sulfinyl)-1H-benzimidazole sodium salt

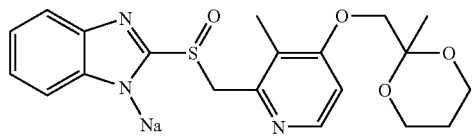
[Formula 179]

(33a) (2-methyl-1,3-dioxan-2-yl)methanol

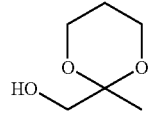
[Formula 180]

The same procedure as in the steps (32a) and (32b) of Example 32 was repeated using 1-benzyloxy-2-propanone to obtain the title compound (1.51 g, total yield: 37%) as a light yellow oil.

$^1$H NMR(400 MHz, CDCl$_3$) δppm; 1.43(3H, s), 1.92-2.20 (2H, m), 3.53(2H, d, J=6 Hz), 3.86-4.06(4H, m).

(33b) 2-(((3-methyl-4-((2-methyl-1,3-dioxan-2-yl)methoxy)pyridin-2-yl)methyl)sulfinyl)-1H-benzimidazole sodium salt

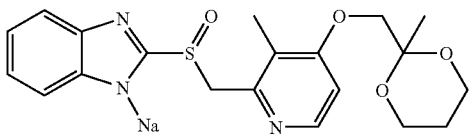
[Formula 181]

The same procedure as in the steps (6b) to (6f) of Example 6 was repeated using (2-methyl-1,3-dioxan-2-yl)methanol obtained in the step (33a) to obtain the title compound (220 mg, total yield: 8.6%) as a light yellow solid.

$^1$H NMR(400 MHz, DMSO-d$_6$) δppm; 1.45(3H, s), 1.57-1.67(2H, m), 2.19(3H, s), 3.88(4H, t, J=6 Hz), 4.09(2H, s), 4.36(1H, d, J=13 Hz), 4.80(1H, d, J=13 Hz), 6.84(2H, dd, J=3, 6 Hz), 6.98(1H, d, J=6 Hz), 7.42(2H, dd, J=3, 6 Hz), 8.25(1H, d, J=6 Hz).

Example 34

2-(((3-methyl-4-(2-(2,5,5-trimethyl-1,3-dioxan-2-yl)ethoxy)pyridin-2-yl)methyl)sulfinyl)-1H-benzimidazole sodium salt

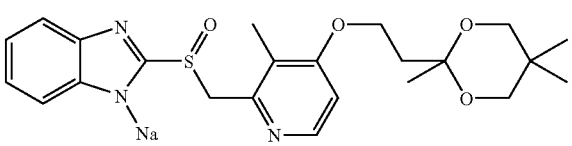
[Formula 182]

(34a) 2-(2,5,5-trimethyl-1,3-dioxan-2-yl)ethanol

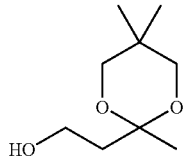
[Formula 183]

The same procedure as in the steps (8a) and (8b) of Example 8 was repeated using ethyl acetoacetate, and 2,2-dimethyl-1,3-propanediol to obtain the title compound (7.3 g, total yield: 55%) as a light yellow oil.

$^1$H NMR(400 MHz, CDCl$_3$) δppm; 0.81(3H, s), 1.16(3H, s), 1.44(3H, s), 1.93(2H, t, J=6 Hz), 3.06(1H, t, J=6 Hz), 3.42(2H, d, J=12 Hz), 3.68(2H, d, J=12 Hz), 3.82-3.92(2H, m).

(34b) 2-(((3-methyl-4-(2-(2,5,5-trimethyl-1,3-dioxan-2-yl)ethoxy)pyridin-2-yl)methyl)sulfinyl)-1H-benzimidazole sodium salt

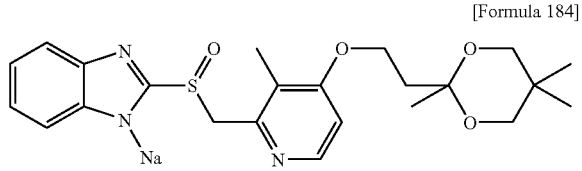

[Formula 184]

The same procedure as in the steps (6b) to (6f) of Example 6 was repeated using 2-(2,5,5-trimethyl-1,3-dioxan-2-yl)ethanol obtained in the step (34a) to obtain the title compound (196 mg, total yield: 7.2%) as a light yellow solid.

$^1$H NMR(400 MHz, DMSO-$d_6$) δppm; 0.83(3H, s), 0.94 (3H, s), 1.38(3H, s), 2.12-2.20(2H, m), 2.16(3H, s), 3.39(2H, d, J=11 Hz), 3.51(2H, d, J=11 Hz), 4.13(2H, t, J=3 Hz), 4.38(1H, d, J=13 Hz), 4.78(1H, d, J=13 Hz), 6.84(2H, dd, J=3, 6 Hz), 6.88(1H, d, J=6 Hz), 7.42(2H, dd, J=3, 6 Hz), 8.25(1H, d, J=6 Hz).

Example 35

2-(((3-methyl-4-(2-(6-methyl-5,7-dioxaspiro[2.5]oct-6-yl)ethoxy)pyridin-2-yl)methyl)sulfinyl)-1H-benzimidazole sodium salt

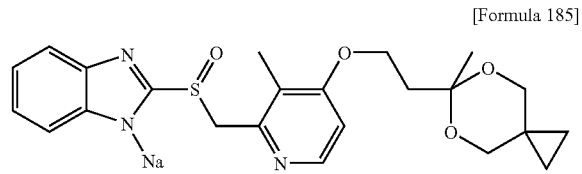

[Formula 185]

(35a) 2-(6-methyl-5,7-dioxaspiro[2.5]oct-6-yl)ethanol

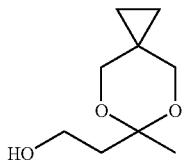

[Formula 186]

The same procedure as in the steps (8a) and (8b) of Example 8, was repeated using ethyl acetoacetate and 1,1-bis(hydroxymethylcyclopropane) to obtain the title compound (2.9 g, total yield: 36%) as a light yellow oil.

$^1$H NMR(400 MHz, CDCl$_3$) δppm; 0.38(2H, t, J=6 Hz), 0.62(2H, t, J=6 Hz), 1.54(3H, s), 1.96(2H, t, J=6 Hz), 3.04 (1H, t, J=6 Hz), 3.16(2H, d, J=12 Hz), 3.84-3.92(2H, m), 4.20(2H, d, J=12 Hz).

(35b) 2-(((3-methyl-4-(2-(6-methyl-5,7-dioxaspiro[2.5]oct-6-yl)ethoxy)pyridin-2-yl)methyl)sulfinyl)-1H-benzimidazole sodium salt

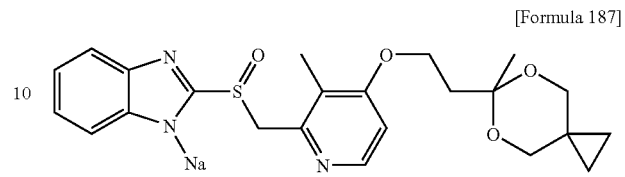

[Formula 187]

The same procedure as in the steps (6b) to (6f) of Example 6 was repeated using 2-(6-methyl-5,7-dioxaspiro[2.5]oct-6-yl)ethanol obtained in the step (35a) to obtain the title compound (163 mg, total yield: 5.5%) as a light yellow solid.

$^1$H NMR(400 MHz, DMSO-$d_6$) δppm; 0.34-0.50(4H, m), 1.46(3H, s), 2.18(3H, s), 2.22(2H, t, J=6 Hz), 3.45(2H, d, J=11 Hz), 3.76(2H, d, J=11 Hz), 4.16(2H, t, J=7 Hz), 4.39 (1H, d, J=13 Hz), 4.78(1H, d, J=13 Hz), 6.86(2H, dd, J=3, 6 Hz), 6.91(1H, d, J=6 Hz), 7.43(2H, dd, J=3, 6 Hz), 8.26(1H, d, J=6 Hz).

Example 36

2-(((4-(2-(2-(methoxymethyl)-1,3-dioxan-2-yl)ethoxy)-3-methylpyridin-2-yl)methyl)sulfinyl)-1H-benzimidazole sodium salt

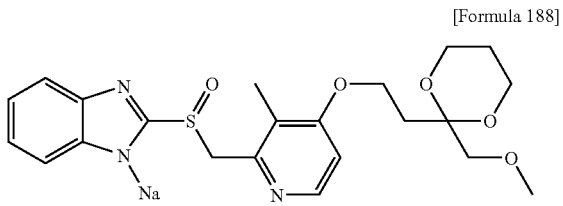

[Formula 188]

(36a) 2-(2-(methoxymethyl)-1,3-dioxan-2-yl)ethanol

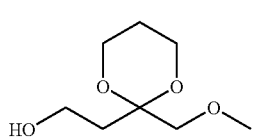

[Formula 189]

The same procedure as in the steps (8a) and (8b) of Example 8 was repeated using methyl 4-methoxyacetoacetate to obtain the title compound (4.5 g, total yield: 34%) as a light yellow oil.

$^1$H NMR(400 MHz, CDCl$_3$) δppm; 1.58-1.70(1H, m), 1.80-1.96(1H, m), 2.03(2H, t, J=6 Hz), 2.86(1H, t, J=6 Hz), 3.43(3H, s), 3.62(2H, s), 3.76-3.84(2H, m), 3.90-4.04(4H, m).

(36b) 2-(((4-(2-(2-(methoxymethyl)-1,3-dioxan-2-yl)ethoxy)-3-methylpyridin-2-yl)methyl)sulfinyl)-1H-benzimidazole sodium salt

[Formula 190]

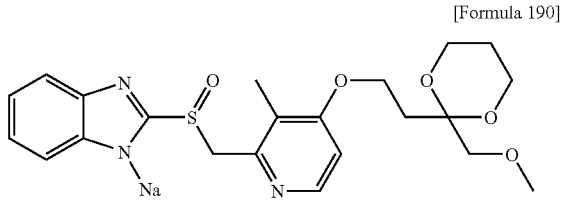

The same procedure as in the steps (6b) to (6f) of Example 6 was repeated using 2-(2-(methoxymethyl)-1,3-dioxan-2-yl)ethanol obtained in the step (36a) to obtain the title compound (304 mg, total yield: 7.0%) as a light yellow solid.

$^1$H NMR(400 MHz, DMSO-d$_6$) δppm; 1.50-1.70(2H, m), 2.16(3H, s), 2.20(2H, t, J=7 Hz), 3.29(3H, s), 3.52(2H, s), 3.80-3.90(4H, m), 4.09(2H, t, J=7 Hz), 4.37(1H, d, J=13 Hz), 4.78(1H, d, J=13 Hz), 6.83(2H, dd, J=3, 6 Hz), 6.87(1H, d, J=6 Hz), 7.41(2H, dd, J=3, 6 Hz), 8.25(1H, d, J=6 Hz).

Example 37

2-(((4-((1-cyclopropyl-2,6,7-trioxabicyclo[2.2.2]oct-4-yl)methoxy)-3-methylpyridin-2-yl)methyl)sulfinyl)-1H-benzimidazole sodium salt

[Formula 191]

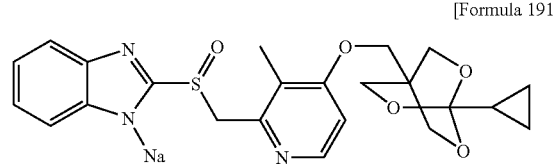

(37a) Methyl cyclopropanecarboxyimidate hydrochloride

[Formula 192]

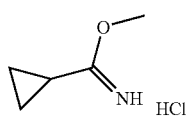

To a solution mixture of cyclopropanecarbonitrile (15 g, 224 mmol), diethyl ether (200 ml), and methanol (10 ml), hydrogen chloride was injected under ice-cool and the mixture was stirred at room temperature for 17 hours. After the solvent of the reaction mixture was distilled off under reduced pressure, diethyl ether was added to the residue and generated solid was collected by filtration under nitrogen atmosphere to obtain the title compound (29 g, yield: 95.5%) as a light yellow solid.

$^1$H NMR(400 MHz, DMSO-d$_6$) δppm; 1.10-1.24(4H, m), 2.06-2.38(1H, m), 3.99(3H, s), 10.8(1H, br s), 12.1(1H, br s).

(37b) (trimethoxymethyl)cyclopropane

[Formula 193]

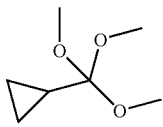

To a n-hexane (75 ml) solution of methyl cyclopropanecarboxyimidate hydrochloride (17.4 g, 128 mmol) obtained in the step (37a), methanol (25.9 ml, 640 mml) was added and the mixture was stirred at room temperature for 3.5 days. The ammonium chloride precipitated was removed by filtration and the filtrate was concentrated under reduced pressure to obtain a crude product of the title compound (7.5 g, yield: 40%) as a light yellow oil.

$^1$H NMR(400 MHz, CDCl$_3$) δppm; 0.47-0.56(2H, m), 0.58-0.67(2H, m), 0.84-0.94(1H, m), 3.29(9H, s).

(37c) (1-cyclopropyl-2,6,7-trioxabicyclo[2.2.2]oct-4-yl)methanol

[Formula 194]

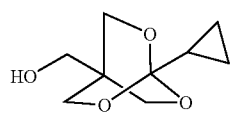

The same procedure as in the step (24a) of Example 24 was repeated using (trimethoxymethyl)cyclopropane (9.8 g, 67.2 mmol) obtained in the step (37b) to obtain the title compound (11.9 g, yield: 95%) as a light yellow oil.

$^1$H NMR(400 MHz, CDCl$_3$) δppm; 0.42-0.52(2H, m), 0.58-0.68(2H, m), 0.86-0.96(1H, m), 3.46(2H, s), 4.02(6H, s).

(37d) 2-(((4-((1-cyclopropyl-2,6,7-trioxabicyclo[2.2.2]oct-4-yl)methoxy)-3-methylpyridin-2-yl)methyl)sulfinyl)-1H-benzimidazole sodium salt

[Formula 195]

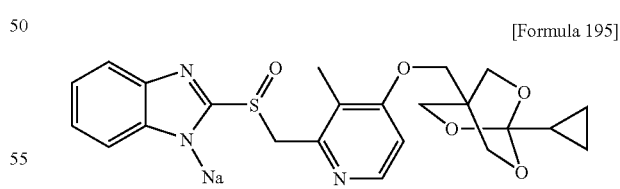

The same procedure as in the steps (24b) to (24f) of Example 24 was repeated using (1-cyclopropyl-2,6,7-trioxabicyclo[2.2.2]oct-4-yl)methanol obtained in the step (37c) above to obtain the title compound (147 mg, total yield: 3.2%) as a light yellow solid.

$^1$H NMR(400 MHz, DMSO-d$_6$) δppm; 0.35-0.54(4H, m), 1.06-1.18(1H, m), 2.19(3H, s), 3.92(2H, s), 4.04(6H, s), 4.38 (1H, d, J=13 Hz), 4.80(1H, d, J=13 Hz), 6.82-6.94(3H, m), 7.44(2H, dd, J=3, 6 Hz), 8.27(1H, d, J=6 Hz).

Example 38

2-(((4-((1-cyclobutyl-2,6,7-trioxabicyclo[2.2.2]oct-4-yl)methoxy)-3-methylpyridin-2-yl)methyl)sulfinyl)-1H-benzimidazole sodium salt

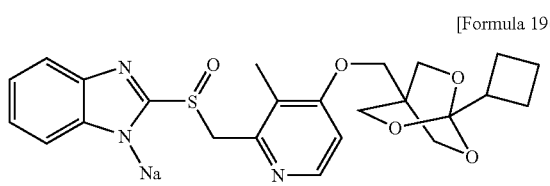

[Formula 196]

(38a) (1-cyclobutyl-2,6,7-trioxabicyclo[2.2.2]oct-4-yl)methanol

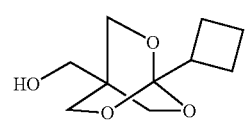

[Formula 197]

The same procedure as in the steps (37a) to (37c) of Example 37 was repeated using cyclobutanecarbonitrile to obtain the title compound (15 g, total yield: 51%) as a light yellow oil.

$^1$H NMR(400 MHz, CDCl$_3$) δppm; 1.70-2.30(7H, m), 3.47 (2H, s), 4.03(6H, s).

(38b) 2-(((4-((1-cyclobutyl-2,6,7-trioxabicyclo[2.2.2]oct-4-yl)methoxy)-3-methylpyridin-2-yl)methyl)sulfinyl)-1H-benzimidazole sodium salt

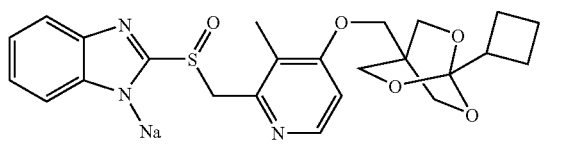

[Formula 198]

The same procedure as in the steps (24b) to (24f) of Example 24 was repeated using (1-cyclobutyl-2,6,7-trioxabicyclo[2.2.2]oct-4-yl)methanol obtained in the step (38a) above to obtain the title compound (56 mg, 2.3%) as a light yellow solid.

$^1$H NMR(400 MHz, DMSO-d$_6$) δppm; 1.60-1.86(4H, m), 1.94-2.07(3H, m), 2.19(3H, s), 3.92(2H, s), 4.05(6H, s), 4.33 (1H, d, J=13 Hz), 4.83(1H, d, J=13 Hz), 6.78-6.90(3H, m), 7.38-7.48(2H, m), 8.26(1H, d, J=6 Hz).

Example 39

2-(((4-(2-(2-ethyl-1,3-dioxolan-2-yl)ethoxy)-3-methylpyridin-2-yl)methyl)sulfinyl)-1H-benzimidazole sodium salt

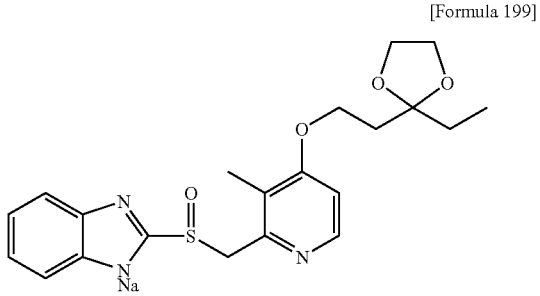

[Formula 199]

(39a) Ethyl(2-ethyl-1,3-dioxolan-2-yl)acetate

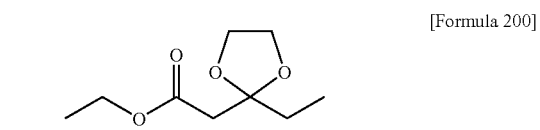

[Formula 200]

A mixture of ethyl 3-oxopentanoate (5 g, 34.7 mmol), ethylene glycol (10.8 g, 174 mmol), triethyl orthoformate (5.14 g, 34.7 mmol), and p-toluenesulfonic acid monohydrate (598 mg, 3.14 mmol) was stirred at room temperature overnight. To the reaction mixture, heptane and ethyl acetate were added to dilute solution, which was washed with water. The organic layer was washed with a saturated saline solution, dried over magnesium sulfate, filtrated and the filtrate was concentrated under reduced pressure. The residue was dissolved in heptane and subjected to NH silica gel column chromatography (elution solvent: n-heptane/ethyl acetate=1/0→10/1) to obtain the title compound (3.85 g, yield: 58.9%) as colorless oil.

$^1$H NMR(400 MHz, CDCl$_3$) δppm; 0.94(3H, t, J=8 Hz), 1.27(3H, t, J=7 Hz), 1.83(2H, q, J=8 Hz), 2.65(2H, s), 3.89-4.03(4H, m), 4.15(2H, q, J=7 Hz).

(39b) 2-(2-ethyl-1,3-dioxolan-2-yl)ethanol

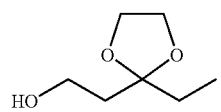

[Formula 201]

To a tetrahydrofuran (50 ml) suspension of lithium aluminum hydride (800 mg, 21.1 mmol), ethyl(2-ethyl-1,3-dioxolan-2-yl)acetate (3.85 g, 20.5 mmol) was added under ice-cool. The mixture was stirred at room temperature for one hour and 30 minutes and cooled on ice. Thereafter, water (0.8 ml), a 15% aqueous sodium hydroxide solution (0.8 ml), and water (2.4 ml) were sequentially added to the mixture under ice cool. Magnesium sulfate was added to the mixture and filtrated through silica gel. The filtrate was concentrated under reduced pressure to obtain the title compound (2.76 g, 92.1%) as an oil.

$^1$H NMR(400 MHz, CDCl$_3$) δppm; 0.92(3H, t, J=8 Hz), 1.68(2H, q, J=8 Hz), 1.93(2H, t, J=5 Hz), 2.82(1H, t, J=5 Hz), 3.76(2H, q, J=5 Hz), 3.96-4.05(4H, m).

(39c) 2-(((3-methyl-4-(2-(2-propyl-1,3-dioxolan-2-yl)ethoxy)pyridin-2-yl)methyl)sulfinyl)-1H-benzimidazole sodium salt

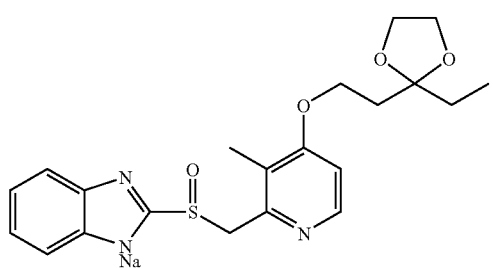

[Formula 202]

The same procedure as in the steps (3c) to (3h) of Example 3 was repeated using 4-chloro-2,3-dimethylpyridine 1-oxide and 2-(2-ethyl-1,3-dioxolan-2-yl)ethanol to obtain the title compound (422 mg, 6 steps: 25%) as a light yellow solid.

$^1$H NMR(400 MHz, DMSO-d$_6$) δppm; 0.87(3H, t, J=8 Hz), 1.64(2H, q, J=8 Hz), 2.07(2H, t, J=7 Hz), 2.17(3H, s), 3.85-3.94(4H, m), 4.09(2H, t, J=7 Hz), 4.40(1H, d, J=13 Hz), 4.80(1H, d, J=13 Hz), 6.83-6.90(2H,m), 6.94(1H, d, J=6 Hz), 7.41-7.49(2H, m), 8.27(1H, d, J=6 Hz).

Example 40

2-(((4-((2-ethyl-1,3-dioxolan-2-yl)methoxy)-3-methylpyridin-2-yl)methyl)sulfinyl)-1H-benzimidazole sodium salt

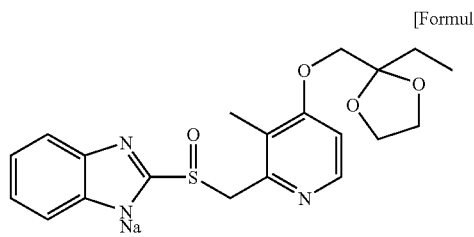

[Formula 203]

(40a) 2-oxobutyl acetate

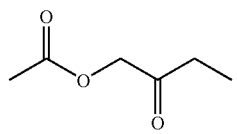

[Formula 204]

A mixture of 1-bromobutan-2-one (10 g, 66.2 mmol), potassium acetate (7.8 g, 79.4 mmol), and N,N-dimethylformamide (50 ml) was stirred at room temperature for 5 days. Water was added to the reaction mixture and extracted with diethyl ether twice. The organic layers were combined and washed with a saturated saline solution, dried over magnesium sulfate, and filtrated. The filtrate was concentrated under reduced pressure to obtain the title compound (8.24 g) in the form of a mixture with N,N-dimethylformamide.

$^1$H NMR(400 MHz, CDCl$_3$) δppm; 1.10(3H, t, J=7 Hz), 2.14(3H, s), 2.45 (2H, q, J=7 Hz), 4.66(2H, s).

(40b) (2-ethyl-1,3-dioxolan-2-yl)methyl acetate

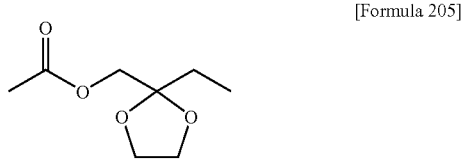

[Formula 205]

A mixture of 2-oxobutyl acetate (4 g) obtained in the step (40a), ethylene glycol (7.82 g, 126 mmol), triethyl orthoformate (3.73 g, 25.2 mmol) and p-toluenesulfonic acid monohydrate (479 mg, 2.52 mmol) was stirred at room temperature overnight. To the reaction mixture, water and ethyl acetate were added, and partitioned. The aqueous layer was extracted again with ethyl acetate. The organic layers were combined, dried over magnesium sulfate and filtrated. The filtrate was concentrated under reduced pressure. The residue was dissolved in heptane-ethyl acetate and subjected to NH silica gel column chromatography (elution solvent: n-heptane/ethyl acetate=20/1→5/1) to obtain the title compound (1.4 g, yield of 2 steps: 25%).

$^1$H NMR(400 MHz, CDCl$_3$) δppm; 0.93(3H, t, J=7 Hz), 1.73(2H, q, J=7 Hz), 2.09(3H, s), 3.96-4.03(4H, m), 4.03(2H, s).

(40c) (2-ethyl-1,3-dioxolan-2-yl)methanol

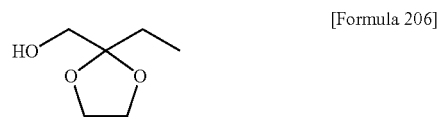

[Formula 206]

A mixture of methyl(2-ethyl-1,3-dioxolan-2-yl) acetate (1.39 g, 7.94 mmol), potassium carbonate (2.19 g, 15.9 mmol), tetrahydrofuran (20 ml) and water (10 ml) was stirred at room temperature for 6 hours and 50 minutes. The reaction mixture was concentrated under reduced pressure, ethyl acetate was added to the residue, which was subjected to NH silica gel pad filtration. The filtrate was concentrated under reduced pressure to obtain the title compound (0.75 g, 71.5%) as colorless oil.

$^1$H NMR(400 MHz, CDCl$_3$) δppm; 0.93(3H, t, J=8 Hz), 1.71(2H, q, J=8 Hz), 1.95-2.03(1H, br), 3.53(2H, d, J=4 Hz), 3.96-4.06(4H, m).

(40d) 2-(((4-((2-ethyl-1,3-dioxolan-2-yl)methoxy)-3-methylpyridin-2-yl)methyl)sulfinyl)-1H-benzimidazole sodium salt

[Formula 207]

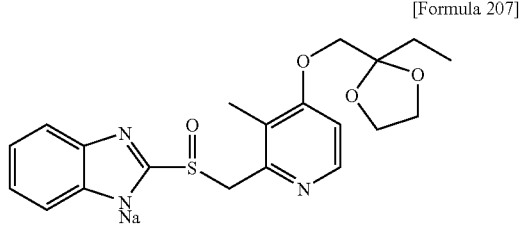

The same procedure as in the steps (3c) to (3h) of Example 3 was repeated using 4-chloro-2,3-dimethylpyridine 1-oxide and (2-ethyl-1,3-dioxolan-2-yl)methanol to obtain the title compound (355 mg, 6 steps: 9.6%) as a white solid.

$^1$H NMR(400 MHz, DMSO-$d_6$) δppm; 0.87(0.3H, t, J=8 Hz), 1.74(2H, q, J=8 Hz), 2.17(3H, s), 3.87-4.00(4H, m), 3.96(2H, s), 4.39(1H, d, J=13 Hz), 4.80(1H, d, J=13 Hz), 6.84-6.91(2H, m), 6.94(1H, d, J=6 Hz), 7.41-7.47(2H, m), 8.25(1H, d, J=6 Hz).

Example 41

2-(((4-(2-(2-ethyl-1,3-dioxolan-2-yl)ethoxy)-3-methylpyridin-2-yl)methyl)sulfinyl)-4-methyl-1H-benzimidazole sodium salt

[Formula 208]

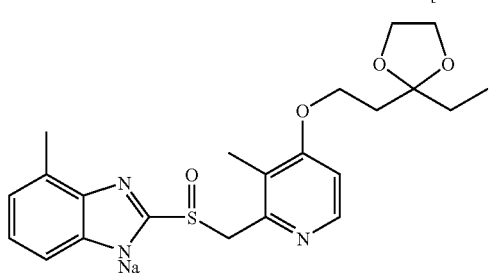

The same procedure as in the step (39c) was repeated using 4-chloro-2,3-dimethylpyridine 1-oxide and 2-(2-ethyl-1,3-dioxolan-2-yl)ethanol except that 4-methyl-1H-benzimidazole-2-thiol obtained in the step (54a) of Example 54 was used instead of 2-mercaptobenzimidazole in the step (39c) of Example 39 to obtain the title compound (490 mg, 6 steps: 27%) as a white powder.

$^1$H NMR(400 MHz, DMSO-$d_6$) δppm; 0.85(3H, t, J=8 Hz), 1.62(2H, q, J=8 Hz), 2.05(2H, t, J=7 Hz), 2.17(3H, s), 2.45(3H, s), 3.83-3.92(4H, m), 4.07(2H, t, J=7 Hz), 4.42(1H, d, J=13 Hz), 4.75(1H, d, J=13 Hz), 6.63(1H, d, J=7 Hz), 6.73(1H, t, J=7 Hz), 6.91(1H, d, J=6 Hz), 7.24(1H, d, J=8 Hz), 8.25(1H, d, J=6 Hz).

Example 42

2-(((4-((2-ethyl-1,3-dioxan-2-yl)methoxy)-3-methylpyridin-2-yl)methyl)sulfinyl)-1H-benzimidazole sodium salt

[Formula 209]

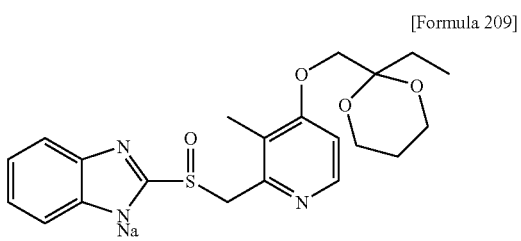

(42a) 2-oxobutyl benzoate

[Formula 210]

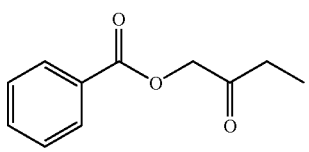

A mixture of 1-bromobutan-2-one (7.2 g, 47.7 mmol), sodium benzoate (7.56 g, 52.4 mmol), and N,N-dimethylformamide (72 ml) was stirred at room temperature for 3 hours and 45 minutes. Diethyl ether was added to the reaction mixture and the mixture was washed with water and a saturated saline solution, dried over magnesium sulfate, and filtrated. The filtrate was concentrated under reduced pressure to obtain the title compound (9.5 g, quantitatively) as a light brown oil.

$^1$H NMR(400 MHz, CDCl$_3$) δppm; 1.13(3H, t, J=7 Hz), 2.54(2H, q, J=7 Hz), 4.89(2H, s), 7.43-7.49(2H, m), 7.57-7.62(1H, m), 8.08-8.12(2H, m).

(42b) (2-ethyl-1,3-dioxan-2-yl)methyl benzoate

[Formula 211]

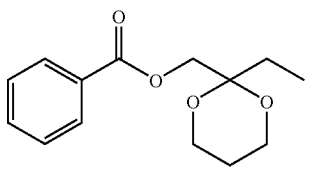

A mixture of 2-oxobutyl benzoate (5 g, 26 mmol), 1,3-propanediol (5.94 g, 78 mmol), triethyl orthoformate (3.85 g, 26 mmol) and p-toluenesulfonic acid monohydrate (448 mg, 2.36 mmol) was stirred at room temperature for 3 hours and 30 minutes. To the reaction mixture, ethyl acetate and diethyl ether were added and the mixture was washed with water and a saturated saline solution. The organic layer was dried over sodium sulfate and filtrated. The filtrate was concentrated under reduced pressure. The residue was dissolved in heptane/ethyl acetate (12/1) and subjected to NH silica gel column chromatography (elution solvent: n-heptane/ethyl acetate=12/1) to obtain the title compound (4.33 g, 65.5%) as a colorless viscous oil.

$^1$H NMR(400 MHz, CDCl$_3$) δppm; 0.98(3H, t, J=8 Hz), 1.63-1.87(2H, m), 1.89(2H, q, J=8 Hz), 3.90-4.06(4H, m), 4.52(2H, s), 7.42-7.48(2H, m), 7.54-7.60(1H, m), 8.06-8.09 (2H, m).

(42c)(2-ethyl-1,3-dioxan-2-yl)methanol

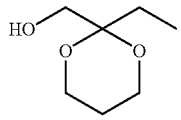

[Formula 212]

A mixture of (2-ethyl-1,3-dioxan-2-yl)methyl benzoate (4.33 g, 17.3 mmol), potassium carbonate (4.95 g, 35.9 mmol), tetrahydrofuran (50 ml), and water (20 ml) was stirred at room temperature for 11 hours. A 5N aqueous sodium hydroxide solution (2 ml) was added to the mixture, which was stirred at room temperature for 7 hours and then methanol (50 ml) was added thereto, which was stirred at room temperature for 4 hours. The reaction mixture was concentrated under reduced pressure. Ethyl acetate was added to the residue and insoluble matter was removed by filtration. The filtrate was concentrated under reduced pressure. The residue was dissolved in heptane/ethyl acetate and subjected to silica gel column chromatography (elution solvent: n-heptane/ethyl acetate=2/1→1/1) to obtain the title compound (2.35 g, 92.9%) as a colorless oil.

$^1$H NMR(400 MHz, CDCl$_3$) δppm; 0.89(3H, t, J=8 Hz), 1.52-1.60(1H, m), 1.83-1.95(4H, m), 3.58(2H, d, J=6 Hz), 3.86-4.01(4H, m).

(42d) 2-(((4-((2-ethyl-1,3-dioxan-2-yl)methoxy)-3-methylpyridin-2-yl)methyl)sulfinyl)-1H-benzimidazole sodium salt

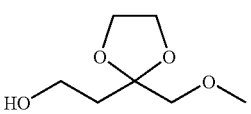

[Formula 213]

The same procedure as in the steps (3c) to (3h) of Example 3 was repeated using 4-chloro-2,3-dimethylpyridine 1-oxide and (2-ethyl-1,3-dioxan-2-yl)methanol to obtain the title compound (305 mg, 6 steps: 9.6%) as a solid.

$^1$H NMR(400 MHz, DMSO-d$_6$) δppm; 0.83(3H, t, J=8 Hz), 1.51-1.71(2H, m), 1.83(2H, q, J=8 Hz), 2.15(3H, s), 3.79-3.94(4H, m), 4.15(2H, s), 4.45(1H, d, J=13 Hz), 4.78(— H, d, J=13 Hz), 6.93-7.00(2H, m), 7.04(1H, d, J=5 Hz), 7.45-7.52(2H, m), 8.26(1H, d, J=5 Hz).

Example 43

2-(((4-(2-(2-(methoxymethyl)-1,3-dioxolan-2-yl) ethoxy)-3-methylpyridin-2-yl)methyl)sulfinyl)-1H-benzimidazole sodium salt

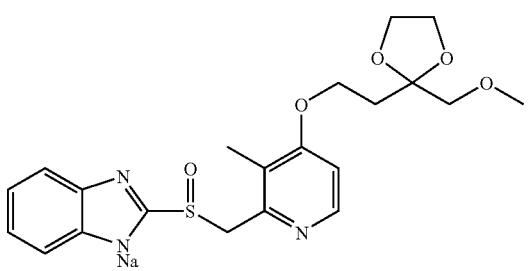

[Formula 214]

(43a) 2-(2-(methoxymethyl)-1,3-dioxolan-2-yl)ethanol

[Formula 215]

The same procedure as in the step (39a) and (39b) of Example 39 was repeated using methyl 4-methoxyacetoacetate to obtain the title compound (5.3 g, 2 steps: 50%) as a colorless oil.

$^1$H NMR(400 MHz, CDCl$_3$) δppm; 2.01(2H, t, J=5 Hz), 2.74-2.80(1H, br), 3.38(2H, s), 3.42(3H, s), 3.74-3.80(2H, br), 4.01-4.06(4H, m).

(43b) 2-(((4-(2-(2-(methoxymethyl)-1,3-dioxolan-2-yl)ethoxy)-3-methylpyridin-2-yl)methyl)sulfinyl)-1H-benzimidazole sodium salt

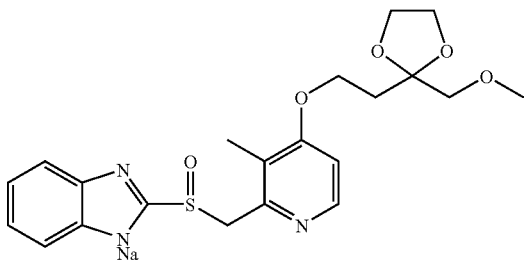

[Formula 216]

The same procedure as in the steps (5d) to (5h) of Example 5 was repeated using 4-chloro-2,3-dimethylpyridine 1-oxide and 2-(2-(methoxymethyl)-1,3-dioxolan-2-yl)ethanol to obtain the title compound (312 mg, 5 steps 3.9%) as a light yellow foam.

$^1$H NMR(400 MHz, DMSO-d$_6$) δppm; 2.10(2H, t, J=7 Hz), 2.15(3H, s), 3.27(3H, s), 3.30(2H, s), 3.86-3.91(4H, m), 4.09(2H, t, J=7 Hz), 4.38(1H, d, J=13 Hz), 4.76(1H, d, J=13 Hz), 6.81-6.88(2H, m), 6.92(1H, d, J=6 Hz), 7.40-7.46(2H, m), 8.26(1H, d, J=6 Hz).

Example 44

2-(((4-((2-(fluoromethyl)-1,3-dioxan-2-yl)methoxy)-3,5-dimethylpyridin-2-yl)methyl)sulfinyl)-1H-benzimidazole sodium salt

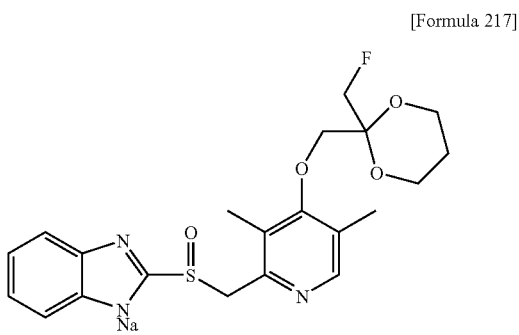

[Formula 217]

(44a) (2-(hydroxymethyl)-1,3-dioxan-2-yl)methyl benzoate

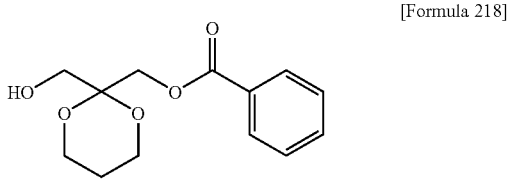

[Formula 218]

To a pyridine (200 ml) solution of dihydroxyacetone (20 g, 222 mmol), benzoyl chloride (25.8 ml, 222 mmol) was added under ice-cool, which was stirred at room temperature for 4 hours. The reaction mixture was concentrated under reduced pressure and ethyl acetate and water were added to dissolve it. The organic layer was taken out and the aqueous layer was extracted with ethyl acetate. The organic layers were combined, washed with a saturated saline solution, dried over magnesium sulfate, and filtrated. The filtrate was concentrated under reduced pressure. The residue was suspended in n-heptane/ethyl acetate (1/1) and insoluble matter was removed by filtration. The filtrate was concentrated and dissolved in ethyl acetate. Silica gel was added to the resultant solution, which was concentrated, and subjected to silica gel column chromatography (elution solvent: n-heptane/ethyl acetate=3/1→2/1→1/1→0/1) to obtain a mixture (16.5 g) containing 3-hydroxy-2-oxopropyl benzoate, as a white solid.

A mixture of the mixture (0.5 g) containing 3-hydroxy-2-oxopropyl benzoate, 1,3-propanediol (0.932 ml, 12.9 mmol), triethyl orthoformate (0.428 ml, 2.58 mmol), and p-toluenesulfonic acid monohydrate (44.5 mg, 0.234 mmol) was stirred at room temperature for 4 days. Another mixture consisting of the mixture (4 g) containing 3-hydroxy-2-oxopropyl benzoate, 1,3-propanediol (7.46 ml, 103 mmol), triethyl orthoformate (3.42 ml, 20.6 mmol), and p-toluenesulfonic acid monohydrate (356 mg, 1.87 mmol) was stirred at 40° C. overnight. Two reaction mixtures were combined, water and ethyl acetate were added, and the organic layer was taken out. The organic layer was dried over magnesium sulfate and filtrated. The filtrate was concentrated under reduced pressure. The residue was dissolved in n-heptane/ethyl acetate (2/1) and toluene and subjected to silica gel column chromatography (elution solvent: n-heptane/ethyl acetate=3/2) to obtain the title compound (4.2 g).

$^1$H NMR(400 MHz, CDCl$_3$) δppm; 1.58-2.04(2H, m), 3.72 (2H, s), 3.92-3.99(2H, m), 4.05-4.13(2H, m), 4.66(2H, s), 7.41-7.48(2H, m), 7.56-7.60(1H, m), 8.02-8.07(2H, m).

(44b) (2-(fluoromethyl)-1,3-dioxan-2-yl)methyl benzoate

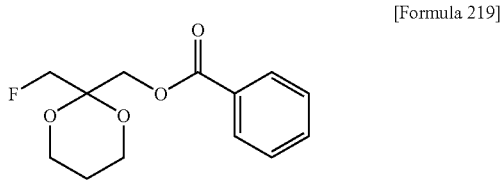

[Formula 219]

To a toluene (100 ml) solution of (2-(hydroxymethyl)-1,3-dioxan-2-yl)methyl benzoate (4.76 g, 18.8 mmol), 1,8-diazabicyclo[5.4.0]undec-7-ene (8.43 ml, 56.4 mmol) was added, cooled on ice and nonafluoro-1-butanesulfonyl chloride (5.06 ml, 28.2 mmol) was added. The mixture was stirred under ice-cool for 15 minutes, and at 40° C. for 20 hours, and further stirred at room temperature for 8 days. The reaction mixture was extracted by adding water and ethyl acetate. The organic layer was washed with a saturated saline solution, dried over magnesium sulfate, and filtrated through silica gel, and then, the filtrate was concentrated. The residue was subjected twice to silica gel column chromatography (elution solvent: n-heptane/ethyl acetate=4/1) to obtain the title compound (2.22 g, yield: 46.4%).

$^1$H NMR(400 MHz, CDCl$_3$) δppm; 1.63-1.74(1H, m), 1.89-2.01(1H, m), 3.93-4.01(2H, m), 4.05-4.13(2H, m), 4.56 (2H, d, J=47 Hz), 4.66(2H, d, J=2 Hz), 7.42-7.48(2H, m), 7.54-7.61(1H, m), 8.03-8.08(2H, m).

(44c) (2-(fluoromethyl)-1,3-dioxan-2-yl)methanol

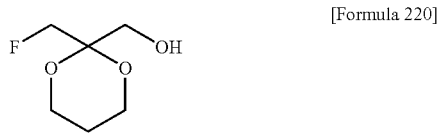

[Formula 220]

A mixture of (2-(fluoromethyl)-1,3-dioxan-2-yl)methyl benzoate (2.22 g, 8.73 mmol), methanol (20 ml) and a 1N-aqueous sodium hydroxide solution (13.1 ml) was stirred at room temperature overnight. Ammonium chloride was added to the reaction mixture, which was concentrated. The residue was suspended in tetrahydrofuran and ethyl acetate, and then magnesium sulfate was added and the mixture was stirred for 5 minutes. After NH silica gel filtration was performed, the filtrate was concentrated to obtain the title compound (1.17 g, 89.3%) as a colorless liquid.

$^1$H NMR(400 MHz, CDCl$_3$) δppm; 1.65-1.75(1H, m), 1.85-1.96(1H, m), 3.71(2H, d, J=3 Hz), 3.94-4.05(4H, m), 4.57(2H, d, J=47 Hz).

(44d) 2-(((4-((2-(fluoromethyl)-1,3-dioxan-2-yl)methoxy)-3,5-dimethylpyridin-2-yl)methyl)sulfinyl)-1H-benzimidazole sodium salt

[Formula 221]

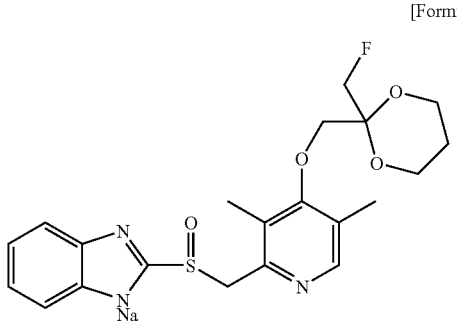

The same procedure as in the steps (1c) to (1g) of Example 1 was repeated using 4-chloro-2,3,5-trimethylpyridine 1-oxide and (2-(fluoromethyl)-1,3-dioxan-2-yl)methanol to obtain the title compound (331 mg, 5 steps: 12%) as a yellow solid.

$^1$H NMR(400 MHz, DMSO-d$_6$) δppm; 1.61-1.74(2H, m), 2.22(3H, s), 2.25(3H, s), 3.86-3.95(4H, m), 3.96(2H, s), 4.41 (1H, t, J=13 Hz), 4.64(2H, d, J=47 Hz), 4.75(1H, d, J=13 Hz), 6.81-6.88(2H, m), 7.39-7.46(2H, m), 8.21(1H, s).

Example 45

2-(((4-((2-(fluoromethyl)-1,3-dioxolan-2-yl)methoxy)-3-methylpyridin-2-yl)methyl)sulfinyl)-1H-benzimidazole sodium salt

[Formula 222]

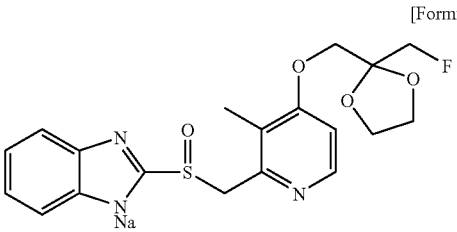

(45a) (2-(fluoromethyl)-1,3-dioxolan-2-yl)methanol

[Formula 223]

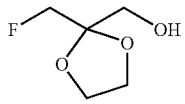

The same procedure as in the steps (44a) to (44c) using dihydroxyacetone except that ethylene glycol was used instead of 1,3-propanediol used in Example 44 to obtain the title compound (543 mg, total yield: 13.8%).

$^1$H NMR(400 MHz, CDCl$_3$) δppm; 1.70-1.82(1H, br), 3.66 (2H, d, J=2 Hz), 4.06(4H, s), 4.37(2H, d, J=47 Hz).

(45b) 2-(((4-((2-(fluoromethyl)-1,3-dioxolan-2-yl)methoxy)-3-methylpyridin-2-yl)methyl)sulfinyl)-1H-benzimidazole sodium salt

[Formula 224]

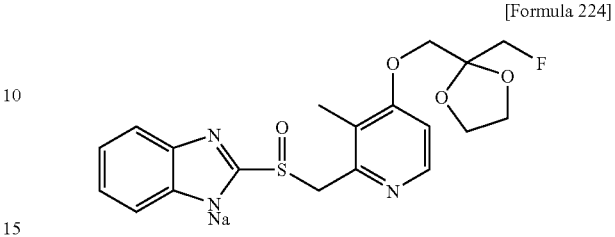

The same procedure as in the steps (3c) to (3h) of Example 3 was repeated using 4-chloro-2,3-dimethylpyridine 1-oxide and (2-(fluoromethyl)-1,3-dioxolan-2-yl)methanol to obtain the title compound (140 mg, 6 steps 8.2%) as a light yellow solid.

$^1$H NMR(400 MHz, DMSO-d$_6$) δppm; 2.20(3H, s), 3.95-4.05(4H, m), 4.10(2H, d, J=2 Hz), 4.38(1H, d, J=13 Hz), 4.48(2H, d, J=47 Hz), 4.83(1H, d, J=13 Hz), 6.81-6.88(2H, m), 6.96(1H, d, J=6 Hz), 7.39-7.46(2H, m), 8.27(1H, d, J=6 Hz).

Example 46

2-(((4-((5,5-difluoro-1,3-dioxan-2-yl)methoxy)-3-methylpyridin-2-yl)methyl)sulfinyl)-1H-benzimidazole sodium salt

[Formula 225]

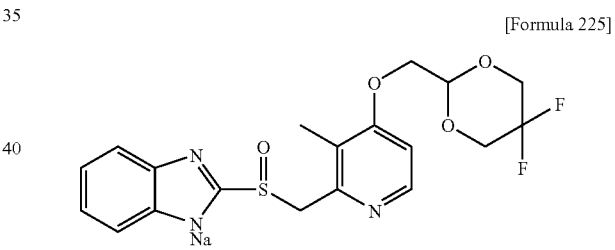

(46a) 2,2-difluoropropane-1,3-diyl diacetate

[Formula 226]

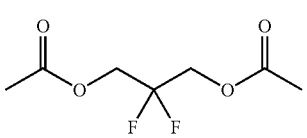

A mixture of 2-oxopropane-1,3-diyl diacetate (10.6 g, 60.8 mmol) and diethylaminosulfur trifluoride (24.2 ml, 182 mmol) was stirred at room temperature for 4 days. The reaction mixture was diluted with ethyl acetate, which was cooled on ice, and then a saturated sodium bicarbonate solution was added and the organic layer was taken out. The organic layer was washed twice with water, dried over magnesium sulfate and filtrated. The filtrate was concentrated under reduced pressure to obtain the title compound (10.92 g, 91.6%).

$^1$H NMR(400 MHz, CDCl$_3$) δppm; 2.13(6H, s), 4.35(4H, t, J=12 Hz).

(46b) 2,2-difluoropropane-1,3-diol

[Formula 227]

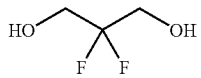

A mixture of 2,2-difluoropropane-1,3-diyl diacetate (10.9 g, 55.7 mmol), methanol (300 ml), and a 28% sodium methoxide methanol solution (32.2 g, 167 mmol) was stirred at room temperature for 2 hours. DOWEX 50W-X8 (100-200 mesh, H form) was added to the reaction mixture to adjust pH to 5. The mixture was filtrated and the filtrate was concentrated. To the residue, tetrahydrofuran and ethyl acetate were added to dissolve it. The solution was dried over magnesium sulfate and filtrated, and then the filtrate was concentrated. The residue was dissolved in ethyl acetate and filtrated through glass fiber filter paper. The filtrate was concentrated under reduced pressure to obtain the title compound (5.3 g, 84.9%).

$^1$H NMR(400 MHz, CDCl$_3$) δppm; 2.07-2.20(2H, br), 3.92 (4H, dt, J=1, 12 Hz).

(46c) 2-((benzyloxy)methyl)-5,5-difluoro-1,3-dioxane

[Formula 228]

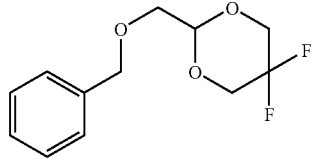

A mixture of 2,2-difluoropropane-1,3-diol (1 g, 8.9 mmol), benzyloxyacetaldehyde (1.34 g, 8.9 mmol), p-toluenesulfonic acid monohydrate (154 mg, 0.81 mmol) and toluene (20 ml) was heated under reflux by a condenser equipped with a Dean-Stark apparatus for one hour. The resultant mixture was stirred at room temperature overnight and then the reaction mixture was concentrated under reduced pressure. The residue was dissolved in ethyl acetate and silica gel was added thereto. The resultant mixture was concentrated to dryness and subjected to silica gel column chromatography (elution solvent: n-heptane/ethyl acetate=10/1) to obtain the title compound (930 mg, 42.8%).

$^1$H NMR(400 MHz, CDCl$_3$) δppm; 3.61(2H, d, J=5 Hz), 3.75-3.88(2H, m), 4.13-4.22(2H, m), 4.61(2H, s), 4.76(1H, t, J=5 Hz), 7.21-7.40(5H, m).

(46d) (5,5-difluoro-1,3-dioxan-2-yl)methanol

[Formula 229]

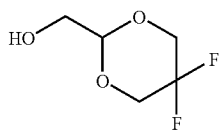

A mixture of 2-((benzyloxy)methyl)-5,5-difluoro-1,3-dioxane (930 mg, 3.81 mmol), 20% palladium hydroxide (353 mg), and ethyl acetate (30 ml) was stirred in a hydrogen atmosphere at room temperature for 4 hours and 25 minutes. The reaction mixture was filtrated and the filtrate was concentrated under reduced pressure to obtain the title compound (572 mg, 97.4%) as a colorless oil.

$^1$H NMR(400 MHz, CDCl$_3$) δppm; 3.72(2H, d, J=5 Hz), 3.78-3.90(2H, m), 4.16-4.23(2H, m), 4.69(1H, t, J=4 Hz).

(46e) 2-(((4-((5,5-difluoro-1,3-dioxan-2-yl)methoxy)-3-methylpyridin-2-yl)methyl)sulfinyl)-1H-benzimidazole sodium salt

[Formula 230]

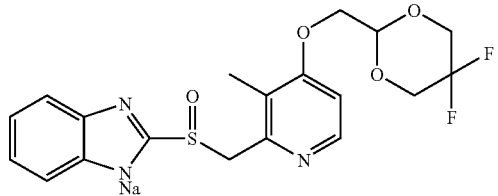

The same procedure as in the steps (1c) to (1g) of Example 1 was repeated using 4-chloro-2,3-dimethylpyridine 1-oxide and (5,5-difluoro-1,3-dioxan-2-yl)methanol to obtain the title compound (375 mg, 5 steps: 22.7%) as a white powder.

$^1$H NMR(400 MHz, DMSO-d$_6$) δppm; 2.19(3H, s), 4.00-4.25(6H, m), 4.38(1H, d, J=13 Hz), 4.83(1H, d, J=13 Hz), 5.17(1H, t, J=4 Hz), 6.81-6.87(2H, m), 6.96(1H, d, J=6 Hz), 7.39-7.45(2H, m), 8.27(1H, d, J=6 Hz).

Example 47

2-(((4-(2-(2,2-dimethyl-1,3-dioxolan-4-yl)ethoxy)-3-methylpyridin-2-yl)methyl)sulfinyl)-5-methyl-1H-benzimidazole sodium salt

[Formula 231]

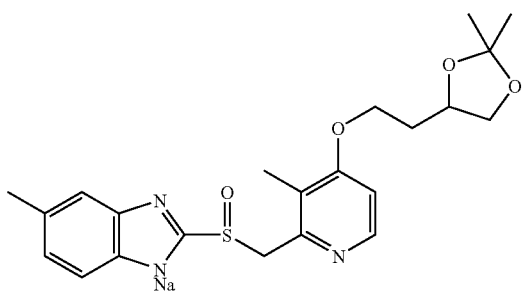

(47a) 5-methyl-1H-benzimidazole-2-thiol

[Formula 232]

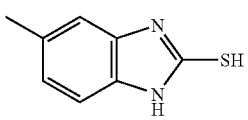

First, 3-amino-4-nitrotoluene (6.3 g, 41.4 mmol) and 10% palladium carbon (900 mg) were suspended in methanol (70 ml) and the mixture was stirred in a hydrogen atmosphere for 3 hours. The reaction vessel was purged with nitrogen and a catalyst was removed by filtration and washed with ethanol. To the reaction mixture, carbon disulfide (20 ml) was added and the mixture was stirred at room temperature for 5 days. After the reaction mixture was concentrated, diethyl ether was added to the residue. The generated solid was collected by filtration to obtain the title compound (6.1 g, yield: 89.7%) was obtained as a light yellow solid.

$^1$H NMR(400 MHz, DMSO-d$_6$) δppm; 2.33(3H, s), 6.90-6.93(2H, m), 7.00(1H, d, J=8 Hz).

(47b) 2-(((4-(2-(2,2-dimethyl-1,3-dioxolan-4-yl)ethoxy)-3-methylpyridin-2-yl)methyl)sulfinyl)-5-methyl-1H-benzimidazole sodium salt

[Formula 233]

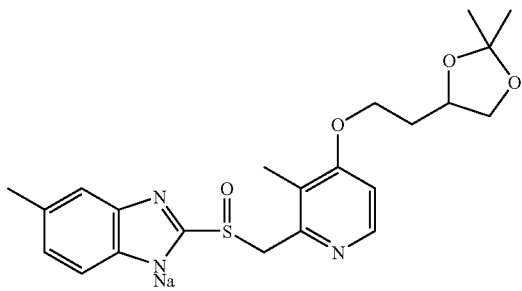

The same procedure as in the steps (1e) to (1g) of Example 1 was repeated using 5-methyl-1H-benzimidazole-2-thiol (309 mg, 1.88 mmol) obtained in the step (47a) and (4-(2-(2,2-dimethyl-1,3-dioxolan-4-yl)ethoxy)-3-methylpyridin-2-yl)methanol (501 mg, 1.88 mmol) to obtain the title compound (118 mg) as a white solid. Note that the operation of solidifying the title compound was performed as follows. Ether was added to the residue and ultrasonic wave was applied to the resultant mixture. The obtained suspension solution was allowed to stand and then the supernatant was removed. These operations were repeated twice. The resultant precipitate was subjected to aspiration to dryness to obtain the title compound.

$^1$H NMR(400 MHz, DMSO-d$_6$) δppm; 1.27(3H, s), 1.33 (3H, s), 1.96-2.04(2H, m), 2.18(3H, s), 2.36(3H, s), 3.59(1H, t, J=8 Hz), 4.04-4.14(3H, m), 4.21-4.26(1H, m), 4.37(1H, dd, J=4, 13 Hz), 4.80(1H, dd, J=2, 13 Hz), 6.69(1H, d, J=8 Hz), 6.92(1H, d, J=6 Hz), 7.22(1H, s), 7.31(1H, d, J=8 Hz), 8.28 (1H, d, J=6 Hz).

Example 48

2-(((4-((2,2-dimethyl-1,3-dioxan-5-yl)methoxy)-3-methylpyridin-2-yl)methyl)sulfinyl)-4-methoxy-1H-benzimidazole sodium salt

[Formula 234]

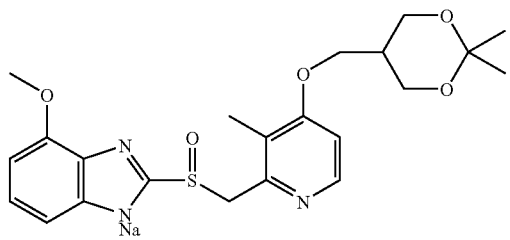

(48a) 4-methoxy-1H-benzimidazole-2-thiol

[Formula 235]

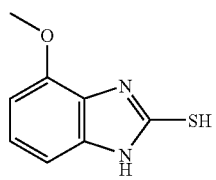

A mixture of 2-methoxy-6-nitroaniline (1 g, 5.95 mmol), 10% palladium carbon (300 mg) and methanol (25 ml) was stirred in a hydrogen atmosphere for 4 hours. The reaction vessel was purged with nitrogen and a catalyst was removed by filtration. To the reaction mixture, carbon disulfide (15 ml) was added and the mixture was stirred at room temperature overnight. Triethylamine (1 ml) was added to the reaction mixture, which was stirred at 50° C. for 3 hours. After the reaction mixture was concentrated, methanol (2 ml) and diethyl ether (20 ml) were added to the residue. The generated solid was collected by filtration to obtain the title compound (950 mg, yield: 88.6%) as a light orange solid.

$^1$H NMR(400 MHz, DMSO-d$_6$) δppm; 3.86(3H, s), 6.74 (1H, d, J=8 Hz), 6.75(1H, d, J=8 Hz), 7.05(1H, t, J=8 Hz).

(48b) 2-(((4-((2,2-dimethyl-1,3-dioxan-5-yl)methoxy)-3-methylpyridin-2-yl)methyl)sulfinyl)-4-methoxy-1H-benzimidazole sodium salt

[Formula 236]

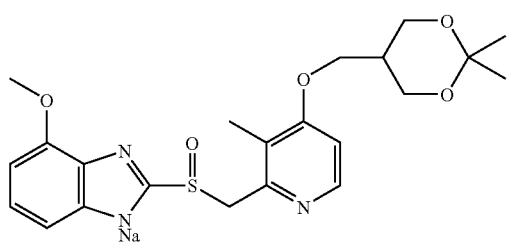

The same procedure as in the steps (1e) to (1g) of Example 1 was repeated using 4-methoxy-1H-benzimidazole-2-thiol (260 mg, 1.44 mmol) obtained in accordance with the method of the step (48a) and (4-((2,2-dimethyl-1,3-dioxan-5-yl)methoxy)-3-methylpyridin-2-yl)methanol (350 mg, 1.31 mmol) to obtain the title compound (326 mg) as a white solid.

$^1$H NMR(400 MHz, DMSO-d$_6$) δppm; 1.33(3H, s), 1.36 (3H, t, J=6 Hz), 2.06-2.14(1H, m), 2.20(3H, s), 3.75-3.80(2H, m), 3.88(3H, s), 3.97-4.01(2H, m), 4.10(2H, d, J=7 Hz), 4.35 (1H, d, J=13 Hz), 4.83(1H, d, J=13 Hz), 6.33(1H, d, J=8 Hz), 6.74(1H, t, J=8 Hz), 6.94(1H, d, J=6 Hz), 7.05(1H, d, J=8 Hz), 8.27(1H, d, J=6 Hz).

Example 49

2-(((4-((5,5-dimethyl-1,3-dioxan-2-yl)methoxy)-3,5-dimethylpyridin-2-yl)methyl)sulfinyl)-5-(trifluoromethyl)-1H-benzimidazole sodium salt

[Formula 237]

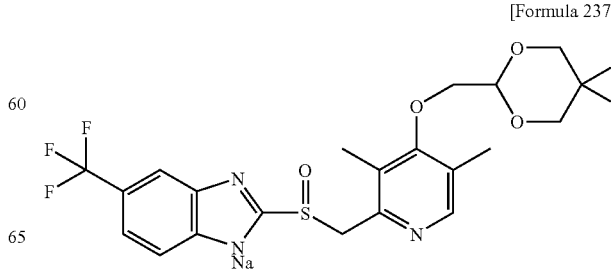

(49a) 5-(trifluoromethyl)-1H-benzimidazole-2-thiol

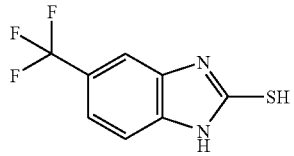

[Formula 238]

A mixture of 4-amino-3-nitrobenzotrifluoride (7 g, 34 mmol), 10% palladium carbon (1.3 g) and methanol (70 ml) was stirred in a hydrogen atmosphere for 5 hours. The reaction vessel was purged with nitrogen and a catalyst was removed by filtration. To the reaction mixture, carbon disulfide (30 ml) was added and the mixture was stirred at room temperature overnight, and thereafter the reaction mixture was concentrated. Methanol (60 ml), carbon disulfide (20 ml) and triethylamine (15 ml) were added to the residue and the mixture was stirred at 50° C. overnight. After the reaction mixture was concentrated, the residue was purified by silica gel column chromatography (silica gel 200 g, elution solvent: ethyl acetate/heptane=1/3→7/3. When Ethyl acetate/heptane=7/3, a little amount of methanol was added to the elution solvent) to obtain the title compound (5.3 g, yield: 71.4%) as a white solid.

$^1$H NMR(400 MHz, DMSO-$d_6$) δppm; 7.29(1H, d, J=8 Hz), 7.35(1H, s), 7.45(1H, d, J=8 Hz), 12.86(1H, br s).

(49b) 2-(((4-((5,5-dimethyl-1,3-dioxan-2-yl)methoxy)-3,5-dimethylpyridin-2-yl)methyl)sulfinyl)-5-(trifluoromethyl)-1H-benzimidazole sodium salt

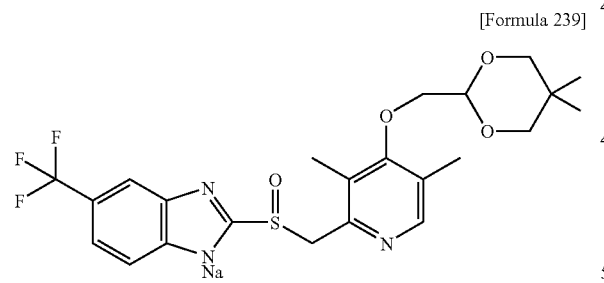

[Formula 239]

The same procedure as in the steps (1e) to (1 g) of Example 1 was repeated using 5-(trifluoromethyl)-1H-benzimidazole-2-thiol (137 mg, 0.626 mmol) obtained by the method of the step (49a) and (4-((5,5-dimethyl-1,3-dioxan-2-yl)methoxy)-3,5-dimethylpyridin-2-yl)methanol (176 mg, 0.626 mmol) to obtain the title compound (104 mg) as a light yellow solid. Note that when the title compound was solidified, heptane (10 ml) and diethyl ether (2 ml) were added and ultrasonically treated.

$^1$H NMR(400 MHz, DMSO-$d_6$) δppm; 0.70(3H, s), 1.10 (3H, s), 2.20(3H, s), 2.21(3H, s), 3.48(2H, d, J=11 Hz), 3.57 (2H, d, J=11 Hz), 3.82(2H, d, J=4 Hz), 4.76(1H, t, J=4 Hz), 7.14(1H, dd, J=2, 8 Hz), 7.59(1H, d, J=8 Hz), 7.77(1H, s), 8.21(1H, s).

Example 50

2-(((4-(5,7-dioxaspiro[2.5]oct-6-ylmethoxy)pyridin-2-yl)methyl)sulfinyl)-1H-benzimidazole sodium salt

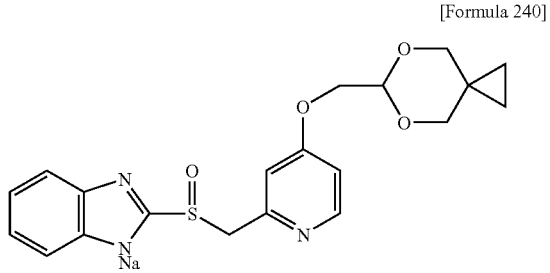

[Formula 240]

The same procedure as in the steps (10d) to (10f) of Example 10 was repeated using 2-mercaptobenzimidazole (291 mg, 1.94 mmol) and (4-(5,7-dioxaspiro[2.5]oct-6-ylmethoxy)pyridin-2-yl)methanol (443 mg, 1.76 mmol) to obtain the title compound (300 mg) as a white solid. Note that, in the same process as in the step (10d), 2-mercaptobenzimidazole was added to the reaction mixture and further 2 equivalents of triethylamine was added. The mixture was stirred at room temperature for 2 days.

$^1$H NMR(400 MHz, DMSO-$d_6$) δppm; 0.30-0.34(2H, m), 0.56-0.60(2H, m), 3.24(2H, d, J=12 Hz), 3.99(2H, t, J=4 Hz), 4.08(2H, d, J=12 Hz), 4.94(1H, t, J=4 Hz), 6.85-6.88(3H, m), 6.92(1H, dd, J=3, 6 Hz), 7.45(2H, dd, J=3, 6 Hz), 8.37(1H, d, J=6 Hz).

Example 51

2-(((4-((2,2-dimethyl-1,3-dioxolan-4-yl)methoxy)-3-ethylpyridin-2-yl)methyl)sulfinyl)-1H-benzimidazole sodium salt

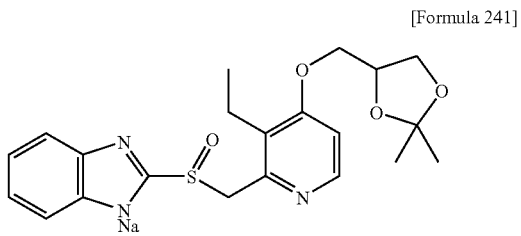

[Formula 241]

(51a) 2-methylpyridin-3-yl trifluoromethanesulfonate

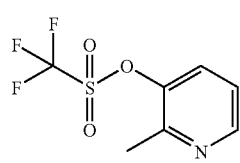

[Formula 242]

First, 3-hydroxy-2-methylpyridine (16.2 g, 148 mmol) and N-phenyltrifluoromethanesulfonimide (53.2 g, 149 mmol) were dissolved in dichloromethane (dehydrated) (450 ml). To the mixture, triethylamine (31 ml, 222 mmol) was added in a nitrogen atmosphere at 1 to 3° C. The mixture was stirred for 13 hours and 20 minutes while raising the temperature to room temperature. The reaction mixture was washed twice with a 1N aqueous sodium hydroxide solution, dried over anhydrous sodium sulfate, filtrated and concentrated to obtain the title compound (34.3 g, yield: 96.1%) as brown oil.

$^1$H NMR(400 MHz, DMSO-d$_6$) δppm; 2.54(3H, s), 7.44-7.52(1H, m), 7.90-7.96(1H, m), 8.56-8.60(1H, m).

(51b) 2-methyl-3-((trimethylsilyl)ethynyl)pyridine

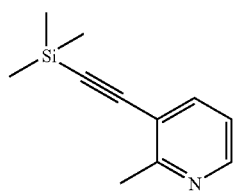

[Formula 243]

First, 2-methylpyridin-3-yl trifluoromethanesulfonate (34.3 g, 142 mmol), trimethylsilylacetylene (30 ml, 212 mmol), bis(triphenylphosphine)palladium (II) chloride (10.0 g, 14.2 mmol), and copper (I) iodide (2.75 g, 14.4 mmol) were dissolved in N,N-dimethyl formamide (150 ml). Thereafter, triethylamine (43 ml, 309 mmol) was added in a nitrogen atmosphere at room temperature to the mixture. The mixture was then stirred for 3 hours (exothermic reaction took place). The reaction mixture was separated by ethyl acetate and a saturated aqueous ammonium chloride solution and insoluble substance was removed by filtration. The organic layer of the filtrate was washed twice with a saturated aqueous ammonium chloride solution, dried over anhydrous magnesium sulfate, filtrated and concentrated to obtain the title compound (22.6 g, yield: 84.1%) as brown oil.

$^1$H NMR(400 MHz, DMSO-d$_6$) δppm; 0.25(9H, s), 2.57 (3H, s), 7.22(1H, dd, J=5, 8 Hz), 7.79(1H, dd, J=2, 8 Hz), 8.43(1H, dd, J=2, 5 Hz).

(51c) 3-ethyl-2-methylpyridine

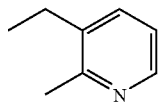

[Formula 244]

First, 2-methyl-3-((trimethylsilyl)ethynyl)pyridine (22.6 g, 119 mmol) was dissolved in tetrahydrofuran (dehydrated) (200 ml). To the mixture, tetrabutyl ammonium fluoride (1N tetrahydrofuran solution) (150 ml, 150 mmol) was added. The mixture was stirred at room temperature for one hour. The reaction mixture was partitioned by ethyl acetate and a saturated aqueous ammonium chloride solution. The aqueous layer was extracted with ethyl acetate. The organic layers were combined and washed twice with a saturated aqueous ammonium chloride solution, dried over anhydrous magnesium sulfate, and distilled by a rotary evaporator. To the obtained fraction, 10% palladium/carbon (900 mg) was added and stirred in a hydrogen atmosphere at room temperature for 2 hours. The reaction mixture was filtrated through anhydrous magnesium sulfate and cerite. To the filtrate, 10% palladium/carbon (810 mg) was added and the mixture was stirred in a hydrogen atmosphere at room temperature for 4 hours. The reaction mixture was filtrated through anhydrous magnesium sulfate and celite and thereafter the filtrate was concentrated to obtain the title compound (7.25 g, yield: 51.1%) as a colorless oil.

$^1$H NMR(400 MHz, DMSO-d$_6$) δppm; 1.16(3H, t, J=8 Hz), 2.45(3H, s), 2.60(2H, q, J=8 Hz), 7.14(1H, dd, J=5, 7 Hz), 7.51(1H, dd, J=1, 7 Hz), 8.26(1H, dd, J=1, 5 Hz).

(51d) 3-ethyl-2-methylpyridine1-oxide

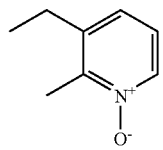

[Formula 245]

First, 3-ethyl-2-methylpyridine (7.25 g, 59.8 mmol) was dissolved in dichloromethane (dehydrated)(100 ml) and 3-chloroperbenzoic acid (19.0 g, 71.6 mmol, as the content was regarded as 65%) was added in a nitrogen atmosphere at ice-cooling temperature. The mixture was stirred at room temperature for 90 hours. To the reaction mixture, a saturated aqueous sodium hydrogen carbonate solution was added. The aqueous layer was extracted twice with dichloromethane and three times with chloroform. The organic layers were combined, dried over anhydrous magnesium sulfate, filtrated and concentrated. The residue was purified by silica gel column chromatography (silica gel: 100 g, elution solvent: heptane, ethyl acetate/methanol=10/1) to obtain the title compound (7.35 g, yield: 89.6%) as a reddish solid.

$^1$H NMR(400 MHz, DMSO-d$_6$) δppm; 1.14(3H, t, J=8 Hz), 2.35(3H, s), 2.64(2H, q, J=8 Hz), 7.12-7.24(2H, m), 8.10-8.16(1H, m).

(51e) 3-ethyl-2-methyl-4-nitropyridine1-oxide

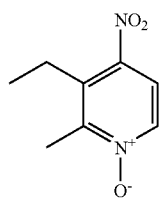

[Formula 246]

While cooling a mixture of 3-ethyl-2-methylpyridine 1-oxide (7.35 g, 53.6 mmol) and sulfuric acid (22.7 g, 231=mmol) in an ice bath, fuming nitric acid (3.64 ml, 87.9 mmol) was added dropwise, which was stirred at 80° C. for 8 hours. The reaction mixture was cooled to room temperature and then poured into ice. The obtained aqueous solution was extracted three times with chloroform. The organic layers were combined, dried over anhydrous magnesium sulfate, filtrated and concentrated to obtain the title compound (3.37 g, yield: 34.5%) as yellow solid.

$^1$H NMR(400 MHz, DMSO-d$_6$) δppm; 1.21(3H, t, J=7 Hz), 2.45(3H, s), 2.80(2H, q, J=7 Hz), 7.88(1H, d, J=7 Hz), 8.36(1H, d, J=7 Hz).

(51f) 4-chloro-3-ethyl-2-methylpyridine 1-oxide

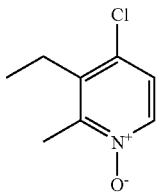
[Formula 247]

First, 3-ethyl-2-methyl-4-nitropyridine 1-oxide (3.37 g, 18.5 mmol) was added to acetyl chloride (20 ml, 281 mmol) in a nitrogen atmosphere at −30° C. The mixture was stirred at −30 to 0° C. for 3 hours. After the reaction mixture was concentrated, the residue was partitioned by chloroform and a saturated aqueous sodium hydrogen carbonate solution. After insoluble substance was removed by filtration, the aqueous layer was extracted twice with chloroform. The organic layers were combined and dried over anhydrous magnesium sulfate, filtrated and concentrated. The residue was purified by silica gel column chromatography (NH silica gel: 100 g, elution solvent: heptane, heptane/ethyl acetate=50/50) to obtain the title compound (2.10 g, yield: 66.1%) as a yellow oil.

$^1$H NMR(400 MHz, DMSO-$d_6$) δppm; 1.10(3H, t, J=8 Hz), 2.42(3H, s), 2.77(2H, q, J=8 Hz), 7.41(1H, d, J=7 Hz), 8.16(1H, d, J=7 Hz).

(51g) 2-(((4-((2,2-dimethyl-1,3-dioxolan-4-yl)methoxy)-3-ethylpyridin-2-yl)methyl)sulfinyl)-1H-benzimidazole sodium salt

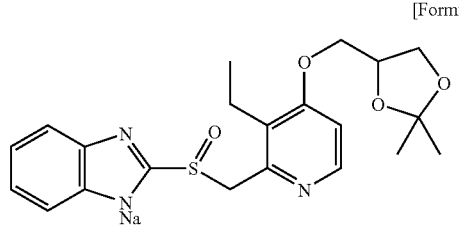
[Formula 248]

The same procedure as in the step (10b) of Example 10 and the steps (11f)-(11i) of Example 11 was repeated using 4-chloro-3-ethyl-2-methylpyridine 1-oxide, solketal and 2-mercaptobenzimidazole to obtain the title compound (122 mg, yield: 5.6%) as a white solid.

$^1$H NMR(400 MHz, DMSO-$d_6$) δppm; 1.07(3H, t, J=7 Hz), 1.30(3H, s), 1.35(3H, s), 2.60-2.83(2H, m), 3.81(1H, t, J=7 Hz), 4.01-4.18(3H, m), 4.32-4.47(2H, m), 4.67-4.77(1H, m), 6.79-6.89(2H, m), 6.95(1H, d, J=5H), 7.38-7.49(2H, m), 8.29(1H, d, J=5 Hz).

Example 52

2-(((4-((2,2-dimethyl-1,3-dioxolan-4-yl)methoxy)-3-methylpyridin-2-yl)methyl)sulfinyl)-5-fluoro-1H-benzimidazole sodium salt

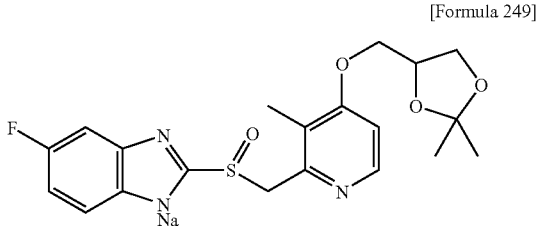
[Formula 249]

(52a) 5-fluoro-1H-benzimidazole-2-thiol

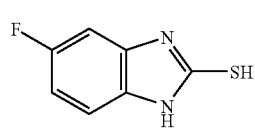
[Formula 250]

A mixture of 3,4-diamino-1-fluorobenzene (10 g, 79.3 mmol), carbon disulfide (70 ml, 1164 mmol), and methanol (100 ml) was stirred at room temperature for 86 hours and 50 minutes. After the reaction mixture was concentrated, the residue was suspended in hexane. The resultant precipitate was collected by filtration and washed with hexane to obtain the title compound (13.1 g, yield: 98.2%) as a brown solid.

$^1$H NMR(400 MHz, DMSO-$d_6$) δppm; 6.90-6.99(2H, m), 7.06-7.13(1H, m), 12.58(1H, s), 12.61(1H, s).

(52b) 2-(((4-((2,2-dimethyl-1,3-dioxolan-4-yl)methoxy)-3-methylpyridin-2-yl)methyl)sulfinyl)-5-fluoro-1H-benzimidazole sodium salt

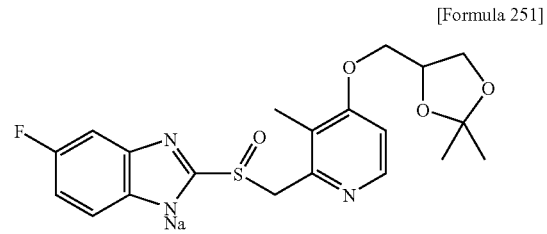
[Formula 251]

The same procedure as in the step (10b) of Example 10 and the step (14b) of Example 14, the step (5f) of Example 5, the steps (11h) and (11i) of Example 11 was repeated using solketal, 4-chloro-2,3-dimethylpyridine 1-oxide, and 5-fluoro-1H-benzimidazole-2-thiol to obtain the title compound (210 mg, yield: 14.1%) as a white solid. Note that methanol was used as a solvent instead of ethanol in the same operation as in the step (5f).

$^1$H NMR(400 MHz, DMSO-$d_6$) δppm; 1.29(3H, s), 1.30-1.40(3H, m), 2.17(3H, s), 3.80(1H, dd, J=6, 8 Hz), 4.00-4.16 (3H, m), 4.37(1H, d, J=13 Hz), 4.42(1H, quint, J=6 Hz), 4.70-4.79(1H, m), 6.62-6.73(1H, m), 6.94(1H, d, J=5 Hz), 7.08-7.16(1H, m), 7.33-7.43(1H, m), 8.27(1H, d, J=5 Hz).

Example 53

2-(((4-(1,3-dioxan-5-ylmethoxy)-3-methylpyridin-2-yl)methyl)sulfinyl)-1H-benzimidazole sodium salt

[Formula 252]

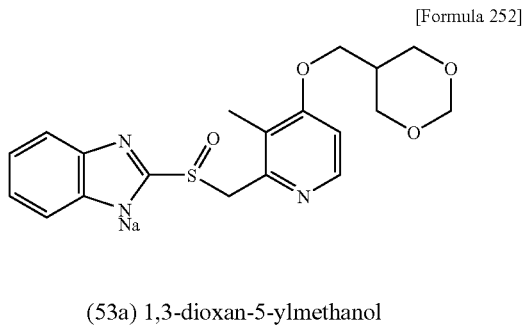

(53a) 1,3-dioxan-5-ylmethanol

[Formula 253]

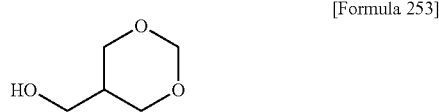

A mixture of 2-(hydroxymethyl)-1,3-propanediol (3.06 g, 28.8 mmol), formaldehyde dimethylacetal (9 ml, 102 mmol), lithium bromide (488 mg, 5.62 mmol), p-toluenesulfonic acid monohydrate (491 mg, 2.58 mmol), and dichloromethane (dehydrate)(15 ml) was stirred for 7 days. After adding triethylamine (1 ml), the reaction mixture was concentrated. The residue was purified by silica gel column chromatography (silica gel: 100 g, elution solvent: heptane, heptane/ethyl acetate=1/1, 1/3) to obtain the title compound (1.37 g, yield: 40.3%) as a colorless oil.

$^1$H NMR(400 MHz, DMSO-d$_6$) δppm; 1.76-1.86(1H, m), 3.36(2H, t, J=6 Hz), 3.57(2H, dd, J=8, 11 Hz), 3.90(2H, dd, J=4, 8 Hz), 4.58(1H, t, J=6 Hz), 4.63(1H, d, J=6 Hz), 4.79(1H d, J=6 Hz).

(53b) 2-(((4-(1,3-dioxan-5-ylmethoxy)-3-methylpyridin-2-yl)methyl)sulfinyl)-1H-benzimidazole sodium salt

[Formula 254]

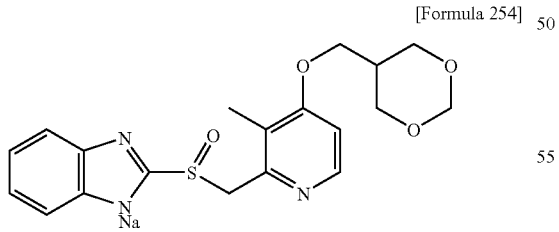

The same procedure as in the step (10b) of Example 10 and the steps (11f)-(11i) of Example 11 was repeated using 1,3-dioxan-5-ylmethanol, 4-chloro-2,3-dimethylpyridine 1-oxide, and 2-mercaptobenzimidazole to obtain the title compound (927 mg, yield: 24.2%) as a white solid.

$^1$H NMR(400 MHz, DMSO-d$_6$) δppm; 2.15-2.27(1H, m), 2.19(3H, s), 3.73-3.85(2H, m), 3.98-4.06(2H, m), 4.11(2H, d, J=7 Hz), 4.40(1H, d, J=13 Hz), 4.75(1H, d, J=6 Hz), 4.77(1H, d, J=13 Hz), 4.83(1H, d, J=6 Hz), 6.80-6.91(2H, m), 6.96(1H, d, J=6 Hz), 7.40-7.51(2H, m), 8.30(1H, d, J=6 Hz).

Example 54

2-(((4-((2,2-dimethyl-1,3-dioxan-5-yl)methoxy)-3-methylpyridin-2-yl)methyl)sulfinyl)-4-methyl-1H-benzimidazole sodium salt

[Formula 255]

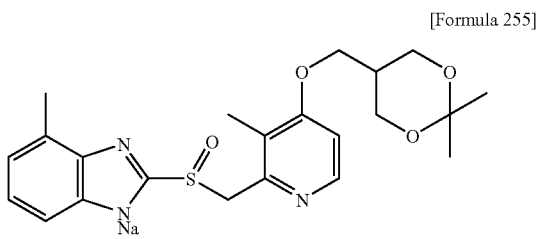

(54a) 4-methyl-1H-benzimidazole-2-thiol

[Formula 256]

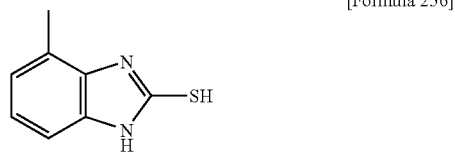

First, 2-methyl-6-nitroaniline (7 g, 46 mmol) and 10% palladium carbon (900 mg) were suspended in methanol (70 ml) and which was stirred in a hydrogen atmosphere for 5 hours. The reaction vessel was purged with nitrogen and a catalyst was removed by filtration. To the reaction mixture, carbon disulfide (30 ml) was added and the mixture was stirred at room temperature overnight. After the solvent was distilled off under reduced pressure, diethyl ether was added to the residue. The generated solid was collected by filtration to obtain the title compound (6.9 g, yield: 92.7%) as a light blue solid.

$^1$H NMR(400 MHz, DMSO-d$_6$) δppm; 2.37(3H, s), 6.91 (1H, t, J=8 Hz), 6.94(1H, d, J=8 Hz), 7.00(1H, d, J=8 Hz).

(54b) 2-(((4-((2,2-dimethyl-1,3-dioxan-5-yl)methoxy)-3-methylpyridin-2-yl)methyl)sulfinyl)-4-methyl-1H-benzimidazole sodium salt

[Formula 257]

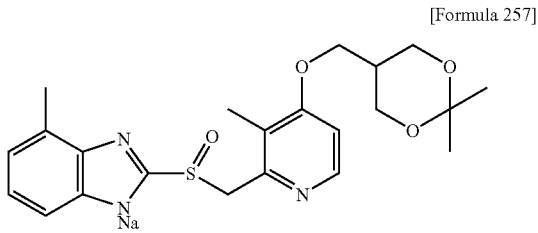

The same procedure as in the steps (11g)-(11i) of Example 11 was repeated using 4-methyl-1H-benzimidazole-2-thiol and (4-((2,2-dimethyl-1,3-dioxan-5-yl)methoxy)-3-methylpyridin-2-yl)methanol to obtain the title compound (327 mg, yield: 36.5%) as a white solid.

$^1$H NMR(400 MHz, DMSO-d$_6$) δppm; 1.33(3H, s), 1.36 (3H, s), 2.05-2.14(1H, m), 2.21(3H, s), 2.48(3H, s), 3.75-3.82 (2H, m), 3.97-4.02(2H, m), 4.11(2H, d, J=7 Hz), 4.44(1H, d, J=13 Hz), 4.77(1H, d, J=13 Hz), 6.65(1H, d, J=7 Hz), 6.75 (1H, dd, J=7, 8 Hz), 6.95(1H, d, J=6 Hz), 7.26(1H, d, J=8 Hz), 8.29(1H, d, J=6 Hz).

Example 55

2-(((4-((2,2-dimethyl-1,3-dioxan-5-yl)methoxy)-3-methylpyridin-2-yl)methyl)sulfinyl)-5-methyl-1H-benzimidazole sodium salt

[Formula 258]

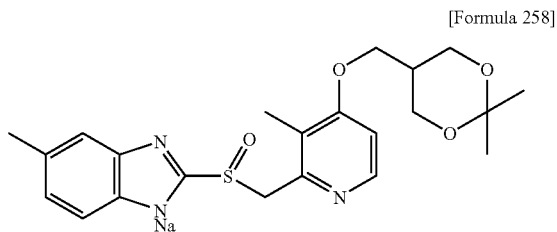

The same procedure as in the steps (11g)-(11i) of Example 11 was repeated using 5-methyl-1H-benzimidazole-2-thiol and (4-((2,2-dimethyl-1,3-dioxan-5-yl)methoxy)-3-methylpyridin-2-yl)methanol to obtain the title compound (330 mg, yield: 35.6%) as a white solid.

$^1$H NMR(400 MHz, DMSO-$d_6$) δppm; 1.33(3H, s), 1.36 (3H, s), 2.06-2.15(1H, m), 2.17(3H, s), 2.36(3H, s), 3.75-3.82 (2H, m), 3.97-4.02(2H, m), 4.11(2H, d, J=7 Hz), 4.38(1H, d, J=13 Hz), 4.77(1H, d, J=13 Hz), 6.69(1H, dd, J=2, 8 Hz), 6.95(1H, d, J=6 Hz), 7.23(1H, d, J=2 Hz), 7.32(1H, d, J=8 Hz), 8.29(1H, d, J=6 Hz).

Example 56

2-(((4-((2,2-dimethyl-1,3-dioxan-5-yl)methoxy)-3,5-dimethylpyridin-2-yl)methyl)sulfinyl)-5-fluoro-1H-benzimidazole sodium salt

[Formula 259]

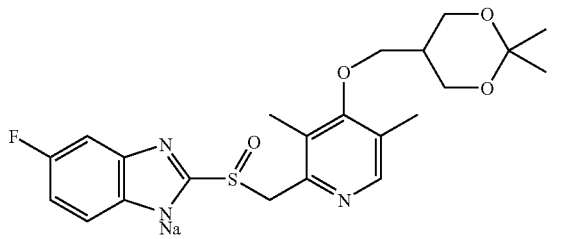

The same procedure as in the steps (11g)-(11i) of Example 11 was repeated using 5-fluoro-1H-benzimidazole-2-thiol and (4-((2,2-dimethyl-1,3-dioxan-5-yl)methoxy)-3,5-dimethylpyridin-2-yl)methanol to obtain the title compound (169 mg, yield: 33.7%) as a white solid.

$^1$H NMR(400 MHz, DMSO-$d_6$) δppm; 1.33(3H, s), 1.36 (3H, s), 2.03-2.13(1H, m), 2.20(6H, s), 3.76-3.87(4H, m), 4.00(2H, dd, J=4, 11 Hz), 4.38(1H, d, J=13 Hz), 4.74(1H, d, J=13 Hz), 6.65-6.74(1H, m), 7.10-7.17(1H, m), 7.36-7.43 (1H, m), 8.22(1H, s).

Example 57

2-(((4-(5,9-dioxaspiro[3.5]non-7-ylmethoxy)pyridin-2-yl)methyl)sulfinyl)-1H-benzimidazole sodium salt

[Formula 260]

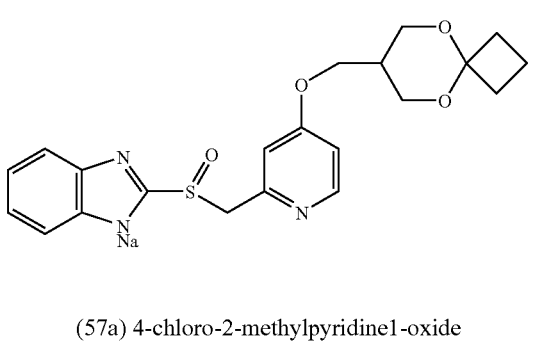

(57a) 4-chloro-2-methylpyridine1-oxide

[Formula 261]

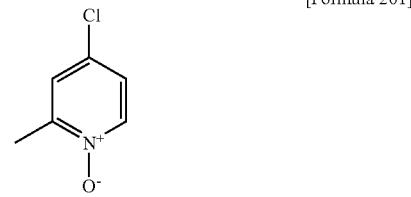

4-nitro-2-picoline N-oxide (20 g, 130 mmol) was added to acetyl chloride (120 ml, 1688 mmol) in a nitrogen atmosphere at −25° C. The mixture was stirred at −30 to 5° C. for 4 hours and 15 minutes. After the reaction mixture was diluted with ethyl acetate (about 150 ml) and chloroform (about 100 ml), the mixture was concentrated. The residue was purified by silica gel column chromatography (NH silica gel: 200 g, elution solvent: heptane, heptane/ethyl acetate=75/25, 50/50, 25/75, ethyl acetate, ethyl acetate/methanol=20/1) to obtain the title compound (3.14 g) as brown oil. Simultaneously, a crude product (about 17 g) was obtained. The crude product thus obtained was further purified by silica gel column chromatography (NH silica gel: 300 g, elution solvent: heptane, heptane/ethyl acetate=75/25, 40/60, 25/75, ethyl acetate) to obtain the title compound (5.39 g) separately as brown oil.

$^1$H NMR(400 MHz, DMSO-$d_6$) δppm; 2.33(3H, s), 7.41 (1H, dd, J=3, 7 Hz), 7.68(1H, d, J=3 Hz), 8.25(1H, d, J=7 Hz).

(57b) 2-(((4-(5,9-dioxaspiro[3.5]non-7-ylmethoxy)pyridin-2-yl)methyl)sulfinyl)-1H-benzimidazole sodium salt

[Formula 262]

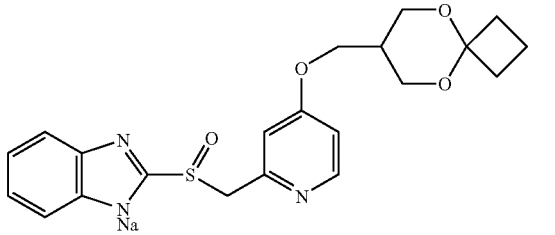

The same procedure as in the step (10b) of Example 10 and the steps (11f)-(11i) of Example 11 was repeated using 4-chloro-2-methylpyridine1-oxide, 5,9-dioxaspiro[3.5]non-7-ylmethanol obtained in the same method as in the step (13a), and 2-mercaptobenzimidazole to obtain the title compound (274 mg, yield: 11.4%) as a white solid. Note that in the same operation as in the step (11g), after 2-mercaptobenzimidazole was added to the reaction mixture, the mixture was stirred at room temperature for one day and further 2 equivalent of triethylamine based on the alcohol was added and stirred at 50° C. for 8 hours and 35 minutes and at room temperature for 84 hours and 40 minutes.

$^1$H NMR(400 MHz, DMSO-$d_6$) δppm; 1.64(2H, quint, J=8 Hz), 1.88-1.97(1H, m), 2.13(2H, t, J=8 Hz), 2.15(2H, t, J=8 Hz), 3.47-3.62(3H, m), 3.75-3.85(3H, m), 4.45(1H, d, J=12 Hz), 4.90(1H, d, J=12 Hz), 6.58(1H, d, J=2 Hz), 6.82(1H, dd, J=2, 6 Hz), 6.84-6.91(2H, m), 7.42-7.48(2H, m), 8.31(1H, d, J=6 Hz).

Example 58

2-(((4-(6,10-dioxaspiro[4.5]dec-8-ylmethoxy)pyridin-2-yl)methyl)sulfinyl)-1H-benzimidazole sodium salt

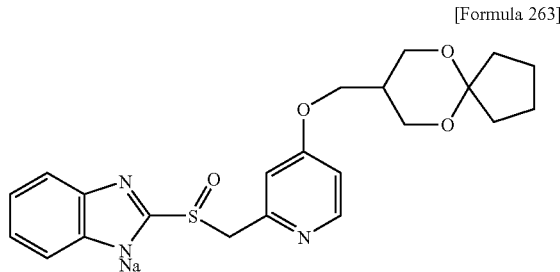

[Formula 263]

The same procedure as in the step (10b) of Example 10 and the steps (11f)-(11i) of Example 11 was repeated using 4-chloro-2-methylpyridine1-oxide, 6,10-dioxaspiro[4.5]dec-8-ylmethanol obtained in the same method as in the step (21a), and 2-mercaptobenzimidazole to obtain the title compound (427 mg, yield: 15.6%) as a white solid.

$^1$H NMR(400 MHz, DMSO-$d_6$) δppm; 1.52-1.63(4H, m), 1.73-1.86(4H, m), 1.88-1.98(1H, m), 3.52-3.66(3H, m), 3.78-3.88(3H, m), 4.45(1H, d, J=12 Hz), 4.59(1H, d, J=12 Hz), 6.60(1H, d, J=3 Hz), 6.82 (1H, dd, J=3, 6 Hz), 6.84-6.91(2H, m), 7.42-7.49(2H, m), 8.32(1H, d, J=6 Hz).

Example 59

2-(((4-((2,2-bis(fluoromethyl)-1,3-dioxan-5-yl)methoxy)pyridin-2-yl)methyl)sulfinyl)-1H-benzimidazole sodium salt

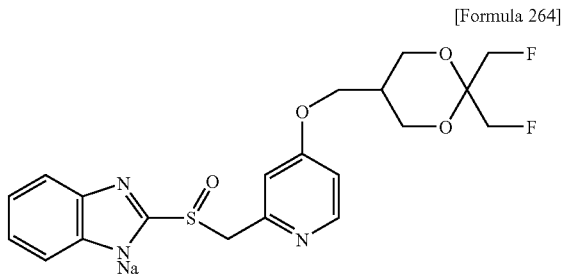

[Formula 264]

The same procedure as in the step (10b) of Example 10 and the steps (11f)-(11i) of Example 11 was repeated using 4-chloro-2-methylpyridine1-oxide, (2,2-bis(fluoromethyl)-1,3-dioxan-5-yl)methanol obtained in the same method as in the step (7a), and 2-mercaptobenzimidazole to obtain the title compound (326 mg, yield: 12.5%) as a white solid.

$^1$H NMR(400 MHz, DMSO-$d_6$) δppm; 2.02-2.12(1H, m), 3.68-3.78(3H, m), 3.90(1H, dd, J=7, 10 Hz), 3.97-4.06(2H, m), 4.40-4.65(6H, m), 6.66(1H, d, J=2 Hz), 6.83-6.92(3H, m), 7.43-7.50(2H, m), 8.34(1H, d, J=6 Hz).

Example 60

2-(((4-(1,5,9-trioxaspiro[5.5]undec-3-ylmethoxy)pyridin-2-yl)methyl)sulfinyl)-1H-benzimidazole sodium salt

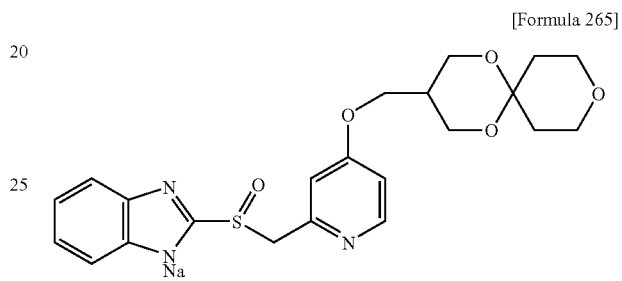

[Formula 265]

The same procedure as in the step (10b) of Example 10 and the steps (11f)-(11i) of Example 11 was repeated using 4-chloro-2-methylpyridine1-oxide, 1,5,9-trioxaspiro[5.5]undec-3-ylmethanol obtained in the same method as in the step (10a), and 2-mercaptobenzimidazole to obtain the title compound (313 mg, yield: 7.1%) as a white solid. Note that in the same operation as in the step (11g), after 2-mercaptobenzimidazole was added to the reaction mixture, the mixture was stirred at room temperature for 86 hours and 30 minutes and further 2 equivalents of triethylamine relative to the alcohol was added and stirred at 50° C. for 10 hours and at room temperature for 14 hours and 30 minutes.

$^1$H NMR(400 MHz, DMSO-$d_6$) δppm; 1.76(2H, t, J=5 Hz), 1.81(2H, t, J=5 Hz), 1.91-2.02 (1H, m), 3.55(4H, t, J=5 Hz), 3.58-3.75(3H, m), 3.83-3.96(3H, m), 4.44(1H, d, J=12 Hz), 4.58(1H, d, J=12 Hz), 6.64(1H, d, J=2 Hz), 6.82-6.91 (3H, m), 7.43-7.49(2H, m), 8.33(1H, d, J=6 Hz).

Example 61

2-(((4-(2,3-dihydro-1,4-benzodioxin-2-ylmethoxy)-3-methylpyridin-2-yl)methyl)sulfinyl)-1H-benzimidazole sodium salt

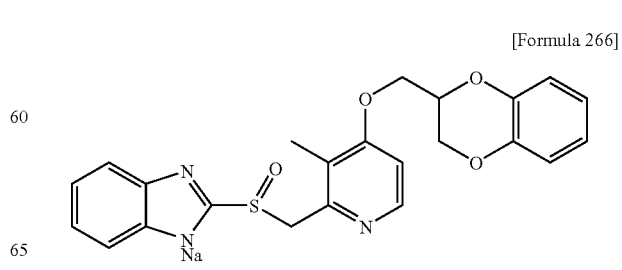

[Formula 266]

The same procedure as in the steps (8c) to (8g) of Example 8 was repeated using 2-hydroxymethyl-1,4-benzodioxane to obtain the title compound (141 mg, total yield: 3%) as a white solid.

¹H NMR(400 MHz, DMSO-d₆) δppm; 2.20(3H, s), 4.19 (1H, dd, J=7, 12 Hz), 4.30-4.34(2H, m), 4.38(1H, dd, J=5, 13 Hz), 4.46(1H, dd, J=2, 12 Hz), 4.61-4.63(1H, m), 4.82(1H, dd, J=5, 13 Hz), 6.82-6.93(6H, m), 6.98(1H, d, J=6 Hz), 7.43(2H, dd, J=3, 6 Hz), 8.29(1H, d, J=6 Hz).

Example 62

2-(((4-(1,4-dioxan-2-ylmethoxy)-3-methylpyridin-2-yl)methyl)sulfinyl)-1H-benzimidazole sodium salt

[Formula 267]

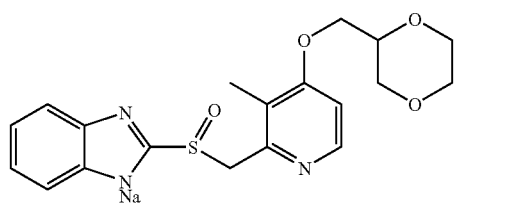

(62a) 2-iodomethyl-1,4-dioxane

[Formula 268]

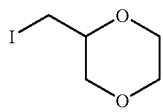

To an acetonitrile (420 mL) solution of 2-(allyloxy)ethanol (14 g, 137 mmol), sodium hydrogen carbonate (34.6 g, 410 mmol) and iodine (104 g, 410 mmol) were added and stirred at room temperature for 20 hours. To the reaction mixture, water was added and was extracted with ethyl acetate. Thereafter, the organic layer was washed with an aqueous sodium thiosulfate solution and a saturated saline solution, dried over magnesium sulfate, and filtrated through a silica gel column pad, and the filtrate was concentrated to obtain the title compound (26.5 g, yield 85%) as a yellow liquid.

¹H NMR(400 MHz, CDCl₃) δppm; 3.10(2H, d, J=8 Hz), 3.34(1H, dd, J=8, 13 Hz), 3.66-3.98 (6H, m).

(62b) 2-hydroxymethyl-1,4-dioxane

[Formula 269]

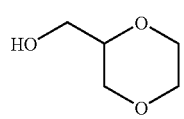

To the 2-iodomethyl-1,4-dioxane (15 g, 65.8 mmol) obtained in the step (62a), potassium acetate (64.6 g, 658 mmol), 18-crown-6 (1.74 g, 6.58 mmol), and N,N-dimethylformamide (220 mL) were added and stirred at 80° C. for 24 hours. To the reaction mixture, water was added and extracted with ethyl acetate. The organic layers were combined and washed with water and a saturated saline solution, dried over magnesium sulfate to obtain an acetoxy compound (5 g). The acetoxy compound was dissolved in methanol (60 mL) and hydrochloric acid (1 mL) was added dropwise. The mixture was stirred at room temperature for one hour and at 40° C. for one hour, and then neutralized by adding triethylamine. The mixture was concentrated and the residue was extracted with ether. Insoluble substance was filtered off, and the filtrate was concentrated and the residue was purified by silica gel column chromatography (silica gel: 500 ml, elution solvent: heptane/ethyl acetate=3/2, 1/1, 0/1) to obtain the title compound (2.15 g, yield: 27%) as colorless liquid.

¹H NMR(400 MHz, CDCl₃) δppm; 3.44-3.89(9H, m).

(62c) 4-(1,4-dioxan-2-ylmethoxy)-2,3-dimethylpyridine 1-oxide

[Formula 270]

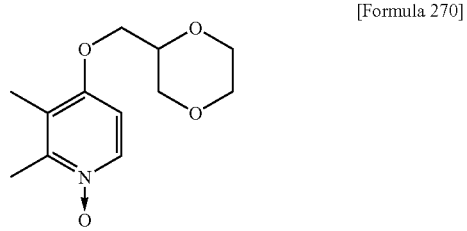

A toluene solution of the 2-hydroxymethyl-1,4-dioxane (2.24 g, 19 mmol) obtained in the step (62b) and 4-chloro-2,3-dimethylpyridine 1-oxide (2.5 g, 15.8 mmol) was heated to 140° C. To the solution, KOH (2 g, 34.8 mmol) was added in twice and the resultant mixture was heated under reflux at the same temperature for 3 hours while removing water from the reaction system by use of a Dean-Stark apparatus. To the reaction mixture, NH silica gel was added and the solvent was removed. The mixture of the crude reaction product and NH silica gel was subjected to purification by silica gel column chromatography (NH silica gel, elution solvent: ethyl acetate/methanol=9/1 to 4/1) to obtain the title compound (2.9 g, yield: 77%) as a light yellow solid.

¹H NMR(400 MHz, DMSO-d₆) δppm; 2.11(3H, s), 2.32 (3H, s), 3.37-3.50(2H, m), 3.58-3.88(5H, m), 4.01-4.02(2H, m), 6.93(1H, d, J=7 Hz), 8.06(1H, d, J=7 Hz).

(62d) 2-(((4-(1,4-dioxan-2-ylmethoxy)-3-methylpyridin-2-yl)methyl)sulfinyl)-1H-benzimidazole sodium salt

[Formula 271]

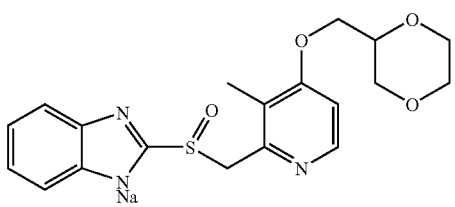

The same procedure as in the steps (8d) to (8g) of Example 8 was repeated using the 4-(4-(1,4-dioxan-2-ylmethoxy))-2, 3-dimethylpyridine1-oxide obtained in the step (62c) to obtain the title compound (385 mg, total yield: 24%) as a white solid.

$^1$H NMR(400 MHz, DMSO-$d_6$) δppm; 2.17(3H, s), 3.35-3.51(2H, m), 3.59-3.90(5H, m), 4.02(2H, br s), 4.36(1H, d, J=12 Hz), 4.80(1H, d, J=12 Hz), 6.83(2H, dd, J=4, 6 Hz), 6.91(1H, d, J=6 Hz), 7.42(2H, dd, J=4, 6 Hz), 8.26(1H, d, J=6 Hz).

Example 63

2-(((4-(1,4-dioxan-2-ylmethoxy)-3,5-dimethylpyridin-2-yl)methyl)sulfinyl)-1H-benzimidazole sodium salt

[Formula 272]

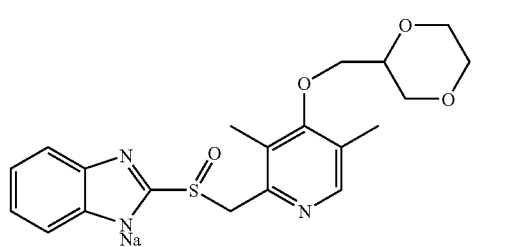

The same procedure as in the steps (62a) to (62d) of Example 62 was repeated using 4-chloro-2,3,5-trimethylpyridine 1-oxide to obtain the title compound (355 mg, total yield: 18%) as a white solid.

$^1$H NMR(400 MHz, DMSO-$d_6$) δppm; 2.18(3H, s), 2.21 (3H, d, J=2 Hz), 3.29-3.82(9H, m), 4.36(1H, dd, J=2, 13 Hz), 4.75(1H, dd, J=2, 13 Hz), 6.82(2H, dd, J=3, 6 Hz), 7.41(2H, dd, J=3, 6 Hz), 8.19(1H, s).

Example 64

2-(((4-(2-(2,2-dimethyl-1,3-dioxolan-4-yl)ethoxy)-3-methylpyridin-2-yl)methyl)sulfinyl)-1H-benzimidazole sodium salt

[Formula 273]

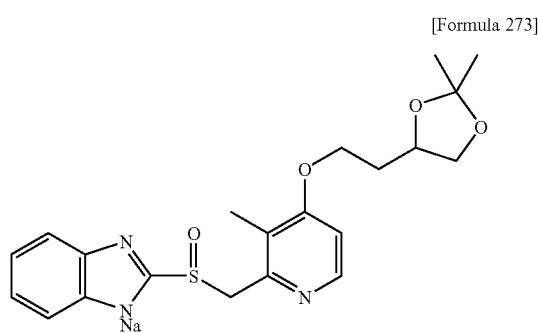

The same procedure as in the steps (4f) to (4j) of Example 4 (a reprecipitation operation was not performed in oxidation step with 3-chloroperbenzoic acid) was repeated using 4-(2-hydroxyethyl)-2,2-dimethyl-1,3-dioxolan to obtain the title compound (412 mg, total yield: 8.7%) as a light yellow solid.

$^1$H NMR(400 MHz, DMSO-$d_6$) δppm; 1.25(3H, s), 1.31 (3H, s), 1.90-2.04(2H, m), 2.17(3H, s), 3.57(1H, t, J=8 Hz), 3.98-4.26(4H, m), 4.36(0.5H, d, J=13 Hz), 4.37(0.5H, d, J=13 Hz), 4.78(0.5H, d, J=13 Hz), 4.78(0.5H, d, J=13 Hz), 6.79-6.87(2H, m), 6.91(1H, d, J=6 Hz), 7.37-7.47(2H, m), 8.26 (1H, d, J=6 Hz).

Example 65

2-(((4-((2,2-diethyl-1,3-dioxolan-4-yl)methoxy)-3-methylpyridin-2-yl)methyl)sulfinyl)-1H-benzimidazole sodium salt

[Formula 274]

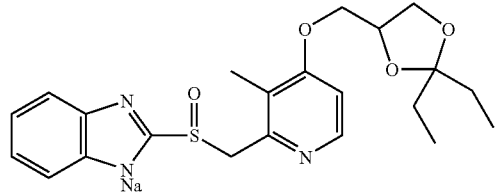

(65a) 4-((benzyloxy)methyl)-2,2-diethyl-1,3-dioxolane

[Formula 275]

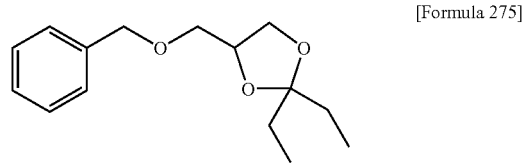

To a tetrahydrofuran (30 ml) solution of DL-α-O-benzyl glycerol (3 g, 16.5 mmol), 3-pentanone (17.5 ml, 165 mmol) and p-toluenesulfonic acid monohydrate (300 mg, 1.58 mmol) were added at room temperature and the mixture was stirred at the same temperature for 22 hours. To the reaction mixture, a saturated aqueous sodium hydrogen carbonate solution (5 ml) was added to adjust pH to about 8. The generated precipitate was removed by filtration and the filtrate was concentrated. The obtained residue was purified by silica gel column chromatography (NH silica gel, elution solvent: heptane/ethyl acetate=1/0 to 3/1 gradient). A desired fraction was concentrated to obtain the title compound (2.77 g, 67.1% yield) as a colorless oil.

$^1$H NMR(400 MHz, DMSO-$d_6$) δppm; 0.75-0.83(6H, m), 1.46-1.58(4H, m), 3.41-3.50(2H, m), 3.52-3.58(1H, m), 3.96-4.02(1H, m), 4.15-4.23(1H, m), 4.49(2H, s), 7.24-7.36(5H, m).

(65b) (2,2-diethyl-1,3-dioxolan-4-yl)methanol

[Formula 276]

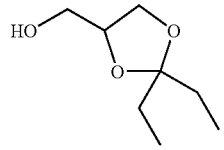

To a methanol (40 ml) solution of the 4-((benzyloxy)methyl)-2,2-diethyl-1,3-dioxolane (2.77 g, 11.1 mmol) obtained in the step (65a) above, palladium hydroxide (20 wt. % Pd (dry basis) on carbon, wet (water max. 50%))(400 mg) was added and the mixture was stirred in a hydrogen atmosphere at room temperature for 16 hours. The reaction vessel was purged with nitrogen and a catalyst was removed by filtration through celite, and then, washed with methanol. The filtrate was concentrated and dried under reduced pressure to obtain the title compound (1.593 g, 89.6% yield) as a colorless oil.

$^1$H NMR(400 MHz, CDCl$_3$) δppm; 0.91(3H, t, J=7 Hz), 0.93(3H, t, J=7 Hz), 1.60-1.72(4H, m), 1.86(1H, t, J=6 Hz), 3.55-3.64(1H, m), 3.67-3.84(2H, m), 4.01-4.08(1H, m), 4.20-4.28(1H, m).

(65c) 2-(((4-((2,2-diethyl-1,3-dioxolan-4-yl)methoxy)-3-methylpyridin-2-yl)methyl)sulfinyl)-1H-benzimidazole sodium salt

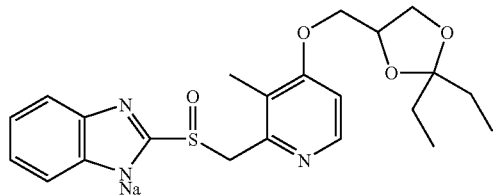

[Formula 277]

The same procedure as in the steps (4f) to (4j) of Example 4 (a reprecipitation operation was not performed in oxidation step with 3-chloroperbenzoic acid) was repeated using (2,2-diethyl-1,3-dioxolan-4-yl)methanol obtained in the step (65b) above to obtain the title compound (418 mg, total 14.3% yield) as a light yellow solid.

$^1$H NMR(400 MHz, DMSO-d$_6$) δppm; 0.78-0.88(6H, m), 1.51-1.66(4H, m), 2.18(1.5H, s), 2.18 (1.5H, s), 3.76(1H, t, J=8 Hz), 4.02-4.20(3H, m), 4.32-4.48(2H, m), 4.76(0.5H, d, J=13 Hz), 4.78(0.5H, d, J=13 Hz), 6.78-6.88(2H, m), 6.94 (1H, d, J=6 Hz), 7.37-7.47(2H, m), 8.26(1H, d, J=6 Hz).

Example 66

2-(((4-(1,3-dioxolan-2-ylmethoxy)-3-methylpyridin-2-yl)methyl)sulfinyl)-1H-benzimidazole sodium salt

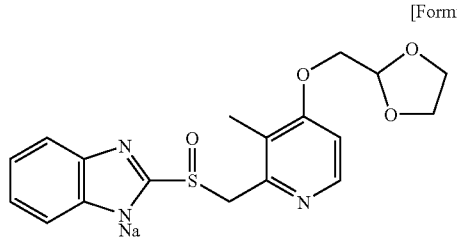

[Formula 278]

(66a) 2-((benzyloxy)methyl)-1,3-dioxolane

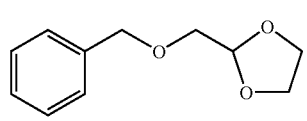

[Formula 279]

A mixture of benzyloxyacetaldehyde (3 g, 20 mmol), ethylene glycol (1.23 ml, 22 mmol), p-toluenesulfonic acid monohydrate (344 mg, 1.8 mmol), and toluene (15 ml) was stirred at 140° C. for 2 hours and further stirred at 150° C. for 3 hours. After cooled on ice, a 2N aqueous sodium hydroxide solution and ethyl acetate were added to the reaction mixture. An organic layer was separated, washed with water (three times) and a saturated saline solution. The organic layer was dried over anhydrous sodium sulfate and concentrated. The crude product was purified by silica gel column chromatography (NH silica gel, elution solvent: heptane/ethyl acetate=1/0 to 9/1 gradient). Desired fractions were concentrated to obtain the title compound (3.01 g, 77.5% yield) as a light yellow oil.

$^1$H NMR(400 MHz, DMSO-d$_6$) δppm; 3.45(2H, d, J=4 Hz), 3.74-3.92(4H, m), 4.51(2H, s), 4.98(1H, t, J=4 Hz), 7.24-7.38(5H, m).

(66b) 1,3-dioxolan-2-ylmethanol

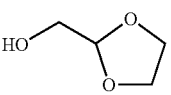

[Formula 280]

To a methanol (100 ml) solution of 2-((benzyloxy)methyl)-1,3-dioxolane (3.01 g, 15.5 mmol) obtained in the step (66a) above, palladium hydroxide (20 wt. % Pd (dry basis) on carbon, wet (water max. 50%))(300 mg) was added and the mixture was stirred in a hydrogen atmosphere at room temperature for 15 hours. The reaction vessel was purged with nitrogen and a catalyst was removed by filtration through celite, and then, washed with methanol. The filtrate was concentrated and dried under reduced pressure to obtain the title compound (1.57 g, 97.3% yield) as a light yellow oil.

$^1$H NMR(400 MHz, CDCl$_3$) δppm; 1.89(1H, br s), 3.66-3.72(2H, m), 3.88-4.08(4H, m), 5.01(1H, t, J=3 Hz).

(66c) 2-(((4-(1,3-dioxolan-2-ylmethoxy)-3-methylpyridin-2-yl)methyl)sulfinyl)-1H-benzimidazole sodium salt

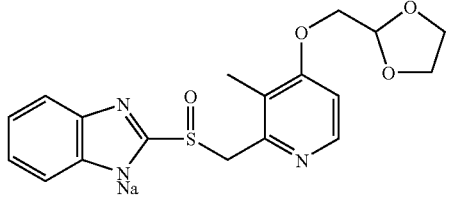

[Formula 281]

The same procedure as in the steps (4f) to (4j) described in Example (a reprecipitation operation was not performed in oxidation step with 3-chloroperbenzoic acid) was repeated using 1,3-dioxolan-2-ylmethanol obtained in the step (66b) above to obtain the title compound (411 mg, total 17.2% yield) as a white solid.

$^1$H NMR(400 MHz, DMSO-d$_6$) δppm; 2.17(3H, s), 3.80-4.00(4H, m), 4.07(2H, d, J=4 Hz), 4.39(1H, d, J=13 Hz), 4.79(1H, d, J=13 Hz), 5.24(1H, t, J=4 Hz), 6.80-6.89(2H, m), 6.94(1H, d, J=6 Hz), 7.38-7.46(2H, m), 8.26(1H, d, J=6 Hz).

Example 67

2-(((3-methyl-4-((2-methyl-1,3-dioxolan-2-yl)methoxy)pyridin-2-yl)methyl)sulfinyl)-1H-benzimidazole sodium salt

[Formula 282]

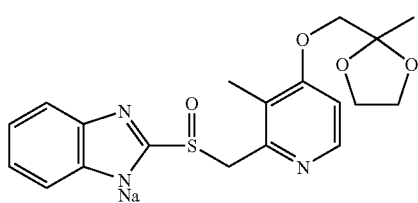

(67a) 2-((benzyloxy)methyl)-2-methyl-1,3-dioxolane

[Formula 283]

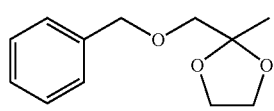

A mixture of 1-benzyloxy-2-propanone (4.94 g, 30.1 mmol), ethylene glycol (20 ml, 359 mmol), triethyl orthoformate (5 ml, 30.1 mmol), and p-toluenesulfonic acid monohydrate (130 mg, 0.683 mmol) was stirred at room temperature for 61.5 hours. To the reaction mixture, a saturated aqueous sodium hydrogen carbonate solution (20 ml) was added and the mixture was extracted twice with chloroform (50 ml) and the organic layer was dried over anhydrous sodium sulfate and concentrated. The crude product was purified by silica gel column chromatography (NH silica gel, elution solvent: heptane/ethyl acetate=1/0 to 4/1 gradient). Desired fractions were concentrated to obtain the title compound (5.67 g, 90.5% yield) as a colorless oil.

$^1$H NMR(400 MHz, DMSO-d$_6$) δppm; 1.26(3H, s), 3.34 (2H, s), 3.85(4H, s), 4.51(2H, s), 7.22-7.38(5H, m).

(67b) (2-methyl-1,3-dioxolan-2-yl)methanol

[Formula 284]

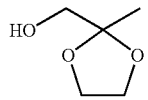

To a methanol (100 ml) solution of 2-((benzyloxy)methyl)-2-methyl-1,3-dioxolane (5.66 g, 27.2 mmol) obtained in the step (67a) above, palladium hydroxide (20 wt. % Pd (dry basis) on carbon, wet (water max. 50%))(500 mg) was added and the mixture was stirred in a hydrogen atmosphere at room temperature for 17 hours. The reaction vessel was purged with nitrogen and a catalyst was removed by filtration through celite, and then, washed with methanol. The filtrate was concentrated and dried under reduced pressure to obtain the title compound (2.96 g, 92.1% yield) as a light green oil.

$^1$H NMR(400 MHz, CDCl$_3$) δppm; 1.35(3H, s), 1.82-1.90 (1H, br), 3.54(2H, d, J=6 Hz), 4.01(4H, s).

(67c) 2-(((3-methyl-4-((2-methyl-1,3-dioxolan-2-yl)methoxy)pyridin-2-yl)methyl)sulfinyl)-1H-benzimidazole sodium salt

[Formula 285]

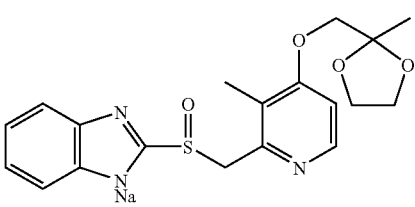

The same procedure as in the steps (4f) to (4j) of Example 4 (a reprecipitation operation was not performed in oxidation step with 3-chloroperbenzoic acid) was repeated using (2-methyl-1,3-dioxolan-2-yl)methanol obtained in the step (67b) above to obtain the title compound (263 mg, total 12.9% yield) as a light yellow solid.

$^1$H NMR(400 MHz, DMSO-d$_6$) δppm; 1.39(3H, s), 2.19 (3H, s), 3.88-4.00(4H, m), 3.96(2H, s), 4.37(1H, d, J=13 Hz), 4.79(1H, d, J=13 Hz), 6.78-6.88(2H, m), 6.92(1H, d, J=6 Hz), 7.37-7.46(2H, m), 8.25(1H, d, J=6 Hz).

Example 68

2-(((4-((2S)-1,4-dioxaspiro[4.5]dec-2-ylmethoxy)-3-methylpyridin-2-yl)methyl)sulfinyl)-1H-benzimidazole sodium salt

[Formula 286]

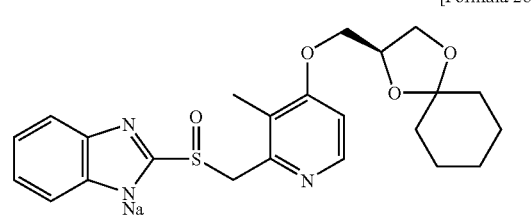

The same procedure as in the steps (4f) to (4j) of Example 4 (a reprecipitation operation was not performed in oxidation step with 3-chloroperbenzoic acid) was repeated using (+)-1,4-dioxaspiro[4.5]decane-2-methanol to obtain the title compound (500 mg, total 16.8% yield) as a white solid.

$^1$H NMR(400 MHz, DMSO-d$_6$) δppm; 1.24-1.63(10H, m), 2.18(3H, s), 3.76-3.84(1H, m), 4.01-4.14(3H, m), 4.37(0.5H, d, J=13 Hz), 4.38(0.5H, d, J=13 Hz), 4.38-4.46(1H, m), 4.77 (0.5H, d, J=13 Hz), 4.78(0.5H, d, J=13 Hz), 6.79-6.87(2H, m), 6.94(1H, d, J=6 Hz), 7.37-7.46(2H, m), 8.26(1H, d, J=6 Hz).

Example 69

2-(((3-methyl-4-(2-(2-methyl-1,3-dioxolan-2-yl)ethoxy)pyridin-2-yl)methyl)sulfinyl)-1H-benzimidazole sodium salt

[Formula 287]

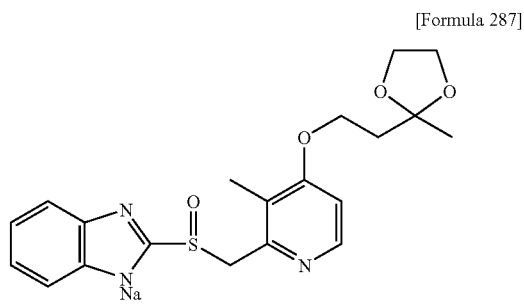

(69a) 2-(2-(benzyloxy)ethyl)-2-methyl-1,3-dioxolane

[Formula 288]

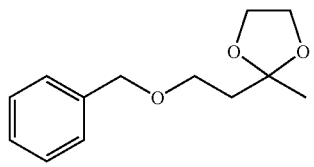

A mixture of 4-benzyloxy-2-butanone (10 g, 56.1 mmol), ethylene glycol (40 ml, 718 mmol), triethyl orthoformate (9.3 ml, 55.9 mmol) and p-toluenesulfonic acid monohydrate (290 mg, 1.52 mmol) was stirred at room temperature for 13.5 hours. To the reaction mixture, a saturated aqueous sodium hydrogen carbonate solution (40 ml) was added and the mixture was extracted three times with chloroform (50 ml). The organic layer was dried over anhydrous sodium sulfate and concentrated. The crude product was purified by silica gel column chromatography (NH silica gel, elution solvent: heptane/ethyl acetate=1/0 to 4/1 gradient). Desired fractions were concentrated to obtain the title compound (10.08 g, 80.8% yield) as a colorless oil.

$^1$H NMR(400 MHz, DMSO-$d_6$) δppm; 1.23(3H, s), 1.86 (2H, t, J=7 Hz), 3.48(2H, t, J=7 Hz), 3.75-3.86(4H, m), 4.42 (2H, s), 7.22-7.36(5H, m).

(69b) 2-(2-methyl-1,3-dioxolan-2-yl)ethanol

[Formula 289]

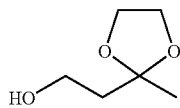

To a methanol (150 ml) solution of 2-(2-(benzyloxy) ethyl)-2-methyl-1,3-dioxolane (10.1 g, 45.4 mmol) obtained in the step (69a), palladium hydroxide (20 wt. % Pd (dry basis) on carbon, wet (water max. 50%))(900 mg) was added and the mixture was stirred in a hydrogen atmosphere at room temperature for 16 hours. The reaction vessel was purged with nitrogen and a catalyst was removed by filtration through celite, and then, washed with methanol. The filtrate was concentrated. The resultant residue was purified by silica gel column chromatography (silica gel, elution solvent: heptane/ethyl acetate=1/0→1/1→0/1 gradient). Desired fractions were concentrated to obtain the title compound (3.5 g, 58.3% yield) as a light yellow oil.

$^1$H NMR(400 MHz, DMSO-$d_6$) δppm; 1.21(3H, s), 1.73 (2H, t, J=7 Hz), 3.40-3.50(2H, m), 3.75-3.86(4H, m), 4.30 (1H, t, J=5 Hz).

(69c) 2-(((3-methyl-4-(2-(2-methyl-1,3-dioxolan-2-yl)ethoxy)pyridin-2-yl)methyl)sulfinyl)-1H-benzimidazole sodium salt

[Formula 290]

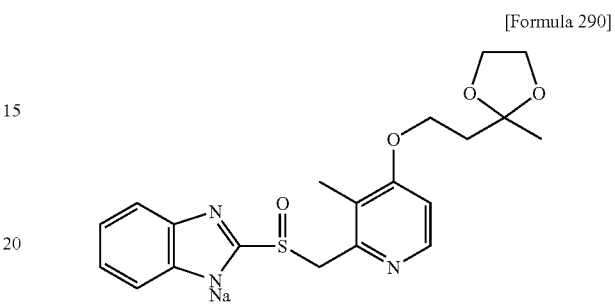

The same procedure as in the steps (4f) to (4j) of Example 4 (a reprecipitation operation was not performed in oxidation step with 3-chloroperbenzoic acid) was repeated using 2-(2-methyl-1,3-dioxolan-2-yl)ethanol obtained in the step (69b) to obtain the title compound (410 mg, total 14.4% yield) as a light yellow solid.

$^1$H NMR(400 MHz, DMSO-$d_6$) δppm; 1.31(3H, s), 2.08 (2H, t, J=7 Hz), 2.15(3H, s), 3.87(4H, s), 4.10(2H, t, J=7 Hz), 4.38(1H, d, J=13 Hz), 4.75(1H, d, J=13 Hz), 6.77-6.89(2H, m), 6.92(1H, d, J=6 Hz), 7.35-7.49(2H, m), 8.26(1H, d, J=6 Hz).

Example 70

Sodium Salt of an Optical Isomer of 2-(((3-methyl-4-((2-methyl-1,3-dioxolan-2-yl)methoxy)pyridin-2-yl)methyl)sulfinyl)-1H-benzimidazole

[Formula 291]

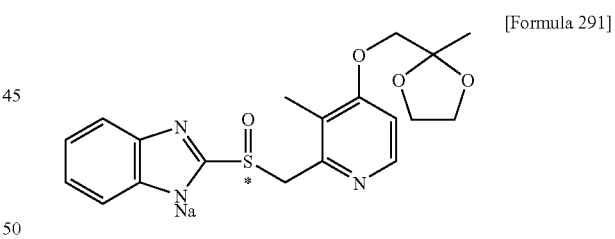

2-(((3-methyl-4-((2-methyl-1,3-dioxolan-2-yl)methoxy) pyridin-2-yl)methyl)sulfinyl)-1H-benzimidazole sodium salt (racemate)(185 mg) obtained in the same manner as in the steps (67a) to (67c) was dissolved in water. To the solution, dichloromethane and a saturated aqueous ammonium chloride solution were added. The aqueous layer was extracted further with dichloromethane. The organic layers were combined and dried over anhydrous sodium sulfate and concentrated.

To the resultant free form, a small amount of diethylamine was added and the mixture was separated by HPLC (column: CHIRALCEL OD-H 2 cmφ×25 cm (manufactured by Daicel Chemical Industries, Ltd.), mobile phase: hexane/ethanol/diethylamine=80/20/0.1 (v/v/v), flow rate: 9 ml/min, detection: 254 nm). On the other hand, aqueous sodium hydroxide solution (100 μl) was placed in each of test tubes, in advance. A fraction of an optical isomer having a short retention time, and a fraction of an optical isomer having a long retention time were separately concentrated and the residues were separately dissolved in water. To each of the solutions, dichloromethane and a saturated aqueous ammonium chloride solution were added. The aqueous layers were separately extracted further with dichloromethane. The organic layers were separately combined and dried over anhydrous sodium sulfate and concentrated. In the manner mentioned above, a free form (59 mg) of the optical isomer having a short retention time and a free form (56 mg) of the optical isomer having a long retention time were obtained each as a light gray foam.

Each of the optical isomer free forms was subjected to the same operation to obtain sodium salt as performed in the step (4j) (sodium salt formation) to obtain a sodium salt (58 mg) of the optical isomer having a short retention time and a sodium salt (53 mg) of the optical isomer having a long retention time each as light yellow solid.

$^1$H NMR(400 MHz, DMSO-d$_6$) δppm; The charts of the both isomers are the same as that of 2-(((3-methyl-4-((2-methyl-1,3-dioxolan-2-yl)methoxy)pyridin-2-yl)methyl)sulfinyl)-1H-benzimidazole sodium salt (racemate).

HPLC;

(Conditions) column: CHIRALCEL OD-H (manufactured by Daicel Chemical Industries, Ltd.) (0.46 cmφ×25 cm), eluant: hexane/ethanol=4/1 (v/v), flow rate: 0.6 ml/min, detection: UV 254 nm).

(Analysis results) The retention time of a sodium salt of the optical isomer having a short retention time: 16 minutes, enantiomeric excess: 100% ee; and the retention time of a sodium salt of the optical isomer having a long retention time: 22 minutes, enantiomeric excess: 100% ee.

Example 71

2-(((4-(2-((4R)-2,2-dimethyl-1,3-dioxolan-4-yl)ethoxy)-3-methylpyridin-2-yl)methyl)sulfinyl)-1H-benzimidazole sodium salt

[Formula 292]

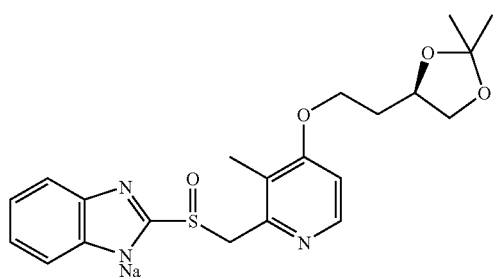

(71a) 2-((4R)-2,2-dimethyl-1,3-dioxolan-4-yl)ethanol

[Formula 293]

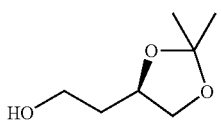

A mixture of (R)-(+)-1,2,4-butanetriol (30 g, 283 mmol), acetone (200 ml, 2724 mmol) and p-toluenesulfonic acid monohydrate (1.4 g, 7.36 mmol) was stirred at room temperature for 16.5 hours. To the reaction mixture, triethylamine was added and the mixture was concentrated. The crude product was purified by silica gel column chromatography (silica gel, elution solvent: heptane/ethyl acetate=1/0→1/1→1/3 gradient). Desired fractions were concentrated to obtain the title compound (29.9 g, 72.3% yield) as a colorless oil.

$^1$H NMR(400 MHz, CDCl$_3$) δppm; 1.37(3H, s), 1.43(3H, s), 1.78-1.95(3H, m), 3.60(1H, t, J=8 Hz), 3.76-3.85(2H, m), 4.09(1H, dd, J=6, 8 Hz), 4.27(1H, quint, J=6 Hz).

(71b) 2-(((4-(2-((4R)-2,2-dimethyl-1,3-dioxolan-4-yl)ethoxy)-3-methylpyridin-2-yl)methyl)sulfinyl)-1H-benzimidazole sodium salt

[Formula 294]

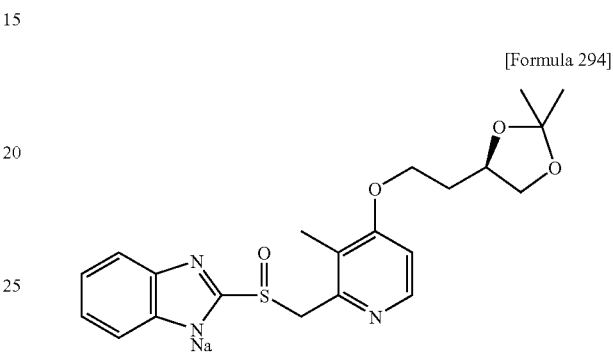

The same procedure as in the steps (4f) to (4j) of Example 4 (recrystallization was performed by use of heptane in the step of obtaining picolyl alcohol; and a reprecipitation operation was not performed in oxidation step with 3-chloroperbenzoic acid) was repeated using 2-((4R)-2,2-dimethyl-1,3-dioxolan-4-yl)ethanol obtained in the step (71a) to obtain the title compound (320 mg, total 8.5% yield) as a light yellow solid.

$^1$H NMR(400 MHz, DMSO-d$_6$) δppm; 1.26(3H, s), 1.32 (3H, s), 1.91-2.04(2H, m), 2.17(3H, s), 3.57(1H, t, J=7 Hz), 3.98-4.28(4H, m), 4.36(0.5H, d, J=13 Hz), 4.37(0.5H, d, J=13 Hz), 4.80(0.5H, d, J=13 Hz), 4.80(0.5H, d, J=13 Hz), 6.78-6.87(2H, m), 6.91(1H, d, J=6 Hz), 7.36-7.46(2H, m), 8.25 (1H, d, J=6 Hz).

Example 72

2-(((4-(2-((4S)-2,2-dimethyl-1,3-dioxolan-4-yl)ethoxy)-3-methylpyridin-2-yl)methyl)sulfinyl)-1H-benzimidazole sodium salt

[Formula 295]

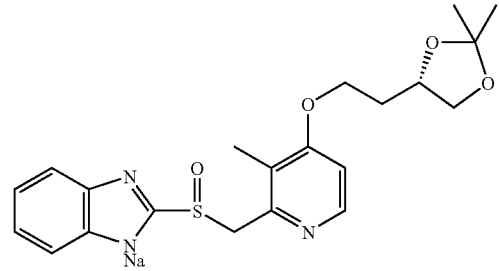

153

(72a) 2-((4S)-2,2-dimethyl-1,3-dioxolan-4-yl)ethanol

[Formula 296]

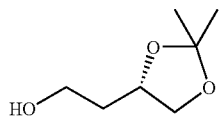

To (S)-(−)-1,2,4-butanetriol (30 g, 283 mmol), acetone (200 ml) and p-toluenesulfonic acid monohydrate (1.4 g, 7.36 mmol) were added and the mixture was stirred at room temperature overnight. To the reaction mixture, triethylamine (4 ml) was added and the mixture was concentrated. The residue was purified by silica gel column chromatography (silica gel 350 g, elution solvent: ethyl acetate/heptane=18/82→6/4) to obtain the title compound (30.2 g, yield: 73%) as a colorless oil.

$^1$H NMR(400 MHz, CDCl$_3$) δppm; 1.37(3H, s), 1.43(3H, s), 1.83(2H, q, J=6 Hz), 2.20(1H, t, J=6 Hz), 3.60(1H, t, J=8 Hz), 3.80(2H, q, J=6 Hz), 4.09(1H, dd, J=6, 8 Hz), 4.27(1H, quint, J=6 Hz).

(72b) 2-(((4-(2-((4S)-2,2-dimethyl-1,3-dioxolan-4-yl)ethoxy)-3-methylpyridin-2-yl)methyl)sulfinyl)-1H-benzimidazole sodium salt

[Formula 297]

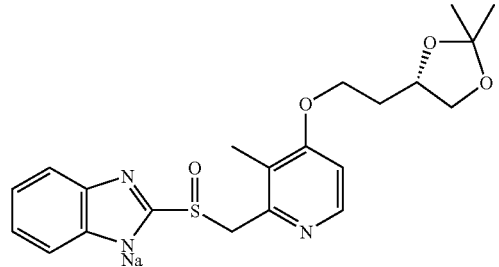

The same procedure as in the steps (4f) to (4j) of Example 4 (recrystallization was performed by use of heptane in the step of obtaining picolyl alcohol; and a reprecipitation operation was not performed in oxidation step with 3-chloroperbenzoic acid) was repeated using 2-((4S)-2,2-dimethyl-1,3-dioxolan-4-yl)ethanol obtained in the step (72a) above to obtain the title compound (386 mg, total 10.1% yield) as a light yellow solid.

$^1$H NMR(400 MHz, DMSO-d$_6$) δppm; 1.25(3H, s), 1.31 (3H, s), 1.90-2.05(2H, m), 2.17(3H, s), 3.57(1H, t, J=8 Hz), 4.00-4.27(4H, m), 4.37(0.5H, d, J=13 Hz), 4.37(0.5H, d, J=13 Hz), 4.78(0.5H, d, J=13 Hz), 4.78(0.5H, d, J=13 Hz), 6.79-6.87(2H, m), 6.91(1H, d, J=6 Hz), 7.38-7.46(2H, m), 8.26 (1H, d, J=6 Hz).

154

Example 73

2-(((3-methyl-4-(2-(8-methyl-1,4,7,9-tetraoxaspiro[4.5]dec-8-yl)ethoxy)pyridin-2-yl)methyl)sulfinyl)-1H-benzimidazole sodium salt

[Formula 298]

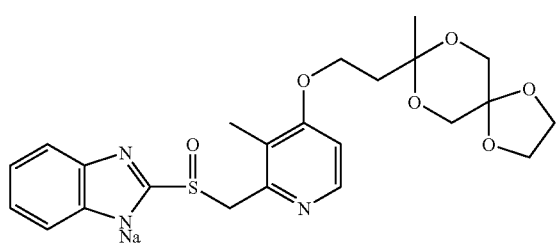

(73a) Methyl(8-methyl-1,4,7,9-tetraoxaspiro[4.5]dec-8-yl)acetate

[Formula 299]

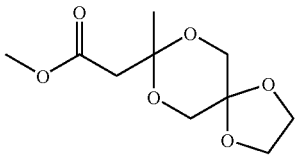

A mixture of 1,3-dioxolane-2,2-diyldimethanol (4 g, 29.8 mmol) separately obtained in the same manner as in the steps (4a) to (4c), methyl acetoacetate (4.9 ml, 45.4 mmol), triethyl orthoformate (5.2 ml, 31.3 mmol), and p-toluenesulfonic acid monohydrate (163 mg, 0.856 mmol) was stirred at room temperature for 3 hours. To the mixture, a saturated aqueous sodium hydrogen carbonate solution and ethyl acetate were added. The organic layer was washed twice with water and with a saline solution, and dried over anhydrous sodium sulfate and concentrated. The crude product was purified by silica gel column chromatography (silica gel, elution solvent: heptane/ethyl acetate=1/0-3/1-1/1 gradient). A desired fraction was concentrated to obtain the title compound (3.46 g, 50.0% yield) as a colorless oil.

$^1$H NMR(400 MHz, DMSO-d$_6$) δppm; 1.41(3H, s), 2.75 (2H, s), 3.57(3H, s), 3.60(2H, d, J=12 Hz), 3.65(2H, d, J=12 Hz), 3.84(4H, s).

(73b) 2-(8-methyl-1,4,7,9-tetraoxaspiro[4.5]dec-8-yl)ethanol

[Formula 300]

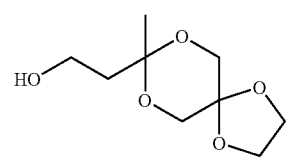

To a THF (40 ml) solution of methyl(8-methyl-1,4,7,9-tetraoxaspiro[4.5]dec-8-yl)acetate (3.46 g, 14.9 mmol) obtained in the step (73a), lithium aluminum hydride (679 mg, 17.9 mmol) was added at 0° C. and the mixture was stirred at 0° C. to room temperature for 3 hours. After the reaction was terminated by sequentially adding water (0.68 ml), a 2N aqueous sodium hydroxide solution (0.68 ml), and water (2 ml), anhydrous sodium sulfate and celite were added thereto. The mixture was filtrated through a glass filter. The precipitate was washed with ethyl acetate and concentrated to obtain the title compound (2.96 g, 97.3% yield) as a colorless oil.

$^1$H NMR(400 MHz, DMSO-$d_6$) δppm; 1.27(3H, s), 1.81 (2H, t, J=7 Hz), 3.44(2H, dt, J=6, 7 Hz), 3.55(2H, d, J=12 Hz), 3.60(2H, d, J=12 Hz), 3.72-3.89(4H, m), 4.31(1H, t, J=6 Hz).

(73c) 2-(((3-methyl-4-(2-(8-methyl-1,4,7,9-tetraoxaspiro[4.5]dec-8-yl)ethoxy)pyridin-2-yl)methyl)sulfinyl)-1H-benzimidazole sodium salt

[Formula 301]

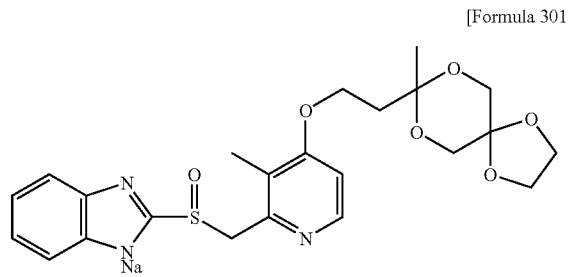

The same procedure as in the steps (4f) to (4j) of Example 4 was repeated using 2-(8-methyl-1,4,7,9-tetraoxaspiro[4.5]dec-8-yl)ethanol obtained in the step (73b) above to obtain the title compound (298 mg, total 15.1% yield) as a white solid.

$^1$H NMR(400 MHz, DMSO-$d_6$) δppm; 1.38(3H, s), 2.11-2.20(5H, m), 3.62(2H, d, J=12 Hz), 3.66(2H, d, J=12 Hz), 3.79-3.90(4H, m), 4.11(2H, t, J=7 Hz), 4.37(1H, d, J=13 Hz), 4.77(1H, d, J=13 Hz), 6.80-6.87(2H, m), 6.90(1H, d, J=6 Hz), 7.38-7.45(2H, m), 8.26(1H, d, J=6 Hz).

Example 74

5-methyl-2-(((3-methyl-4-(2-(8-methyl-1,4,7,9-tetraoxaspiro[4.5]dec-8-yl)ethoxy)pyridin-2-yl)methyl)sulfinyl)-1H-benzimidazole sodium salt

[Formula 302]

The same procedure as in the steps (4f) to (4j) of Example 4 was repeated using 2-(8-methyl-1,4,7,9-tetraoxaspiro[4.5]dec-8-yl)ethanol obtained in the step (73b) above and 5-methyl-1H-benzimidazole-2-thiol obtained in the step (47a) to obtain the title compound (188 mg, total 12.4% yield) as a white solid.

$^1$H NMR(400 MHz, DMSO-$d_6$) δppm; 1.38(3H, s), 2.09-2.20(5H, m), 2.34(3H, s), 3.62(2H, d, J=12 Hz), 3.66(2H, d, J=12 Hz), 3.77-3.92(4H, m), 4.10(2H, t, J=6 Hz), 4.35(1H, d, J=13 Hz), 4.75(1H, d, J=13 Hz), 6.67(1H, d, J=8 Hz), 6.89 (1H, d, J=6 Hz), 7.20(1H, s), 7.29(1H, d, J=8 Hz), 8.25(1H, d, J=6 Hz).

Example 75

2-(((4-(2-(8-methyl-1,4,7,9-tetraoxaspiro[4.5]dec-8-yl)ethoxy)pyridin-2-yl)methyl)sulfinyl)-1H-benzimidazole sodium salt

[Formula 303]

The same procedure as in the steps (5d) to (5h) of Example 5 (a reprecipitation operation was not performed in oxidation step with 3-chloroperbenzoic acid) was repeated using 2-(8-methyl-1,4,7,9-tetraoxaspiro[4.5]dec-8-yl)ethanol obtained in the step (73b) above and 4-chloro-2-methylpyridine1-oxide obtained in the step (57a) to obtain the title compound (860 mg, total 20.2% yield) as a white solid.

$^1$H NMR(400 MHz, DMSO-$d_6$) δppm; 1.31(3H, s), 2.05 (2H, t, J=7 Hz), 3.59(2H, d, J=12 Hz), 3.64(2H, d, J=12 Hz), 3.78-4.03(6H, m), 4.45(1H, d, J=12 Hz), 4.54(1H, d, J=12 Hz), 6.71-6.90(4H, m), 7.37-7.48(2H, m), 8.32(1H, d, J=6 Hz).

Example 76

2-(((4-(2-(9-methyl-1,5,8,10-tetraoxaspiro[5.5]undec-9-yl)ethoxy)pyridin-2-yl)methyl)sulfinyl)-1H-benzimidazole sodium salt

[Formula 304]

(76a) 2,2-bis((benzyloxy)methyl)-1,3-dioxane

[Formula 305]

A mixture of 1,3-bis(benzyloxy)acetone (20 g, 73.9 mmol) obtained in the same manner as in the step (4a) above, 1,3- propanediol (54 ml, 747 mmol), triethyl orthoformate (13 ml, 78.2 mmol), and p-toluenesulfonic acid monohydrate (394 mg, 2.07 mmol) was stirred at 50° C. for 14.5 hours. To the mixture, a saturated aqueous sodium hydrogen carbonate solution and ethyl acetate were added. The organic layer was washed with water and a saline solution, dried over anhydrous sodium sulfate, and concentrated. The obtained crude product was purified by silica gel column chromatography (silica gel, elution solvent: heptane/ethyl acetate=1/0-3/1 gradient). Desired fractions were concentrated to obtain the title compound (17.46 g, 71.9% yield) as a light yellow oil.

$^1$H NMR(400 MHz, DMSO-$d_6$) δppm; 1.60(2H, quint, J=6 Hz), 3.60(4H, s), 3.82(4H, t, J=6 Hz), 4.49(4H, s), 7.22-7.35 (10H, m).

(76b) 1,3-dioxane-2,2-diyldimethanol

[Formula 306]

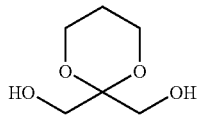

To a ethyl acetate (200 ml) solution of 2,2-bis((benzyloxy) methyl)-1,3-dioxane (17.46 g, 53.2 mmol) obtained in the step (76a) above, palladium hydroxide (20 wt. % Pd (dry basis) on carbon, wet (water max. 50%)) (1.7 g) was added and the mixture was stirred in a hydrogen atmosphere at room temperature for 46 hours. The reaction vessel was purged with nitrogen and a catalyst was removed by filtration, and then, ethyl acetate washing was performed. The filtrate was concentrated to obtain the title compound (7.67 g, 97.3% yield) as a white solid.

$^1$H NMR(400 MHz, DMSO-$d_6$) δppm; 1.58(2H, quint, J=6 Hz), 3.47(4H, d, J=6 Hz), 3.80(4H, t, J=6 Hz), 4.43(2H, t, J=6 Hz).

(76c) methyl(9-methyl-1,5,8,10-tetraoxaspiro[5.5] undec-9-yl)acetate

[Formula 307]

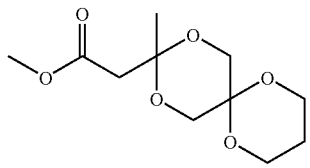

A mixture of 1,3-dioxane-2,2-diyldimethanol (4 g, 27 mmol) obtained in the step (76b) above, methyl acetoacetate (4.4 ml, 40.8 mmol), triethyl orthoformate (4.6 ml, 27.7 mmol), and p-toluenesulfonic acid monohydrate (160 mg, 0.843 mmol) was stirred at room temperature for 4.5 hours. To the mixture, a saturated aqueous sodium hydrogen carbonate solution and ethyl acetate were added. The organic layer was washed twice with water and a saline solution, dried over anhydrous sodium sulfate and concentrated. The crude product obtained was purified by silica gel column chromatography (silica gel, elution solvent: heptane/ethyl acetate=1/0-4/ 1-1/1 gradient). Desired fractions were concentrated to obtain the title compound (1.60 g, 24.1% yield) as a colorless oil.

$^1$H NMR(400 MHz, DMSO-$d_6$) δppm; 1.39(3H, s), 1.53-1.63(2H, m), 2.72(2H, s), 3.56(3H, s), 3.70-3.86(8H, m).

(76d) 2-(9-methyl-1,5,8,10-tetraoxaspiro[5.5]undec-9-yl)ethanol

[Formula 308]

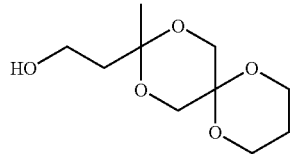

To a THF (20 ml) solution of methyl(9-methyl-1,5,8,10-tetraoxaspiro[5.5]undec-9-yl)acetate (1.6 g, 6.5 mmol) obtained in the step (76c), lithium aluminum hydride (300 mg, 7.9 mmol) was added at 0° C. and the mixture was stirred at 0° C. to room temperature for one hour. After the reaction was terminated by sequentially adding water (0.3 ml), a 2N aqueous sodium hydroxide solution (0.3 ml), and water (0.9 ml), anhydrous sodium sulfate and celite were added thereto. The mixture was filtrated through a glass filter. The precipitate was washed with ethyl acetate and concentrated. The resultant residue was purified by silica gel column chromatography (silica gel, elution solvent: heptane/ethyl acetate=3/ 1-1/4 gradient). Desired fractions were concentrated to obtain the title compound (950 mg, 67.0% yield) as a colorless oil.

$^1$H NMR(400 MHz, DMSO-$d_6$) δppm; 1.24(3 Hz s), 1.53-1.63(2H, m), 1.78(2H, t, J=7 Hz), 3.43(2H, dt, J=6, 7 Hz), 3.67-3.85(8H, m), 4.30(1H, t, J=6 Hz).

(76e) 2-(((4-(2-(9-methyl-1,5,8,10-tetraoxaspiro[5.5] undec-9-yl)ethoxy)pyridin-2-yl)methyl)sulfinyl)-1H-benzimidazole sodium salt

[Formula 309]

The same procedure as in the steps (5d) to (5h) of Example 5 (a reprecipitation operation was not performed in oxidation step with 3-chloroperbenzoic acid) was repeated using 2-(9-methyl-1,5,8,10-tetraoxaspiro[5.5]undec-9-yl)ethanol obtained in the step (76d) above to obtain the title compound (228 mg, total 11.4% yield) as a white solid.

$^1$H NMR(400 MHz, DMSO-$d_6$) δppm; 1.28(3H, s), 1.53-1.64(2H, m), 2.02(2H, t, J=7 Hz), 3.68-4.00(10H, m), 4.46 (1H, d, J=12 Hz), 4.54(1H, d, J=12 Hz), 6.72-6.90(4H, m), 7.36-7.47(2H, m), 8.32(1H, d, J=6 Hz).

Example 77

2-(((4-((2,2-dimethyl-1,3-dioxan-5-yl)methoxy)-3-methylpyridin-2-yl)methyl)sulfinyl)-6,7-dihydro-1H-[1.4]dioxino[2.3-f]benzimidazole sodium salt

[Formula 310]

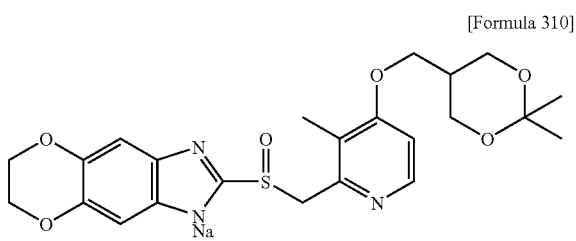

The same procedure as in the steps (5f) to (5h) above (a reprecipitation operation was not performed in oxidation step with 3-chloroperbenzoic acid) was repeated using (4-((2,2-dimethyl-1,3-dioxan-5-yl)methoxy)-3-methylpyridin-2-yl)methanol obtained in the step (12b) and 6,7-dihydro-1H-[1.4]dioxino[2'.3':4.5]benzo[d]imidazole-2-thiol to obtain the title compound (137 mg, total 25.8% yield) as a light yellow solid.

$^1$H NMR(400 MHz, DMSO-d$_6$) δppm; 1.32(3H, s), 1.35 (3H, s), 2.03-2.14(1H, m), 2.16(3H, s), 3.70-3.82(2H, m), 3.92-4.02(2H, m), 4.09(2H, d, J=7 Hz), 4.14(4H, s), 4.32(1H, d, J=13 Hz), 4.75(1H, d, J=13 Hz), 6.83(2H, s), 6.92(1H, d, J=6 Hz), 8.26(1H, d, J=6 Hz).

Example 78

6-(((4-((2,2-dimethyl-1,3-dioxan-5-yl)methoxy)-3-methylpyridin-2-yl)methyl)sulfinyl)-5H-[1.3]dioxolo[4,5-f]benzimidazole sodium salt

[Formula 311]

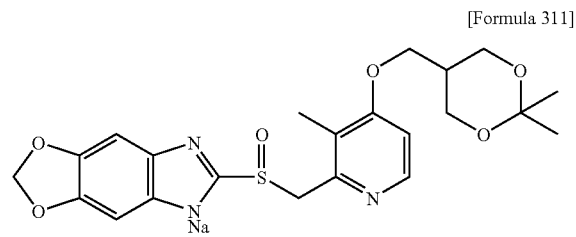

(78a) 5,6-dinitro-1,3-benzodioxol

[Formula 312]

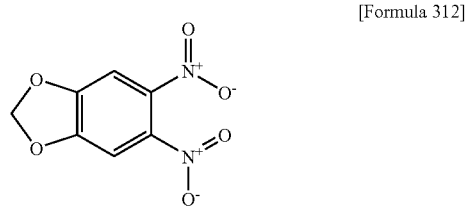

A mixture of 5-nitro-1,3-benzodioxol (10 g, 59.8 mmol), tetramethylammonium nitrate (10.6 g, 77.7 mmol) and dichloromethane (100 ml) was stirred under ice-cool and then trifluoromethanesulfonic anhydride (13.1 ml, 77.7 mmol) was added dropwise thereto below 7° C. The mixture was stirred at room temperature for 30 minutes and heated under reflux overnight. The reaction mixture was stirred under ice-cool and tetramethylammonium nitrate (4.07 g, 29.9 mmol) and trifluoromethanesulfonic anhydride (5.03 ml, 29.9 mmol) were added thereto. The resultant mixture was stirred at 50° C. for 6 hours. The reaction mixture was cooled to room temperature and a saturated aqueous sodium hydrogencarbonate solution and ice were added. The mixture was stirred and the organic layer was taken out. The aqueous layer was extracted with ethyl acetate. The organic layers were combined, dried over sodium sulfate, magnesium sulfate and filtrated by silica gel. The filtrate was concentrated to obtain the title compound (7.4 g, 58.3%) as a yellow solid.

$^1$H NMR(400 MHz, CDCl$_3$) δppm; 6.27(2H, s), 7.31(2H, s).

(78b) 1,3-benzodioxol-5,6-diamine

[Formula 313]

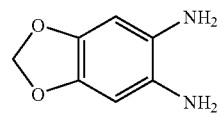

A mixture of 5,6-dinitro-1,3-benzodioxol (7.4 g, 34.9 mmol) obtained in the step (78a) above, and 10% palladium carbon (containing 50% of water, 1.09 g), methanol (200 ml), and tetrahydrofuran (50 ml) was stirred in a hydrogen atmosphere for 3 days. The reaction mixture was filtrated and the filtrate was concentrated to obtain a mixture (6.48 g) containing the title compound as a yellow solid.

$^1$H NMR(400 MHz, DMSO-d$_6$) δppm; 4.10(4H, br s), 5.67(2H,s), 6.23(2H, s).

(78c) 5H-[1,3]dioxolo[4,5-f]benzimidazole-6-thiol

[Formula 314]

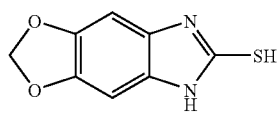

The mixture (6.48 g) containing 1,3-benzodioxol-5,6-diamine obtained in the step (78b) above was dissolved in methanol (100 ml). To the mixture, carbon disulfide (30 ml) was added and the mixture was stirred at room temperature for one day. The reaction mixture was concentrated under reduced pressure. To the solid residue, ethyl acetate was added and filtration was performed. The solid was washed by adding tetrahydrofuran, ethyl acetate and diluted hydrochloric acid and insoluble substance was collected by filtration, dried under reduced pressure at room temperature for 2 hours in a desiccator to obtain the title compound (3.8 g, 56.1% from 5,6-dinitro-1,3-benzodioxol) as a brown solid.

$^1$H NMR(400 MHz, DMSO-d$_6$) δppm; 5.99(2H,s), 6.74 (2H, s), 12.36(2H, br s).

(78d) 6-(((4-((2,2-dimethyl-1,3-dioxan-5-yl)methoxy)-3-methylpyridin-2-yl)methyl)sulfinyl)-5H-[1,3]dioxolo[4,5-f]benzimidazole sodium salt

[Formula 315]

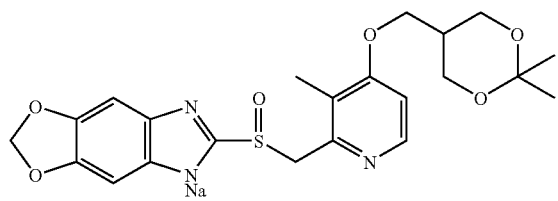

The same procedure as in the steps (5f) to (5h) of Example 5 was repeated using (4-((2,2-dimethyl-1,3-dioxan-5-yl)methoxy)-3-methylpyridin-2-yl)methanol obtained in the step (12b) above and 5H-[1,3]dioxolo[4,5-f]benzimidazole-6-thiol obtained in the step (78c) above to obtain the title compound (347 mg, total 51.9% yield) as a white solid.

$^1$H NMR(400 MHz, DMSO-d$_6$) δppm; 1.32(3H, s), 1.34 (3H, s), 2.03-2.13(1H, m), 2.16(3H, s), 3.71-3.81(2H, m), 3.93-4.02(2H, m), 4.09(2H, d, J=7 Hz), 4.30(1H, d, J=13 Hz), 4.80(1H, d, J=13 Hz), 5.82(2H, s), 6.89(2H, s), 6.92(1H, d, J=6 Hz), 8.26(1H, d, J=6 Hz).

Example 79

2-(((4-((2,2-dimethyl-1,3-dioxan-5-yl)methoxy)pyridin-2-yl)methyl)sulfinyl)-6,7-dihydro-1H-[1,4]dioxino[2,3-f]benzimidazole sodium salt

[Formula 316]

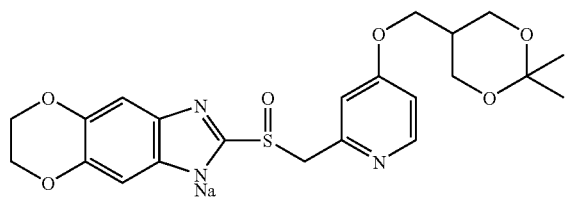

(79a) 4-((2,2-dimethyl-1,3-dioxan-5-yl)methoxy)-N,N-diisopropylpyridine-2-carboxamide

[Formula 317]

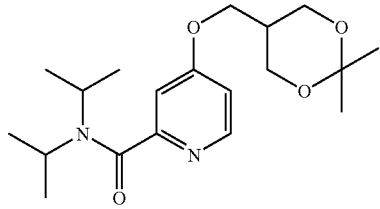

A mixture of the 4-chloro-N,N-diisopropylpyridine-2-carboxamide (5 g, 20.8 mmol) obtained in the same manner as in the step (92a), (2,2-dimethyl-1,3-dioxan-5-yl)methanol (3.34 g, 22.8 mmol) obtained in the same manner as in the step (11a), potassium hydroxide (2.57 g, 45.8 mmol) and toluene (50 ml) was heated under reflux equipped with a Dean-Stark devise for 7 hours and stirred at room temperature for 3 days. The reaction mixture was washed with water and a saturated saline solution, dried over magnesium sulfate and filtrated.

The filtrate was concentrated under reduced pressure and the residue was dissolved in toluene-heptane-ethyl acetate and subjected to NH silica gel column chromatography (elution solvent: n-heptane/ethyl acetate=2/1→1/1). The fraction containing a desired product was concentrated and the solid residue was washed with heptane and collected by filteration to obtain the title compound (5.39 g, 73.9%) as a white solid.

$^1$H NMR(400 MHz, DMSO-d$_6$) Δppm; 1.09(6H, d, J=7 Hz), 1.23(3H, s), 1.36(3H, s), 1.43(6H, d, J=6 Hz), 2.02-2.10 (1H, m), 3.51-3.65(2H, m), 3.74(2H, dd, J=6, 12 Hz), 3.98 (2H, dd, J=4, 12 Hz), 4.16(2H, d, J=7 Hz), 6.95-7.00(2H, m), 8.33(1H, d, J=6 Hz).

(79b) 2-(((4-((2,2-dimethyl-1,3-dioxan-5-yl)methoxy)pyridin-2-yl)methyl)sulfinyl)-6,7-dihydro-1H-[1,4]dioxino[2,3-f]benzimidazole sodium salt

[Formula 318]

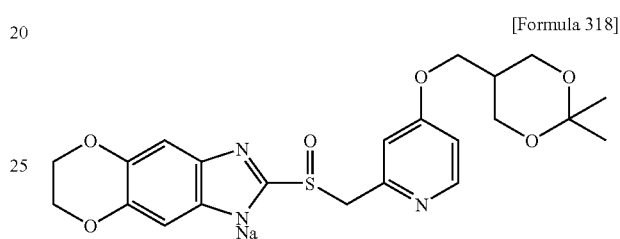

The same procedure as in the same manner as in the steps (92d) and (5f) to (5h) (a reprecipitation operation was not performed in oxidation step with 3-chloroperbenzoic acid) was repeated using 4-((2,2-dimethyl-1,3-dioxan-5-yl)methoxy)-N,N-diisopropylpyridine-2-carboxamide obtained in the step (79a) and 6,7-dihydro-1H-[1,4]dioxino[2',3':4,5]benzo[d]imidazole-2-thiol to obtain the title compound (373 mg, total 40.8% yield) as a white solid.

$^1$H NMR(400 MHz, DMSO-d$_6$) δppm; 1.30(3H, s), 1.33 (3H, s), 1.82-1.95(1H, m), 3.53-3.73(3H, m), 3.79-3.91(3H, m), 4.14 (4H, s), 4.38(1H, d, J=12 Hz), 4.54(1H, d, J=12 Hz), 6.55-6.63(1H, m), 6.74-6.86(1H, m), 6.83(2H, s), 8.28(1H, d, J=6 Hz).

Example 80

2-(((4-(1,4-dioxaspiro[4.4]non-6-ylmethoxy)-3-methylpyridin-2-yl)methyl)sulfinyl)-1H-benzimidazole sodium salt

[Formula 319]

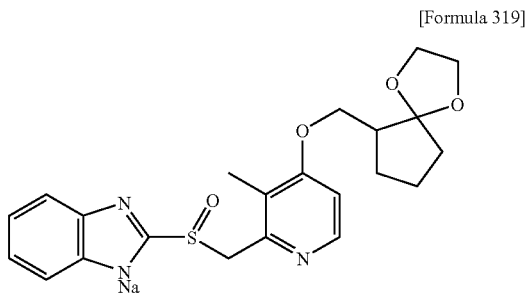

(80a) Methyl 1,4-dioxaspiro[4.4]nonan-6-carboxylate

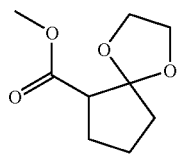

[Formula 320]

A reflux condenser equipped with a Dean-Stark water separator was attached to a round bottom flask containing methyl 2-cyclopentanonecarboxylate (2 ml, 16.2 mmol), ethylene glycol (994 μl, 17.8 mmol), p-toluenesulfonic acid monohydrate (139 mg, 0.73 mmol), and benzene (30 ml). The mixture was heated under reflux for 2 hours. To the reaction mixture, triethylamine (0.22 ml) was added and the mixture was concentrated and purified by silica gel column chromatography (elution solvent: ethyl acetate/heptane=1/9, 1/1) to obtain the title compound (2.12 g, yield 70.3%) as a colorless oil.

$^1$H NMR(400 MHz, CDCl$_3$) δppm; 1.59-1.72(1H, m), 1.77-1.98(4H, m), 2.06-2.18(1H, m), 2.93(1H, t, J=8 Hz), 3.70(3H, s), 3.86-4.06(4H, m).

(80b) 1,4-dioxaspiro[4.4]non-6-ylmethanol

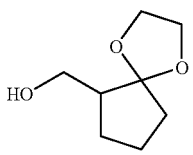

[Formula 321]

To a suspension of lithium aluminum hydride (630 mg, 16.6 mmol) in diethyl ether (30 ml), methyl 1,4-dioxaspiro[4.4]nonane-6-carboxylate (3.1 g, 16.6 mmol) obtained by the method of the step (80a) above was added at 0° C. The mixture was stirred at room temperature for 3 hours. Water (0.6 ml), a 5N aqueous sodium hydroxide solution (0.6 ml), and water (1.8 ml) were sequentially added at 0° C. to the mixture and the mixture was filtrated. After water was added to the filtrate and the organic layer was separated. The aqueous layer was extracted three times with ethyl acetate. The resultant extract was dried over sodium sulfate, concentrated under reduced pressure, and purified by silica gel column chromatography (elution solvent: ethyl acetate/heptane=1/4, 1/1) to obtain the title compound (1.9 g, yield 72.4%) as a colorless oil.

$^1$H NMR(400 MHz, CDCl$_3$) δppm; 1.51-1.92(6H, m), 2.11-2.18(1H, m), 2.53-2.69(1H, br), 3.58-3.73(2H, m), 3.88-4.02(4H, m).

(80c) 2-(((4-(1,4-dioxaspiro[4.4]non-6-ylmethoxy)-3-methylpyridin-2-yl)methyl)sulfinyl)-1H-benzimidazole sodium salt

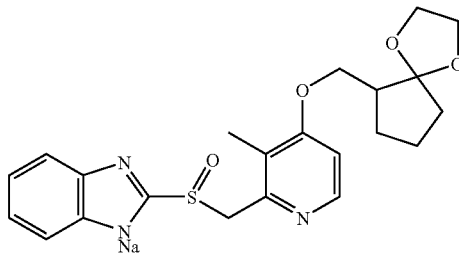

[Formula 322]

The same procedure as in the steps (14a) to (14e) of Example 14 was repeated using the 1,4-dioxaspiro[4.4]non-6-ylmethanol obtained in the step (80b) above to obtain the title compound (383 mg, the total yield of 5 steps: 14.6%) as a light yellow solid. Note that in the same process as in the step (14c), methanol was used as a solvent instead of ethanol.

$^1$H NMR(400 MHz, DMSO-d$_6$) δppm; 1.42-1.80(5H, m), 1.86-2.01(1H, m), 2.15(3H, d, J=7 Hz), 2.28-2.41(1H, m), 3.70-3.93(5H, m), 4.02-4.13(1H, m), 4.38(1H, d, J=13 Hz), 4.77(1H, d, J=13 Hz), 6.79-6.87(2H, m), 6.89(1H, dd, J=2, 6 Hz), 7.37-7.46(2H, m), 8.25(1H, d, J=6 Hz).

Example 81

2-(((4-((3,3-dimethyl-1,5-dioxaspiro[5.5]undec-9-yl)oxy)-3-methylpyridin-2-yl)methyl)sulfinyl)-1H-benzimidazole sodium salt

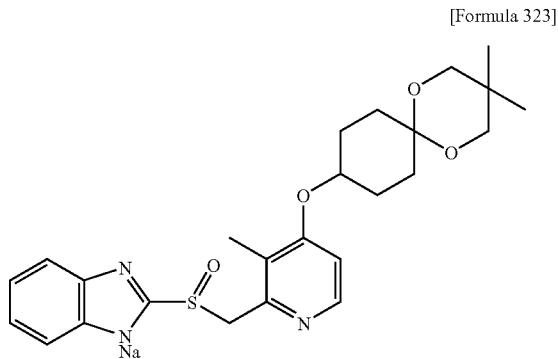

[Formula 323]

(81a) 3,3-dimethyl-1,5-dioxaspiro[5.5]undecan-9-ol

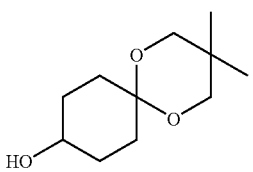

[Formula 324]

To the suspension of lithium aluminum hydride (748 mg, 19.7 mmol) in tetrahydrofuran (40 ml), a tetrahydrofuran solution of 1,4-cyclohexanedione mono-2,2-dimethyltrimethylene ketal (3.9 g, 19.7 mmol) was added at 0° C. The mixture was stirred at room temperature for 3 hours. After water (0.7 ml), a 5N aqueous sodium hydroxide solution (0.7 ml), and water (2.1 ml) were sequentially added at 0° C. to the mixture, the mixture was dried over sodium sulfate, filtrated, concentrated under reduced pressure, and purified by silica gel column chromatography (elution solvent: ethyl acetate/heptane=1/2, 1/1, 2/1) to obtain the title compound (3.6 g, yield: 91.2%) as a colorless oil.

$^1$H NMR(400 MHz, CDCl$_3$) δppm; 0.97(6H, s), 1.51-1.60 (4H, m), 1.74-1.86(2H, m), 2.04-2.14(2H, m), 3.50(4H, d, J=4 Hz), 3.74-3.84(1H, m).

(81b) 2-(((4-((3,3-dimethyl-1,5-dioxaspiro[5.5]un-dec-9-yl)oxy)-3-methylpyridin-2-yl)methyl)sulfi-nyl)-1H-benzimidazole sodium salt

[Formula 325]

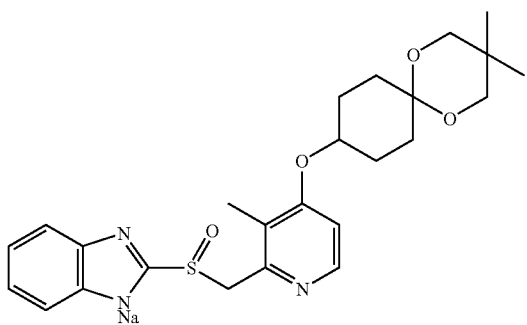

The same procedure as in the steps (14a) to (14e) of Example 14 was repeated using the 3,3-dimethyl-1,5-dioxas-piro[5.5]undecan-9-ol obtained in the step (81a) above to obtain the title compound (275 mg, the total yield of 5 steps: 3.3%) as a white solid. Note that in the same process as in the step (14b), after acetic anhydride was added, 10 equivalents of triethylamine relative to pyridine1-oxide derivative was added to perform the reaction. In the same process as in the step (14c), tetrahydrofuran was used as a solvent instead of ethanol.

$^1$H NMR(400 MHz, DMSO-d$_6$) δppm; 0.90(6H, s), 1.62-1.94(8H, m), 2.18(3H, s), 3.45(4H, d, J=6 Hz), 4.35(1H, d, J=13 Hz), 4.70-4.78(1H, br), 4.81(1H, d, J=13 Hz), 6.81-6.88 (2H, m), 6.97(1H, d, J=6 Hz), 7.39-7.46(2H, m), 8.23(1H, d, J=6 Hz).

Example 82

2-(((4-(1,4-dioxaspiro[4.5]dec-8-ylmethoxy)-3-me-thylpyridin-2-yl)methyl)sulfinyl)-1H-benzimidazole sodium salt

[Formula 326]

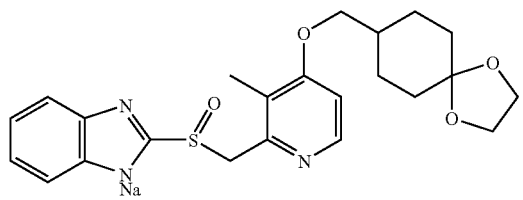

(82a) 1,4-dioxaspiro[4.5]dec-8-ylmethanol

[Formula 327]

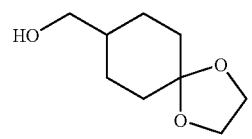

A reflux condenser equipped with a Dean-Stark water separator was attached to a round bottom flask containing ethyl 4-cyclohexanonecarboxylate (5 ml, 31.4 mmol), ethylene glycol (1.93 ml, 34.5 mmol), p-toluenesulfonic acid monohydrate (200 mg, 1.05 mmol), and benzene (30 ml). The mixture was heated under reflux for 3 hours. To the reaction mixture, triethylamine (181 μl, 1.3 mmol) was added and the mixture was concentrated. A tetrahydrofuran solution of the resultant crude substance was added to a tetrahydrofuran (30 ml) suspension of lithium aluminum hydride (1.31 g, 34.5 mmol) at 0° C. After the mixture was stirred at room temperature for 7 hours, water (1.3 ml), a 5N aqueous sodium hydroxide solution (1.3 ml), and water (3.9 ml) were sequentially added to the mixture at 0° C. After dried over sodium sulfate, the mixture was filtrated. The filtrate was concentrated under reduced pressure and purified by silica gel column chromatography (elution solvent: ethyl acetate/heptane=1/2, 1/1, 2/1) to obtain the title compound (4.6 g, yield: 85.1%) as a colorless oil.

$^1$H NMR(400 MHz, CDCl$_3$) δppm; 1.20-1.33(3H, m), 1.48-1.61(2H, m), 1.74-1.82(4H, m), 3.49(2H, t, J=6 Hz), 3.92-3.96(4H, m).

(82b) 2-(((4-(1,4-dioxaspiro[4.5]dec-8-ylmethoxy)-3-methylpyridin-2-yl)methyl)sulfinyl)-1H-benzimi-dazole sodium salt

[Formula 328]

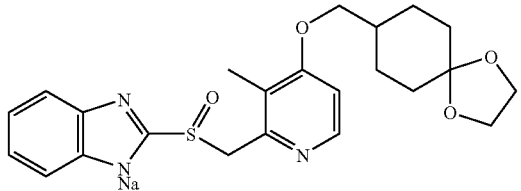

The same procedure as in the steps (14a) to (14b) of Example 14 and the steps (7d) to (7f) of Example 7 was repeated using the 1,4-dioxaspiro[4.5]dec-8-ylmethanol obtained in the step (82a) above to obtain the title compound (115 mg, the total yield of 5 steps: 7.3%) as a white solid. Note that, in the same process as in the step (14b), after acetic anhydride was added, 2 equivalents of triethylamine relative to pyridine1-oxide derivative was added to perform the reaction.

$^1$H NMR(400 MHz, DMSO-d$_6$) δppm; 1.23-1.55(4H, m), 1.65-1.89(5H, m), 2.19(3H, s), 3.81-3.95(6H, m), 4.36(1H, d, J=13 Hz), 4.83(1H, d, J=13 Hz), 6.79-6.88(2H, m), 6.90(1H, d, J=6 Hz), 7.38-7.46(2H, m), 8.24(1H, d, J=6 Hz).

Example 83

2-(((4-(5,9-dioxaspiro[3.5]non-7-yloxy)pyridin-2-yl)methyl)sulfinyl)-1H-benzimidazole sodium salt

[Formula 329]

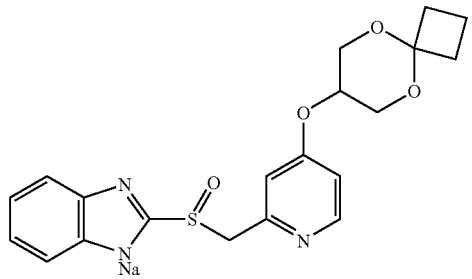

(83a) 4-(5,9-dioxaspiro[3.5]non-7-yloxy)-N,N-diisopropylpyridine-2-carboxamide

[Formula 330]

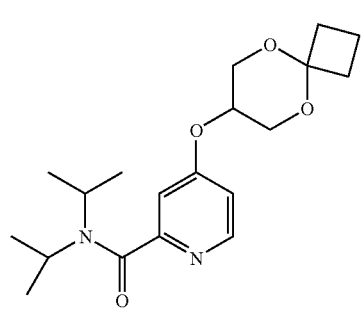

The same procedure as in the step (92c) of Example 92 was repeated using 5,9-dioxaspiro[3.5]nonan-7-ol separately obtained in the method of steps (9a) to (9e) of Example 9, and 4-chloro-N,N-diisopropylpyridine-2-carboxamide obtained in the method of the step (92a) of Example 92 to obtain the title compound (1.69 g, yield 97%) as colorless oil.

$^1$H NMR(400 MHz, CDCl$_3$) δppm; 1.12-1.31(6H, d, J=6 Hz), 1.74-1.82(2H, m), 2.24-2.34(4H, m), 3.45-3.63(1H, m), 3.72-3.87(1H, m), 3.90(2H, dd, J=5, 12 Hz), 4.05-4.15(2H, m), 4.36-4.44(1H, m), 6.88(1H, dd, J=2, 6 Hz), 6.95(1H, d, J=2 Hz), 8.40(1H, d, J=6 Hz).

(6H was missing since it was overlapped with the peak of a H$_2$O content at 1.4-1.7 ppm)

(83b) (4-(5,9-dioxaspiro[3.5]non-7-yloxy)pyridin-2-yl)methanol

[Formula 331]

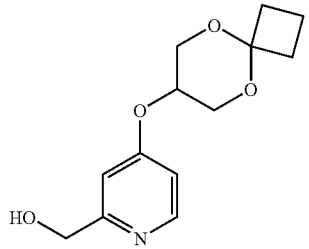

To a tetrahydrofuran (60 ml) solution of 4-(5,9-dioxaspiro[3.5]non-7-yloxy)-N,N-diisopropylpyridine-2-carboxamide (1.69 g, 4.85 mmol) obtained in the step (83a), lithium aluminum hydride (552 mg, 14.5 mmol) was added at −6 to −5° C. and then the mixture was stirred at room temperature for one hour. Water (0.55 ml), a 5N aqueous sodium hydroxide solution (0.55 ml), and water (1.65 ml) were sequentially added to the mixture. After dried over sodium sulfate, the mixture was concentrated under reduced pressure, and purified by silica gel column chromatography (elution solvent: heptane, ethyl acetate/heptane=1/1, ethyl acetate) to obtain the title compound (560 mg, yield 45.9%) as a white solid.

$^1$H NMR(400 MHz, DMSO-d$_6$) δppm; 1.65(2H, quint, J=8 Hz), 2.14(2H, t, J=8 Hz), 2.23(2H, t, J=8 Hz), 3.77(2H, dd, J=3, 13 Hz), 3.99-4.06(2H, m), 4.44-4.49(3H, m), 6.82(1H, dd, J=2, 6 Hz), 6.96(1H, d, J=2 Hz), 8.25(1H, d, J=6 Hz).

(83c) 2-(((4-(5,9-dioxaspiro[3.5]non-7-yloxy)pyridin-2-yl)methyl)sulfinyl)-1H-benzimidazole sodium salt

[Formula 332]

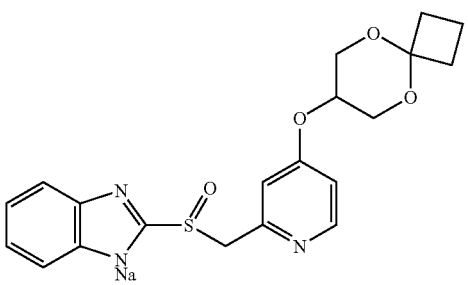

The same procedure as in the steps (9h) to (9j) of Example 9 was repeated using the (4-(5,9-dioxaspiro[3.5]non-7-yloxy)pyridin-2-yl)methanol obtained in the step (83b) above to obtain the title compound (100 mg, the total yield of 3 steps: 50%) as a white solid. Note that, in the same process as in the step (9h), 2-mercaptobenzimidazole was added to the reaction mixture and stirred at room temperature for 25 hours, and thereafter, 3 equivalents of potassium hydroxide relative to the alcohol was added thereto. The mixture was allowed to react at room temperature for 6 hours.

$^1$H NMR(400 MHz, DMSO-d$_6$) δppm; 1.56-1.70(2H, m), 2.04-2.24(4H, m), 3.44-3.53(1H, m), 3.60-3.72(2H, m), 3.80 (1H, dd, J=2, 13 Hz), 3.96(1H, t, J=2 Hz), 4.41(1H, d, J=12 Hz), 4.57(1H, d, J=12 Hz), 6.55(1H, d, J=3 Hz), 6.81-6.91 (3H, m), 7.40-7.48(2H, m), 8.31(1H, d, J=6 Hz).

Example 84

2-(((4-(5,7-dioxaspiro[2.5]oct-6-ylmethoxy)pyridin-2-yl)methyl)sulfinyl)-5-fluoro-1H-benzimidazole sodium salt

[Formula 333]

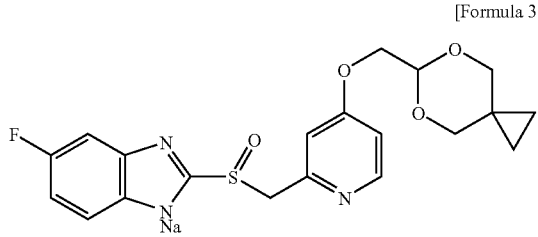

(84a) 2,2-diethoxyethyl benzoate

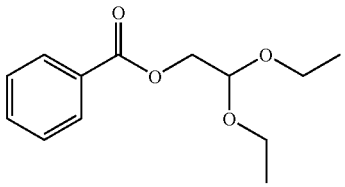

[Formula 334]

To a pyridine (30 ml) solution of glycol aldehyde diethylacetal (19.8 g, 148 mmol), benzoyl chloride (51.7 ml, 444 mmol) was added dropwise at −20 to 30° C. The mixture was stirred at room temperature for 167 hours and 50 minutes. After methanol and water were added to the mixture, extraction with ethyl acetate was performed. The obtained organic layer was washed with a saturated aqueous ammonium chloride solution, saturated aqueous sodium hydrogencarbonate solution, and a saturated saline solution. After dried over anhydrous magnesium sulfate, the mixture was concentrated under reduced pressure and purified by silica gel column chromatography (elution solvent: heptane, ethyl acetate/heptane=1/9). Thereafter, purification by silica gel column chromatography (elution solvent: heptane, ethyl acetate/heptane=1/100, 1/30, 1/10) was performed again to obtain the title compound (34 g, yield: 96.4%) as a light green oil.

$^1$H NMR(400 MHz, CDCl$_3$) δppm; 1.24(6H, t, J=7 Hz), 3.58-3.68(2H, m), 3.72-3.82(2H, m), 4.34(2H, d, J=6 Hz), 4.83(1H, t, J=6 Hz), 7.42-7.48(2H, m), 7.54-7.60(1H, m), 8.02-8.09(2H, m).

(84b) 5,7-dioxaspiro[2.5]oct-6-ylmethyl benzoate

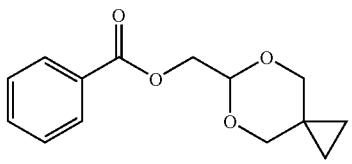

[Formula 335]

A reflux condenser equipped with a Dean-Stark water separator was attached to a round bottom flask containing 2,2-diethoxyethyl benzoate (33 g, 139 mmol) obtained in the step (84a) above, 1,1-bis(hydroxymethyl)cyclopropane (15.6 g, 153 mmol), p-toluenesulfonic acid monohydrate (2.64 g, 13.9 mmol), and toluene (100 ml). The mixture was heated under reflux for 2 hours and cooled to room temperature. To the reaction mixture, triethylamine (10 ml), ethyl acetate (100 ml), and silica gel (50 g) were added. The mixture was concentrated and purified by silica gel column chromatography (elution solvent: ethyl acetate/heptane=1/30, 1/10) to obtain the title compound (25.5 g, yield 73.9%) as a light yellow oil.

$^1$H NMR(400 MHz, CDCl$_3$) δppm; 0.32-0.39(2H, m), 0.68-0.76(2H, m), 3.29(2H, d, J=12 Hz), 4.16(2H, d, J=12 Hz), 4.41(2H, d, J=5 Hz), 4.98(1H, t, J=5 Hz), 7.40-7.46 (2H, m), 7.52-7.58(1H, m), 8.04-8.09(2H, m).

(84c) 5,7-dioxaspiro[2.5]oct-6-ylmethanol

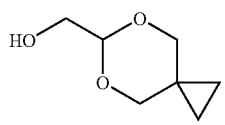

[Formula 336]

To a mixture of 5,7-dioxaspiro[2.5]oct-6-ylmethyl benzoate (25.1 g, 101 mmol) obtained in the step (84b) above and methanol (150 ml), a 2N aqueous sodium hydroxide solution (55.6 ml, 111 mmol) was added at an inner temperature of 0 to 4° C. After the mixture was stirred at room temperature for 3 hours, a saturated aqueous ammonium chloride solution was added to the mixture to adjust pH to about 9. The mixture was concentrated under reduced pressure by about the amount of methanol. Ethyl acetate was added to the residue and the organic layer was separated. The aqueous layer was extracted with ethyl acetate and then sodium chloride was added to the obtained water layer. The mixture was extracted with ethyl acetate and then the organic layers were combined and washed with a saturated saline solution. The organic layer was dried over anhydrous magnesium sulfate and then the solvent was removed by distillation to obtain the title compound (10 g, yield: 68.6%) as a colorless oil.

$^1$H NMR(400 MHz, CDCl$_3$) δppm; 0.33-0.37(2H, m), 0.68-0.72(2H, m), 1.87(1H, t, J=6 Hz), 3.28(2H, d, J=11 Hz), 3.68(2H, dd, J=4, 6 Hz), 4.16(2H, d, J=11 Hz), 4.73(1H, t, J=4 Hz).

(84d)-2-(((4-(5,7-dioxaspiro[2.5]oct-6-ylmethoxy)pyridin-2-yl)methyl)sulfinyl)-5-fluoro-1H-benzimidazole sodium salt

[Formula 337]

The same procedure as in the step (79a) of Example 79, the step (92d) of Example 92, the step (5f) of Example 5, and the steps (9i) to (9j) of Example 9 was repeated using the 5,7-dioxaspiro[2.5]oct-6-ylmethanol obtained in the step (84c) above to obtain the title compound (298 mg, the total yield of 5 steps: 14.1%) as a white solid. Note that in the same operation as in the step (92d), ethanol was used instead of methanol. In the same operation as in the step (5f), 5-fluoro-1H-benzimidazole-2-thiol obtained in the step (52a) of Example 52 was used instead of 2-mercaptobenzimidazole.

$^1$H NMR(400 MHz, DMSO-d$_6$) δppm; 0.33(2H, dd, J=7, 8 Hz), 0.59(2H, dd, J=7, 8 Hz), 3.24(2H, d, J=12 Hz), 3.92-4.04 (2H, m), 4.09(2H, d, J=12 Hz), 4.43(1H, d, J=12 Hz), 4.50 (1H, d, J=12 Hz), 4.94(1H, t, J=4 Hz), 6.64-6.78(1H, m), 6.80-6.98(2H, m), 7.16(1H, dd, J=2, 10 Hz), 7.42(1H, d, J=5, 8 Hz), 8.37(1H, d, J=6 Hz).

Example 85

2-(((4-(6,8-dioxaspiro[3.5]non-7-ylmethoxy)-3-methylpyridin-2-yl)methyl)sulfinyl)-1H-benzimidazole sodium salt

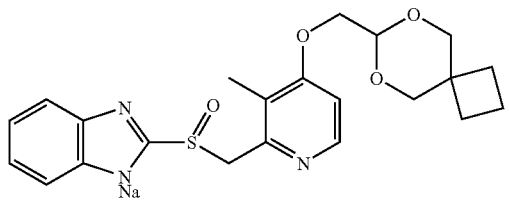
[Formula 338]

(85a) Cyclobutane-1,1-diyldimethanol

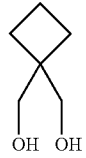
[Formula 339]

A tetrahydrofuran (50 ml) solution of diethyl 1,1-cyclobutanedicarboxylate (4.97 g, 24.8 mmol) was cooled under ice-cool. To the solution, lithium aluminum hydride (1.6 g, 42.2 mmol) was added. The reaction mixture was stirred at 0° C. for 10 minutes and further stirred at room temperature for 15 minutes. The reaction was terminated by adding diethyl ether-water to the reaction mixture. The solution having precipitated inorganic compounds was dried over anhydrous magnesium sulfate and the solvent was distilled off under reduced pressure to obtain the title compound (2.88 g, 100%) as a colorless oil.

$^1$H NMR(400 MHz, CDCl$_3$) δppm; 1.77-1.82(4H, m), 1.90-1.96(2H, m), 2.38(2H, br s), 3.75(4H, s).

(85b) 7-((benzyloxy)methyl)-6,8-dioxaspiro[3.5]nonane

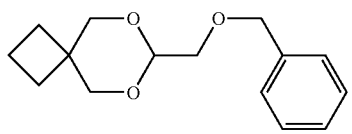
[Formula 340]

A mixture of cyclobutane-1,1-diyldimethanol (2.88 g, 24.8 mmol) obtained in the step (85a) above, benzyloxyacetaldehyde (3.72 g, 24.8 mmol), p-toluenesulfonic acid monohydrate (214 mg, 1.13 mmol) and toluene (70 ml) was heated under reflux for one hour while removing water by a Dean-Stark apparatus. The reaction mixture was cooled to room temperature and triethylamine (3 ml) was added thereto, then the solvent was distilled away. The residue was purified by silica gel column chromatography (silica gel: 200 g, elution solvent: ethyl acetate/heptane=1/50→1/9) to obtain the title compound (3.8 g, yield: 48.7%) as a white solid.

$^1$H NMR(400 MHz, CDCl$_3$) δ ppm; 1.54(2H, t, J=8 Hz), 1.90(2H, quint, J=8 Hz), 2.10(2H, t, J=8 Hz), 3.49(2H, d, J=4 Hz), 3.52(2H, d, J=11 Hz), 4.00(2H, d, J=11 Hz), 4.57(2H, s), 4.67(1H, t, J=4 Hz), 7.25-7.33(5H, m).

(85c) 6,8-dioxaspiro[3.5]non-7-ylmethanol

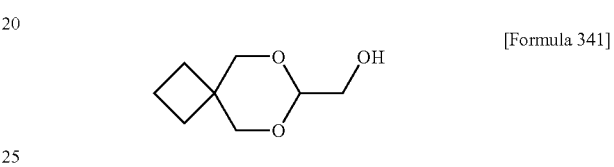
[Formula 341]

A mixture of 7-((benzyloxy)methyl)-6,8-dioxaspiro[3.5]nonane (3.8 g, 15.3 mmol) obtained in the step (85b) above, 20% palladium hydroxide (800 mg), and ethyl acetate (70 ml) was stirred in a hydrogen atmosphere overnight. The reaction vessel was purged with nitrogen and a catalyst was removed by filtration. The filtrate was concentrated to obtain the title compound (2.0 g, yield: 82.6%) as a white solid.

$^1$H NMR(400 MHz, CDCl$_3$) δppm; 1.56(2H, t, J=8 Hz), 1.83(1H, t, J=4 Hz), 1.92(2H, quint, J=8 Hz), 2.10(2H, t, J=8 Hz), 3.54(2H, d, J=11 Hz), 3.60(2H, t, J=5 Hz), 4.02(2H, d, J=11 Hz), 4.56(1H, t, J=4 Hz).

(85d) 2-(((4-(6,8-dioxaspiro[3.5]non-7-ylmethoxy)-3-methylpyridin-2-yl)methyl)sulfinyl)-1H-benzimidazole sodium salt

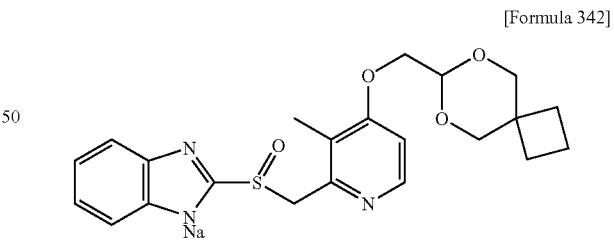
[Formula 342]

The same manner as in the steps (62c) and (8d) to (8g) was repeated using alcohol obtained in the step (85c) above to obtain the title compound (198 mg, total yield 13.6%) as a white solid.

$^1$H NMR(400 MHz, DMSO-d$_6$) δppm; 1.51(2H, t, J=8 Hz), 1.85(2H, quint, J=8 Hz), 1.98(2H, t, J=8 Hz), 2.16(3H, s), 3.54(2H, d, J=10 Hz), 3.97(2H, d, J=10 Hz), 4.01(2H, d, J=4 Hz), 4.38(1H, d, J=13 Hz), 4.76(1H, d, J=13 Hz), 4.86 (1H, t, J=4 Hz), 6.83-6.85(2H, m), 6.92(1H, d, J=6 Hz), 7.41-7.43(2H, m), 8.25(1H, d, J=6 Hz).

Example 86

2-(((4-(2-(5,5-dimethyl-1,3-dioxan-2-yl)ethoxy)-3-methylpyridin-2-yl)methyl)sulfinyl)-1H-benzimidazole sodium salt

[Formula 343]

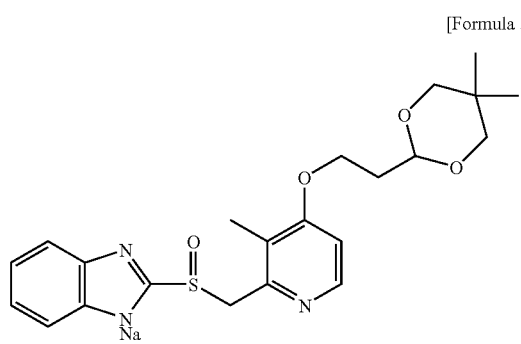

The same procedure as in the steps (1c) to (1g) of Example 1 was repeated using 5,5-dimethyl-1,3-dioxane-2-ethanol (1.00 g, 6.24 mmol) to obtain the title compound (138 mg, 0.31 mmol) as a beige solid.

$^1$H NMR(400 MHz, DMSO-d$_6$) δppm; 0.68(3H, s), 1.09 (3H, s), 1.96-2.07(2H, m), 2.16(3H, s), 3.41(2H, d, J=11 Hz), 3.53(2H, d, J=11 Hz), 4.10(2H, t, J=6 Hz), 4.38(1H, d, J=13 Hz), 4.65(1H, t, J=5 Hz), 4.74(1H, d, J=13 Hz), 6.79-6.88 (2H, m), 6.90(1H, d, J=6 Hz), 7.38-7.47(2H, m), 8.25(1H, d, J=6 Hz).

Example 87

2-(((4-(1,3-dioxolan-4-ylmethoxy)-3-methylpyridin-2-yl)methyl)sulfinyl)-1H-benzimidazole sodium salt

[Formula 344]

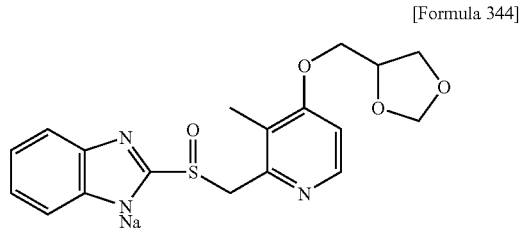

The same procedure as in the steps (1c) to (1 g) of Example 1 was repeated using glycerol formal (1.76 ml, 20.3 mmol) to obtain the title compound (87 mg, 0.22 mmol) as a beige solid.

$^1$H NMR(400 MHz, DMSO-d$_6$) δppm; 2.18(3H, s), 3.68-3.74(1H, m), 4.01(1H, t, J=8 Hz), 4.06-4.17(2H, m), 4.33-4.43(2H, m), 4.78(1H, d, J=3 Hz), 4.85(1H, s), 4.94(1H, s), 6.78-6.88(2H, m), 6.93(1H, d, J=6 Hz), 7.36-7.46(2H, m), 8.26(1H, d, J=6 Hz).

Example 88

Sodium Salt of an Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 345]

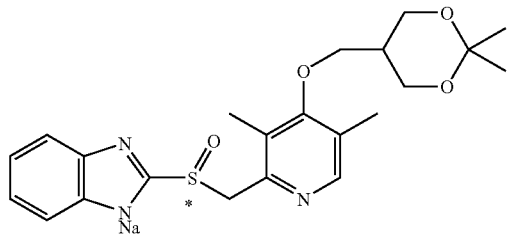

Another method of synthesis performed in Example 20 is described below.

(88a) Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 346]

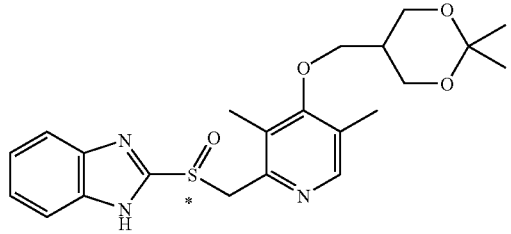

A toluene (4 ml) solution of 2-(((4-(2,2-dimethyl-1,3-dioxan-5-yl)methoxy)-3,5-dimethylpyridin-2-yl)methyl)thio)-1H-benzimidazole (500 mg, 1.21=mmol), zirconium(IV) isopropoxide isopropanol complex (295 mg, 0.76 mmol) and N,N,N',N'-(−)-tetramethyl-(D)-tartaramide (396 mg, 1.94 mmol) was stirred in a nitrogen atmosphere at 40° C. for one hour. After the solution was cooled to room temperature, N,N-diisopropylethylamine (91 µl, 0.52 mmol) was added and subsequently, cumene hydroperoxide (243 µl, 1.32 mmol as the content was regarded as 80%) was added dropwise to the mixture and then the mixture was stirred at room temperature for 22 hours. After a saturated aqueous sodium hydrogen carbonate solution and a saturated aqueous sodium thiosulfate solution were added, the mixture was extracted with ethyl acetate. The organic layer was dried over anhydrous sodium sulfate, filtrated, and concentrated. The residue was purified by silica gel column chromatography (NH silica gel: 30 g, elution solvent: ethyl acetate, ethyl acetate/methanol 7:3, 1;1 gradient). The fractions containing the title compound were collected with ethyl acetate and concentrated to obtain the title compound (328 mg, yield: 63%) as a colorless foam.

HPLC (Conditions) column: CHIRALPAK IA (manufactured by Daicel Chemical Industries, Ltd.)(0.46 cmφ×25 cm)

eluant: hexane/ethanol=3/2 (v/v), flow rate: 0.5 ml/min, detection: UV (254 nm).

(Analysis Results)

The retention time: 17.5 minutes, enantiomeric excess: 99% ee.

(88b) Sodium Salt of an Optical Isomer (Short in Retention Time) 2-(((4-((2,2-dimethyl-1,3-dioxan-5-yl)methoxy)-3,5-dimethylpyridin-2-yl)methyl)sulfinyl)-1H-benzimidazole

[Formula 347]

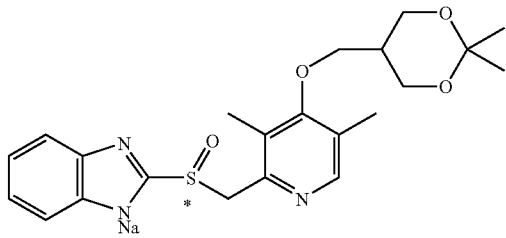

The same procedure as in Example 20b was repeated to form a sodium salt to obtain the title compound (299 mg, yield: 88%) as a white solid.

HPLC (Conditions) column: CHIRALPAK IA (manufactured by Daicel Chemical Industries, Ltd.)(0.46 cmφ×25 cm)

eluant: hexane/ethanol=3/2 (v/v), flow rate: 0.5 ml/min, detection: UV (254 nm).

(Analysis Results)

The retention time: 18.0 minutes, enantiomeric excess: 99% ee.

Specific rotation: $\alpha_D^{22.4}$=+78.51 (c=0.5, EtOH).

Example 89

Sodium Salt of an Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 348]

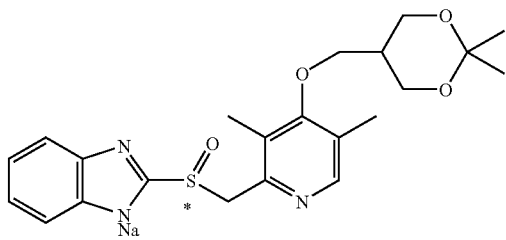

Another method of synthesis performed in Example 20 is described below.

(89a) Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 349]

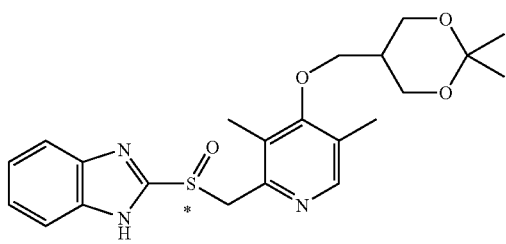

A mixture of 2-(((4-((2,2-dimethyl-1,3-dioxan-5-yl)methoxy)-3,5-dimethylpyridin-2-yl)methyl)thio)-1H-benzimidazole (500 mg, 1.21 mmol) and N,N,N',N'-(−)-tetramethyl-(D)-tartaramide (396 mg, 1.94 mmol) in toluene (4 ml) was dissolved by heating at 40° C. for 10 minutes in a nitrogen atmosphere. Hafnium tetrabutoxide (315 μL, 0.78 mmol) was added to the mixture and further stirred at the same temperature for one hour. After the reaction mixture was cooled to room temperature, N,N-diisopropylethylamine (90 μl, 0.52 mmol) was added and subsequently, cumene hydroperoxide (267 μl, 1.46 mmol as the content was regarded as 80%) was added dropwise to the mixture and then the mixture was stirred at room temperature for 22 hours. After a saturated aqueous sodium hydrogen carbonate solution and a saturated aqueous sodium thiosulfate solution were added, the mixture was extracted with ethyl acetate. The organic layer was dried over anhydrous sodium sulfate, filtrated, and concentrated. The residue was purified by silica gel column chromatography (NH silica gel: 30 g, elution solvent: ethyl acetate, ethyl acetate/methanol 7:3, 1;1 gradient). The fractions containing the title compound were collected with ethyl acetate and concentrated to obtain the title compound (206 mg, yield: 40%) as a colorless foam.

HPLC (Conditions) column: CHIRALPAK IA (manufactured by Daicel Chemical Industries, Ltd.)(0.46 cmφ×25 cm)

eluant: hexane/ethanol=3/2 (v/v), flow rate: 0.5 ml/min, detection: UV (254 nm).

(Analysis Results)

The retention time: 17.2 minutes, enantiomeric excess: 90% ee.

(89b) Sodium Salt of an Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 350]

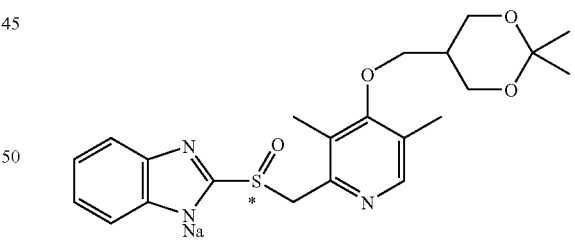

The same procedure as in Example 20b was repeated to form a sodium salt to obtain the title compound (182 mg, yield: 84%) as a white solid.

HPLC (Conditions) column: CHIRALPAK IA (manufactured by Daicel Chemical Industries, Ltd.)(0.46 cmφ×25 cm)

eluant: hexane/ethanol=3/2 (v/v), flow rate: 0.5 ml/min, detection: UV (254 nm).

(Analysis Results)

The retention time: 18.1 minutes, enantiomeric excess: 89% ee.

Example 90

Optical Isomer (Short in Retention Time) of 2-(((4-((2,2-dimethyl-1,3-dioxan-5-yl)methoxy)-3,5-dimethylpyridin-2-yl)methyl)sulfinyl)-1H-benzimidazole

[Formula 351]

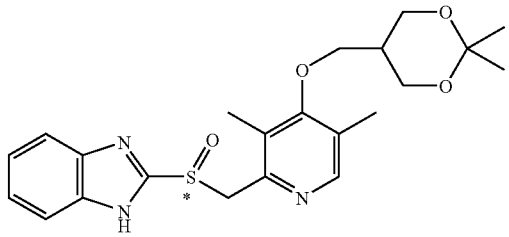

Another method of synthesis performed in Example 20a is described below.

To a flask, (S)-(−)-2-(3,5-di-tert-butylsalicylideneamino)-3,3-dimethyl-1-butanol (115 mg, 0.35 mmol), vanadyl acetylacetone (64 mg, 0.24 mmol), and acetonitrile (0.8 mL) were added and the mixture was stirred at room temperature for 30 minutes. The mixture was added to a dichloromethane (3 mL) solution of 2-(((4-((2,2-dimethyl-1,3-dioxan-5-yl)methoxy)-3,5-dimethylpyridin-2-yl)methyl)thio)-1H-benzimidazole (500 mg, 1.21 mmol) prepared in another flask, and the result mixture was stirred at room temperature for 30 minutes. An aqueous hydrogen peroxide solution (150 μl) was added by dividing the amount of the solution into 15 times (10 μl per time) for 20 hours and the mixture was further stirred for 24 hours. After a 1N aqueous sodium hydroxide solution (3 mL) was added and the mixture was stirred for 48 hours, a saturated aqueous sodium hydrogen carbonate solution and a saturated aqueous sodium thiosulfate solution were added to the mixture and then the mixture was extracted with ethyl acetate. The organic layer was dried over anhydrous sodium sulfate, filtrated, and concentrated. The residue was purified by silica gel column chromatography (NH silica gel 30 g, elution solvent: ethyl acetate, ethyl acetate/methanol 7:3, 1;1 gradient). The fractions containing the title compound were collected with ethyl acetate and concentrated to obtain the title compound (76 mg, yield: 15%) as colorless foam.

HPLC (Conditions) column: CHIRALPAK IA (manufactured by Daicel Chemical Industries, Ltd.)(0.46 cmφ×25 cm)

eluant: hexane/ethanol=3/2 (v/v), flow rate: 0.5 ml/min, detection: UV (254 nm).

(Analysis Results)

The retention time: 19.9 minutes, enantiomeric excess: 45% ee.

Example 91

Sodium Salt of an Optical Isomer of 2-(((3-methyl-4-(1,5,9-trioxaspiro[5.5]undec-3-ylmethoxy)pyridin-2-yl)methyl)sulfinyl)-1H-benzimidazole

[Formula 352]

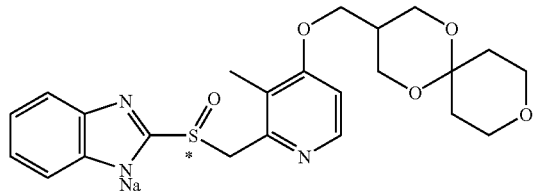

An ethanol solution of a sodium salt (racemate) of 2-(((3-methyl-4-(1,5,9-trioxaspiro[5.5]undec-3-ylmethoxy)pyridin-2-yl)methyl)sulfinyl)-1H-benzimidazole (192 mg) was prepared and separated by HPLC (column: CHIRALCEL OD-H 2 cmφ×25 cm (manufactured by Daicel Chemical Industries, Ltd.), mobile phase: ethanol/n-hexane=3/2, flow rate: 3.0 ml/min, detection wavelength: 254 nm). Immediately after fractions were obtained, a 1N aqueous sodium hydroxide solution (1 ml) was added to each of the fractions. The fractions containing optical isomers short and long in retention time were collected respectively and separated with ethyl acetate and a saturated aqueous ammonium chloride solution. The organic layer of each of the fractions was dried over anhydrous sodium sulfate, concentrated and subjected to azeotropic distillation with diethyl ether.

The residue of the optical isomer short in retention time was subjected to the same HPLC fraction, separation, drying and concentration operations as mentioned above. The obtained residue was purified by silica gel column chromatography (NH silica gel 20 g, elution solvent: dichloromethane, dichloromethane/methanol=10/1). Thereafter, the same HPLC fraction, separation, drying, concentration and azeotropic distillation with diethyl ether as mentioned above were performed to obtain a free form of the optical isomer (20 mg) short in retention time as a colorless solid.

The residue of the optical isomer long in retention time was subjected to the same HPLC fraction, separation, drying, concentration, and azeotropic distillation with diethyl ether as mentioned above to obtain a free form of the optical isomer (14 mg) long in retention time as a colorless solid.

Each of the free optical isomers was subjected to the operation for converting into a sodium salt in the same manner as in the step (11i) of Example 11 to obtain a sodium salt (18 mg) of the optical isomer short in retention time and a sodium salt (14 mg) of the optical isomer long in retention time, both as a colorless solid.

$^1$H NMR(400 MHz, DMSO-$d_6$); With respect to the sodium slats of both optical isomers, the same chart was obtained as in the case of the sodium salt (recemate) of 2-(((3-methyl-4-(1,5,9-trioxaspiro[5.5]undec-3-ylmethoxy)pyridin-2-yl)methyl)sulfinyl)-1H-benzimidazole.

HPLC (Conditions) column: CHIRALPAK OD-H (manufactured by Daicel Chemical Industries, Ltd.)(0.46 cmφ×25 cm)

eluant: hexane/ethanol=4/1 (v/v), flow rate: 0.5 ml/min, detection: UV: (280 nm).

(Analysis Results)

With respect to the sodium salt of an optical isomer short in retention time, the retention time: 36 minutes, enantiomeric excess: >98.0% ee.

specific rotation: $\alpha_D^{25.5}$=+107.73 (c=0.32, EtOH).

With respect to the sodium salt of an optical isomer long in retention time, the retention time: 44 minutes, enantiomeric excess: >98.0% ee.

specific rotation: $\alpha_D^{25.0}$=−115.85 (c=0.19, EtOH).

Example 92

2-(((4-((2,2-dimethyl-1,3-dioxan-5-yl)methoxy)-3-ethylpyridin-2-yl)methyl)sulfinyl)-1H-benzimidazole sodium salt

[Formula 353]

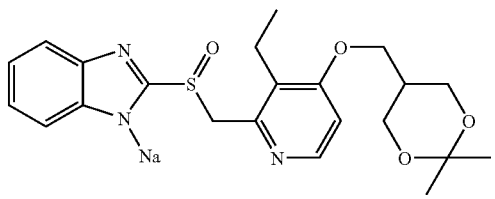

(92a) 4-chloro-N,N-diisopropylpyridine-2-carboxamide

[Formula 354]

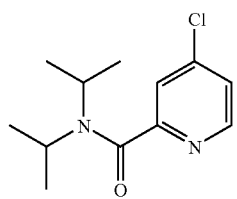

Thionyl chloride (60 ml, 823 mmol) was diluted with toluene (100 ml) and heated to 45° C. To the mixture, N,N-dimethylformamide (16 ml, 207 mmol) was added and the resultant mixture was stirred in the same conditions for one hour. To the mixture, picolinic acid (25 g, 203 mmol) was added and the resultant mixture was stirred at 80° C. for one hour and 20 minutes. After the reaction mixture was concentrated and diisopropylamine (185 ml, 807 mmol) and acetonitrile (500 ml) were added to the residue, the mixture was stirred at room temperature for 21 hours and 30 minutes. After the reaction mixture was concentrated, the residue was separated with ethyl acetate and water. The organic layer was washed with a saturated saline solution, dried over anhydrous magnesium sulfate, filtrated and concentrated. The residue was purified by silica gel column chromatography (elution solvent: heptane/ethyl acetate) to obtain the title compound (31.1 g, yield: 63.6%) as a pale brown solid.

$^1$H NMR(400 MHz, DMSO-$d_6$) δppm; 1.11(6H, d, J=7 Hz), 1.43(6H, d, J=6 Hz), 3.54-3.66(2H, m), 7.56-7.62(2H, m), 8.51-8.56(1H, m).

(92b) 4-chloro-3-ethyl-N,N-diisopropylpyridine-2-carboxamide

[Formula 355]

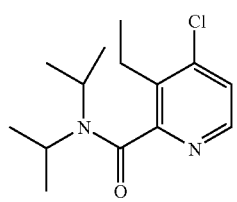

To a tetrahydrofuran (dehydrated) (50 ml) solution of diisopropylamine (1.35 g, 13.3 mmol), n-butyllithium (1.6 M hexane solution, 6.75 ml, 10.8 mmol) was added dropwise under ice-cool in a nitrogen atmosphere and the resultant mixture was stirred under the same conditions for 30 minutes. After the reaction mixture was cooled to −70° C., a tetrahydrofuran solution of the 4-chloro-N,N-diisopropylpyridine-2-carboxamide (2 g, 8.31 mmol) obtained in the step (92a) above was added to the mixture and the resultant mixture was stirred at −70° C. for 1.5 hours. To the reaction mixture, ethyl iodide (798 µl, 10 mmol) was added and the resultant mixture was stirred at −70° C. to 0° C. for 3 hours. To the reaction mixture, a saturated aqueous ammonium chloride solution was added and extracted with ethyl acetate. The organic layer was dried over anhydrous magnesium sulfate, filtrated and concentrated. The residue was purified by silica gel column chromatography (elution solvent: heptane/ethyl acetate) to obtain the title compound (1.9 g, yield: 85.1%) as a light yellow solid.

$^1$H NMR(400 MHz, CDCl$_3$) δppm; 1.15(6H, d, J=7 Hz), 1.25(3H, t, J=7 Hz), 1.58(6H, d, J=7 Hz), 2.70-2.84(2H, m), 3.42-3.60(2H, m), 7.26(1H, d, J=6 Hz), 8.28(1H, d, J=6 Hz).

(92c) 4-((2,2-dimethyl-1,3-dioxan-5-yl)methoxy)-3-ethyl-N,N-diisopropylpyridine-2-carboxamide

[Formula 356]

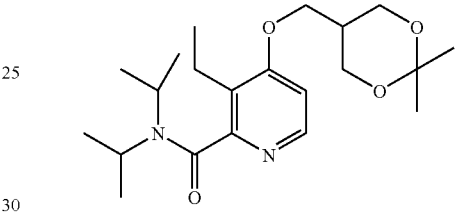

To a dimethylsulfoxide (20 ml) solution of the 4-chloro-3-ethyl-N,N-diisopropylpyridine-2-carboxamide (1 g, 3.72 mmol) obtained in the step (92b) above, oily sodium hydride, in oil (195 mg, 4.46 mmol as the content was regarded as 55%) was added at room temperature. To the mixture, the (2,2-dimethyl-1,3-dioxan-5-yl)methanol (598 mg, 4.09 mmol) obtained in Example (11a) was added and the mixture was stirred at room temperature for 16.5 hours. Ethyl acetate was added to the reaction mixture. The mixture was washed twice with a saturate saline solution. The organic layer was dried over anhydrous magnesium sulfate, filtrated, and concentrated. The residue was washed with diethyl ether to obtain the title compound (520 mg, yield: 36.9%) as a light yellow solid.

$^1$H NMR(400 MHz, CDCl$_3$) δppm; 1.10-1.22(9H, m), 1.44 (3H, s), 1.49(3H, s), 1.58(6H, d, J=7 Hz), 2.14-2.22(1H, m), 2.55-2.66(2H, m), 3.46-3.60(2H, m), 3.86-3.98(2H, m), 4.10-4.26(4H, m), 6.77(1H, d, J=6 Hz), 8.32(1H, d, J=6 Hz).

(92d) (4-((2,2-dimethyl-1,3-dioxan-5-yl)methoxy)-3-ethylpyridin-2-yl)methanol

[Formula 357]

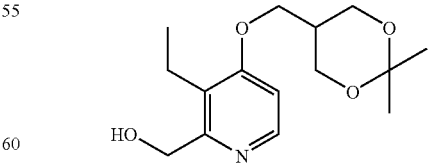

To a tetrahydrofuran (10 ml) solution of the 4-((2,2-dimethyl-1,3-dioxan-5-yl)methoxy)-3-ethyl-N,N-diisopropylpyridine-2-carboxamide (520 mg, 1.37 mmol) obtained in the step (92c) above, lithium aluminum hydride (156 mg, 4.11 mmol) was added under ice-cool and the mixture was stirred under ice-cool for one hour. To the reaction mixture, water (0.2 ml), a 2N aqueous sodium hydroxide solution (0.2 ml), and water (0.6 ml) were sequentially added. Then, mixture was filtrated through celite and the solvent was distilled off from the filtrate under reduced pressure. To a methanol (20 ml) solution of the residue, sodium borohydride (51.8 mg, 1.37 mmol) was added and the mixture was stirred at room temperature for one hour. A saturated saline solution was added to the reaction mixture. The mixture was extracted with ethyl acetate. The organic layer was dried over anhydrous magnesium sulfate, filtrated, and concentrated to obtain a crude product of the title compound (456 mg, yield: 118%) as a light yellow solid.

$^1$H NMR(400 MHz, CDCl$_3$) δppm; 1.09(3H, t, J=7 Hz), 1.43(3H, s), 1.49(3H, s), 2.14-2.22(1H, m), 2.52(2H, q, J=7 Hz), 3.90(2H, dd, J=5, 12 Hz), 4.08-4.22(4H, m), 4.71(2H, s), 6.76(1H, d, J=6 Hz), 8.31(1H, d, J=6 Hz).

(92e) 2-(((4-((2,2-dimethyl-1,3-dioxan-5-yl)methoxy)-3-ethylpyridin-2-yl)methyl)sulfinyl)-1H-benzimidazole sodium salt

[Formula 358]

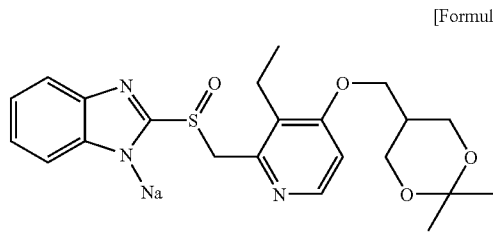

The same procedure as in the steps (6d), (6e), and (6f) of Example 6 was repeated using the (4-((2,2-dimethyl-1,3-dioxan-5-yl)methoxy)-3-ethylpyridin-2-yl)methanol obtained in the step (92d) above to obtain the title compound (159 mg, overall yield: 25%) as a light yellow solid.

$^1$H NMR(400 MHz, DMSO-d$_6$) δppm; 1.07(3H, t, J=7 Hz), 1.33(3H, s), 1.35(3H, s), 2.06-2.16(1H, m), 2.62-2.82(2H, m), 3.78(2H, dd, J=6, 12 Hz), 3.98(2H, dd, J=4, 12 Hz), 4.09(2H, d, J=10 Hz), 4.36(1H, d, J=13 Hz), 4.77(1H, d, J=13 Hz), 6.80-6.98(2H, m), 6.93(1H, d, J=6 Hz), 7.38-7.48(2H, m), 8.28(1H, d, J=6 Hz).

Example 93

2-(((4-((2,2-dimethyl-1,3-dioxan-5-yl)methoxy)-3,5-dimethylpyridin-2-yl)methyl)sulfinyl)-6,7-dihydro-1H-[1,4]dioxino[2,3-f]benzimidazole sodium salt

[Formula 359]

The same procedure as in the steps (5f) to (5h) was repeated using the (4-((2,2-dimethyl-1,3-dioxan-5-yl)methoxy)-3,5-dimethylpyridin-2-yl)methanol, which was obtained by subjecting (4-((2,2-dimethyl-1,3-dioxan-5-yl)methoxy)-3,5-dimethylpyridin-2-yl)methanol monohydrate obtained in the same manner as in Example 96(5) to azeotropic distillation with toluene, and 6,7-dihydro-1H-[1,4]dioxino[2',3':4,5]benzo[d]imidazole-2-thiol, to obtain the title compound (395 mg, total 61.7% yield) as a white solid.

$^1$H NMR(400 MHz, DMSO-d$_6$) δppm; 1.32(3H, s), 1.35(3H, s), 2.00-2.13(1H, m), 2.18(6H, s), 3.69-3.86(4H, m), 3.91-4.03(2H, m), 4.14(4H, s), 4.31(1H, d, J=12 Hz), 4.70(1H, d, J=12 Hz), 6.82(2H, s), 8.19(1H, s).

Example 94

2-(((3-methyl-4-(2-(8-methyl-1,4,7,9-tetraoxaspiro[4.5]dec-8-yl)ethoxy)pyridin-2-yl)methyl)sulfinyl)-6,7-dihydro-1H-[1,4]dioxino[2,3-f]benzimidazole sodium salt

[Formula 360]

The same procedure as in the steps (5d) to (5h) was repeated using the 2-(8-methyl-1,4,7,9-tetraoxaspiro[4.5]dec-8-yl)ethanol and 6,7-dihydro-1H-[1,4]dioxino[2',3':4,5]benzo[d]imidazole-2-thiol obtained in Example (73b) to obtain the title compound (110 mg, content: 93.5%, total 9.2% yield) as a white solid.

$^1$H NMR(400 MHz, DMSO-d$_6$) δppm; 1.39(3H, s), 2.05-2.23(5H, m), 3.56-3.72(4H, m), 3.75-3.93(4H, m), 4.02-4.22(6H, m), 4.31(1H, d, J=13 Hz), 4.75(1H, d, J=13 Hz), 6.82(2H, s), 6.88(1H, d, J=5 Hz), 8.24(1H, d, J=5 Hz).

Example 95

2-(((4-(5,7-dioxaspiro[2.5]oct-6-ylmethoxy)-3-methylpyridin-2-yl)methyl)sulfinyl)-6,7-dihydro-1H-[1,4]dioxino[2,3-f]benzimidazole sodium salt

[Formula 361]

The same procedure as in the steps (5f) to (5h) was repeated using the (4-(5,7-dioxaspiro[2.5]oct-6-ylmethoxy)-3-methylpyridin-2-yl)methanol obtained in Example (2d) and 6,7-dihydro-1H-[1,4]dioxino[2',3':4,5]benzo[d]imidazole-2-thiol to obtain the title compound (364 mg, total 55.6% yield) as a light pink solid.

$^1$H NMR(400 MHz, DMSO-d$_6$) δ ppm; 0.26-0.40(2H, m), 0.50-0.66(2H, m), 2.16(3H, s), 3.26(2H, d, J=12 Hz), 4.09 (2H, d, J=4 Hz), 4.12(2H, d, J=12 Hz), 4.15(4H, s), 4.33(1H, d, J=13 Hz), 4.76(1H, d, J=13 Hz), 5.02(1H, t, J=4 Hz), 6.83(2H, s), 6.94(1H, d, J=6 Hz), 8.26(1H, d, J=6 Hz).

Example 96

Sodium Salt of an Optical Isomer (Short in Retention Time) of 2-(((4-((2,2-dimethyl-1,3-dioxan-5-yl) methoxy)-3,5-dimethylpyridin-2-yl)methyl)sulfinyl)-1H-benzimidazole

[Formula 362]

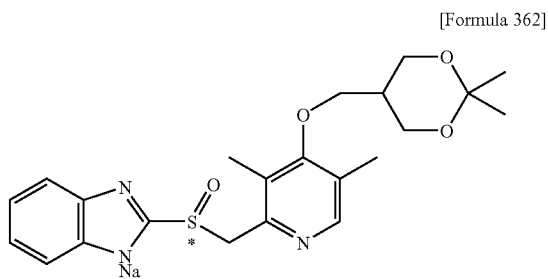

(1) Optical isomer (short in retention time) of 2-(((4-((2,2-dimethyl-1,3-dioxan-5-yl)methoxy)-3,5-dimethylpyridin-2-yl)methyl)sulfinyl)-1H-benzimidazole (429 mg, 1 mmol) was dissolved in ethanol (0.85 ml) and a 1N aqueous sodium hydroxide solution (1 ml, 1 mmol) was added thereto. After the mixture was concentrated under reduced pressure and ethanol (0.85 ml) was added thereto, the mixture was concentrated under reduced pressure. Tetrahydrofuran (0.85 ml) was added, and then, tert-butylmethyl ether (8 ml) was added to make the mixture cloudy (white turbid). After the mixture was allowed to stand at room temperature overnight, the generated precipitate was collected by filtration to obtain the title compound (191 mg, yield 42%)(lot A) as a white solid.

(2) Optical isomer (short in retention time) of 2-(((4-((2,2-dimethyl-1,3-dioxan-5-yl)methoxy)-3,5-dimethylpyridin-2-yl)methyl)sulfinyl)-1H-benzimidazole (490 mg, 1.14 mmol, enantiomeric excess: 98% ee) was dissolved in ethanol (0.98 ml) and a 1N aqueous sodium hydroxide solution (1.14 ml, 1.14 mmol) was added thereto. After the mixture was concentrated under reduced pressure and ethanol (0.98 ml) was added thereto, the mixture was concentrated under reduced pressure. This operation was repeated twice. After ethyl acetate (6 ml) was added, the title compound obtained in the step (1) (lot A) was added as a seed to the mixture. The mixture was concentrated under reduced pressure. After ethyl acetate (8 ml) was added, the title compound obtained in the step (1) (lot A) was added as a seed to the mixture, the mixture was allowed to stand at room temperature for one hour and 13 minutes. Ethyl acetate (2 ml) was further added to the mixture, the mixture was allowed to stand at room temperature overnight. The generated precipitate was collected by filtration to obtain the title compound (309 mg, yield 60%)(lot B) as white crystal.

(3) To an ethanol (8 ml) solution of an optical isomer (short in retention time) of 2-(((4-((2,2-dimethyl-1,3-dioxan-5-yl) methoxy)-3,5-dimethylpyridin-2-yl)methyl)sulfinyl)-1H-benzimidazole (4 g, 9.31 mmol), a 1N aqueous sodium hydroxide solution (9.31 mmol, 9.31 mmol) was added thereto. After the mixture was stirred under the same conditions for 2 hours, the solvent was distilled off under reduced pressure. Ethanol (8 ml) was added to the residue and distilled under reduced pressure. After this operation was repeated twice, ethyl acetate (80 ml) was added to the residue, the title compound (lot B) obtained in the step (2) was added as seed crystal and the resultant mixture was allowed to stand at room temperature overnight. After allowed to further stand still at 4° C. overnight, the precipitate generated was collected by filtration to obtain the title compound (1.1 g, yield: 25.9%) (lot C) as light yellow crystal. Part of the solvent of the filtrate thus obtained was distilled off under reduced pressure. The resultant crystal, after it was allowed to stand at room temperature for 2 hours, was collected by filtration to obtain the title compound (2.5 g, yield: 59.5%)(lot D) as light yellow crystal.

(4) To an ethanol (10 ml) solution of an optical isomer (short in retention time) of 2-(((4-((2,2-dimethyl-1,3-dioxan-5-yl) methoxy)-3,5-dimethylpyridin-2-yl)methyl)sulfinyl)-1H-benzimidazole (200 mg, 0.466 mmol, enantiomeric excess: 77.1% ee), a 1N aqueous sodium hydroxide solution (466 μl, 0.466 mmol) was added at room temperature, and thereafter, the mixture was concentrated under reduced pressure. After ethanol (10 ml) was added, the mixture was concentrated under reduced pressure. This operation was repeated twice. To the residue, ethyl acetate (40 ml) was added, and the resultant suspension was dissolved in ethanol. The mixture was concentrated under reduced pressure and dissolved in ethyl acetate (4 ml) and ethanol (2 ml). Then, the title compound (lot D) obtained in the step (3) was added as a seed and the mixture was concentrated under reduced pressure. The residue was dissolved in 2-propanol (0.4 ml) and ethyl acetate (4 ml) and then, the title compound (lot D) obtained in the step (3) was added as a seed. After allowed to stand at room temperature, the mixture was concentrated under reduced pressure. After the resultant mixture was dissolved in ethanol (0.2 ml) and ethyl acetate (3 ml), the title compound (lot D) obtained in the step (3) was added at room temperature as a seed while stirring. In about 10 minutes, a precipitate started to emerge. After further stirred for about 10 minutes, the precipitate generated was collected by filtration to obtain the title compound (44 mg, yield 21%)(lot E) as white crystal.

(5) Optical isomer (short in retention time) of 2-(((4-((2,2-dimethyl-1,3-dioxan-5-yl)methoxy)-3,5-dimethylpyridin-2-yl)methyl)sulfinyl)-1H-benzimidazole (340 mg, 0.792 mmol, enantiomeric excess, 47% ee) was dissolved in ethanol (4.5 ml) at room temperature and a 1N aqueous sodium hydroxide solution (792 μL, 0.792 mmol) was added dropwise thereto. The mixture was concentrated at 40° C. under reduced pressure. After ethanol (0.9 ml) was added, the mixture was concentrated under reduced pressure. This operation was repeated twice to azeotropically remove water. After ethyl acetate was added to the mixture, the mixture was stirred at room temperature, collected by filtration, and washed with ethyl acetate (4.5 ml) to obtain the title compound (lot F) (230 mg, yield 64.3%) as a light yellow solid. The filtrate was subjected to the same operation to obtain the title compound (lot G)(47 mg, yield: 13.1%) as a light yellow solid.

HPLC (Conditions) column: CHIRALPAK AD-H (manufactured by Daicel Chemical Industries, Ltd.)(0.46 cmφ×25 cm)

eluant: hexane/ethanol=1/1 (v/v), flow rate: 0.6 ml/min, detection: UV 254 nm).

(Analysis Results)

Lot B: the retention time: 16.7 minutes, enantiomeric excess: 100% ee;

Lot C: the retention time: 17.2 minutes, enantiomeric excess: 100% ee;
Lot D: the retention time: 16.8 minutes, enantiomeric excess: 100% ee;
Lot E: the retention time: 18.0 minutes, enantiomeric excess: 100% ee;
Lot F: the retention time: 17.1 minutes, enantiomeric excess: 39% ee;
Lot G: the retention time: 17.1 minutes, enantiomeric excess: 62% ee.

Example 97

Sodium Salt of an Optical Isomer (Short in Retention Time) of 2-(((4-((2,2-dimethyl-1,3-dioxan-5-yl) methoxy)-3,5-dimethylpyridin-2-yl)methyl)sulfinyl)-1H-benzimidazole (1) 2,3,5-trimethylpyridine1-oxide

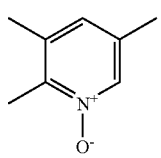

[Formula 363]

To acetic acid (1.43 kg, 23.83 mol), 2,3,5-trimethylpyridine (1.43 kg, 11.80 mol) was added over 15 minutes. After 15 minutes, a 35% hydrogen peroxide solution (1.38 kg, 14.2 mol) was added dropwise over 30 minutes, the mixture was stirred at 90° C. to 95° C. overnight. To the reaction mixture, sodium sulfite (220 g) was added. The reaction mixture was poured into a mixture of sodium carbonate (2.5 kg) and water (12 L) and the mixture was extracted with chloroform (3.0 L×4). The organic layer obtained was concentrated until crystal precipitated. To the precipitate, n-hexane (2.5 L) was added. The resultant mixture was stirred under ice-cool overnight The resultant solid was filtrated to obtain a desired compound (1.53 kg).

(2) 2,3,5-trimethyl-4-nitropyridine1-oxide

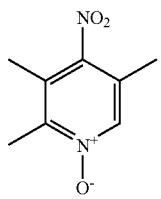

[Formula 364]

To 98% sulfuric acid (4.93 kg, 49.3 mol), 2,3,5-trimethylpyridine1-oxide (1.38 kg, 10.1 mol) was added. After 97% nitric acid (1.44 kg) was added dropwise thereto over 50 minutes, the mixture was heated at 85° C. for 4 hours. The reaction mixture was poured to a mixture of ammonium hydrogen carbonate (10.6 kg) and water (9.0 L). The mixture was extracted with ethyl acetate (3.0 L×3). The obtained organic layer was concentrated and dried under vacuum overnight to obtain a desired product (1.50 kg).

(3) 4-chloro-2,3,5-trimethylpyridine1-oxide

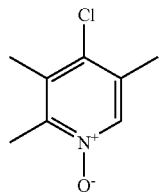

[Formula 365]

To 2,3,5-trimethyl-4-nitropyridine1-oxide (850 g, 4.67 mol), water (400 g) and 36% concentrated hydrochloric acid (1.69 kg) was added and the mixture was heated to 70° C. To the mixture, N,N-dimethylformamide (115 mL) was added and then the resultant mixture was heated to 100° C. After completion of the reaction, the reaction mixture was cooled to 20° C. and poured into a mixture of potassium carbonate (1.40 kg) and water (7 L). The mixture was extracted with chloroform (1.0 L×3), the organic layer dried over sodium sulfate and concentrated. The obtained crude product was stirred for 2 hours in a mixture of diisopropyl ether (500 mL) and n-hexane (1.0 L), and thereafter, sucking filtration was performed. The obtained wet product was dried under vacuum overnight to obtain a desired product (666.4 g).

(4) 4-(2,2-dimethyl-1,3-dioxan-5-ylmethoxy)-2,3,5-trimethylpyridine 1-oxide

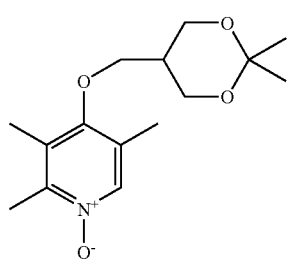

[Formula 366]

A mixture of 4-chloro-2,3,5-trimethylpyridine 1-oxide (840 g), (2,2-dimethyl-1,3-dioxan-5-yl)methanol (688 g) and toluene (2.52 L) was heated under reflux while removing a water content. While azeotropical dehydration was continued, potassium hydroxide (0.58 kg) was added to the reaction mixture over 3 hours and 45 minutes, and azeotropic dehydration was continued for 2.5 hours. The mixture was cooled to 30° C. or less, and ethyl acetate (2.5 L) and a 17% saline solution (3.5 L) were added to the mixture and then the mixture was allowed to stand for overnight. The ethyl acetate layer was separated and the aqueous layer was extracted with ethyl acetate (1.0 L×3). The ethyl acetate layers were combined, filtrated through celite, and concentrated under reduced pressure to obtain a desired product (1.20 kg).

(5) (4-(2,2-dimethyl-1,3-dioxan-5-yl)methoxy-3,5-dimethylpyridin-2-yl)methanol monohydrate

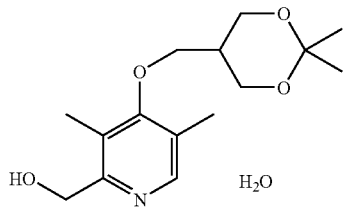

[Formula 367]

To a mixture of 4-(2,2-dimethyl-1,3-dioxan-5-yl)methoxy-2,3,5-trimethylpyridine N-oxide (1.20 kg) and sodium acetate (0.18 kg) heated at 50° C. to 60° C., acetic anhydride (1.10 kg) was added dropwise over 1.5 hours. After 0.5 hours, the mixture was heated at 80° C. for 4.5 hours and cooled to an inner temperature below 30° C. or less, allowed to stand, and concentrated under reduced pressure. The obtained residue was dissolved in methanol (1.0 L) and the solution was added to a mixture of a 48% aqueous sodium hydroxide solution (0.71 kg) and cold water (2.85 L) for one hour. After stirred at room temperature for 5 hours and 45 minutes, the mixture was concentrated under reduced pressure. To the residue thus concentrated, water (3.0 L) was added and the mixture was extracted with toluene (2.3 L×4). The toluene layers were combined and washed with water (1.2 L). The obtained organic layer was filtrated through celite and concentrated. To the residue obtained, diisopropyl ether (1.15 L) was added at a room temperature and further warm water (45° C., 74 mL) was added. After crystal precipitation was confirmed, the mixture was stirred at 25° C. for one hour. After heptane (3.6 L) was poured, the mixture was stirred overnight. The mixture was further stirred under ice-cool for 5 hours and then filtrated to obtain yellow crystal. To the yellow crystal obtained, diisopropylether (3.5 L) was added and the mixture was dissolved at 50° C. After insoluble substance was removed by filtration, the mixture was gradually cooled and allowed to stand at 5° C. overnight. The obtained crystal was filtrated and washed with heptane (0.5 L) and dried by air to obtain a desired product (0.69 kg).

(6) 2-(((4-(2,2-dimethyl-1,3-dioxan-5-yl)methoxy-3,5-dimethylpyridin-2-yl)methyl)thio)-1H-benzimidazole

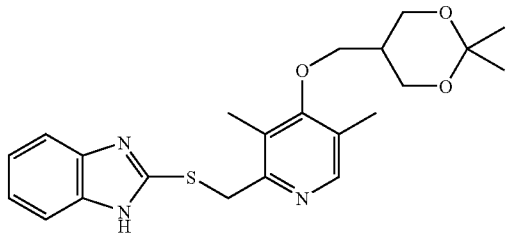

[Formula 368]

To (4-(2,2-dimethyl-1,3-dioxan-5-yl)methoxy-3,5-dimethylpyridin-2-yl)methanol monohydrate (690 g), toluene was added to perform azeotropic dehydration (2.1 L×5, 1.75 L×1). To the concentrated product obtained, toluene (393 mL) was added to obtain a toluene solution (921 g) of (4-(2,2-dimethyl-1,3-dioxan-5-yl)methoxy-3,5-dimethylpyridin-2-yl)methanol.

To the toluene solution of (4-(2,2-dimethyl-1,3-dioxan-5-yl)methoxy-3,5-dimethylpyridin-2-yl)methanol (845.7 g, content: 61.7%, amount: 521.8 g, 1.855 mol), tetrahydrofuran (2609 mL), toluene (669 mL) and triethylamine (375.3 g, 3.709 mol) were sequentially added in a nitrogen atmosphere. The mixture was stirred while cooling with dry ice/ethanol. From 30 minutes after initiation of cooling, methanesulfonyl chloride (254.9 g, 2.226 mol) was added dropwise for 42 minutes. After completion of dropwise addition, the mixture was stirred under cooling by an ice bath. After about 1.5 hours, a tetrahydrofuran (3653 mL) solution of 2-mercaptobenzimidazole (334.28 g, 2.226 mol) was poured to the mixture for 2 minutes and the mixture was stirred at room temperature for about 18 hours. To the reaction mixture, toluene (3653 mL) was poured and a 20% w/w aqueous sodium hydroxide solution (1852.4 g) and further $H_2O$ (2322 mL) were added. In this way, extraction and separation were performed. The organic layer was washed twice with a 20% w/w aqueous ammonium chloride solution (4174 g) and further washed with $H_2O$ (4174 ml).

The obtained organic layer was concentrated under reduced pressure (40° C.) to obtain brown oil substance (2.40 kg, containing toluene 1446 mL, tetrahydrofuran 168 mL, calculated from 1H—NMR spectrum).

The brown oil thus obtained was transferred to a crystallization container, washed down with toluene (119 mL), and the mixture was stirred at room temperature. After 10 minutes, tert-butyl methyl ether (134 mL) was poured and the mixture was continuously stirred at room temperature. After 20 minutes, further tert-butyl methyl ether (127 mL) was added and the mixture was continuously stirred at room temperature. After 30 minutes, further tert-butyl methyl ether (266 mL) was added dropwise for 20 minutes, and the mixture was continuously stirred at room temperature. After one minute, further dropwise addition of tert-butyl methyl ether (522 mL) was started. After 8 minutes, crystal precipitation was confirmed. The dropwise addition was terminated in one hour and 20 minutes. After the resultant mixture was stirred at room temperature for 40 minutes, heptane (2348 mL) was added dropwise for one hour and 17 minutes and the mixture was stirred at room temperature overnight.

About 15.5 hours after dropwise addition of heptane, the crystal precipitated was subjected to suction filtration, rinsed with toluene/tert-butyl methyl ether/heptane (587 mL/391 mL/587 mL) and dried with vacuum. The wet crystal thus obtained was air-dried (50° C.) to obtain a desired product.

Yield: 619.0 g, content: 96.5%, amount: 597.3 g, yield: 77.8% (amount base), HPLC purity: 98.0%

<HPLC Analysis Conditions (Reaction Check, HPLC Purity Measurement and Quantification)>

Column: YMC-Pack Pro C18 AS-302 (5 μm, 150 mm×4.6 mm I.D.)

Eluent: A solution (MeCN/20 mM AcONH4 aq.=100/900 (v/v)), B solution (MeCN/20 mM AcONH4 aq.=800/200 (v/v))

Flow rate: 1.0 mL/min

Detection: UV 254 nm

Oven temp.: 25° C.

Sample temp.: 25° C.

Gradient condition (time/B solution conc.): 0.01 min/0%→25 min/100%→30 min/100%→30.01 min/0%→40 min/stop RT=18.4 min (7) Crude Sodium Salt of an Optical Isomer (Short in Retention Time) of 2-(((4-(2,2-dimethyl-1,3-dioxan-5-yl)methoxy-3,5-dimethylpyridin-2-yl)methyl)sulfinyl)-1H-benzimidazole

[Formula 369]

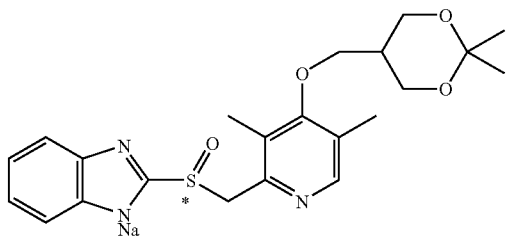

The water content of 2-(((4-(2,2-dimethyl-1,3-dioxan-5-yl) methoxy-3,5-dimethylpyridin-2-yl)methyl)thio)-1H-benzimidazole, toluene, diethyl L-(+)-tartrate, and N,N-diisopropylethylamine used in the reaction was measured by the Karl Fischer technique (total amount: 0.885 g).

2-(((4-(2,2-dimethyl-1,3-dioxan-5-yl)methoxy-3,5-dimethylpyridin-2-yl)methyl)thio)-1H-benzimidazole (580.3 g, content: 96.5%, amount: 560.0 g, 1.354 mol), toluene (3864 mL), and H₂O (2.81 g, 0.156 mol) were sequentially added in a nitrogen atmosphere and the mixture was stirred while heating at 60° C. After 6 minutes, diethyl L-(+)-tartrate (122.9 g, 0.596 mol) was added with toluene (560 mL) to the resultant suspension, and the bottle of the reagent was washed down. After 30 minutes, dissolution was confirmed. After 8 minutes, titanium (IV) tetraisopropoxide (77.0 g, 0.271 mol) was added and the bottle of the reagent was washed down with toluene (56 mL). The resultant mixture was stirred while heating at the same temperature for about one hour. The mixture was cooled to 8° C. and N,N-diisopropylethylamine with toluene (280 mL) was added (56.01 g, 0.742 mol), and then, the bottle of the reagent was washed down. After 10 minutes, a toluene solution (840 mL) of cumene hydroperoxide (259.2 g, 1.422 mol) was added dropwise for 47 minutes and the mixture was stirred at 8° C. for about 18.5 hours. A 30% w/w aqueous sodium thiosulfate solution (2240 g) cooled was poured and the mixture was stirred for 12 minutes, and then the aqueous layer was discarded. To the organic layer, a 4% w/w aqueous sodium hydroxide solution (2240 g) was poured and the mixture was stirred, and allowed to stand. The aqueous layer was separated to obtain an aqueous solution of an optical isomer (short in retention time) of 2-(((4-(2,2-dimethyl-1,3-dioxan-5-yl)methoxy-3,5-dimethylpyridin-2-yl)methyl)sulfinyl)-1H-benzimidazole extracted with the aqueous sodium hydroxide solution as a brown-yellow suspension. To toluene (7840 mL), the solution (2.98 kg) of an optical isomer (short in retention time) of 2-(((4-(2,2-dimethyl-1,3-dioxan-5-yl)methoxy-3,5-dimethylpyridin-2-yl)methyl)sulfinyl)-1H-benzimidazole extracted with the aqueous sodium hydroxide solution was poured and the mixture was stirred. To the mixture, a 20% w/w aqueous acetic acid solution (400 mL), a 8% aqueous NaOH solution (50 mL), and a 20% w/w aqueous acetic acid solution (8 mL) were sequentially added while stirring and pH was adjusted to 8.64. The mixture was allowed to stand and separated, and the aqueous layer was discarded. The organic layer was washed with a 5% w/w aqueous saline solution (2240 g), separated to obtain a toluene extraction solution of an optical isomer (short in retention time) of 2-(((4-(2,2-dimethyl-1,3-dioxan-5-yl) methoxy-3,3-dimethylpyridin-2-yl)methyl)sulfinyl)-1H-benzimidazole (7.31 kg) (the content thereof: 567.7 g, 1.322 mol) as a brown-yellow solution.

To the toluene extraction solution obtained, a 28.3% methanol solution of sodium methoxide (245.6 g, 1.286 mol) was added for one minute while stirring at room temperature. Subsequently, to this solution, tert-butyl methyl ether (1120 mL) was added dropwise for 3 minutes, and the mixture was stirred at room temperature. After 6 minutes, it was confirmed that crystal was precipitated. The mixture was continuously stirred for about 30 minutes. Furthermore, tert-butyl methyl ether (7840 mL) was added dropwise over 2 hours and 40 minutes and continuously stirred at room temepautre overnight.

About 13 hours after tert-butylmethyl ether was added dropwise, the crystal precipitated was subjected to suction filtration, rinsed with toluene/tert-butyl methyl ether (1047 mL/1193 mL) and dried with vacuum for 15 minutes. The wet crystal thus obtained was dried under reduced pressure (40° C.) to obtain a desired product.

Yield: 546.8 g, content: 101.7%, amount: 546.8 g (as the content was regarded as 100%), yield: 90.9% (amount base), HPLC purity: 98.2%, enantiomeric excess: 100% ee <HPLC Analysis Conditions (Reaction Check, HPLC Purity Measurement and Quantification)>

Column: YMC-Pack Pro C18 AS-302 (5 μm, 150 mm×4.6 mm I.D.)
Eluent: A solution (MeCN/20 mM AcONH4 aq.=100/900 (v/v)), B solution (MeCN/20 mM AcONH4 aq.=800/200 (v/v))
Flow rate: 1.0 mL/min
Detection: UV 254 nm
Oven temp.: 25° C.
Sample temp.: 25° C.
Gradient condition (time/B solution conc.): 0.01 min/0%→25 min/100%→30 min/100%→30.01 min/0%→40 min/stop
RT=14.1 min <HPLC Analysis Conditions (Enantiomeric Excess)>
Column: DAICEL CHIRALPAK IA (250 mm×4.6 mm I.D.)
Eluent: EtOH/MTBE=150/850 (v/v)
Flow rate: 1.0 mL/min
Detection: UV 284 nm
Oven temp.: 25° C.
Sample temp.: 25° C.

(8) Purified Sodium Salt of an Optical Isomer (Short in Retention Time) of 2-(((4-(2,2-dimethyl-1,3-dioxan-5-yl)methoxy-3,5-dimethylpyridin-2-yl)methyl)sulfinyl)-1H-benzimidazole

[Formula 370]

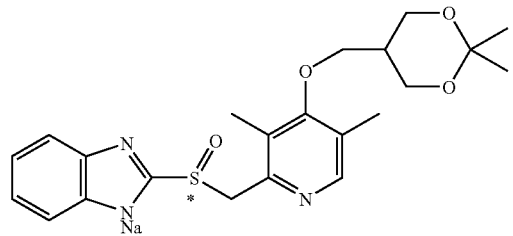

To a crude optical isomer (short in retention time) of sodium 2-(((4-(2,2-dimethyl-1,3-dioxan-5-yl)methoxy-3,5-dimethylpyridin-2-yl)methyl)sulfinyl)-1H-benzimidazole (536.8 g, 1.189 mol), ethanol (1074 mL) was added. The crude isomer was dissolved in ethanol at room temperature. To the solution, further tert-butyl methyl ether (1074 mL) was poured. The solution thus obtained was subjected to suction filtration through Hyflo Super-Cel bed (107.4 g, washed sequentially with ethanol/tert-butyl methyl ether (1074 mL/1074 mL) and tert-butyl methyl ether (537 mL)), and rinsed with ethanol/tert-butyl methyl ether (215 mL/215 mL).

The filtrate obtained was transferred to a crystallization container and washed down with ethanol/tert-butyl methyl ether (54 mL/54 mL) for full transfer and started stirring at room temperature. Then, tert-butyl methyl ether (1610 mL) was added dropwise for 6 minutes and the mixture was continuously stirred at room temperature. After 11 minutes, tert-butyl methyl ether (268 mL) was added dropwise for 2 minutes and the mixture was continuously stirred. After one minute, crystal precipitation was confirmed. The mixture was continuously stirred for 31 minutes and tert-butyl methyl ether (268 mL) was added dropwise for 9 minutes. After the mixture was stirred at room temperature for 8 minutes, further tert-butyl methyl ether (8589 mL) was added dropwise for one hour and 10 minutes and the mixture was continuously stirred at room temperature.

About 22 hours after dropwise addition of tert-butyl methyl ether was completed, the precipitated crystal was subjected suction filtration while spraying nitrogen, washed sequentially with ethanol/tert-butylmethyl ether (107 mL/966 mL), and tert-butyl methyl ether (1074 mL), and dried with vacuum for 8 minutes. Of the wet crystal obtained (584.54 g), the wet crystal (531.10 g) was dried under reduced pressure (50° C.) to obtain a desired product.

Yield: 419.6 g, HPLC purity:99.4%

<HPLC analysis conditions (HPLC purity measurement and quantification)>

Column: YMC-Pack Pro C18 AS-302 (5 μm, 150 mm×4.6 mm I.D.)

Eluent: A solution (MeCN/20 mM AcONH4 aq.=100/900 (v/v)), B solution (MeCN/20 mM AcONH4 aq.=800/200 (v/v))

Flow rate: 1.0 mL/min

Detection: UV 254 nm

Oven temp.: 25° C.

Sample temp.: 25° C.

Gradient condition (time/B solution conc.): 0.01 min/0%→25 min./100%→30 min/100%→30.01 min/0%→40 min/stop RT=14.1 min Production Example 1

2-(((4-((2,2-dimethyl-1,3-dioxan-5-yl)methoxy)-3,5-dimethylpyridin-2-yl)methyl)thio)-1H-benzimidazole

[Formula 371]

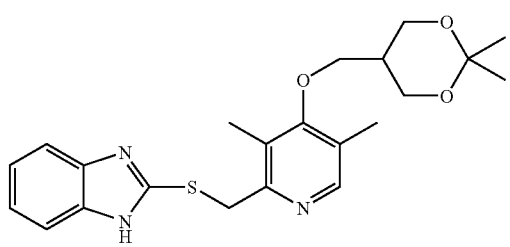

(1a) (4-((2,2-dimethyl-1,3-dioxan-5-yl)methoxy)-3,5-dimethylpyridin-2-yl)methyl methanesulfonate

[Formula 372]

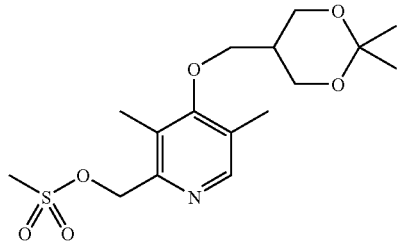

(4-((2,2-dimethyl-1,3-dioxan-5-yl)methoxy)-3,5-dimethylpyridin-2-yl)methanol (2.5 g, 8.35 mmol as the water content was regarded as 7.28%) was dissolved in toluene and the mixture was subjected twice to azeotropic dehydration. The residue was dissolved in tetrahydrofuran (30 ml). To the solution, triethylamine (2.33 ml, 16.7=mol) was added and the mixture was stirred in nitrogen atmosphere under ice-cool. Further, methanesulfonyl chloride (0.766 ml, 10 mmol) was added dropwise at an inner temperature below 11.5° C. for 2 minutes. The reaction mixture was stirred for 13 minutes under the same conditions, diluted with ethyl acetate and washed with a saturated aqueous sodium hydrogencarbonate solution and a saturated saline solution. The organic layer was dried over magnesium sulfate and filtrated through silica gel and the filtrate was concentrated under reduced pressure to obtain the title compound (2.8 g, 93.3%) as a light orange solid.

$^1$H NMR(400 MHz, DMSO-d$_6$) δppm; 1.33(3H, s), 1.37 (3H, s), 2.07-2.15(1H, m), 2.23(3H, s), 2.26(3H, s), 3.22(3H, s), 3.81(2H, dd, J=6, 12 Hz), 3.89(2H, d, J=7 Hz), 4.02(2H, dd, J=4, 12 Hz), 5.29(2H, s), 8.24(1H, s).

(1b) 2-(((4-((2,2-dimethyl-1,3-dioxan-5-yl)methoxy)-3,5-dimethylpyridin-2-yl)methyl)thio)-1H-benzimidazole

[Formula 373]

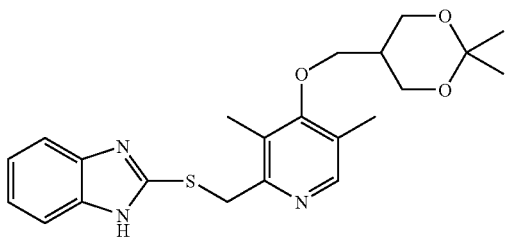

To a mixture of (4-((2,2-dimethyl-1,3-dioxan-5-yl)methoxy)-3,5-dimethylpyridin-2-yl)methyl methanesulfonate (500 mg, 1.39=mmol), 2-mercaptobenzimidazole (209 mg, 1.39 mmol) and tetrahydrofuran (5 ml), triethylamine (0.387 ml, 2.78 mmol) was added and the mixture was stirred at room temperature for 14 hours and 25 minutes. The reaction mixture was concentrated under reduced pressure, and toluene and a 0.1N aqueous sodium hydroxide solution were added to the residue and insoluble substance was removed by filtration. The organic layer was taken out and the aqueous layer was extracted again with toluene. The organic layers were combined, washed with a saturated saline solution, dried over sodium sulfate, and filtrated. The filtrate was concentrated under reduced pressure. The residue was dissolved in n-heptane/ethyl acetate (1/1) and subjected to silica gel column chromatography (elution solvent: n-heptane/ethyl acetate=1/1→0/1) to obtain the title compound (549 mg, 95.5%) as a colorless viscous oil.

$^1$H NMR(400 MHz, DMSO-d$_6$) δppm; 1.33(3H, s), 1.36 (3H, s), 2.05-2.16(1H, m), 2.20(3H, s), 2.28(3H, s), 3.80(2H, dd, J=6, 12 Hz), 3.86(2H, d, J=7 Hz), 4.01(2H, dd, J=4, 12 Hz), 4.68(2H, s), 7.08-7.14(2H, m), 7.38-7.50(2H, m), 8.17 (1H, s).

Production Example 2

2-(((4-((2,2-dimethyl-1,3-dioxan-5-yl)methoxy)-3,5-dimethylpyridin-2-yl)methyl)thio)-1H-benzimidazole

[Formula 374]

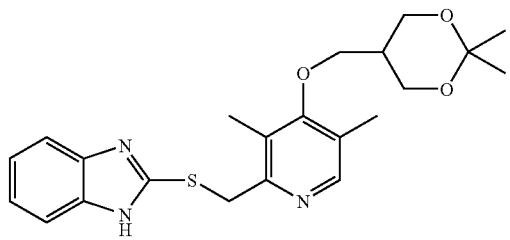

(2a) (4-((2,2-dimethyl-1,3-dioxan-5-yl)methoxy)-3,5-dimethylpyridin-2-yl)methyl 4-methylbenzenesulfonate

[Formula 375]

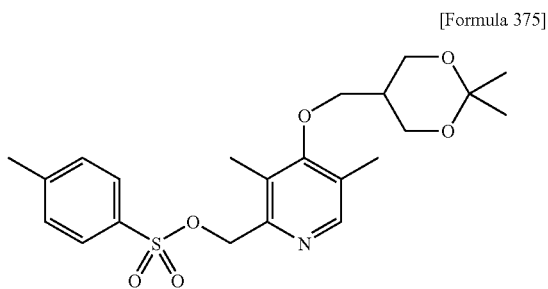

To a tetrahydrofuran (30 ml) solution of (4-((2,2-dimethyl-1,3-dioxan-5-yl)methoxy)-3,5-dimethylpyridin-2-yl)methanol (738 mg, 2.61 mmol), powdered sodium hydroxide (313 mg, 7.84 mmol) was added and the mixture was stirred at room temperature for 35 minutes. The mixture was further stirred for 10 minutes under ice-cool and p-toluenesulfonyl chloride (1.09 g, 5.74 mmol) was added little by little for one minute. The reaction mixture was stirred at room temperature for 17 hours and 40 minutes and diluted with tetrahydrofuran, and then insoluble substance was removed by filtration. To the filtrate, silica gel was added, and the mixture was concentrated, and subjected to silica gel column chromatography (elution solvent: n-heptane/ethyl acetate=1/1) to obtain the title compound (1.00 g, 88%) as a white solid.

$^1$H NMR(400 MHz, DMSO-d$_6$) δppm; 1.33(3H, s), 1.37 (3H, s), 2.03-2.11(1H, m), 2.07(3H, s), 2.18(3H, s), 2.41(3H, s), 3.76-3.81(4H, m), 4.00(2H, dd, J=4, 12 Hz), 5.13(2H, s), 7.42(2H, d, J=8 Hz), 7.73(2H, d, J=8 Hz), 8.14(1H, s).

(2b) 2-(((4-((2,2-dimethyl-1,3-dioxan-5-yl)methoxy)-3,5-dimethylpyridin-2-yl)methyl)thio)-1H-benzimidazole

[Formula 376]

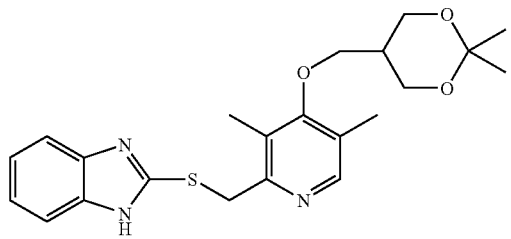

To a mixture of (4-((2,2-dimethyl-1,3-dioxan-5-yl)methoxy)-3,5-dimethylpyridin-2-yl)methyl 4-methylbenzenesulfonate (457 mg, 1.05 mmol), 2-mercaptobenzimidazole (158 mg, 1.05 mmol), and tetrahydrofuran (5 ml), triethylamine (0.293 ml, 2.1 mmol) was added and the mixture was stirred at room temperature for 15 hours and 30 minutes. To the reaction mixture, toluene and a diluted aqueous sodium hydroxide solution were added and the organic layer was taken out. The aqueous layer was extracted again with toluene. The organic layers were combined and washed with a saturated saline solution, dried over sodium sulfate, and filtrated. The filtrate was concentrated under reduced pressure. The residue was dissolved in n-heptane/ethyl acetate (1/1) and subjected to silica gel column chromatography (elution solvent: n-heptane/ethyl acetate=1/1→0/1) to obtain the title compound (419 mg, 96.5%) as a colorless viscous oil.

$^1$H NMR(400 MHz, DMSO-d$_6$) δppm; 1.33(3H, s), 1.36 (3H, s), 2.05-2.16(1H, m), 2.20(3H, s), 2.28(3H, s), 3.80(2H, dd, J=6, 12 Hz), 3.86(2H, d, J=7 Hz), 4.01(2H, dd, J=4, 12 Hz), 4.68(2H, s), 7.08-7.14(2H, m), 7.38-7.50(2H, m), 8.17 (1H, s)

Production Example 3

2-(((4-((2,2-dimethyl-1,3-dioxan-5-yl)methoxy)-3,5-dimethylpyridin-2-yl)methyl)thio)-1H-benzimidazole

[Formula 377]

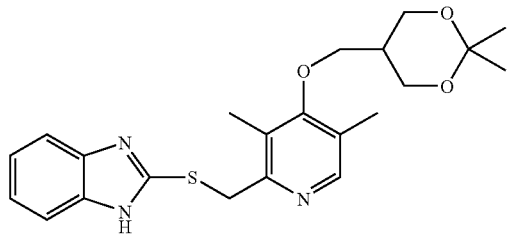

(3a) 2-(chloromethyl)-(4-((2,2-dimethyl-1,3-dioxan-5-yl)methoxy)-3,5-dimethylpyridine

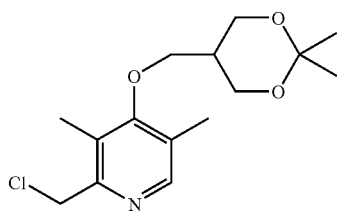

[Formula 378]

To a toluene (16 ml) solution of (4-((2,2-dimethyl-1,3-dioxan-5-yl)methoxy)-3,5-dimethylpyridin-2-yl)methanol (800 mg, 2.85 mmol), triethylamine (0.397 ml, 2.85 mmol) was added and the mixture was stirred in a nitrogen atmosphere under ice-cool. Thionyl chloride (0.208 ml, 2.85 mmol) was added dropwise for 2 minutes at an inner temperature below 7.7° C. and the mixture was stirred at room temperature for 20 minutes. The reaction mixture was diluted with ethyl acetate under ice-cool and washed with a saturated aqueous sodium hydrogencarbonate solution and a saline solution. The organic layer was dried over sodium sulfate, and filtrated with silica gel. The filtrate was concentrated under reduced pressure to obtain the title compound (0.837 g, 98%) as a light brown oil substance.

$^1$H NMR(400 MHz, DMSO-$d_6$) δppm; 1.33(3H, s), 1.37 (3H, s), 2.05-2.16(1H, m), 2.21(3H, s), 2.28(3H, s), 3.81(2H, dd, J=6, 12 Hz), 3.88(2H, d, J=7 Hz), 4.01(2H, dd, J=4, 12 Hz), 4.76(2H, s), 8.19(1H, s).

(3b) 2-(((4-((2,2-dimethyl-1,3-dioxan-5-yl)methoxy)-3,5-dimethylpyridin-2-yl)methyl)thio)-1H-benzimidazole

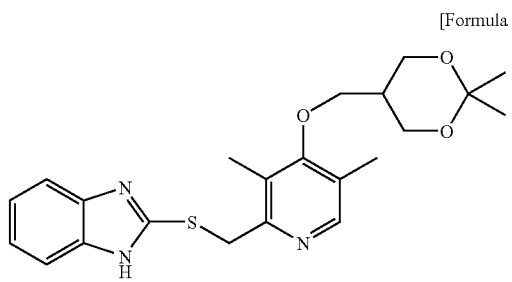

[Formula 379]

To a mixture of 2-(chloromethyl)-(4-((2,2-dimethyl-1,3-dioxan-5-yl)methoxy)-3,5-dimethylpyridine (837 mg, 2.79 mmol), 2-mercaptobenzimidazole (419 mg, 2.79 mmol) and sodium hydroxide (223 mg, 5.58 mmol), methanol (20 ml) was added and the mixture was stirred at room temperature for 12 hours and 55 minutes. The reaction mixture was concentrated under reduced pressure. Toluene and a 0.1N aqueous sodium hydroxide solution were added to the residue and insoluble substance was removed by filtration, and then, the organic layer was taken out. The aqueous layer was extracted again with toluene. The organic layers were combined and washed with a saturated saline solution, dried over sodium sulfate, and filtrated. The filtrate was concentrated under reduced pressure. The residue was dissolved in n-heptane/ethyl acetate (1/1) and subjected to silica gel column chromatography (elution solvent: n-heptane/ethyl acetate=1/1→0/1) to obtain the title compound (980 mg, 84.9%) as a white foam.

$^1$H NMR(400 MHz, DMSO-$d_6$) δppm; 1.33(3H, s), 1.36 (3H, s), 2.05-2.16(1H, m), 2.20(3H, s), 2.28(3H, s), 3.81(2H, dd, J=6, 12 Hz), 3.86(2H, d, J=7 Hz), 4.01(2H, dd, J=4, 12 Hz), 4.68(2H, s), 7.08-7.14(2H, m), 7.38-7.50(2H, m), 8.17 (1H, s).

Production Example 4

2-(((4-((2,2-dimethyl-1,3-dioxan-5-yl)methoxy)-3,5-dimethylpyridin-2-yl)methyl)thio)-1H-benzimidazole

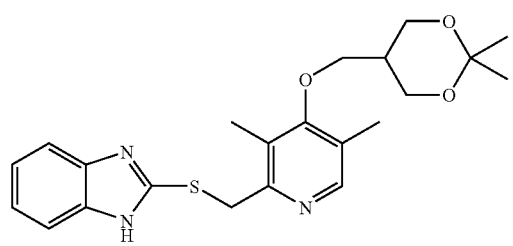

[Formula 380]

(4a) (4-((2,2-dimethyl-1,3-dioxan-5-yl)methoxy)-3,5-dimethylpyridin-2-yl)methyl acetate

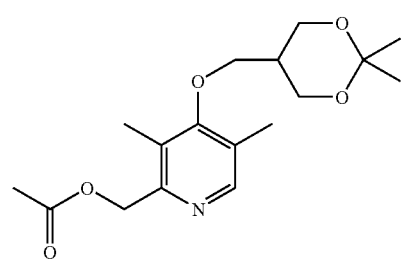

[Formula 381]

4-((2,2-dimethyl-1,3-dioxan-5-yl)methoxy)-2,3,5-trimethylpyridine1-oxide (10.5 g, 37.4 mmol) was dissolved in acetic anhydride (100 mL) and the solution was stirred at 85° C. for 1.5 hours. After the reaction mixture was concentrated, the residue was purified by silica gel column chromatography (elution solvent: n-heptane/ethyl acetate=1/1→0/1) and a desired fraction was concentrated to obtain the title compound (6.1 g, 50.4%) as a light yellow solid.

$^1$H NMR(400 MHz, DMSO-$d_6$) δppm; 1.31(3H, s), 1.35 (3H, s), 2.04(3H, s), 2.05-2.13(1H, m), 2.17(3H, s), 2.19(3H, s), 3.79(2H, dd, J=6, 12 Hz), 3.85(2H, d, J=7 Hz), 4.00(2H, dd, J=4, 12 Hz), 5.09(2H, s), 8.17(1H, s).

(4b) 2-(((4-((2,2-dimethyl-1,3-dioxan-5-yl)methoxy)-3,5-dimethylpyridin-2-yl)methyl)thio)-1H-benzimidazole

[Formula 382]

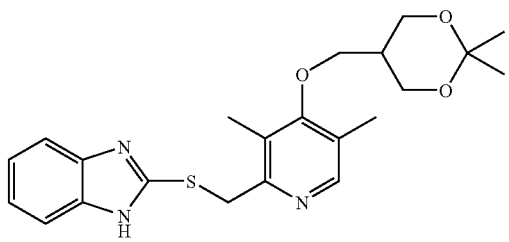

To a dimethylsulfoxide (10 ml) solution of potassium t-butoxide (262 mg, 2.33 mmol) and 2-mercaptobenzimidazole (349 mg, 2.33 mmol), (4-((2,2-dimethyl-1,3-dioxan-5-yl)methoxy)-3,5-dimethylpyridin-2-yl)methyl acetate (500 mg, 1.55 mmol) was added and the mixture was stirred in a nitrogen atmosphere at 150° C. for 3 hours and 10 minutes. After cooled to room temperature, the reaction mixture was diluted with toluene and washed with a diluted aqueous sodium hydroxide solution and a saturated saline solution, dried over sodium sulfate, and filtrated. The filtrate was concentrated under reduced pressure. The residue was subjected twice to silica gel column chromatography (elution solvent: n-heptane/ethyl acetate=1/1) to obtain the title compound (441 mg, 68.8%) as a white foam.

$^1$H NMR(400 MHz, DMSO-$d_6$) δppm; 1.33(3H, s), 1.36 (3H, s), 2.05-2.16(1H, m), 2.20(3H, s), 2.28(3H, s), 3.80(2H, dd, J=6, 12 Hz), 3.86(2H, d, J=7 Hz), 4.01(2H, dd, J=4, 12 Hz), 4.68(2H, s), 7.08-7.14(2H, m), 7.38-7.50(2H, m), 8.17 (1H, s).

Experimental Example 1

Inhibitory Effect of Gastric Acid Secretion in a Dog Having a Chronic Gastric Fistula (1) Method Compounds according to the Examples were investigated for an inhibitory effect against gastric acid secretion and persistency of the effect against gastric acid secretion by use of large dogs (body weight: about 14 to 19 kg) having a chronic gastric fistula. An experiment was performed for 2 days. On the first day, histamine (50 or 75 μg/kg/h) was intravenously administered continuously for 3 hours. During the histamine administration, the gastric juice was collected every 20 minutes. One hour after initiation of histamine administration, a test compound (which is a compound prepared in Examples) suspended or dissolved in a 0.5% methylcellulose solution was administered at a volume of 0.1 ml/kg though an indwelling catheter in the duodenum. The inhibitory effect of the test compound against gastric acid secretion was checked during the 2 hours after administration. On the second day (that is, 24 hours after the administration of the test compound), histamine was intravenously administered continuously for 2 hours. During the histamine administration, the gastric juice was collected every 20 minutes and checked for persistency of the inhibitory effect against gastric acid secretion. After the amount of the gastric juice was measured, a sample of 0.5 ml of the gastric juice was titrated to pH 7.0 with a 0.04 mol/l sodium hydroxide solution. In this manner, the acid concentration of the gastric juice was measured. The gastric acid output (secretion amount) was calculated by multiplying the volume of gastric juice by acid concentration. The inhibitory effect against gastric acid secretion was evaluated based on the inhibitory rate (%) of gastric acid secretion on the first day. The inhibitory effect (%) against gastric acid secretion was obtained in accordance with the following equation. When the number of animals was 2 or more, an average value was obtained.

The inhibitory effect against gastric acid secretion (%)=(A−B)/A×100

[A]: The gastric acid output (secretion amount) for 20 minutes from 40 minutes after initiation of histamine administration to one hour later.

[B]: The gastric acid output for 20 minutes from one hour and 40 minutes after the administration of the test compound to two hours later.

The persistency of the inhibitory effect against gastric acid secretion was evaluated based on the inhibitory rate (%) against gastric acid secretion on the second day. The persistency (%) of inhibitory effect against gastric acid secretion was obtained in accordance with the following equation:

The persistency (%) of the inhibitory effect against gastric acid secretion=(C−D)/C×100.

[C]: The total amount of gastric acid output from the initiation of administration of histamine (on the first day to one hour later).

[D]: The total amount of gastric acid output from the initiation of administration of histamine (on the second day to one hour later).

(2) Results

TABLE 1

| Compound | Dose (mg/kg, i.d.) | Number of animals | Inhibitory effect against gastric acid secretion (%) | Persistency of inhibitory effect against gastric acid secretion (%) |
|---|---|---|---|---|
| Example 1 | 0.4 | 2 | 94 | 76 |
| Example 1 | 0.8 | 2 | 100 | 90 |
| Example 2 | 0.2 | 3 | 83 | 52 |
| Example 2 | 0.4 | 3 | 100 | 90 |
| Example 2 | 0.8 | 2 | 100 | 96 |
| Example 3 | 0.8 | 1 | 100 | 86 |
| Example 4 | 0.8 | 1 | 100 | 93 |
| Example 5 | 0.8 | 2 | 100 | 89 |
| Example 5 | 0.4 | 2 | 54 | 61 |

TABLE 2

| Compound | Dose (mg/kg, i.d.) | Number of animals | Inhibitory effect against gastric acid secretion (%) | Persistency of inhibitory effect against gastric acid secretion (%) |
|---|---|---|---|---|
| Example 6 | 0.8 | 1 | 100 | 89 |
| Example 7 | 0.8 | 1 | 99 | 90 |
| Example 8 | 0.8 | 1 | 100 | 88 |
| Example 9 | 0.8 | 2 | 100 | 90 |
| Example 10 | 0.8 | 2 | 98 | 90 |
| Example 10 | 1.6 | 1 | 100 | 87 |
| Example 11 | 0.4 | 3 | 79 | 65 |
| Example 11 | 0.8 | 3 | 100 | 89 |
| Example 12 | 0.8 | 1 | 100 | 86 |
| Example 13 | 0.8 | 2 | 100 | 74 |
| Example 19 | 0.4 | 4 | 13 | −4 |
| Example 19 | 0.8 | 4 | 82 | 56 |
| Example 20 | 0.1 | 4 | 8 | 6 |
| Example 20 | 0.2 | 4 | 65 | 46 |
| Example 20 | 0.4 | 10 | 97 | 77 |
| Example 20 | 0.8 | 8 | 100 | 89 |
| Example 21 | 1.6 | 1 | 100 | 94 |
| Example 22 | 1.6 | 1 | 100 | 97 |
| Example 23 | 1.6 | 1 | 100 | 92 |
| Example 24 | 1.6 | 1 | 88 | 80 |

TABLE 2-continued

| Compound | Dose (mg/kg, i.d.) | Number of animals | Inhibitory effect against gastric acid secretion (%) | Persistency of inhibitory effect against gastric acid secretion (%) |
|---|---|---|---|---|
| Example 26 | 1.6 | 1 | 100 | 80 |
| Example 27 | 1.6 | 1 | 100 | 92 |
| Example 28 | 1.6 | 1 | 94 | 77 |
| Example 29 | 1.6 | 1 | 100 | 87 |
| Example 30 | 1.6 | 1 | 100 | 95 |
| Example 30 | 0.8 | 1 | 100 | 63 |
| Example 31 | 1.6 | 1 | 100 | 97 |
| Example 32 | 1.6 | 1 | 100 | 83 |
| Example 33 | 1.6 | 1 | 100 | 84 |
| Example 34 | 1.6 | 1 | 100 | 78 |
| Example 36 | 1.6 | 1 | 100 | 90 |
| Example 39 | 1.6 | 1 | 100 | 86 |

TABLE 3

| Compound | Dose (mg/kg, i.d.) | Number of animals | Inhibitory effect against gastric acid secretion (%) | Persistency of inhibitory effect against gastric acid secretion (%) |
|---|---|---|---|---|
| Example 40 | 1.6 | 1 | 100 | 92 |
| Example 40 | 0.8 | 1 | 99 | 66 |
| Example 41 | 1.6 | 1 | 100 | 85 |
| Example 42 | 0.8 | 1 | 60 | 72 |
| Example 46 | 0.8 | 1 | 100 | 95 |
| Example 47 | 1.6 | 1 | 100 | 87 |
| Example 50 | 0.8 | 1 | 79 | 80 |
| Example 51 | 1.6 | 1 | 100 | 83 |
| Example 52 | 1.6 | 1 | 100 | 87 |
| Example 53 | 0.8 | 1 | 99 | 87 |
| Example 55 | 0.8 | 1 | 83 | 75 |
| Example 56 | 0.8 | 1 | 84 | 74 |
| Example 57 | 0.8 | 2 | 98 | 83 |
| Example 58 | 0.8 | 2 | 95 | 77 |
| Example 59 | 0.8 | 1 | 89 | 77 |
| Example 60 | 0.8 | 1 | 89 | 74 |
| Example 61 | 1.6 | 2 | 100 | 90 |
| Example 64 | 0.8 | 2 | 100 | 78 |
| Example 65 | 1.6 | 1 | 100 | 91 |
| Example 66 | 1.6 | 1 | 100 | 79 |
| Example 67 | 1.6 | 1 | 100 | 83 |
| Example 69 | 1.6 | 1 | 100 | 78 |
| Example 70 | 1.6 | 1 | 100 | 77 |
| Example 70 | 1.6 | 1 | 100 | 64 |
| Example 73 | 0.8 | 1 | 100 | 94 |
| Example 75 | 0.8 | 1 | 85 | 75 |
| Example 81 | 0.8 | 1 | 96 | 70 |
| Example 83 | 0.8 | 1 | 71 | 94 |
| Example 85 | 0.8 | 1 | 100 | 86 |
| Example 86 | 0.8 | 1 | 100 | 75 |
| Example 87 | 0.8 | 1 | 100 | 92 |

Preparation Example 1

Capsule 30.0 g of 2-(((4-((2,2-dimethyl-1,3-dioxan-5-yl)methoxy)-3,5-dimethylpyridin-2-yl)methyl)sulfinyl)-1H-benzimidazole sodium salt (hereinafter referred to as "Compound A"), 8.1 g of ethylcellulose (trade name: Etcel, manufactured by Dow Chemical Co.) and 16.2 g of hydroxypropylcellulose (trade name: HPC-L, manufactured by Shin-Etsu Chemical Co. Ltd.) were dissolved in 489 g of dehydrated ethanol. This solution was applied to 500.1 g of a core substance, Nonpareil 108 (trade name, manufactured by Freund Corporation) by use of a Wurster-type fluid-bed coating granule machine (trade name: Multiplex, Pawlek) and dried to obtain granules.

Then, 48.6 g of ethylcellulose (trade name: Etcel, Dow Chemical Co.) and 291.9 g of hydroxypropylcellulose (trade name: HPC-L, Shin-Etsu Chemical Co. Ltd.) were dissolved in dehydrated ethanol (6860 g). Further 136.8 g of magnesium stearate (manufactured by Marin Klot) was dispersed in this solution to prepare a coating solution. The granules (554.4 g) prepared above was coated with the coating solution and dried to prepare coated granules of intermediate-layer.

Furthermore, 460.2 g of hydroxypropylmethyl cellulose phthalate (trade name: HP-55S, Shin-Etsu Chemical Co. Ltd.) and 45.3 g of diacetylated monoglyceride (trade name: Mybassett, manufactured by Quest International) were dissolved in a 80% aqueous ethanol solution (11045 g). Furthermore, 42.3 g of talc (trade name: Talc, manufactured by Matsumura Industry) and 24.3 g of titanium oxide (trade name: Titanium (IV) oxide, manufactured by Merck) were dispersed in the ethanol solution obtained above. The coated granules of intermediate-layer (1031.7 g) were coated with the dispersion solution and dried to obtain enteric-coated granules.

To the enteric-coated granules (1603.8 g), 15.0 g of light anhydrous silicic acid (trade name: AEROSIL-200 (Japanese Pharmacopoeia), manufactured by Nippon Aerosil), and 15.0 g of talc (trade name, Hi-filler#17, manufactured by Matsumura Industry) were added and they were mixed by use of a vessel-type mixer (trade name: 2/5 L vessel-type mixer, manufactured by Toyo Packing) to obtain Compound A, which was charged in capsules in an amount of 1 mg/capsule.

Preparation Example 2

Capsule

Granules were prepared in accordance with the following recipe in the same manner as in Preparation Example 1. Compound A was charged in capsules in an amount of 10 mg/capsule.

TABLE 4

| Component | |
|---|---|
| Nonpareil 108 | 465.0 |
| Main ingredient layer | |
| Compound A | 500.0 |
| Ethylcellulose | 135.0 |
| HPC-L | 270.0 |
| Intermediate layer | |
| Ethylcellulose | 40.0 |
| HPC-L | 240.0 |
| Mg Stearate | 112.5 |
| External layer | |
| HP-55S | 380.0 |
| Mybassett | 37.5 |
| Talc | 35.0 |
| Titanium oxide | 20.0 |
| AEROSIL-200 | 30.0 |
| Talc | 30.0 |

Unit: g

Nonpareil 103 (Trade name, Freund Corporation)

INDUSTRIAL APPLICABILITY

The compounds of the present invention highly inhibits gastric acid secretion, persistently inhibits gastric acid secretion, is safer, is appropriately physicochemically stable, and thus can be usefully used as a medicament, especially therapeutic medicament or prophylactic medicament for acid-related diseases or symptoms.

The invention claimed is:

1. 2-(((4-((2,2-dimethyl-1,3-dioxan-5-yl)methoxy)-3,5-dimethylpyridin-2-yl)methyl)sulfinyl)-1H-benzimidazole or a salt thereof.

2. A sodium salt of 2-(((4-((2,2-dimethyl-1,3-dioxan-5-yl)methoxy)-3,5-dimethylpyridin-2-yl)methyl)sulfinyl)-1H-benzimidazole.

* * * * *